(12) United States Patent
Holson et al.

(10) Patent No.: US 10,662,199 B2
(45) Date of Patent: May 26, 2020

(54) INHIBITORS OF HISTONE DEACETYLASE

(71) Applicants: The Broad Institute, Inc., Cambridge, MA (US); The General Hospital Corporation, Boston, MA (US); Massachusetts Institute of Technology, Cambridge, MA (US)

(72) Inventors: Edward Holson, Newton, MA (US); Florence Fevrier Wagner, Ashland, MA (US); Michel Weiwer, Cambridge, MA (US); Li-Huei Tsai, Cambridge, MA (US); Stephen J. Haggarty, Gloucester, MA (US); Yan-Ling Zhang, Lexington, MA (US)

(73) Assignees: The Broad Institute, Inc., Cambridge, MA (US); The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/786,134

(22) Filed: Oct. 17, 2017

(65) Prior Publication Data
US 2018/0099977 A1 Apr. 12, 2018

Related U.S. Application Data

(60) Continuation of application No. 15/147,201, filed on May 5, 2016, now Pat. No. 9,890,172, which is a (Continued)

(51) Int. Cl.
*C07D 491/107* (2006.01)
*C07D 401/12* (2006.01)
(Continued)

(52) U.S. Cl.
CPC ........ *C07D 491/107* (2013.01); *A61K 31/167* (2013.01); *A61K 31/351* (2013.01); *A61K 31/352* (2013.01); *A61K 31/381* (2013.01); *A61K 31/397* (2013.01); *A61K 31/402* (2013.01); *A61K 31/403* (2013.01); *A61K 31/4035* (2013.01); *A61K 31/415* (2013.01); *A61K 31/4178* (2013.01); *A61K 31/437* (2013.01); *A61K 31/439* (2013.01); *A61K 31/445* (2013.01); *A61K 31/4418* (2013.01); *A61K 31/4433* (2013.01); *A61K 31/4439* (2013.01); *A61K 31/4535* (2013.01); *A61K 31/4545* (2013.01); *A61K 31/496* (2013.01); (Continued)

(58) Field of Classification Search
USPC .................................................. 514/210.17
See application file for complete search history.

(56) References Cited

U.S. PATENT DOCUMENTS

| 3,689,550 A | 9/1972 | Schellenbaum et al. |
| 3,850,931 A | 11/1974 | Kim et al. |

(Continued)

FOREIGN PATENT DOCUMENTS

| BE | 891537 | 4/1982 |
| DE | 670 584 C | 1/1939 |

(Continued)

OTHER PUBLICATIONS

STN Registry Database record for RN 737809-68-6, "N-[2-(acetylamino)phenyl]-cyclohexanecarboxamide", Entered into database on Sep. 2, 2004. (Year: 2004).*
STN Registry Database record for RN 1153257-67-0, "N-(2-aminophenyl)-1,2,3,4-tetrahydro-1-naphthalenecarboxamide", Entered into database on Jun. 7, 2009. (Year: 2009).*
Ei-Sayed; Bulletin of the Chemical Society of Japan 1979, 52, 3092-3095. (Year: 1979).*
Chemical Abstracts STN Registry Database, record for RN 926231-00-7, Entered into STN on Mar. 13, 2007. (Year: 2007).*
Chemical Abstracts STN Registry Database, record for RN 1218208-54-8, Entered into STN on Apr. 11, 2010. (Year: 2010).*
Chemical Abstracts STN Registry Database, record for RN 926217-21-2, entered into STN Mar. 13, 2007. (Year: 2007).*
Chemical Abstracts STN Registry Database, record for RN 695166-87-1, entered into STN Jun. 18, 2004. (Year: 2004).*

(Continued)

*Primary Examiner* — Daniel R Carcanague
(74) *Attorney, Agent, or Firm* — Wolf, Greenfield & Sacks, P.C.

(57) ABSTRACT

The present invention relates to compounds of formula (I):

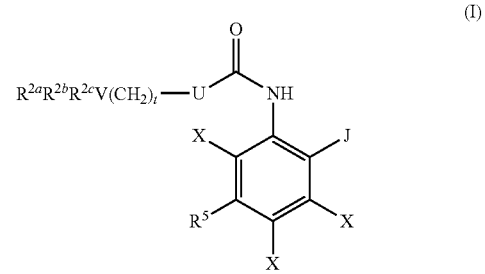

or a pharmaceutically acceptable salt, hydrate, solvate, or prodrug thereof, wherein U, J, V, X, $R^{2a}$, $R^{2b}$, $R^{2c}$, $R^5$ and t are as described herein. The present invention relates generally to inhibitors of histone deacetylase and to methods of making and using them. These compounds are useful for promoting cognitive function and enhancing learning and memory formation. In addition, these compounds are useful for treating, alleviating, and/or preventing various conditions, including for example, neurological disorders, memory and cognitive function disorders/impairments, extinction learning disorders, fungal diseases and infections, inflammatory diseases, hematological diseases, and neoplastic diseases in humans and animals.

39 Claims, 10 Drawing Sheets

Related U.S. Application Data division of application No. 14/065,278, filed on Oct. 28, 2013, now Pat. No. 9,365,498, which is a continuation of application No. PCT/US2012/035814, filed on Apr. 30, 2012.

(60) Provisional application No. 61/480,133, filed on Apr. 28, 2011.

(51) Int. Cl.
| | | |
|---|---|---|
| C07D 403/12 | (2006.01) | |
| C07D 309/08 | (2006.01) | |
| C07D 311/82 | (2006.01) | |
| C07D 333/20 | (2006.01) | |
| C07D 405/12 | (2006.01) | |
| C07D 493/08 | (2006.01) | |
| C07D 211/22 | (2006.01) | |
| C07D 213/40 | (2006.01) | |
| C07C 271/28 | (2006.01) | |
| C07C 275/30 | (2006.01) | |
| C07C 275/40 | (2006.01) | |
| C07C 281/06 | (2006.01) | |
| C07C 211/52 | (2006.01) | |
| C07C 233/43 | (2006.01) | |
| C07C 233/56 | (2006.01) | |
| C07C 233/62 | (2006.01) | |
| C07C 235/82 | (2006.01) | |
| C07D 409/12 | (2006.01) | |
| C07C 237/20 | (2006.01) | |
| C07D 205/06 | (2006.01) | |
| C07D 213/56 | (2006.01) | |
| C07D 241/12 | (2006.01) | |
| C07D 333/24 | (2006.01) | |
| C07C 237/24 | (2006.01) | |
| C07D 205/04 | (2006.01) | |
| C07D 209/44 | (2006.01) | |
| C07D 209/52 | (2006.01) | |
| C07D 211/34 | (2006.01) | |
| C07D 211/62 | (2006.01) | |
| C07D 295/195 | (2006.01) | |
| C07D 471/04 | (2006.01) | |
| A61K 31/167 | (2006.01) | |
| A61K 31/402 | (2006.01) | |
| A61K 31/403 | (2006.01) | |
| A61K 31/4035 | (2006.01) | |
| A61K 31/437 | (2006.01) | |
| A61K 31/445 | (2006.01) | |
| A61K 31/351 | (2006.01) | |
| A61K 31/352 | (2006.01) | |
| A61K 31/381 | (2006.01) | |
| A61K 31/397 | (2006.01) | |
| A61K 31/415 | (2006.01) | |
| A61K 31/4178 | (2006.01) | |
| A61K 31/439 | (2006.01) | |
| A61K 31/4418 | (2006.01) | |
| A61K 31/4433 | (2006.01) | |
| A61K 31/4439 | (2006.01) | |
| A61K 31/4535 | (2006.01) | |
| A61K 31/4545 | (2006.01) | |
| A61K 31/496 | (2006.01) | |
| A61K 31/4965 | (2006.01) | |
| A61K 31/50 | (2006.01) | |
| A61K 31/501 | (2006.01) | |
| A61K 31/519 | (2006.01) | |
| A61K 31/5377 | (2006.01) | |
| C07C 233/42 | (2006.01) | |
| C07D 231/04 | (2006.01) | |
| C07D 237/04 | (2006.01) | |
| C07D 295/185 | (2006.01) | |
| C07D 311/04 | (2006.01) | |
| C07D 407/12 | (2006.01) | |
| C07D 487/04 | (2006.01) | |
| C07D 487/10 | (2006.01) | |
| C07D 491/08 | (2006.01) | |

(52) U.S. Cl.
CPC .......... *A61K 31/4965* (2013.01); *A61K 31/50* (2013.01); *A61K 31/501* (2013.01); *A61K 31/519* (2013.01); *A61K 31/5377* (2013.01); *C07C 211/52* (2013.01); *C07C 233/42* (2013.01); *C07C 233/43* (2013.01); *C07C 233/56* (2013.01); *C07C 233/62* (2013.01); *C07C 235/82* (2013.01); *C07C 237/20* (2013.01); *C07C 237/24* (2013.01); *C07C 271/28* (2013.01); *C07C 275/30* (2013.01); *C07C 275/40* (2013.01); *C07C 281/06* (2013.01); *C07D 205/04* (2013.01); *C07D 205/06* (2013.01); *C07D 209/44* (2013.01); *C07D 209/52* (2013.01); *C07D 211/22* (2013.01); *C07D 211/34* (2013.01); *C07D 211/62* (2013.01); *C07D 213/40* (2013.01); *C07D 213/56* (2013.01); *C07D 231/04* (2013.01); *C07D 237/04* (2013.01); *C07D 241/12* (2013.01); *C07D 295/185* (2013.01); *C07D 295/195* (2013.01); *C07D 309/08* (2013.01); *C07D 311/04* (2013.01); *C07D 311/82* (2013.01); *C07D 333/20* (2013.01); *C07D 333/24* (2013.01); *C07D 401/12* (2013.01); *C07D 403/12* (2013.01); *C07D 405/12* (2013.01); *C07D 407/12* (2013.01); *C07D 409/12* (2013.01); *C07D 471/04* (2013.01); *C07D 487/04* (2013.01); *C07D 487/10* (2013.01); *C07D 491/08* (2013.01); *C07D 493/08* (2013.01); *C07C 2601/02* (2017.05); *C07C 2601/08* (2017.05); *C07C 2601/10* (2017.05); *C07C 2601/14* (2017.05); *C07C 2601/16* (2017.05); *C07C 2602/08* (2017.05); *C07C 2602/50* (2017.05)

(56) References Cited

U.S. PATENT DOCUMENTS

| | | |
|---|---|---|
| 4,404,356 A | 9/1983 | Andrews |
| 5,135,949 A | 8/1992 | von der Saal et al. |
| 5,137,918 A | 8/1992 | Weiershausen et al. |
| 5,284,656 A | 2/1994 | Platz et al. |
| 5,451,569 A | 9/1995 | Wong et al. |
| 5,525,727 A | 6/1996 | Bodor |
| 5,618,803 A | 4/1997 | Bodor |
| 5,635,503 A | 6/1997 | Poindexter et al. |
| 5,783,522 A | 7/1998 | Schaefer et al. |
| 5,886,044 A | 3/1999 | Widdowson et al. |
| 6,313,122 B1 * | 11/2001 | Beight ................ C07D 405/14 514/237.5 |
| 6,407,137 B2 | 6/2002 | Shashoua |
| 6,645,990 B2 | 11/2003 | Askew et al. |
| 6,653,309 B1 | 11/2003 | Saunders et al. |
| 6,946,462 B2 | 9/2005 | Haag et al. |
| 7,119,074 B2 | 10/2006 | Ekwuribe et al. |
| 7,550,490 B2 | 6/2009 | Lu et al. |
| 8,138,138 B2 | 3/2012 | Tjelta et al. |
| 8,138,168 B1 * | 3/2012 | Jones ................ C07D 235/14 514/211.08 |
| 8,158,825 B2 | 4/2012 | Grimm et al. |
| 8,211,901 B2 | 7/2012 | Lu et al. |

(56) References Cited

U.S. PATENT DOCUMENTS

| | | | |
|---|---|---|---|
| 8,450,525 | B2 | 5/2013 | Rajagopal et al. |
| 8,598,168 | B2 | 12/2013 | Moradei et al. |
| 8,957,066 | B2 | 2/2015 | Jacques et al. |
| 9,265,734 | B2 | 2/2016 | Rusche et al. |
| 9,365,498 | B2 | 6/2016 | Holson et al. |
| 9,447,030 | B2 | 9/2016 | Holson et al. |
| 9,790,184 | B2 | 10/2017 | Holson et al. |
| 9,890,172 | B2 | 2/2018 | Holson et al. |
| 9,914,717 | B2 | 3/2018 | Holson et al. |
| 9,988,343 | B2 | 6/2018 | Mazitschek et al. |
| 2002/0173507 | A1 | 11/2002 | Santora et al. |
| 2002/0193367 | A1 | 12/2002 | Adam et al. |
| 2003/0027862 | A1 | 2/2003 | Haning et al. |
| 2003/0159221 | A1 | 8/2003 | Lang |
| 2003/0166639 | A1 | 9/2003 | Adam et al. |
| 2006/0008517 | A1 | 1/2006 | Lynch et al. |
| 2007/0054904 | A1 | 3/2007 | Knolle et al. |
| 2008/0070954 | A1 | 3/2008 | Lim et al. |
| 2008/0132503 | A1 | 6/2008 | Moradei et al. |
| 2009/0118303 | A1 | 5/2009 | Jikyo et al. |
| 2010/0009990 | A1 | 1/2010 | Venkataramani et al. |
| 2010/0029615 | A1* | 2/2010 | Munchhof ........... C07D 235/14 514/212.08 |
| 2010/0144732 | A1* | 6/2010 | Krueger ............... C07D 239/48 514/235.8 |
| 2010/0216806 | A1 | 8/2010 | Liang et al. |
| 2010/0298358 | A1 | 11/2010 | Lu et al. |
| 2010/0324046 | A1 | 12/2010 | Harrington et al. |
| 2011/0306591 | A1* | 12/2011 | Allen ................... C07D 401/14 514/210.18 |
| 2014/0080800 | A1 | 3/2014 | Holson et al. |
| 2014/0080802 | A1 | 3/2014 | Holson et al. |
| 2014/0335550 | A1 | 11/2014 | Zhang et al. |
| 2015/0191427 | A1 | 7/2015 | Holson et al. |
| 2015/0368221 | A1 | 12/2015 | Holson et al. |
| 2016/0251351 | A1 | 9/2016 | Holson et al. |
| 2016/0272579 | A1 | 9/2016 | Mazitschek et al. |
| 2016/0347761 | A1 | 12/2016 | Holson et al. |
| 2018/0016282 | A9 | 1/2018 | Holson et al. |
| 2018/0072671 | A1 | 3/2018 | Holson et al. |
| 2018/0215726 | A1 | 8/2018 | Holson et al. |
| 2019/0216754 | A1* | 7/2019 | Holson .............. A61K 2300/00 |

FOREIGN PATENT DOCUMENTS

| | | |
|---|---|---|
| DE | 1108213 | 6/1961 |
| DE | 2163381 | 7/1972 |
| EP | 0 196 005 A1 | 10/1986 |
| EP | 0 199 393 A1 | 10/1986 |
| EP | 0 309 423 | 3/1989 |
| EP | 1 402 888 A1 | 3/2004 |
| GB | 2 086 905 A | 5/1982 |
| JP | 3-232868 A | 10/1991 |
| JP | H06-122669 A | 5/1994 |
| JP | 9-503748 A | 4/1997 |
| JP | 9-227495 A | 9/1997 |
| JP | 2000-302765 | 10/2000 |
| JP | 2004-521072 A | 7/2004 |
| JP | 2005-508311 A | 3/2005 |
| JP | 2005-522440 A | 7/2005 |
| JP | 2007-506785 | 3/2007 |
| JP | 2008-502719 | 1/2008 |
| JP | 2008-509075 A | 3/2008 |
| JP | 2008-094847 A | 4/2008 |
| JP | 2009-523726 A | 6/2009 |
| JP | 2009-536615 A | 10/2009 |
| JP | 2010-531359 A | 9/2010 |
| JP | 2011-528039 | 11/2011 |
| JP | 2012-510512 A | 5/2012 |
| JP | 2012-518612 A | 8/2012 |
| WO | WO 01/70675 | 9/2001 |
| WO | WO 2002/14311 A2 | 2/2002 |
| WO | WO 03/013484 | 2/2003 |
| WO | WO 2003/066623 A1 | 8/2003 |
| WO | WO 2004/073599 A2 | 9/2004 |
| WO | WO 2005/025557 | 3/2005 |
| WO | WO 2005/030705 A1 | 4/2005 |
| WO | WO 2005/034880 A2 | 4/2005 |
| WO | WO 2005/066151 A2 | 7/2005 |
| WO | WO 2006/001958 | 1/2006 |
| WO | WO 2006/016680 A1 | 2/2006 |
| WO | WO 2007/087130 A2 | 8/2007 |
| WO | WO 2007/118137 A1 | 10/2007 |
| WO | WO 2008/113255 | 9/2008 |
| WO | WO 2009/002534 A1 | 12/2008 |
| WO | WO 2009/055917 A1 | 5/2009 |
| WO | WO 2009/076234 A2 | 6/2009 |
| WO | WO-2009104819 A1 * | 8/2009 ........... C07D 401/12 |
| WO | WO 2010/014054 A1 | 2/2010 |
| WO | WO 2010/028192 | 3/2010 |
| WO | WO 2010/065117 A1 | 6/2010 |
| WO | WO 2010/094678 A1 | 8/2010 |
| WO | WO 2010/142426 A1 | 12/2010 |
| WO | WO 2011/009084 A2 | 1/2011 |
| WO | WO 2011/053876 | 5/2011 |
| WO | WO 2012/112447 A2 | 8/2012 |
| WO | WO 2012/118782 A1 | 9/2012 |
| WO | WO 2012/149540 | 11/2012 |
| WO | WO 2012/155806 A1 | 11/2012 |
| WO | WO 2013/059582 A2 | 4/2013 |
| WO | WO 2013/067391 A1 | 5/2013 |
| WO | WO 2015/134973 A1 | 9/2015 |

OTHER PUBLICATIONS

Dobrota; Tetrahedron Letters 51 (2010) 1262-1264, with pp. 1-14 of Supplementary material. doi:10.1016/j.tetlet.2009.11.080 (Year: 2010).*
Charton; Bioorganic & Medicinal Chemistry 2006, 14, 4490-4518. doi:10.1016/j.bmc.2006.02.028 (Year: 2006).*
Chemical Abstracts, STN Registry Database, Record for 1218056-74-6, Entered on Apr. 11, 2010. (Year: 2010).*
European Communication Pursuant to Article 94(3) EPC dated Mar. 27, 2018, with Office Action Annex for Application No. 13745773.5.
Canadian Office Action dated Apr. 17, 2018 for Application No. 2,834,548.
[No Author Listed], Benzoxazole derivatives. CAPLUS Accession No. 1983:179360 of JP 58004778; Jan. 11, 1983. 1page.
Supplementary European Search Report dated Apr. 13, 2015 for Application No. EP 12775936.3.
Office Communication dated May 30, 2016 for Application No. EP 12775936.3.
European Search Report dated Mar. 4, 2014 for Application No. EP 13194971.1.
Office Communication dated Jul. 15, 2015 for Application No. EP 13194971.1.
European Communication Pursuant to Article 94(3) EPC dated Nov. 20, 2017 for Application No. 13194971.1.
Japanese Office Action dated Oct. 14, 2015 for Application No. JP 2014-508179.
International Search Report and Written Opinion dated Jul. 20, 2012 for Application No. PCT/US2012/035814.
International Preliminary Report on Patentability dated Nov. 7, 2013 for Application No. PCT/US2012/035814.
European Office Communication for European Application No. 13745773.5 dated Dec. 21, 2016.
International Search Report and Written Opinion dated Oct. 22, 2013 for Application No. PCT/US2013/052572.
International Preliminary Report on Patentability dated Feb. 5, 2015 for Application No. PCT/US2013/052572.
International Search Report and Written Opinion dated Mar. 13, 2014 for Application No. PCT/US2013/076618.
International Preliminary Report on Patentability dated Jul. 2, 2015 for Application No. PCT/US2013/076618.
[No Author Listed], Database Accession No. 341032-95-9. Database Registry Chemical Abstracts Service. Jun. 14, 2001. STN File CASREACT: XP002720214. 2 pages.
Abramson et al., Blocking the effects of IL-1 in rheumatoid arthritis protects bone and cartilage. Rheumatology (Oxford). Sep. 2002;41(9):972-80. Review.

(56) References Cited

OTHER PUBLICATIONS

Abuchowski et al., Soluble Polymer-Enzyme Adducts. In: Enzymes as Drugs. 1981. Hocenberg et al., Eds. 367-83.
Acharya et al., Rational development of histone deacetylase inhibitors as anticancer agents: a review. Mol Pharmacol. Oct. 2005;68(4):917-32. Epub Jun. 14, 2005. Review.
Adjei et al., Bioavailability of leuprolide following intratracheal administration to beagle dogs. Int J Pharm. Jun. 11, 1990;61:135-44.
Adjei et al., Pulmonary delivery of peptide drugs: effect of particle size on bioavailability of leuprolide acetate in healthy male volunteers. Pharm Res. Jun. 1990;7(6):565-9.
Alberini, Transcription factors in long-term memory and synaptic plasticity. Physiol Rev. Jan. 2009;89(1):121-45. doi: 10.1152/physrev.00017.2008. Review.
Alenghat et al., Nuclear receptor corepressor and histone deacetylase 3 govern circadian metabolic physiology. Nature. Dec. 18, 2008;456(7224):997-1000. doi: 10.1038/nature07541. Epub Nov. 26, 2008.
Arts et al., Histone deacetylase inhibitors: from chromatin remodeling to experimental cancer therapeutics. Curr Med Chem. Nov. 2003;10(22):2343-50. Review.
Banker et al., Modern Pharmaceutics, 3rd ed. Marcel Dekker. 1996;451, 596.
Bannister et al., Regulation of chromatin by histone modifications. Cell Res. Mar. 2011;21(3):381-95. doi: 10.1038/cr.2011.22. Epub Feb. 15, 2011. Review.
Bantscheff et al., Chemoproteomics profiling of HDAC inhibitors reveals selective targeting of HDAC complexes. Nat Biotechnol. Mar. 2011;29(3):255-65. doi: 10.1038/nbt.1759. Epub Jan. 23, 2011.
Barrett et al., Beyond transcription factors: the role of chromatin modifying enzymes in regulating transcription required for memory. Learn Mem. Jun. 26, 2008;15(7):460-7. doi: 10.1101/lm.917508. Print Jul. 2008 Review.
Berge et al., Pharmaceutical salts. J Pharm Sci. Jan. 1977;66(1):1-19.
Blanchard et al., Histone deacetylase inhibitors: new drugs for the treatment of inflammatory diseases? Drug Discov Today. Feb. 1, 2005;10(3):197-204. Review.
Bradner et al., Chemical genetic strategy identifies histone deacetylase 1 (HDAC1) and HDAC2 as therapeutic targets in sickle cell disease. Proc Natl Acad Sci U S A. Jul. 13, 2010;107(28):12617-22. doi: 10.1073/pnas.1006774107. Epub Jun. 28, 2010.
Bradner et al., Chemical phylogenetics of histone deacetylases. Nat Chem Biol. Mar. 2010;6(3):238-243. Epub Sep.1, 2010. 14 pages.
Braquet et al., Effect of endothelin-1 on blood pressure and bronchopulmonary system of the guinea pig. J Cardiovasc Pharmacol. 1989;13 Suppl 5:S143-6.
Bredt et al., 1-Epicamphor (1-β-camphor). Chemical Abstracts STN Database Record for RN 1914:9447. Oxford and Manchester. J. Chem. Soc. 1914;103:2182-25. Abstract Only.
Bredt et al., 1-Epicamphor (1-β-camphor). J Chem Soc Trans. 1913;103:2182-225.
Broide et al., Distribution of histone deacetylases 1-11 in the rat brain. J Mol Neurosci. 2007;31(1):47-58.
Brukshtus et al., Synthesis of N-acetyl derivatives of 5-and 6-ethoxy-2-methylthiobenzimidazole and their cardiotonic activity. Chem Heterocyclic Compounds. Jun. 1, 1997;33(6):665-71.
Bunn, Pathogenesis and treatment of sickle cell disease. N Engl J Med. Sep. 11, 1997;337(11):762-9. Review.
Burger et al., Is IL-1 a good therapeutic target in the treatment of arthritis? Best Pract Res Clin Rheumatol. Oct. 2006;20(5):879-96. Review.
Cargin et al., Mild memory impairment in healthy older adults is distinct from normal aging. Brain Cogn. 2006;60(2):146-55.
Chang et al., Differential response of cancer cells to HDAC inhibitors trichostatin A and depsipeptide. Br J Cancer. Jan. 3, 2012;106(1):116-25. doi: 10.1038/bjc.2011.532. Epub Dec. 8, 2011.
Chang et al., Synthesis and bioevaluation of novel 3,4,5-trimethoxybenzylbenzimidazole derivatives that inhibit Helicobacter pylori-induced pathogenesis in human gastric epithelial cells. European Journal of Medicinal Chemistry. Feb. 2012;48:244-54.
Charache et al., Effect of hydroxyurea on the frequency of painful crises in sickle cell anemia. Investigators of the Multicenter Study of Hydroxyurea in Sickle Cell Anemia. N Engl J Med. May 18, 1995;332(20):1317-22.
Chemical Abstracts STN Database Record for RN 1019377-02-6. May 6, 2008. 1 page.
Chemical Abstracts STN Database Record for RN 1038237-56-7. Aug. 3, 2008. 1 page.
Chemical Abstracts STN Database Record for RN 1095240-42-8. Jan. 22, 2009. 1 page.
Chemical Abstracts STN Database Record for RN 1152996-49-0. Jun. 7, 2009. 1 page.
Chemical Abstracts STN Database Record for RN 1153085-77-8. Jun. 7, 2009. 1 page.
Chemical Abstracts STN Database Record for RN 1154691-98-1. Jun. 9, 2009. 1 page.
Chemical Abstracts STN Database Record for RN 1156303-71-7. Jun. 12, 2009. 1 page.
Chemical Abstracts STN Database Record for RN 1182778-35-3. Sep. 11, 2009. 1 page.
Chemical Abstracts STN Database Record for RN 1262320-49-9. Feb. 8, 2011. 1 page.
Chemical Abstracts STN Database Record for RN 128691-95-2. Aug. 10, 1990. 1 page.
Chemical Abstracts STN Database Record for RN 1350126-66-7. Dec. 7, 2011. 1 page.
Chemical Abstracts STN Database Record for RN 157026-22-7. Aug. 16, 1994. 1 page.
Chemical Abstracts STN Database Record for RN 169604-52-8. Nov. 3, 1995. 1 page.
Chemical Abstracts STN Database Record for RN 22380-13-8. Nov. 16, 1984. 1 page.
Chemical Abstracts STN Database Record for RN 76280-05-2. Nov. 16, 1984. 1 page.
Chemical Abstracts STN Database Record for RN 865837-30-5. Oct. 24, 2005. 1 page.
Chemical Abstracts STN Database Record for RN 926186-52-9. Mar. 13, 2007.
Chemical Abstracts STN Database Record for RN 926189-39-1. Mar. 13, 2007.
Chemical Abstracts STN Database Record for RN 926194-42-5. Mar. 13, 2007. 1 page.
Chemical Abstracts STN Database Record for RN 926196-62-5. Mar. 13, 2007. 1 page.
Chemical Abstracts STN Database Record for RN 926204-50-4. Mar. 13, 2007.
Chemical Abstracts STN Database Record for RN 926206-09-. Mar. 13, 2007. 1 page.
Chemical Abstracts STN Database Record for RN 926214-21-3. Mar. 13, 2007.
Chemical Abstracts STN Database Record for RN 926217-10-9. Mar. 13, 2007. 1 page.
Chemical Abstracts STN Database Record for RN 926219-65-0. Mar. 13, 2007.
Chemical Abstracts STN Database Record for RN 926219-90-1. Mar. 13, 2007. 1 page.
Chemical Abstracts STN Database Record for RN 926233-05-8. Mar. 13, 2007. 1 page.
Chemical Abstracts STN Database Record for RN 926246-05-1. Mar. 13, 2007. 1 page.
Chemical Abstracts STN Database Record for RN 926247-11-2. Mar. 13, 2007.
Chemical Abstracts STN Database Record for RN 926260-48-2. Mar. 13, 2007.
Chemical Abstracts STN Database Record for RN 926260-89-1. Mar. 13, 2007.
Chemical Abstracts STN Database Record for RN 926264-98-4. Mar. 13, 2007. 1 page.
Chemical Abstracts STN Database Record for RN 926272-49-3. Mar. 13, 2007.

(56) References Cited

OTHER PUBLICATIONS

Chemical Abstracts STN Database Record for RN 937607-77-7. Jun. 17, 2007. 1 page.
Chemical Abstracts STN Database Record for RN 937619-64-2 Jun. 17, 2007. 1 page.
Chemical Abstracts STN Database Record for RN 937624-40-3 Jun. 17, 2007. 1 page.
Chemical Abstracts STN Database Record for RN 953731-76-5 Nov. 15, 2007. 1 page.
Chemical Abstracts STN Database Record for RN 953741-80-5 Nov. 15, 2007. 1 page.
Chemical Abstracts STN Database Record for RN 953747-99-4. Nov. 15, 2007. 1 page.
Chou et al., Pimelic diphenylamide 106 is a slow, tight-binding inhibitor of class I histone deacetylases. J Biol Chem. Dec. 19, 2008;283(51):35402-9. doi: 10.1074/jbc.M807045200.
Citrome, Schizophrenia and valproate. Psychopharmacol Bull. 2003;37 Suppl 2:74-88. Review.
Conti et al., Design and synthesis of novel isoxazole-based HDAC inhibitors. Eur J Med Chem. Sep. 2010;45(9):4331-8. doi: 10.1016/j.ejmech.2010.06.035. Epub Jun. 30, 2010.
Dayer et al., Anti-interleukin-1 therapy in rheumatic diseases. Curr Opin Rheumatol. May 2001;13(3):170-6. Review.
Debs et al., Lung-specific delivery of cytokines induces sustained pulmonary and systemic immunomodulation in rats. J Immunol. May 15, 1988;140(10):3482-8.
Dehaene et al., Reward-dependent learning in neuronal networks for planning and decision making. Brain Res. 2000;126:217-29.
Diao et al., Assembly of substituted 1H-benzimidazoles and 1,3-dihydrobenzimidazol-2-ones via CuI/L-proline catalyzed coupling of aqueous ammonia with 2-iodoacetanilides and 2-iodophenylcarbamates. J Org Chem. Oct. 16, 2009;74(20):7974-7. doi: 10.1021/jo9017183.
Dörwald, Chapter 1: Organic Synthesis: General Remarks. Side Reactions in Organic Synthesis. A Guide to Successful Synthesis Design. Wiley-VCH Verlag GmbH & Co. KGaA. 2005. 32 pages.
D'Ydewalle et al., Charcot-Marie-Tooth disease: emerging mechanisms and therapies. Int J Biochem Cell Biol. Aug. 2012;44(8):1299-304. doi: 10.1016/j.biocel.2012.04.020. Epub Apr. 30, 2012. Review.
D'Ydewalle et al., HDAC6 at the Intersection of Neuroprotection and Neurodegeneration. Traffic. Jun. 2012;13(6):771-9. doi: 10.1111/j.1600-0854.2012.01347.x. Epub Mar. 26, 2012. Review.
Fischer et al., Cyclin-dependent kinase 5 is required for associative learning. J Neurosci. May 1, 2002;22(9):3700-7.
Fischer et al., Recovery of learning and memory is associated with chromatin remodelling. Nature. May 10, 2007;447(7141):178-82. Epub Apr. 29, 2007.
Fischle et al., Enzymatic activity associated with class II HDACs is dependent on a multiprotein complex containing HDAC3 and SMRT/N-CoR. Mol Cell. Jan. 2002;9(1):45-57.
Foster, Deuterium Isotope Effects in the Metabolism of Drugs and Xenobiotics: Implications for Drug Design. Adv Drug Res. 1985;14:1-40.
Fray et al., CANTAB battery: proposed utility in neurotoxicology. Neurotoxicol Teratol. Jul.-Aug. 1996;18(4):499-504. Review.
Glaser et al., Differential protein acetylation induced by novel histone deacetylase inhibitors. Biochem Biophys Res Commun. Dec. 17, 2004;325(3):683-90.
Govindarajan et al., Reducing HDAC6 ameliorates cognitive deficits in a mouse model for Alzheimer's disease. EMBO Mol Med. Jan. 2013;5(1):52-63. Doi: 10.1002/emmm.201201923. Epub Nov. 26, 2012.
Grundmann et al., Nitrile Oxides. XII. Cycloaliphatic and Alipathic Stable Nitrile Oxides. J Org Chem. Jan. 1, 1969;34(6):2016-8.
Guan et al., HDAC2 negatively regulates memory formation and synaptic plasticity. Nature. May 7, 2009;459(7243):55-60. doi: 10.1038/nature07925.
Guenther et al., A core SMRT corepressor complex containing HDAC3 and TBL1, a WD40-repeat protein linked to deafness. Genes Dev. May 1, 2000;14(9):1048-57.
Hancock et al., HDAC inhibitor therapy in autoimmunity and transplantation. Ann Rheum Dis. Apr. 2012;71 Suppl 2:i46-54. doi: 10.1136/annrheumdis-2011-200593. Review.
Hnilicováet al., Histone deacetylase activity modulates alternative splicing. PloS One. Feb. 2, 2011;6(2):e16727. Doi: 10.1371/journal.pone.0016727. 11 pages.
Hubbard et al., Anti-neutrophil-elastase defenses of the lower respiratory tract in alpha 1-antitrypsin deficiency directly augmented with an aerosol of alpha 1-antitrypsin. Ann Intern Med. Aug. 1, 1989;111(3):206-12.
Iverson, Interpreting change on the WAIS-III/WMS-III in clinical samples. Arch Clin Neuropsychol. Feb. 2001;16(2):183-91.
Jochems et al., Antidepressant-like properties of novel HDAC6-selective inhibitors with improved brain bioavailability. Neuropsychopharmacology. Jan. 2014;39(2):389-400. doi: 10.1038/npp.2013.207. Epub Aug. 19, 2013.
Johannessen et al., Valproate: past, present, and future. CNS Drug Rev. 2003 Summer;9(2):199-216. Review.
Kalin et al., Development and therapeutic implications of selective histone deacetylase 6 inhibitors. J Med Chem. Aug. 22, 2013;56(16):6297-313. doi: 10.1021/jm4001659. Epub May 15, 2013. Review.
Karagianni et al., HDAC3: taking the SMRT-N-CoRrect road to repression. Oncogene. Aug. 13, 2007;26(37):5439-49. Review.
Katragadda et al., Hydrophobic effect and hydrogen bonds account for the improved activity of a complement inhibitor, compstatin. J Med Chem. Jul. 27, 2006;49(15):4616-22.
Katsura et al., Studies on antiulcer drugs. II. Synthesis and antiulcer activities of imidazo[1,2-alpha]pyridinyl-2-alkylaminobenzoxazoles and 5,6,7,8-tetrahydroimidazo[1,2-alpha]pyridinyl derivatives. Chem Pharm Bull (Tokyo). Feb. 1992;40(2):371-80.
Kilgore et al., Inhibitors of class 1 histone deacetylases reverse contextual memory deficits in a mouse model of Alzheimer's disease. Neuropsychopharmacology. Mar. 2010;35(4):870-80. doi: 10.1038/npp.2009.197. Epub Dec. 9, 2009.
Kouzarides, Chromatin modifications and their function. Cell. Feb. 23, 2007;128(4):693-705. Review.
Kreutzberger et al., Antiinflammatory Agents, VII: Aroylation of 5-Chlorobenzotriazole [Published in German as Entzündungshemmende Wirkstoffe, 7. Mitt. Aroylierung von 5-Chlorbenzotriazol]. Arch. Pharm. 1980;313(3): 255-259. doi: 10.1002/ardp.19803130311.
Kuhn et al., Stalling of spliceosome assembly at distinct stages by small-molecule inhibitors of protein acetylation and deacetylation. RNA. Jan. 2009;15(1):153-75. doi: 10.1261/rna.1332609. Epub Nov. 24, 2008.
Lane et al., Histone deacetylase inhibitors in cancer therapy. J Clin Oncol. Nov. 10, 2009;27(32):5459-68. doi: 10.1200/JCO.2009.22.1291. Epub Oct. 13, 2009.
Langer, New methods of drug delivery. Science. Sep. 28, 1990;249(4976):1527-33. Review.
Langley et al., Remodeling chromatin and stress resistance in the central nervous system: histone deacetylase inhibitors as novel and broadly effective neuroprotective agents. Curr Drug Targets CNS Neurol Disord. Feb. 2005;4(1):41-50. Review.
Lattal et al., Systemic or intrahippocampal delivery of histone deacetylase inhibitors facilitates fear extinction. Behav Neurosci. Oct. 2007;121(5):1125-31.
Leoni et al., The antitumor histone deacetylase inhibitor suberoylanilide hydroxamic acid exhibits antiinflammatory properties via suppression of cytokines. Proc Natl Acad Sci U S A. Mar. 5, 2002;99(5):2995-3000. Epub Feb. 26, 2002.
Lettre et al., DNA polymorphisms at the BCL11A, HBS1L-MYB, and beta-globin loci associate with fetal hemoglobin levels and pain crises in sickle cell disease. Proc Natl Acad Sci U S A. Aug. 19, 2008;105(33):11869-74. doi: 10.1073/pnas.0804799105. Epub Jul. 30, 2008.
Letvin et al., Augmentation of fetal-hemoglobin production in anemic monkeys by hydroxyurea. N Engl J Med. Apr. 5, 1984;310(14):869-73.
Levenson et al., Regulation of histone acetylation during memory formation in the hippocampus. J Biol Chem. Sep. 24, 2004;279(39):40545-59. Epub Jul. 23, 2004.

(56) References Cited

OTHER PUBLICATIONS

Li et al., Both corepressor proteins SMRT and N-CoR exist in large protein complexes containing HDAC3. EMBO J. Aug. 15, 2000;19(16):4342-50.
Locock et al., γ-aminobutyric acid(C) ($GABA_c$) selective antagonists derived from the bioisosteric modification of 4-aminocyclopent-1-enecarboxylic acid: amides and hydroxamates. J Med Chem. Jul. 11, 2013;56(13):5626-30. doi: 10.1021/jm4006548. Epub Jun. 27, 2013.
Malvaez et al., Modulation of chromatin modification facilitates extinction of cocaine-induced conditioned place preference. Biol Psychiatry. Jan. 1, 2010;67(1):36-43. doi: 10.1016/j.biopsych.2009.07.032. Epub.
Marks et al., Histone deacetylase inhibitors. Adv Cancer Res. 2004;91:137-68. Review.
Marks et al., Histone deacetylases and cancer: causes and therapies. Nat Rev Cancer. Dec. 2001;1(3):194-202. Review.
Matsushita et al., Smart cleavage reactions: the synthesis of benzimidazoles and benzothiazoles from polymer-bound esters. Tetrahedron Lett. 2004;45(2):313-6.
McKay et al., A bird's-eye view of post-translational modifications in the spliceosome and their roles in spliceosome dynamics. Mol Biosyst. Nov. 2010;6(11):2093-102. doi: 10.1039/c002828b. Epub Jun. 22, 2014. 20 pages.
McQuown et al., HDAC3 is a critical negative regulator of long-term memory formation. J Neurosci. Jan. 12, 2011;31(2):764-74. doi: 10.1523/JNEUROSCI.5052-10.2011.
Menzel et al., A QTL influencing F cell production maps to a gene encoding a zinc-finger protein on chromosome 2p15. Nat Genet. Oct. 2007;39(10):1197-9. Epub Sep. 2, 2007.
Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8. doi: 10.1016/j.bmcl.2007.12.031. Epub Jan. 7, 2008.
Miller et al., Histone deacetylase inhibitors. J Med Chem. Nov. 20, 2003;46(24):5097-116. Review.
Monfils et al., Extinction-reconsolidation boundaries: key to persistent attenuation of fear memories. Science. May 15, 2009;324(5929):951-5. doi: 10.1126/science.1167975. Epub Apr. 2, 2009.
Mullin, Crystallization and precipitation. In: Ullmann's encyclopedia of industrial chemistry. 2002;1-51.
Mullin, Crystallization. In: Kirk-Othmer encyclopedia of chemical technology. 2002;95-147.
Namdar et al., Selective inhibition of histone deacetylase 6 (HDAC6) induces DNA damage and sensitizes transformed cells to anticancer agents. Proc Natl Acad Sci U S A. Nov. 16, 2010;107(46):20003-8. doi: 10.1073/pnas.1013754107. Epub Oct. 29, 2010.
Newmark et al., Preparation and properties of adducts of streptokinase-plasmin complex with polyethylene glycol and pluronic polyol F 38. J Appl Biochem. 1982;4:185-9.
Ogino et al., Syntheses and structure-activity relationships of novel, potent, and selective trans-2-[3-oxospiro[isobenzofuran-1(3H),1'-cyclohexan]-4'-yl]benzimidazole NPY Y5 receptor antagonists. Bioorg Med Chem Lett. Sep. 15, 2008;18(18):4997-5001. doi: 10.1016/j.bmcl.2008.08.021.
O'Malley et al., Virtual medicinal chemistry: in silico pre-docking functional group transformation for discovery of novel inhibitors of botulinum toxin serotype A light chain. Bioorg Med Chem Lett. May 1, 2013;23(9):2505-11. doi: 10.1016/j.bmcl.2013.03.030. Epub Mar. 18, 2013.
Oehme et al., Histone deacetylase 8 in neuroblastoma tumorigenesis. Clin Cancer Res. Jan. 1, 2009;15(1):91-9. doi: 10.1158/1078-0432.CCR-08-0684.
Olson et al., Discovery of the first histone deacetylase 6/8 dual inhibitors. J Med Chem. Jun. 13, 2013;56(11):4816-20. doi: 10.1021/jm400390r. Epub May 29, 2013. Supplementary Information. S1-20.
Oswein et al., Aerosolization of Protein Pharmaceuticals. Proceedings of Symposium on Respiratory Drug Delivery II. Keystone, Colorado. Mar. 1990 34 pages.
Park et al., Histone deacetylases 1, 6 and 8 are critical for invasion in breast cancer. Oncol Rep. Jun. 2011;25(6):1677-81. doi: 10.3892/or.2011.1236. Epub Mar. 28, 2011.
Platt et al., Hydroxyurea enhances fetal hemoglobin production in sickle cell anemia. J Clin Invest. Aug. 1984;74(2):652-6.
Rai et al., Two new pimelic diphenylamide HDAC inhibitors induce sustained frataxin upregulation in cells from Friedreich's ataxia patients and in a mouse model. PLoS One. Jan. 21, 2010;5(1):e8825. doi: 10.1371/journal.pone.0008825.
Rivieccio et al., HDAC6 is a target for protection and regeneration following injury in the nervous system. Proc Natl Acad Sci U S A. Nov. 17, 2009;106(46):19599-604. doi: 10.1073/pnas.0907935106. Epub Nov. 2, 2009.
Roozendaal et al., Membrane-associated glucocorticoid activity is necessary for modulation of long-term memory via chromatin modification. J Neurosci. Apr. 7, 2010;30(14):5037-46. doi: 10.1523/JNEUROSCI.5717-09.2010.
Rouhi, The right stuff, from research and development to the clinic, getting drug crystals right is full of pitfalls. Chem. Eng. News. Feb. 24, 2003;81(8):32-5.
Sankaran et al., Developmental and species-divergent globin switching are driven by BCL11A. Nature. Aug. 27, 2009;460(7259):1093-7. doi: 10.1038/nature08243. Epub Aug. 5, 2009.
Sankaran et al., Human fetal hemoglobin expression is regulated by the developmental stage-specific repressor BCL11A. Science. Dec. 19, 2008;322(5909):1839-42. doi: 10.1126/science.1165409. Epub Dec. 4, 2008.
Schultz et al., Kinetics and comparative reactivity of human class I and class IIb histone deacetylases. Biochemistry. Aug. 31, 2004;43(34):11083-91.
Silverman, Prodrugs and drug delivery systems. In: The organic chemistry of drug design and drug action. 1992. Chapter 8:354-5.
Smith et al., Pulmonary deposition and clearance of aerosolized alpha-1-proteinase inhibitor administered to dogs and to sheep. J Clin Invest. Oct. 1989;84(4):1145-54.
Song et al., Synthesis of New Crown Ethers Containing Appended Pyridine, 10-hydroxybenzoquinoline, 8-hydroxyquinoline and 2-amino-1-hydroxybiphenyl Sidearms. Supramolecular Chemistry. 2002;14(2-3):263-269.
Stefanko et al., Modulation of long-term memory for object recognition via HDAC inhibition. Proc Natl Acad Sci U S A. Jun. 9, 2009;106(23):9447-52. doi: 10.1073/pnas.0903964106. Epub May 26, 2009.
Steinberg et al., Effect of hydroxyurea on mortality and morbidity in adult sickle cell anemia: risks and benefits up to 9 years of treatment. JAMA. Apr. 2, 2003;289(13):1645-51. Erratum in: JAMA. Aug. 13, 2003;290(6):756.
Steinberg et al., Management of sickle cell disease. N Engl J Med. Apr. 1, 1999;340(13):1021-30. Review.
Suuronen et al., Regulation of microglial inflammatory response by histone deacetylase inhibitors. J Neurochem. Oct. 2003;87(2):407-16.
Tsankova et al., Sustained hippocampal chromatin regulation in a mouse model of depression and antidepressant action. Nat Neurosci. Apr. 2006;9(4):519-25. Epub Feb. 26, 2006.
Turconi et al., Synthesis of a New Class of 2,3-Dihydro-2-oxo-1H-benzimidazole-1-carboxylic Acid Derivatives as Highly Potent $5\text{-}HT_3$ Receptor Antagonists. J Med Chem. 1990;33:2101-8.
Uda et al., Genome-wide association study shows BCL11A associated with persistent fetal hemoglobin and amelioration of the phenotype of beta-thalassemia. Proc Natl Acad Sci U S A. Feb. 5, 2008;105(5):1620-5. doi: 10.1073/pnas.0711566105. Epub Feb. 1, 2008.
Vecsey et al., Histone deacetylase inhibitors enhance memory and synaptic plasticity via CREB:CBP-dependent transcriptional activation. J Neurosci. Jun. 6, 2007;27(23):6128-40.
Wagner et al., An Isochemogenic Set of Inhibitors to Define the Therapeutic Potential of Histone Deacetylases in β-Cell Protection. ACS Chem Biol. Feb. 19, 2016;11(2):363-74. doi: 10.1021/acschembio.5b00640.

(56) References Cited

OTHER PUBLICATIONS

Wagner et al., Potent and selective inhibition of histone deacetylase 6 (HDAC6) does not require a surface-binding motif. J Med Chem. Feb. 28, 2013;56(4):1772-6. doi: 10.1021/jm301355j. Epub Feb. 18, 2013.

Wagner et al., Small molecule inhibitors of zinc-dependent histone deacetylases. Neurotherapeutics. Oct. 2013;10(4):589-604. doi: 10.1007/s13311-013-0226-1.

Weïwer et al., Therapeutic potential of isoform selective HDAC inhibitors for the treatment of schizophrenia. Future Med Chem. Sep. 2013;5(13):1491-508. doi: 10.4155/fmc.13.141.

Wolff, Burger's Medicinal Chemistry, 5th ed. Part I. John Wiley & Sons. 1995;975-7.

Xiong et al., HDAC6 mutations rescue human tau-induced microtubule defects in *Drosophila*. Proc Natl Acad Sci U S A. Mar. 19, 2013;110(12):4604-9. doi: 10.1073/pnas.1207586110. Epub Mar. 4, 2013. 6 pages.

European Communication dated Jul. 17, 2018 for Application No. 13194971.1.

Capkova et al., Synthesis and structure-activity relationships of second-generation hydroxamate botulinum neurotoxin A protease inhibitors. Bioorganic & Medicinal Chemistry Letters. 2007;10:6463-6466.

Canadian Office Action for Application No. 2834548 dated Jul. 15, 2019.

Japanese Decision of Rejection dated Jun. 10, 2019 for Application No. JP 2017-212845.

Canadian Examination Report dated Jul. 30, 2019 for Application No. 2,880,117.

[No Author Listed] Chemical Abstracts STN Database Record for RN 926190-69-4 and 926236-00-2. Mar. 13, 2007.

[No Author Listed] Chemical Abstracts STN Database Record for RN 1039887-48-3. Aug. 20, 2008.

\* cited by examiner

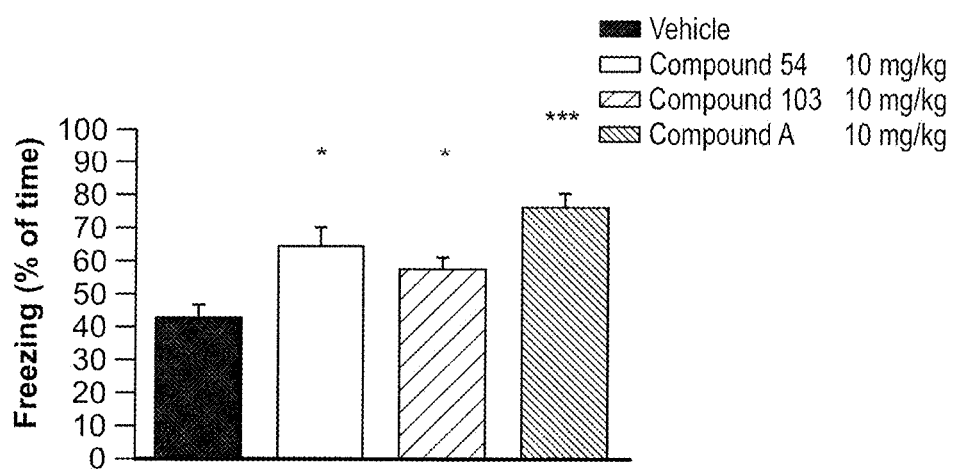
FIG. 4
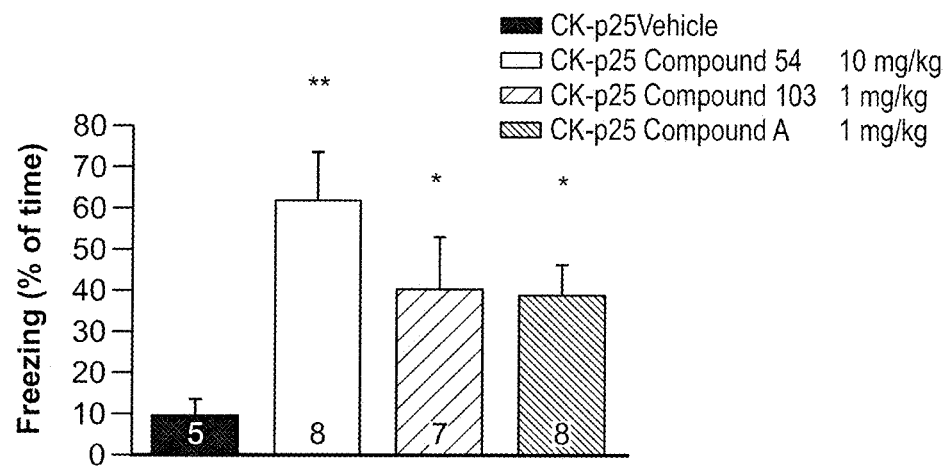
FIG. 5
FIG. 6A
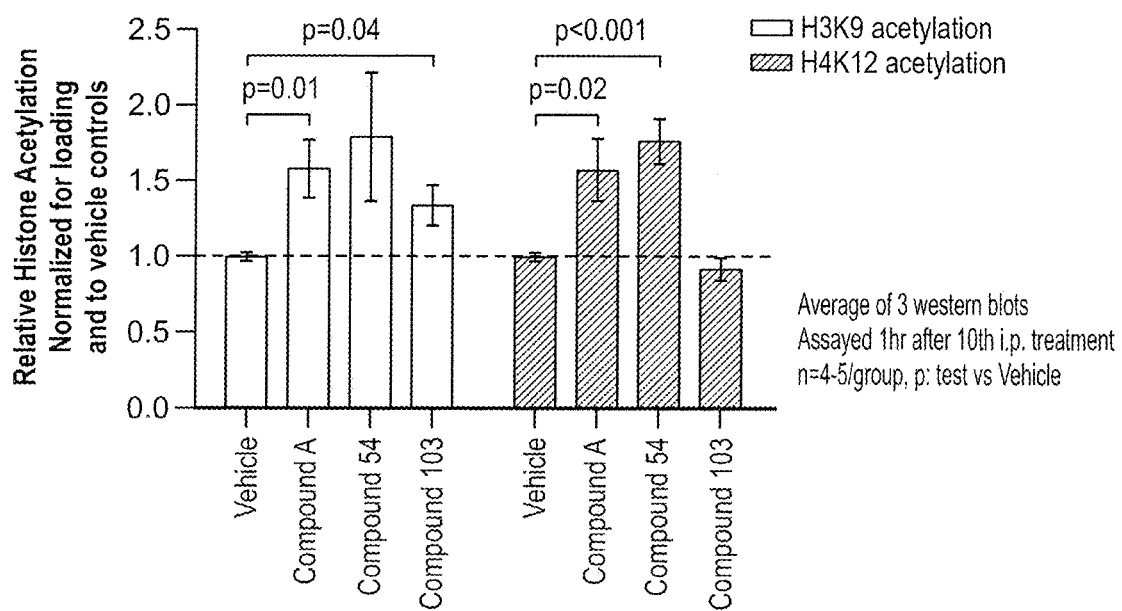

INHIBITORS OF HISTONE DEACETYLASE

CROSS-REFERENCE TO RELATED APPLICATION

This application is a continuation of and claims priority under 35 U.S.C. § 120 to U.S. patent application Ser. No. 15/147,201, filed May 5, 2016, which is a division of and claims priority under 35 U.S.C. § 120 to U.S. patent application Ser. No. 14/065,278, filed Oct. 28, 2013 and issued as U.S. Pat. No. 9,365,498, which is a continuation of International PCT Application No. PCT/US2012/035814, filed on Apr. 30, 2012, which claims priority to and the benefit of U.S. Provisional Application No. 61/480,133, filed on Apr. 28, 2011, the entire contents of each of which are incorporated herein by reference.

FIELD OF THE INVENTION

The present invention relates generally to inhibitors of histone deacetylase and to methods of making and using them. These compounds are useful for promoting cognitive function and enhancing learning and memory formation. These compounds are useful for treating, alleviating, and/or preventing various conditions, including for example, neurological disorders, memory and cognitive function disorders/impairments, extinction learning disorders, fungal diseases and infections, inflammatory diseases, hematological diseases, and neoplastic diseases in humans and animals.

BACKGROUND OF THE INVENTION

Inhibitors of histone deacetylases (HDAC) have been shown to modulate transcription and to induce cell growth arrest, differentiation and apoptosis. HDAC inhibitors also enhance the cytotoxic effects of therapeutic agents used in cancer treatment, including radiation and chemotherapeutic drugs. Marks, P., Rifkind, R. A., Richon, V. M., Breslow, R., Miller, T., Kelly, W. K. Histone deacetylases and cancer: causes and therapies. Nat Rev Cancer, 1, 194-202, (2001); and Marks, P. A., Richon, V. M., Miller, T., Kelly, W. K. Histone deacetylase inhibitors. Adv Cancer Res, 91, 137-168, (2004). Moreover, recent evidence indicates that transcriptional dysregulation may contribute to the molecular pathogenesis of certain neurodegenerative disorders, such as Huntington's disease, spinal muscular atrophy, amyotropic lateral sclerosis, and ischemia. Langley, B., Gensert, J. M., Beal, M. F., Ratan, R. R. Remodeling chromatin and stress resistance in the central nervous system: histone deacetylase inhibitors as novel and broadly effective neuroprotective agents. Curr Drug Targets CNS Neurol Disord, 4, 41-50, (2005). A recent review has summarized the evidence that aberrant histone acetyltransferase (HAT) and histone deacetylases (HDAC) activity may represent a common underlying mechanism contributing to neurodegeneration. Moreover, using a mouse model of depression, Nestler has recently highlighted the therapeutic potential of histone deacetylation inhibitors (HDAC5) in depression. Tsankova, N. M., Berton, O., Renthal, W., Kumar, A., Neve, R. L., Nestler, E. J. Sustained hippocampal chromatin regulation in a mouse model of depression and antidepressant action. Nat Neurosci, 9, 519-525, (2006).

There are 18 known human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to class IIa and have homology to yeast. HDAC6 and HDAC10 contain two catalytic sites and are classified as class IIb. Class III (the sirtuins) includes SIRT1, SIRT2, SIRT3, SIRT4, SIRT5, SIRT6, and SIRT7. HDAC11 is another recently identified member of the HDAC family and has conserved residues in its catalytic center that are shared by both class I and class II deacetylases and is sometimes placed in class IV.

There is still much to be understood about the family of HDACs, including the varying functions of different HDACs and the range of HDAC substrates. In order to learn more about the role that the individual HDACs play, it is important to develop compounds showing selectivity for individual isoforms or small subsets of these isoforms. While some degree of isoform selectivity has been shown by a few compounds, this problem of identifying selective inhibitors is far from solved, and the problem is complicated by the interactions of the HDACs with each other as well as other proteins (cofactors) that can possibly alter their interaction with various inhibitors (Glaser, et al., Biochem. Biophys. Res. Commun., 325, 683-690 (2004). Clinically, the optimal dose, timing and duration of therapy, as well as the most appropriate agents to combine with HDAC inhibitors, are also still to be defined.

The findings to date suggest that HDAC inhibitors have great therapeutic potential in promoting cognitive function, enhancing learning and memory, and treating disease. There is a need to identify specific/selective HDAC inhibitors and to identify the structural features required for potent HDAC inhibitory activity.

SUMMARY OF THE INVENTION

The present invention provides compounds useful for the inhibition of histone deacetylase (HDAC). The invention provides a compound having the formula I:

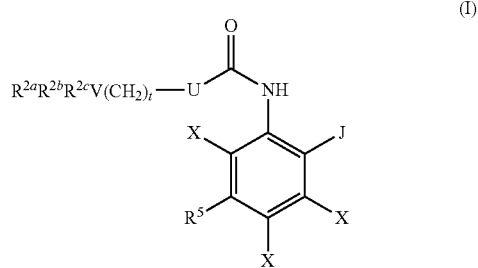

or a pharmaceutically acceptable salt, hydrate, solvate, or prodrug thereof. In formula I, the variables U, J, V, X, $R^{2a}$, $R^{2b}$, $R^{2c}$, $R^5$ and t can be selected from the respective groups of chemical moieties later defined in the detailed description.

In addition, the invention provides pharmaceutical compositions comprising an effective amount of a compound of the invention and a pharmaceutical carrier, diluent, or excipient.

In one aspect, the invention provides a method of treating, alleviating, and/or preventing a condition in a subject comprising administering to a subject in need thereof an effective amount of a compound of the invention or a pharmaceutically acceptable salt, hydrate, solvate or prodrug thereof. In one aspect, the condition is selected from a neurological disorder, memory or cognitive function disorder or impairment, extinction learning disorder, fungal disease or infection, inflammatory disease, hematological disease, and neoplastic disease.

In one aspect, the invention provides a method of improving memory in a normal subject comprising administering to the subject in need thereof an effective amount of a compound of the invention or a pharmaceutically acceptable salt, hydrate, solvate, or prodrug thereof.

In one aspect, the invention provides a method of treating, alleviating, and/or preventing memory loss or impairment in a subject comprising administering to the subject in need thereof an effective amount of a compound of the invention or a pharmaceutically acceptable salt, hydrate, solvate, or prodrug thereof.

In one aspect, the invention provides a method of treating, alleviating, and/or preventing a cognitive function disorder or impairment in a subject in need thereof comprising administering to the subject an effective amount of a compound of the invention or a pharmaceutically acceptable salt, hydrate, solvate, or prodrug thereof. In one aspect, the cognitive function disorder or impairment is associated with Alzheimer's disease, Huntington's disease, seizure induced memory loss, schizophrenia, Rubinstein Taybi syndrome, Rett Syndrome, Fragile X, Lewy body dementia, vascular dementia, ADHD, dyslexia, bipolar disorder and social, cognitive and learning disorders associated with autism, traumatic head injury, or attention deficit disorder. In one aspect, the cognitive function disorder or impairment is associated with an anxiety disorder, conditioned fear response, panic disorder, obsessive compulsive disorder, post-traumatic stress disorder, phobia, social anxiety disorder, substance dependence recovery or Age Associated Memory Impairment (AAMI), or Age Related Cognitive Decline (ARCD).

In one aspect, the invention provides a method of treating, alleviating, and/or preventing an inflammatory disease in a subject in need thereof comprising administering to the subject an effective amount of a compound or a pharmaceutically acceptable salt, hydrate, solvate, or prodrug thereof.

In one aspect, the invention provides a method of treating, alleviating, and/or preventing a fungal disease or infection in a subject in need thereof comprising administering to the subject an effective amount of a compound of the invention or a pharmaceutically acceptable salt, hydrate, solvate, or prodrug thereof.

In one aspect, the invention provides a method of treating, alleviating, and/or preventing a hematological disease in a subject comprising administering to the subject in need thereof an effective amount of a compound of the invention or a pharmaceutically acceptable salt, hydrate, solvate, or prodrug thereof. In one aspect, the hematological disease is selected from acute myeloid leukemia, acute promyelocytic leukemia, acute lymphoblastic leukemia, chronic myelogenous leukemia, myelodysplastic syndromes, and sickle cell anemia. In one aspect, the hematological disease is sickle cell anemia.

In one aspect, the invention provides a method of treating, alleviating, and/or preventing a neoplastic disease in a subject comprising administering to the subject in need thereof an effective amount of a compound of the invention or a pharmaceutically acceptable salt, hydrate, solvate, or prodrug thereof. In one aspect, the neoplastic disease is cancer.

In one aspect, the invention provides a method of treating, alleviating, and/or preventing a psychiatric disease (depression, mood, mania disorders etc.) in a subject comprising administering to the subject in need thereof an effective amount of a compound of the invention or a pharmaceutically acceptable salt, hydrate, solvate, or prodrug thereof.

In one aspect, the invention provides a method, wherein the method is a combination therapy further comprising administering to the subject (1) a pharmaceutically active ingredient or exposing the subject to (2) cognitive behavioral therapy (CBT), (3) psychotherapy, (4) behavioral exposure treatments, (5) virtual reality exposure (VRE) or (6) cognitive remediation therapy or (7) any combination thereof.

In one aspect, the invention provides a combination therapy for treating, alleviating, and/or preventing post-traumatic stress disorder (PTSD) or Alzheimer's disease in a subject comprising administering to the subject in need thereof an effective amount of (1) a compound of the invention or a pharmaceutically acceptable salt, hydrate, solvate, or prodrug thereof and (2) a pharmaceutically active ingredient administered selected from Aricept®, memantine, and galantamine.

In one aspect, the invention provides a method of treating extinction learning disorders in a subject in need thereof comprising administering to the subject an effective amount of a compound of the invention or a pharmaceutically acceptable salt, hydrate, solvate, or prodrug thereof. In one aspect, the extinction learning disorder is fear extinction deficit. In one aspect, the extinction learning disorder is post-traumatic stress disorder. In one aspect, the method is a combination therapy for treating extinction learning disorders in a subject in need thereof comprising administering to the subject (1) an effective amount of a compound of the invention or a pharmaceutically acceptable salt, hydrate, solvate, or prodrug thereof and (2) exposing the subject to cognitive behavioral therapy (CBT), psychotherapy, behavioral exposure treatments, virtual reality exposure (VRE) or cognitive remediation therapy.

In one aspect, the invention provides a method wherein the compound of the invention or a pharmaceutically acceptable salt, hydrate, solvate, or prodrug thereof is administered by a route selected from oral, parenteral, intramuscular, intranasal, sublingual, intratracheal, inhalation, ocular, vaginal, rectal, and intracerebroventricular.

In one aspect, the invention provides a method, wherein the subject is a human.

In one aspect, the invention provides a method of synthesizing a compound of the invention or a pharmaceutically acceptable salt, hydrate, solvate, or prodrug thereof.

In one aspect, the invention provides a kit containing one or more compounds of the invention or a pharmaceutically acceptable salt, hydrate, solvate, or prodrug thereof. In one aspect, the kit further contains a pharmaceutically active ingredient.

In one aspect, the invention provides a method of increasing synaptic density in a subject comprising administering to the subject in need of such increase an effective amount of a compound of the invention or a pharmaceutically acceptable salt, hydrate, solvate, or prodrug thereof. In one aspect, the invention provides a method of increasing synaptic plasticity in a subject comprising administering to the subject in need of such increase an effective amount of a compound of the invention or a pharmaceutically acceptable salt, hydrate, solvate, or prodrug thereof. In one aspect, the invention provides a method of increasing dendritic density in neurons in a subject comprising administering to the subject in need of such increase an effective amount of a compound of the invention or a pharmaceutically acceptable salt, hydrate, solvate, or prodrug thereof.

BRIEF DESCRIPTION OF THE DRAWINGS

FIG. 4 is a bar chart indicating increased freezing in a contextual fear conditioning paradigm following administration of compounds of the invention or compound A (positive control; 10 mg/kg) in wild type mice.

FIG. 5 is a bar chart indicating increased freezing in a contextual fear conditioning paradigm following administration of compounds of the invention or compound A (positive control; 1 mg/kg) in 6-week induced CK-p25 mice (neurodegenerative mouse model).

FIG. 6A is a bar chart indicating the relative histone acetylation of H3K9 and H4K12 in C57BL/6 mouse cortex following chronic administration of compounds of the invention or compound A (positive control) compared to untreated (vehicle) mice.

DETAILED DESCRIPTION OF THE INVENTION

Figure 1A:
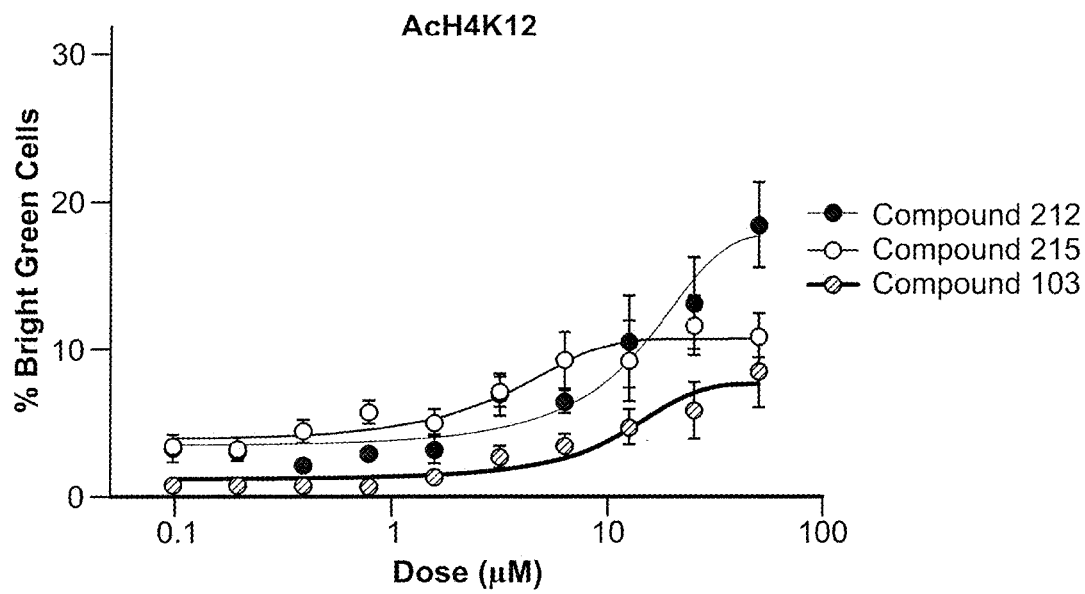
FIGS. 1A and 1C are dose response curves of histone acetylation (AcH4K12) in primary neuronal cultures by compounds of the invention.

The invention provides compounds, pharmaceutical compositions and methods for inhibiting class I histone deacetylase enzymatic activity. The invention also provides compounds, pharmaceutical compositions and methods for promoting cognitive function and treating, alleviating and/or preventing various conditions disease e.g., neurological disorders, memory and cognitive function disorders/impairments, extinction learning disorders, fungal diseases, inflammatory diseases, hematological diseases, and neoplastic diseases. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having from 1, 2, 3, 4, 5, 6, 7, or 8 carbon atoms. "$C_1$-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, isopropyl, n-butyl, isobutyl, sec-butyl, and tert-butyl. The term "$C_1$-$C_4$ n-alkyl" refers to straight chain hydrocarbon moieties having from 1 to 4 carbon atoms including methyl, ethyl, n-propyl, and n-butyl. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. The term "$C_3$-$C_8$ cycloalkyl" also includes cyclooctyl. Cycloalkylalkyl refers to cycloalkyl moieties linked through an alkyl linker chain, as for example, but without limitation, cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. Each alkyl, cycloalkyl, and cycloalkylalkyl group may be optionally substituted as specified herein.

The term "$C_4$-$C_8$ cycloalkenyl" refers to cyclobutenyl, cyclopentyl, cyclohexenyl, cycloheptenyl, and cyclooctenyl rings having one or more sites of unsaturation e.g., one or more double bonds.

The term "3 to 8 membered ring" includes a 3, 4, 5, 6, 7, and 8-membered ring.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom.

The term "halogen" refers to fluoro, chloro, bromo, or iodo.

The term "hydroxyl" means OH.

The term "aryl" or "aromatic ring" alone or in combination, means a carbocyclic aromatic system containing one, two or three rings wherein such rings may be attached together in a pendent manner or may be fused. The term "aryl" or "aromatic ring" embraces aromatic radicals such as phenyl (e.g., $C_6H_5$—), naphthyl, tetrahydronapthyl, indane and biphenyl, and includes carbocyclic aryl, heterocyclic aryl and biaryl groups, all of which may be optionally substituted.

The term "heteroaryl" or "heteroaromatic ring" as used herein includes 5-, 6- and 7-membered single-ring aromatic groups that may include from 1, 2, 3, or 4 heteroatoms, for example, pyrrole, furan, thiophene, imidazole, oxazole, thiazole, triazole, pyrazole, pyridine, pyrazine, pyridazine, azepine, oxepine, oxazine, triazine and pyrimidine, and the like. Those aryl groups having heteroatoms in the ring structure may also be referred to as "aryl heterocycles" or "heteroaromatics." A heteroaryl or heteroaromatic ring can be monocyclic, bicyclic, or tricyclic, wherein such rings may be attached together in a pendent manner or may be fused. In one aspect, the heteroaryl or heteroaromatic ring is a 5-, 6-, or 7-membered single ring that includes from 1, 2, 3, or 4 heteroatoms. A heteroaryl or heteroaromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like.

The term "heterocyclic ring" or "heterocycle" is taken to mean a saturated, unsaturated, or partially unsaturated containing from 1, 2, 3, or 4 heteroatoms selected from nitrogen, oxygen and sulfur, said ring optionally being benzofused. A heterocylic ring can be multicyclic e.g., bicyclic or tricyclic. The term "3- to 8-membered heterocyclic ring" refers to a ring having from 3, 4, 5, 6, 7 or 8 atoms. The term "3- to 6-membered heterocyclic ring" refers to a ring having from 3, 4, 5, or 6 atoms. The term "5- to 6-membered heterocyclic ring" refers to a ring having 5 or 6 atoms. Exemplary heterocyclic rings, for the purposes of the present invention, include furanyl, thiophenyl (thienyl or thiopheneyl), pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. Heterocyclic rings include bicyclic rings for example, 3-azabicyclo[3.1.0]hexane, 8-oxa-3-azabicyclo[3.2.1]octane. Benzofused heterocyclic rings include isoquinolinyl, benzoxazolyl, benzodioxolyl, benzothiazolyl, quinolinyl, benzofuranyl, benzothiophenyl, indolyl, and the like, all of which may be optionally substituted, which also of course includes optionally substituted on the benzo ring when the heterocycle is benzofused.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds unless otherwise specified. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient(s) and salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

The term "acid addition salt" refers to a salt of a compound of the invention prepared by reaction of a compound of the invention with a mineral or organic acid. For exemplification of pharmaceutically acceptable acid addition salts see, e.g., Berge, S. M, Bighley, L. D., and Monkhouse, D. C., *J. Pharm. Sci.,* 66:1, 1977. Compounds of this invention which are amines, are basic in nature and accordingly react with any of a number of inorganic and organic acids to form pharmaceutically acceptable acid addition salts.

Pharmaceutically acceptable acid addition salts of the invention can be formed by reacting a compound of the invention with an equimolar or excess amount of acid. Alternatively, hemi-salts can be formed by reacting a compound of the invention with the desired acid in a 2:1 ratio, compound to acid. The reactants are generally combined in a mutual solvent such as diethylether, tetrahydrofuran, methanol, ethanol, isopropanol, benzene, or the like. The salts normally precipitate out of solution within about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

Some of the compounds of the present invention may exist in unsolvated as well as solvated forms such as, for example, hydrates.

Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the compounds of the invention, methods of delivering the same and compositions containing the same. "Prodrugs" are intended to include any covalently bonded carriers that release an active parent drug of the present invention in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the invention wherein a hydroxyl or amino, group is bonded to any group that, when the prodrug of the present invention is administered to a mammalian subject, it cleaves to form a free hydroxyl or free amino group, respectively. Examples of prodrugs include, but are not limited to, acetate, formate, and benzoate derivatives of alcohol and amine functional groups in the compounds of the present invention.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "suitable solvent" refers to any solvent, or mixture of solvents, inert to the ongoing reaction that sufficiently solubilizes the reactants to afford a medium within which to effect the desired reaction.

The compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention. Furthermore, the invention also includes metabolites of the compounds described herein.

The invention also comprehends isotopically-labeled compounds, which are identical to those recited in the formulae of the invention, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$, $^{14}C$, $^2H$ and $^{18}F$.

Compounds of the present invention and salts, hydrates, solvates or prodrugs of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., 3H, and carbon-14, i.e., $^{14}C$, isotopes are particularly preferred for their ease of preparation and detectability. $^{11}C$ and $^{18}F$ isotopes are particularly useful in PET (positron emission tomography). PET is useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances, isotopically labeled compounds of this invention can generally be prepared by carrying out the procedures disclosed in the Schemes and/or in the Examples below, by substituting a readily available isotopically labeled reagent for a non-isotopically labeled reagent. In one embodiment, the compounds of the invention, salts, hydrates, solvates, or prodrugs thereof are not isotopically labelled.

When any variable (e.g., $R^x$) occurs more than one time in any constituent or formula for a compound, its definition at each occurrence is independent of its definition at every other occurrence. Thus, for example, if a group is shown to be substituted with one or more $R^X$ moieties, then $R^X$ at each occurrence is selected independently from the definition of $R^X$. Also, combinations of substituents and/or variables are permissible, but only if such combinations result in stable compounds within a designated atom's normal valency.

As used herein, the term "treat," "treating," "alleviate," or "alleviating" herein, is meant decreasing the symptoms, markers, and/or any negative effects of a condition in any appreciable degree in a patient who currently has the condition. In some embodiments, treatment may be administered to a subject who exhibits only early signs of the condition for the purpose of decreasing the risk of developing the disease, disorder, and/or condition.

As used herein, the term "prevent," "prevention," or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, "subject" means a human or animal (in the case of an animal, more typically a mammal). In one aspect, the subject is a human. Such subject can be considered to be in need of treatment with an HDAC inhibitor.

As used herein, "unsaturated" refers to compounds or structures having at least one degree of unsaturation (e.g., at least one double or triple bond).

As used herein, the term "Compound A" refers to the known compound CI-994.

Compounds of the Invention

In one aspect, the invention relates to a compound of formula I:

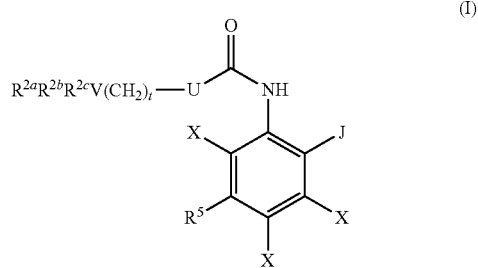

or a pharmaceutically acceptable salt, hydrate, solvate, or prodrug thereof, wherein U is selected from single bond, $CR^{2e}R^{2f}$—$CR^{2g}R^{2h}$, $NR^{2d}$, $NR^{2d}$—$NR^{2d'}$, and O;

J is selected from $NH_2$, OH, and SH;

V is selected from C and N, provided that when V is N, one of $R^{2a}$, $R^{2b}$, or $R^{2c}$ is absent;

X is selected from hydrogen, deuterium, methyl, $CF_3$, and halogen;

$R^{2a}$ is selected from hydrogen, halogen, OH, NH$_2$, and C$_1$-C$_8$ alkyl;
$R^{2b}$ is selected from hydrogen, halogen, OH, NH$_2$, and C$_1$-C$_8$ alkyl;
$R^{2c}$ is selected from hydrogen, halogen, OH, NH$_2$, and C$_1$-C$_8$ alkyl;
$R^{2d}$ is selected from NH$_2$, hydrogen, and C$_1$-C$_8$ alkyl;
$R^{2d'}$ is selected from NH$_2$, hydrogen, and C$_1$-C$_8$ alkyl;
$R^{2e}$, $R^{2f}$, $R^{2g}$, and $R^{2h}$ are each independently selected from hydrogen, halogen, and C$_1$-C$_4$ alkyl;
or taken together two of $R^{2a}$, $R^{2b}$, and $R^{2c}$ form =O,
or taken together two of $R^{2a}$, $R^{2b}$, and $R^{2c}$ form a C$_3$-C$_8$ cycloalkyl ring, C$_4$-C$_8$ cycloalkenyl ring, or 3 to 8 membered saturated or partially unsaturated heterocyclic ring and the remaining $R^{2a}$, $R^{2b}$, or $R^{2c}$ is absent or selected from hydrogen, halogen, OH, NH$_2$, and C$_1$-C$_8$ alkyl, further wherein said cycloalkyl, cycloalkenyl, and heterocyclic ring are unsubstituted or substituted with one or more $R^x$;
or alternatively, taken together two of $R^{2a}$, $R^{2b}$, $R^{2c}$ and $R^{2d}$ form a C$_3$-C$_8$ cycloalkyl ring, C$_4$-C$_8$ cycloalkenyl ring, or 3 to 8 membered saturated or partially unsaturated heterocyclic ring and the remaining $R^{2a}$, $R^{2b}$, or $R^{2c}$ is selected from hydrogen, halogen, OH, NH$_2$, and C$_1$-C$_8$ alkyl or $R^{2d}$ is hydrogen, NH$_2$, or C$_1$-C$_8$ alkyl, further wherein said cycloalkyl, cycloalkenyl, and heterocyclic ring are unsubstituted or substituted with one or more $R^x$;
or taken together two of $R^{2a}$, $R^{2b}$, and $R^{2c}$ form an aromatic or heteroaromatic ring and the remaining $R^{2a}$, $R^{2b}$, or $R^{2c}$ is absent, provided that when two of $R^{2a}$, $R^{2b}$, and $R^{2c}$ form an aromatic or heteroaromatic ring and the remaining $R^{2a}$, $R^{2b}$, or $R^{2c}$ is absent, U is not a single bond when t is 0,
further wherein said aromatic and heteroaromatic ring are unsubstituted or substituted with one or more $R^x$,
or taken together $R^{2e}$ and $R^{2f}$ or $R^{2g}$ and $R^{2h}$ taken together form =O;
or taken together two of $R^{2e}$, $R^{2f}$, $R^{2g}$, and $R^{2h}$ on two adjacent carbon atoms together with the bond between said adjacent carbon atoms form a carbon-carbon double bond;
or taken together two of $R^{2e}$, $R^{2f}$, $R^{2g}$, and $R^{2h}$ on two adjacent carbon atoms together with the intervening atoms to which they are attached form a 3 to 8 membered saturated or partially saturated ring;
each $R^x$ is independently selected from (CH$_2$)$_z$NH$_2$, (CH$_2$)$_z$NHR$^3$, (CH$_2$)$_z$NR$^3$R$^3$, OR$^3$, OCF$_3$, OCH$_2$F, OCHF$_2$, (CH$_2$)$_z$-aromatic ring, (CH$_2$)$_z$-heterocyclic ring, hydroxyl, halogen, C$_1$-C$_8$ alkyl, (C$_1$-C$_8$ alkyl)CF$_3$, (C$_1$-C$_8$ alkyl)OH, C(O)R$^3$, (CH$_2$)$_z$C(O)NH$_2$, (CH$_2$)$_z$C(O)NHR$^3$, (CH$_2$)$_z$C(O)NR$^3$R$^3$, (CH$_2$)$_z$NHC(O)R$^4$, and (CH$_2$)$_z$NR$^4$C(O)R$^4$;
or taken together two $R^x$ attached to the same carbon atom of a cycloalkyl, cycloalkenyl or heterocyclic ring together form =O;
or taken together two $R^x$ form a C$_3$-C$_8$ cycloalkyl ring, C$_4$-C$_8$ cycloalkenyl ring or 3 to 8 membered saturated or partially unsaturated heterocyclic ring, further wherein said cycloalkyl, cycloalkenyl, and heterocyclic ring are unsubstituted or substituted with one or more $R^z$;
or taken together two $R^x$ form an aromatic ring or heteroaromatic ring, further wherein said aromatic and heteroaromatic ring are unsubstituted or substituted with one or more $R^z$;
each $R^z$ is independently selected from halogen, C$_1$-C$_4$ alkyl, OH, OR$^3$, CF$_3$, OCF$_3$, OCH$_2$F, OCHF$_2$, NH$_2$, NHR$^3$, NR$^3$R$^3$, and C(O)CH$_3$;
$R^3$ is selected from C$_1$-C$_8$ alkyl and O(C$_1$-C$_8$ alkyl);

$R^4$ is selected from C$_1$-C$_8$ alkyl and CF$_3$;
$R^5$ is selected from hydrogen, deuterium, halogen, OH, OR$^6$, CF$_3$, C$_1$-C$_8$ alkyl, C$_2$-C$_8$ alkene, (CH$_2$)$_u$-5-6 membered saturated, unsaturated, or partially unsaturated heterocyclic ring, (CH$_2$)$_v$—C$_3$-C$_8$ cycloalkyl ring, (C$_1$-C$_8$-alkyl)$_w$-C$_4$-C$_8$cycloalkenyl ring, (CH$_2$)$_s$-aromatic ring, and (CH$_2$)$_s$-heteroaromatic and wherein said heterocyclic, cycloalkyl, cycloalkenyl, heteroaromatic, and aromatic ring are unsubstituted or substituted with one or more $R^y$ and said alkene is substituted with one or more $R^T$;
each $R^y$ is independently selected from halogen, OR$^6$, NH$_2$, NHR$^6$, NR$^6$R$^6$, OH, CF$_3$, aromatic ring, C(O)R$^6$, C$_1$-C$_8$ alkyl, C$_2$-C$_8$ alkenyl, and C$_2$-C$_8$ alkynyl;
$R^6$ is C$_1$-C$_8$ alkyl;
each $R^T$ is independently selected from hydrogen, halogen, Si(R$^3$)$_3$, phenyl, and C$_1$-C$_8$ alkyl;
u is selected from 0, 1, and 2;
v is selected from 0, 1, and 2;
w is selected from 0, 1, and 2;
s is selected from 0, 1, and 2;
t is selected from 0, 1, and 2, and
z is selected from 0, 1, 2, and 3.

In one aspect, the invention relates to a compound having the formula I or a pharmaceutically acceptable salt, hydrate, solvate, or prodrug thereof, wherein U is selected from single bond, CR$^{2e}$R$^{2f}$—CR$^{2g}$R$^{2h}$, NR$^{2d}$, NR$^{2d}$—NR$^{2d'}$ and O; J is selected from NH$_2$, OH, and SH; V is selected from C and N, provided that when V is N, one of $R^{2a}$, $R^{2b}$, or $R^{2c}$ is absent; X is selected from hydrogen, methyl, CF$_3$, and halogen; $R^{2a}$ is selected from hydrogen, halogen, OH, NH$_2$, and C$_1$-C$_8$ alkyl; $R^{2b}$ is selected from hydrogen, halogen, OH, NH$_2$, and C$_1$-C$_8$ alkyl; $R^{2c}$ is selected from hydrogen, halogen, OH, NH$_2$, and C$_1$-C$_8$ alkyl; $R^{2d}$ is selected from NH$_2$, hydrogen, and C$_1$-C$_8$ alkyl; $R^{2d'}$ is selected from NH$_2$, hydrogen, and C$_1$-C$_8$ alkyl; $R^{2e}$, $R^{2f}$, $R^{2g}$, and $R^{2h}$ are each independently selected from hydrogen, halogen, and C$_1$-C$_4$ alkyl; or taken together two of $R^{2a}$, $R^{2b}$, and $R^{2c}$ form =O; or taken together two of $R^{2a}$, $R^{2b}$, and $R^{2c}$ form a C$_3$-C$_8$ cycloalkyl ring, C$_4$-C$_8$ cycloalkenyl ring, or 3 to 8 membered saturated or partially unsaturated heterocyclic ring, and the remaining $R^{2a}$, $R^{2b}$, or $R^{2c}$ is selected from hydrogen, halogen, OH, NH$_2$, and C$_1$-C$_8$ alkyl; or taken together two of $R^{2a}$, $R^{2b}$, and $R^{2c}$ form an aromatic or heteroaromatic ring and the remaining $R^{2a}$, $R^{2b}$, or $R^{2c}$ is absent, provided that U is not single bond and t is not 0; further, wherein said cycloalkyl, cycloalkenyl, heterocyclic, aromatic and heteroaromatic ring (formed by two of $R^{2a}$, $R^{2b}$, and $R^{2c}$) are unsubstituted or substituted with one or more $R^x$, or taken together two of $R^{2e}$, $R^{2f}$, $R^{2g}$, and $R^{2h}$ on two adjacent carbon atoms together with the bond between said adjacent carbon atoms form a carbon-carbon double bond; or taken together two of $R^{2e}$, $R^{2f}$, $R^{2g}$, and $R^{2h}$ on two adjacent carbon atoms together with the intervening atoms to which they are attached form a 3 to 8 membered saturated or partially saturated ring;
each $R^x$ is independently selected from NH$_2$, NHR$^3$, NR$^3$R$^3$, OR$^3$, (CH$_2$)$_z$C$_6$H$_6$, hydroxyl, halogen, C$_1$-C$_8$ alkyl, (C$_1$-C$_8$)CF$_3$, (C$_1$-C$_8$)OH, C(O)R$^3$ and (CH$_2$)$_z$NHC(O)R$^4$,
or taken together two $R^x$ attached to the same carbon atom of a cycloalkyl, cycloalkenyl or heterocyclic ring together form =O; or taken together two $R^x$ form a C$_3$-C$_8$ cycloalkyl ring, C$_4$-C$_8$ cycloalkenyl ring or 3 to 8 membered saturated or partially unsaturated heterocyclic ring; further wherein said cycloalkyl, cycloalkenyl, and heterocyclic ring (formed by two $R^x$) are optionally substituted with one or more $R^z$; each $R^z$ is independently selected from halogen, C$_1$-C$_4$ alkyl, OH, NH$_2$, and C(O)CH$_3$; $R^3$ is selected from $C_1$-$C_8$ alkyl and O($C_1$-$C_8$ alkyl); $R^4$ is selected from $C_1$-$C_8$ alkyl and $CF_3$; $R^5$ is selected from hydrogen, halogen, OH, $OR^6$, $CF_3$, $CH_3$, $C_{2-8}$ alkene, $(CH_2)_u$-5-6 membered saturated, unsaturated, or partially unsaturated heterocyclic ring, $(CH_2)_v$—$C_3$-$C_8$ cycloalkyl ring, ($C_1$-$C_8$-alkyl)$_w$-$C_4$-$C_8$ cycloalkenyl ring, $(CH_2)_s$-aromatic ring, and $(CH_2)_s$-heteroaromatic, and wherein said heterocyclic, cycloalkyl, cycloalkenyl, aromatic and heteroaromatic ring are unsubstituted or substituted with one or more $R^y$ and said alkene is substituted with one or more $R^T$; each $R^y$ is independently selected from halogen, $OR^6$, $NH_2$, $NHR^6$, $NR^6R^6$, OH, aromatic ring, $C(O)R^6$, $C_1$-$C_8$ alkyl, $C_2$-$C_8$ alkenyl, and $C_2$-$C_8$ alkynyl; $R^6$ is $C_1$-$C_8$ alkyl; each $R^T$ is independently selected from hydrogen, halogen, $Si(R^3)_3$, $C_6H_6$, and $C_1$-$C_8$ alkyl; u is selected from 0, 1, and 2; v is selected from 0, 1, and 2; w is selected from 0, 1, and 2; s is selected from 0, 1, and 2; t is selected from 0, 1, and 2, and z is selected from 0, 1, 2, and 3.

In one aspect, the invention provides a compound of formula I, wherein the moiety:

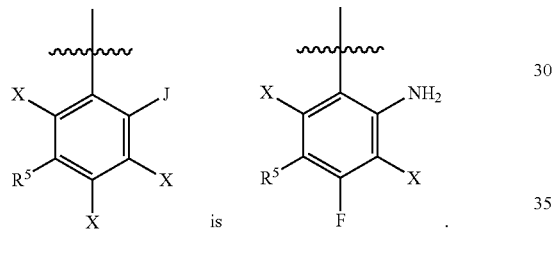

is.

In one aspect, the invention provides a compound having a formula selected from

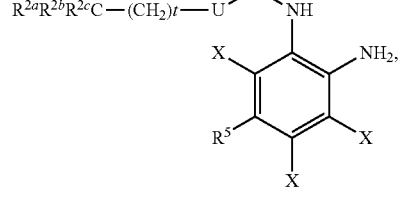

(Ia)

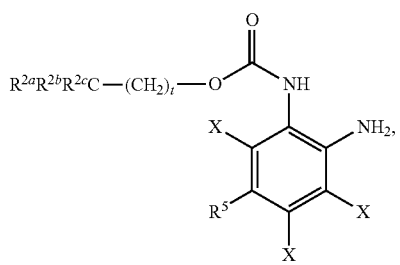

(IIa)

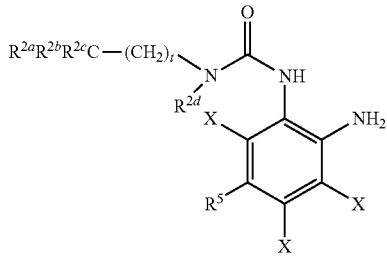

(IIIa)

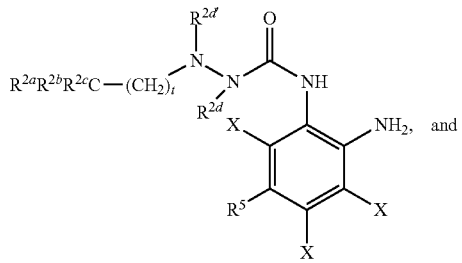

(IVa)

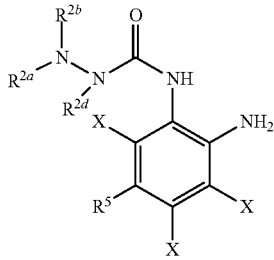

(Va)

or a pharmaceutically acceptable salt, hydrate, solvate, or prodrug thereof, wherein U is selected from single bond and $CR^{2e}R^{2f}$—$CR^{2g}R^{2h}$, and $R^{2a}$, $R^{2b}$, $R^{2c}$, $R^{2d}$, t, X, $R^5$, $R^{2d'}$, $R^{2e}$, $R^{2f}$, $R^{2g}$, and $R^{2h}$ are the same as described for formula I herein.

In one aspect, the invention provides a compound of formulae Ia, IIa, IIIa, IVa, or Va or a pharmaceutically acceptable salt, hydrate, solvate, or prodrug thereof, wherein the moiety:

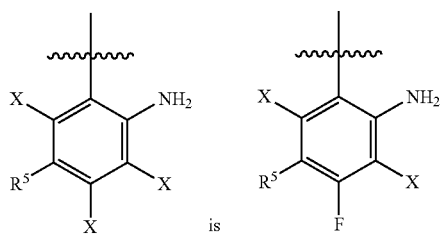

is.

In one aspect, the invention provides a compound having the formula Ib:

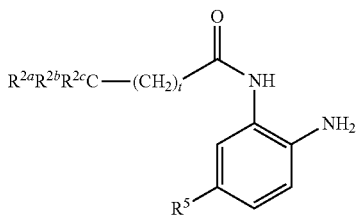

(Ib)

or a pharmaceutically acceptable salt, hydrate, solvate or prodrug thereof, wherein
$R^{2a}$ is selected from hydrogen, OH, $NH_2$, and $C_1$-$C_8$ alkyl;
$R^{2b}$ is selected from hydrogen, OH, $NH_2$, and $C_1$-$C_8$ alkyl;
$R^{2c}$ is selected from hydrogen, OH, $NH_2$, and $C_1$-$C_8$ alkyl;
or taken together two of $R^{2a}$, $R^{2b}$, and $R^{2c}$ form =O,
or taken together two of $R^{2a}$, $R^{2b}$, and $R^{2c}$ form a $C_3$-$C_8$ cycloalkyl ring, $C_4$-$C_8$ cycloalkenyl ring, or 3 to 6 membered saturated or partially unsaturated heterocyclic ring, and the remaining $R^{2a}$, $R^{2b}$ or $R^{2c}$ is selected from hydrogen, OH, $NH_2$, and $C_1$-$C_8$ alkyl,
or taken together two of $R^{2a}$, $R^{2b}$, and $R^{2c}$ form an aromatic or heteroaromatic ring and the remaining $R^{2a}$, $R^{2b}$, or $R^{2c}$ is absent, provided that when two of $R^{2a}$, $R^{2b}$, and $R^{2c}$ form an aromatic ring and the remaining $R^{2a}$, $R^{2b}$, or $R^{2c}$ is absent, t is not 0,
wherein said cycloalkyl, cycloalkenyl, heterocyclic, aromatic, and heteroaromatic ring are unsubstituted or substituted with one or more $R^x$;
each $R^x$ is independently selected from $(CH_2)_zNH_2$, $(CH_2)_zNHR^3$, $(CH_2)_zNR^3R^3$, $OR^3$, $OCF_3$, $OCH_2F$, $OCHF_2$, $(CH_2)_z$-aromatic ring, $(CH_2)_z$-heterocyclic ring, hydroxyl, halogen, $C_1$-$C_8$ alkyl, $(C_1$-$C_8$ alkyl)$CF_3$, $(C_1$-$C_8$ alkyl)OH, $C(O)R^3$, $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_zNR^4C(O)R^4$;
or taken together two $R^x$ attached to the same carbon atom of a cycloalkyl, cycloalkenyl, or heterocyclic ring together form =O;
or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$;
or taken together two $R^x$ form an aromatic ring or heteroaromatic ring, further wherein said aromatic and heteroaromatic ring are unsubstituted or substituted with one or more $R^z$;
each $R^z$ is independently selected from halogen, $C_1$-$C_4$ alkyl, OH, $OR^3$, $OCF_3$, $OCH_2F$, $OCHF_2$, $NH_2$, $NHR^3$, $NR^3R^3$, and $C(O)CH_3$;
$R^3$ is selected from $C_1$-$C_8$ alkyl and $O(C_1$-$C_8$ alkyl);
$R^4$ is selected from $C_1$-$C_8$ alkyl and $CF_3$;
$R^5$ is selected from hydrogen, deuterium, halogen, OH, $OR^6$, $CF_3$, $C_1$-$C_8$ alkyl, $C_{2-8}$ alkene, $(CH_2)_s$-aromatic ring, $(CH_2)_s$-heteroaromatic, $C_3$-$C_6$ cycloalkyl ring, $C_4$-$C_6$ cycloalkenyl ring and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more $R^y$ and said alkene is substituted with one or more $R^T$;
each $R^y$ is independently selected from halogen, $OR^6$, $NH_2$, $NHR^6$, $NR^6R^6$, OH, $C(O)R^6$, $C_1$-$C_8$ alkyl, $C_2$-$C_8$ alkenyl, and $C_2$-$C_8$ alkynyl;

$R^T$ is independently selected from halogen, hydrogen, $C_6H_6$, $Si(R^3)_3$ and $C_1$-$C_8$ alkyl;
$R^6$ is $C_1$-$C_8$ alkyl;
s is selected from 0, 1, and 2,
t is selected from 0, 1, and 2 and
z is selected from 0, 1, 2, and 3.

In one aspect, the invention provides a compound having the formula Ib or a pharmaceutically acceptable salt, hydrate, solvate or prodrug thereof, wherein $R^{2a}$ is selected from hydrogen, OH, $NH_2$, and $C_1$-$C_8$ alkyl; $R^{2b}$ is selected from hydrogen, OH, $NH_2$, and $C_1$-$C_8$ alkyl; $R^{2c}$ is selected from hydrogen, OH, $NH_2$, and $C_1$-$C_8$ alkyl;
or taken together two of $R^{2a}$, $R^{2b}$, and $R^{2c}$ form =O, or taken together two of $R^{2a}$, $R^{2b}$, and $R^{2c}$ form a $C_3$-$C_8$ cycloalkyl ring, $C_4$-$C_8$ cycloalkenyl ring, or 3 to 6 membered saturated or partially unsaturated heterocyclic ring, and the remaining $R^{2a}$, $R^{2b}$ or $R^{2c}$ is selected from hydrogen, OH, $NH_2$, and $C_1$-$C_8$ alkyl, or taken together two of $R^{2a}$, $R^{2b}$, and $R^{2c}$ form an aromatic or heteroaromatic ring and the remaining $R^{2a}$, $R^{2b}$, or $R^{2c}$ is absent,
wherein said cycloalkyl, cycloalkenyl, heterocyclic, aromatic, and heteroaromatic ring are unsubstituted or substituted with one or more $R^x$; each $R^x$ is independently selected from $NH_2$, $NHR^6$, $NR^6$, $R^6$, hydroxyl, halogen, $C_1$-$C_8$ alkyl, $(C_1$-$C_8)CF_3$, $(C_1$-$C_8)OH$, $C(O)R^3$, $OR^3$, $(CH_2)_zC_6H_6$, and $(CH_2)_zNHC(O)R^4$; or taken together two $R^x$ attached to the same carbon atom of a cycloalkyl, cycloalkenyl, or heterocyclic ring together form =O;
or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; each $R^z$ is independently selected from halogen, $C_1$-$C_4$ alkyl, OH, $NH_2$, and $C(O)CH_3$; $R^3$ is selected from $C_1$-$C_8$ alkyl and $O(C_1$-$C_8$ alkyl); $R^4$ is selected from $C_1$-$C_8$ alkyl and $CF_3$; $R^5$ is selected from hydrogen, halogen, OH, $OR^6$, $CF_3$, $CH_3$, $C_{2-8}$ alkene, $(CH_2)_s$-aromatic ring, $(CH_2)_s$-heteroaromatic, $C_3$-$C_6$ cycloalkyl ring, $C_4$-$C_6$ cycloalkenyl ring and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more $R^y$ and said alkene is substituted with one or more $R^T$; each $R^y$ is independently selected from halogen, $OR^6$, $NH_2$, $NHR^6$, $NR^6R^6$, OH, $C(O)R^6$, $C_1$-$C_8$ alkyl, $C_2$-$C_8$ alkenyl, and $C_2$-$C_8$ alkynyl;
$R^T$ is independently selected from halogen, hydrogen, $C_6H_6$, $Si(R^3)_3$ and $C_1$-$C_8$ alkyl; $R^6$ is $C_1$-$C_8$ alkyl; s is selected from 0, 1, and 2, t is selected from 0, 1, and 2 and z is selected from 0, 1, 2, and 3.

In one aspect, the invention provides a compound having the formula Ibb:

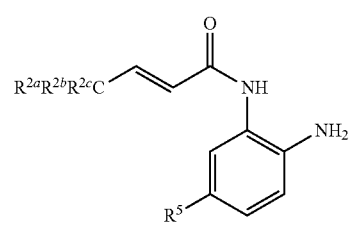

(Ibb)

or a pharmaceutically acceptable salt, hydrate, solvate, or prodrug thereof, wherein $R^{2c}$, $R^{2b}$, $R^{2a}$, and $R^5$ are as described herein.

In one aspect, the invention provides a compound having the formula Ibbb:

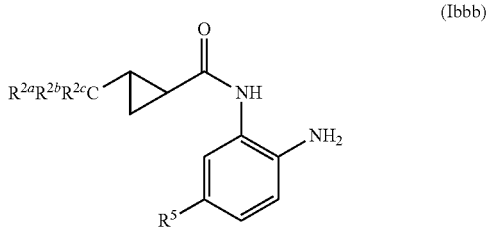

(Ibbb)

or a pharmaceutically acceptable salt, hydrate, solvate, or prodrug thereof, wherein $R^{2c}$, $R^{2b}$, $R^{2a}$, and $R^5$ are as described herein.

In one aspect, the invention provides a compound having the formula IIb:

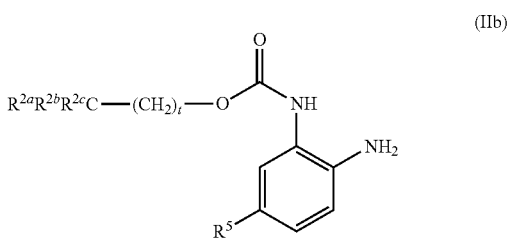

(IIb)

or a pharmaceutically acceptable salt, hydrate, solvate, or prodrug thereof, wherein
$R^{2a}$ is selected from hydrogen, halogen, OH, $NH_2$, and $C_1$-$C_8$ alkyl;
$R^{2b}$ is selected from hydrogen, halogen, OH, $NH_2$, and $C_1$-$C_8$ alkyl;
$R^{2c}$ is selected from hydrogen, halogen, OH, $NH_2$, and $C_1$-$C_8$ alkyl;
or alternatively, taken together two of $R^{2a}$, $R^{2b}$, and $R^{2c}$ form a $C_3$-$C_8$ cycloalkyl ring, $C_4$-$C_8$ cycloalkenyl ring, 3-6 membered saturated or partially unsaturated heterocyclic ring and the remaining $R^{2a}$, $R^{2b}$, and $R^{2c}$ is selected from hydrogen, halogen, OH, $NH_2$, and $C_1$-$C_8$ alkyl, or taken together two of $R^{2a}$, $R^{2b}$, and $R^{2c}$ form an aromatic or heteroaromatic ring and the remaining $R^{2a}$, $R^{2b}$, or $R^{2c}$ is absent;
further, wherein said cycloalkyl, cycloalkenyl, heterocyclic, aromatic and heteroaromatic ring are unsubstituted or substituted with one or more $R^x$;
each $R^x$ is independently selected from $(CH_2)_zNH_2$, $(CH_2)_zNHR^3$, $(CH_2)_zNR^3R^3$, $OR^3$, $OCF_3$, $OCH_2F$, $OCHF_2$, $(CH_2)_z$-aromatic ring, $(CH_2)_z$-heterocyclic ring, hydroxyl, halogen, $C_1$-$C_8$ alkyl, $(C_1$-$C_8$ alkyl)$CF_3$, $(C_1$-$C_8$ alkyl)OH, $C(O)R^3$, $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_zNR^4C(O)R^4$;
$R^3$ is selected from $C_1$-$C_8$ alkyl and $O(C_1$-$C_8$ alkyl);
$R^4$ is selected from $C_1$-$C_8$ alkyl and $CF_3$;
$R^5$ is selected from hydrogen, deuterium, halogen, OH, $OR^6$, $CF_3$, $C_1$-$C_8$ alkyl, $C_{2-8}$ alkene, $(CH_2)_s$-aromatic ring, $(CH_2)_s$-heteroaromatic, $C_3$-$C_6$ cycloalkyl ring, $C_4$-$C_6$ cycloalkenyl ring and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more $R^y$ and said alkene is substituted with one or more $R^T$;
each $R^y$ is independently selected from halogen, $OR^6$, $NH_2$, $NHR^6$, $NR^6R^6$, OH, aromatic ring, $C(O)R^6$, $C_1$-$C_8$ alkyl, $C_2$-$C_8$ alkenyl, and $C_2$-$C_8$ alkynyl;
$R^6$ is $C_1$-$C_8$ alkyl;
each $R^T$ is independently selected from halogen, hydrogen, $C_6H_6$, $Si(R^3)_3$ and $C_1$-$C_8$ alkyl;
s is selected from 0, 1, and 2,
t is selected from 0, 1, and 2, and
z is selected from 0, 1, 2, and 3.

In one aspect, the invention provides a compound having the formula IIb or a pharmaceutically acceptable salt, hydrate, solvate, or prodrug thereof, wherein $R^{2a}$ is selected from hydrogen, halogen, OH, $NH_2$, and $C_1$-$C_8$ alkyl; $R^{2b}$ is selected from hydrogen, halogen, OH, $NH_2$, and $C_1$-$C_8$ alkyl; $R^{2c}$ is selected from hydrogen, halogen, OH, $NH_2$, and $C_1$-$C_8$ alkyl; or alternatively, taken together two of $R^{2a}$, $R^{2b}$, and $R^{2c}$ form a $C_3$-$C_8$ cycloalkyl ring, $C_4$-$C_8$ cycloalkenyl ring, 3-6 membered saturated or partially unsaturated heterocyclic ring and the remaining $R^{2a}$, $R^{2b}$, and $R^{2c}$ is selected from hydrogen, halogen, OH, $NH_2$, and $C_1$-$C_8$ alkyl, or taken together two of $R^{2a}$, $R^{2b}$, and $R^{2c}$ form an aromatic or heteroaromatic ring and the remaining $R^{2a}$, $R^{2b}$, or $R^{2c}$ is absent;
further, wherein said cycloalkyl, cycloalkenyl, heterocyclic, aromatic and heteroaromatic ring are unsubstituted or substituted with one or more $R^x$; each $R^x$ is independently selected from $NH_2$, $NHR^3$, $NR^3R^3$, hydroxyl, halogen, $C_1$-$C_8$ alkyl, $(C_1$-$C_8)CF_3$, $(C_1$-$C_8)OH$, $C(O)R^3$, $OR^3$, $(CH_2)_zC_6H_6$, and $(CH_2)_zNHC(O)R^4$; $R^3$ is selected from $C_1$-$C_8$ alkyl and $O(C_1$-$C_8$ alkyl); $R^4$ is selected from $C_1$-$C_8$ alkyl and $CF_3$; $R^5$ is selected from hydrogen, halogen, OH, $OR^6$, $CF_3$, $CH_3$, $C_{2-8}$ alkene, $(CH_2)_s$-aromatic ring, $(CH_2)_s$-heteroaromatic, $C_3$-$C_6$ cycloalkyl ring, $C_4$-$C_6$ cycloalkenyl ring and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more $R^y$ and said alkene is substituted with one or more $R^T$.
each $R^y$ is independently selected from halogen, $OR^6$, $NH_2$, $NHR^6$, $NR^6R^6$, OH, aromatic ring, $C(O)R^6$, $C_1$-$C_8$ alkyl, $C_2$-$C_8$ alkenyl, and $C_2$-$C_8$ alkynyl;
$R^6$ is $C_1$-$C_8$ alkyl; each $R^T$ is independently selected from halogen, hydrogen, $C_6H_6$, $Si(R^3)_3$ and $C_1$-$C_8$ alkyl; s is selected from 0, 1, and 2; t is selected from 0, 1, and 2, and z is selected from 0, 1, 2, and 3.

In one aspect, the invention provides a compound having the formula IIIb:

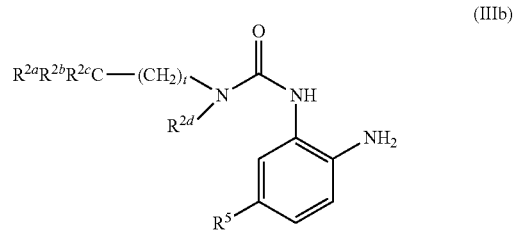

(IIIb)

or a pharmaceutically acceptable salt, hydrate, solvate, or prodrug thereof, wherein $R^{2a}$ is selected from hydrogen, halogen, OH, $NH_2$, and $C_1$-$C_8$ alkyl;

$R^{2b}$ is selected from hydrogen, halogen, OH, $NH_2$, and $C_1$-$C_8$ alkyl;

$R^{2c}$ is selected from hydrogen, halogen, OH, $NH_2$, and $C_1$-$C_8$ alkyl;

$R^{2d}$ is selected from hydrogen, $NH_2$, and $C_1$-$C_8$ alkyl;

or alternatively, taken together two of $R^{2a}$, $R^{2b}$, $R^{2c}$ and $R^{2d}$ form a $C_3$-$C_8$ cycloalkyl ring, $C_4$-$C_8$ cycloalkenyl ring, or 3 to 8 membered saturated or partially unsaturated heterocyclic ring and the remaining $R^{2a}$, $R^{2b}$, or $R^{2c}$ is selected from hydrogen, halogen, OH, $NH_2$, and $C_1$-$C_8$ alkyl or $R^{2d}$ is hydrogen, $NH_2$, or $C_1$-$C_8$ alkyl, or taken together two of $R^{2a}$, $R^{2b}$, and $R^{2c}$ form an aromatic or heteroaromatic ring and the remaining $R^{2a}$, $R^{2b}$, or $R^{2c}$ is absent;

further, wherein said cycloalkyl, cycloalkenyl, heterocyclic, aromatic or heteroaromatic ring are unsubstituted or substituted with one or more $R^x$;

each $R^x$ is independently selected from $(CH_2)_zNH_2$, $(CH_2)_z$ $NHR^3$, $(CH_2)_zNR^3R^3$, $OR^3$, $OCF_3$, $OCH_2F$, $OCHF_2$, $(CH_2)_z$-aromatic ring, $(CH_2)_z$-heterocyclic ring, hydroxyl, halogen, $C_1$-$C_8$ alkyl, $(C_1$-$C_8$ alkyl)$CF_3$, $(C_1$-$C_8$ alkyl)OH, $C(O)R^3$, $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_zNR^4C(O)R^4$;

or taken together two $R^x$ attached to the same carbon atom of a cycloalkyl, cycloalkenyl, or heterocyclic ring together form =O;

or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$;

or taken together two $R^x$ form an aromatic ring or heteroaromatic ring, further wherein said aromatic and heteroaromatic ring are unsubstituted or substituted with one or more $R^z$;

each $R^z$ is independently selected from halogen, $C_1$-$C_4$ alkyl, OH, $OR^3$, $OCF_3$, $OCH_2F$, $OCHF_2$, $NH_2$, $NHR^3$, $NR^3R^3$, and $C(O)CH_3$;

$R^3$ is selected from $C_1$-$C_8$ alkyl and $O(C_1$-$C_8$ alkyl);

$R^4$ is selected from $C_1$-$C_8$ alkyl and $CF_3$;

$R^5$ is selected from hydrogen, deuterium, halogen, OH, $OR^6$, $CF_3$, $C_1$-$C_8$ alkyl, $C_{2-8}$ alkene, $(CH_2)_s$-aromatic ring, $(CH_2)_s$-heteroaromatic, $C_3$-$C_6$ cycloalkyl ring, $C_3$-$C_6$ cycloalkenyl ring and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more $R^y$ and said alkene is substituted with one or more $R^T$;

each $R^y$ is independently selected from halogen, $OR^6$, $NH_2$, $NHR^6$, $NR^6R^6$, OH, aromatic ring, $C(O)R^6$ and $C_1$-$C_8$ alkyl;

$R^T$ is independently selected from halogen, hydrogen, $C_6H_6$, $Si(R^3)_3$ and $C_1$-$C_8$ alkyl;

$R^6$ is $C_1$-$C_8$ alkyl;

s is selected from 0, 1, and 2, t is selected from 0, 1, and 2, and z is selected from 0, 1, 2, and 3.

In one aspect, the invention provides a compound having the formula IIIb or a pharmaceutically acceptable salt, hydrate, solvate, or prodrug thereof, wherein $R^{2a}$ is selected from hydrogen, halogen, OH, $NH_2$, and $C_1$-$C_8$ alkyl; $R^{2b}$ is selected from hydrogen, halogen, OH, $NH_2$, and $C_1$-$C_8$ alkyl; $R^{2c}$ is selected from hydrogen, halogen, OH, $NH_2$, and $C_1$-$C_8$ alkyl;

$R^{2d}$ is selected from hydrogen, $NH_2$, and $C_1$-$C_8$ alkyl;

or alternatively, taken together two of $R^{2a}$, $R^{2b}$, $R^{2c}$ and $R^{2d}$ form a $C_3$-$C_8$ cycloalkyl ring, $C_4$-$C_8$ cycloalkenyl ring, or 3 to 8 membered saturated or partially unsaturated heterocyclic ring and the remaining $R^{2a}$, $R^{2b}$, or $R^{2c}$ is selected from hydrogen, halogen, OH, $NH_2$, and $C_1$-$C_8$ alkyl or $R^{2d}$ is hydrogen, $NH_2$, or $C_1$-$C_8$ alkyl, or taken together two of $R^{2a}$, $R^{2b}$, and $R^{2c}$ form an aromatic or heteroaromatic ring and the remaining $R^{2a}$, $R^{2b}$, or $R^{2c}$ is absent; further, wherein said cycloalkyl, cycloalkenyl, heterocyclic, aromatic or heteroaromatic ring are unsubstituted or substituted with one or more $R^x$; each $R^x$ is independently selected from $NH_2$, $NHR^6$, $NR^6R^6$, hydroxyl, $C_1$-$C_8$ alkyl, $(C_1$-$C_8)CF_3$, $(C_1$-$C_8)OH$, halogen, $C(O)R^3$, $OR^3$, $(CH_2)_zC_6H_6$, and $(CH_2)_zNHC(O)R^4$; $R^3$ is selected from $C_1$-$C_8$ alkyl and $O(C_1$-$C_8$ alkyl); $R^4$ is selected from $C_1$-$C_8$ alkyl and $CF_3$; $R^5$ is selected from hydrogen, halogen, OH, $OR^6$, $CF_3$, $CH_3$, $C_{2-8}$ alkene, $(CH_2)_s$-aromatic ring, $(CH_2)_s$-heteroaromatic, $C_3$-$C_6$ cycloalkyl ring, $C_3$-$C_6$ cycloalkenyl ring and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more $R^y$ and said alkene is substituted with one or more $R^T$; each $R^y$ is independently selected from halogen, $OR^6$, $NH_2$, $NHR^6$, $NR^6R^6$, OH, aromatic ring, $C(O)R^6$ and $C_1$-$C_8$ alkyl; $R^T$ is independently selected from halogen, hydrogen, $C_6H_6$, $Si(R^3)_3$ and $C_1$-$C_8$ alkyl; $R^6$ is $C_1$-$C_8$ alkyl; s is selected from 0, 1, and 2; t is selected from 0, 1, and 2, and z is selected from 0, 1, 2, and 3.

In one aspect, the invention provides a compound having the formula IVb:

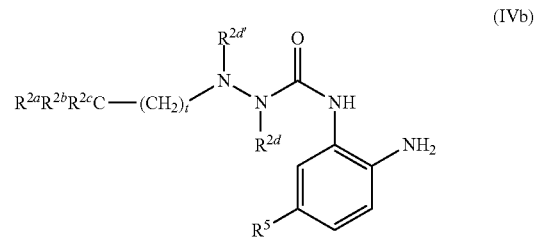

(IVb)

or a pharmaceutically acceptable salt, hydrate, solvate, or prodrug thereof, wherein $R^{2a}$ is selected from hydrogen, $NH_2$, and $C_1$-$C_8$ alkyl;

$R^{2b}$ is selected from hydrogen, $NH_2$, and $C_1$-$C_8$ alkyl;

$R^{2c}$ is selected from hydrogen, $NH_2$, and $C_1$-$C_8$ alkyl;

$R^{2d}$ is selected from hydrogen, $NH_2$, and $C_1$-$C_8$ alkyl;

$R^{2d'}$ is selected from hydrogen, $NH_2$, and $C_1$-$C_8$ alkyl;

or alternatively, taken together two of $R^{2a}$, $R^{2b}$, $R^{2c}$ and $R^{2d}$ form a $C_3$-$C_8$ cycloalkyl ring, $C_4$-$C_8$ cycloalkenyl ring, 3-6 membered saturated, unsaturated, or partially unsaturated heterocyclic ring and the remaining $R^{2a}$, $R^{2b}$, or $R^{2c}$ is selected from hydrogen, halogen, OH, $NH_2$, and $C_1$-$C_8$ alkyl or $R^{2d}$ or $R^{2d'}$ is hydrogen or $C_1$-$C_8$ alkyl, or taken together two of $R^{2a}$, $R^{2b}$, and $R^{2c}$ form aromatic or heteroaromatic ring and the remaining $R^{2a}$, $R^{2b}$, and $R^{2c}$ is absent;

further, wherein said cycloalkyl, cycloalkenyl, heterocyclic, aromatic and heteroaromatic ring are unsubstituted or substituted with one or more $R^x$;

each $R^x$ is independently selected from $(CH_2)_zNH_2$, $(CH_2)_z$ $NHR^3$, $(CH_2)_zNR^3R^3$, $OR^3$, $OCF_3$, $OCH_2F$, $OCHF_2$, (CH$_2$)$_z$-aromatic ring, (CH$_2$)$_z$-heterocyclic ring, hydroxyl, halogen, C$_1$-C$_8$ alkyl, (C$_1$-C$_8$ alkyl)CF$_3$, (C$_1$-C$_8$ alkyl)OH, C(O)R$^3$, (CH$_2$)$_z$C(O)NH$_2$, (CH$_2$)$_z$C(O)NHR$^3$, (CH$_2$)$_z$C(O)NR$^3$R$^3$, (CH$_2$)$_z$NHC(O)R$^4$, and (CH$_2$)$_z$NR$^4$C(O)R$^4$;

R$^3$ is selected from C$_1$-C$_8$ alkyl and O(C$_1$-C$_8$ alkyl);

R$^4$ is selected from C$_1$-C$_8$ alkyl and CF$_3$;

R$^5$ is selected from hydrogen, deuterium, halogen, OH, OR$^6$, CF$_3$, C$_1$-C$_8$ alkyl, C$_{2-8}$ alkene, (CH$_2$)$_s$-aromatic ring, (CH$_2$)$_s$-heteroaromatic, C$_3$-C$_6$ cycloalkyl ring, C$_4$-C$_6$ cycloalkenyl ring, and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more R$^y$ and said alkene is substituted with one or more R$^T$;

each R$^y$ is independently selected from halogen, OR$^6$, NH$_2$, NHR$^6$, NR$^6$R$^6$, OH, aromatic ring, C(O)R$^6$, C$_1$-C$_8$ alkyl, C$_2$-C$_8$ alkenyl, and C$_2$-C$_8$ alkynyl;

R$^6$ is C$_1$-C$_8$ alkyl;

each R$^T$ is independently selected from halogen, hydrogen, C$_6$H$_6$, Si(R$^3$)$_3$ and C$_1$-C$_8$ alkyl;

s is selected from 0, 1, and 2, t is selected from 0, 1, and 2, and z is selected from 0, 1, 2, and 3.

In one aspect, the invention provides a compound having the formula IVb or a pharmaceutically acceptable salt, hydrate, solvate, or prodrug thereof, wherein R$^{2a}$ is selected from hydrogen, NH$_2$, and C$_1$-C$_8$ alkyl; R$^{2b}$ is selected from hydrogen, NH$_2$, and C$_1$-C$_8$ alkyl; R$^{2c}$ is selected from hydrogen, NH$_2$, and C$_1$-C$_8$ alkyl; R$^{2d}$ is selected from hydrogen, NH$_2$, and C$_1$-C$_8$ alkyl; R$^{2d'}$ is selected from hydrogen, NH$_2$, and C$_1$-C$_8$ alkyl;

or alternatively, taken together two of R$^{2a}$, R$^{2b}$, R$^{2c}$ and R$^{2d}$ form a C$_3$-C$_8$ cycloalkyl ring, C$_4$-C$_8$ cycloalkenyl ring, 3-6 membered saturated, unsaturated, or partially unsaturated heterocyclic ring and the remaining R$^{2a}$, R$^{2b}$, or R$^{2c}$ is selected from hydrogen, halogen, OH, NH$_2$, and C$_1$-C$_8$ alkyl or R$^{2d}$ or R$^{2d'}$ is hydrogen or C$_1$-C$_8$ alkyl, or taken together two of R$^{2a}$, R$^{2b}$, and R$^{2c}$ form aromatic or heteroaromatic ring and the remaining R$^{2a}$, R$^{2b}$, and R$^{2c}$ is absent; further, wherein said cycloalkyl, cycloalkenyl, heterocyclic, aromatic and heteroaromatic ring are unsubstituted or substituted with one or more R$^x$; each R$^x$ is independently selected from NH$_2$, NHR$^3$, NR$^3$R$^3$, hydroxyl, halogen, C$_1$-C$_8$ alkyl, (C$_1$-C$_8$)CF$_3$, (C$_1$-C$_8$)OH, C(O)R$^3$, OR$^3$, (CH$_2$)$_z$C$_6$H$_6$, or (CH$_2$)$_z$NHC(O)R$^4$; R$^3$ is selected from C$_1$-C$_8$ alkyl and O(C$_1$-C$_8$ alkyl); R$^4$ is selected from C$_1$-C$_8$ alkyl and CF$_3$; R$^5$ is selected from hydrogen, halogen, OH, OR$^6$, CF$_3$, CH$_3$, C$_{2-8}$ alkene, (CH$_2$)$_s$-aromatic ring, (CH$_2$)$_s$-heteroaromatic, C$_3$-C$_6$ cycloalkyl ring, C$_4$-C$_6$ cycloalkenyl ring, and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more R$^y$ and said alkene is substituted with one or more R$^T$;

each R$^y$ is independently selected from halogen, OR$^6$, NH$_2$, NHR$^6$, NR$^6$R$^6$, OH, aromatic ring, C(O)R$^6$, C$_1$-C$_8$ alkyl, C$_2$-C$_8$ alkenyl, and C$_2$-C$_8$ alkynyl; R$^6$ is C$_1$-C$_8$ alkyl;

each R$^T$ is independently selected from halogen, hydrogen, C$_6$H$_6$, Si(R$^3$)$_3$ and C$_1$-C$_8$ alkyl; s is selected from 0, 1, and 2; t is selected from 0, 1, and 2, and z is selected from 0, 1, 2, and 3.

In one aspect, the invention provides a compound having the formula Vb:

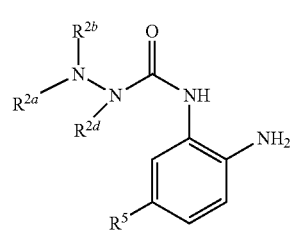

(Vb)

or a pharmaceutically acceptable salt, hydrate, solvate, or prodrug thereof, wherein R$^{2a}$ is selected from hydrogen, NH$_2$, and C$_1$-C$_8$ alkyl;

R$^{2b}$ is selected from hydrogen, NH$_2$, and C$_1$-C$_8$ alkyl;

R$^{2d}$ is selected from hydrogen, NH$_2$, and C$_1$-C$_8$ alkyl;

R$^5$ is selected from hydrogen, deuterium, halogen, OH, OR$^6$, CF$_3$, C$_1$-C$_8$ alkyl, C$_{2-8}$ alkene, (CH$_2$)$_s$-aromatic ring, (CH$_2$)$_s$-heteroaromatic, C$_5$-C$_6$ cycloalkyl ring, C$_5$-C$_6$ cycloalkenyl ring, and 5-6 membered saturated, unsaturated, or partially unsaturated heterocyclic ring, wherein said aromatic, heteroaromatic, cycloalkyl, cycloalkenyl, and heterocyclic ring are unsubstituted or substituted with one or more R$^y$ and said alkene is substituted with one or more R$^T$;

each R$^y$ is independently selected from halogen, OR$^6$, NH$_2$, NHR$^6$, NR$^6$R$^6$, OH, aromatic ring, C(O)R$^6$ and C$_1$-C$_8$ alkyl;

each R$^T$ is independently selected from halogen, hydrogen, C$_6$H$_6$Si(R$^3$)$_3$ and C$_1$-C$_8$ alkyl, and R$^6$ is C$_1$-C$_8$ alkyl.

In one aspect, the invention provides a compound having the formula (Vb) or a pharmaceutically acceptable salt, hydrate, solvate, or prodrug thereof, wherein R$^{2a}$ is selected from hydrogen, NH$_2$, and C$_1$-C$_8$ alkyl; R$^{2b}$ is selected from hydrogen, NH$_2$, and C$_1$-C$_8$ alkyl; R$^{2d}$ is selected from hydrogen, NH$_2$, and C$_1$-C$_8$ alkyl; R$^5$ is selected from hydrogen, halogen, OH, OR$^6$, CF$_3$, CH$_3$, C$_{2-8}$ alkene, (CH$_2$)$_s$-aromatic ring, (CH$_2$)$_s$-heteroaromatic, C$_5$-C$_6$ cycloalkyl ring, C$_5$-C$_6$ cycloalkenyl ring, and 5-6 membered heteroaromatic, cycloalkyl, cycloalkenyl, and heterocyclic ring are unsubstituted or substituted with one or more R$^y$ and said alkene is substituted with one or more R$^T$;

each R$^y$ is independently selected from halogen, OR$^6$, NH$_2$, NHR$^6$, NR$^6$R$^6$, OH, aromatic ring, C(O)R$^6$ and C$_1$-C$_8$ alkyl; each R$^T$ is independently selected from halogen, hydrogen, C$_6$H$_6$Si(R$^3$)$_3$ and R$^6$ is C$_1$-C$_8$ alkyl.

Furthermore, while all of the compounds of this invention are useful as histone deacetylase inhibitors, certain classes of compounds, hydrates, solvates, or prodrugs thereof are preferred. The following paragraphs describe such preferred classes.

1) R$^5$ is selected from hydrogen, deuterium, halogen, OH, OCH$_3$, CF$_3$, CH$_3$, and cyclopropyl;

2) R$^5$ is

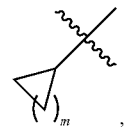

, and m is selected from 1, 2, 3, and 4;

3) $R^5$ is

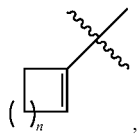

and n is selected from 1, 2, 3, and 4;

4) $R^5$ is

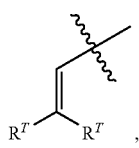

each $R^T$ is independently selected from halogen, hydrogen, $C_6H_6$, $Si(R^3)_3$, phenyl; $C_1$-$C_8$ alkyl and $R_3$ is selected from $C_1$-$C_8$ alkyl and $O(C_1$-$C_8$ alkyl);

5) $R^5$ is selected from

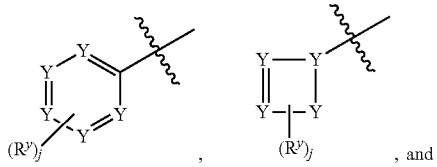, and

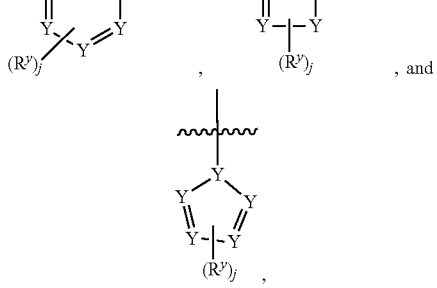

each Y is independently selected from CH, $CR^y$, and N; each j is independently selected from 0, 1, 2, 3, 4, and 5; each $R^y$ is independently selected from halogen, $OR^6$, $NHR^6$, $NR^6R^6$, OH, $CF_3$, aromatic ring, $C(O)R^6$, $C_1$-$C_8$ alkyl, $C_2$-$C_8$ alkenyl, and $C_2$-$C_8$ alkynyl; and $R^6$ is $C_1$-$C_8$ alkyl;

6) $R^5$ is

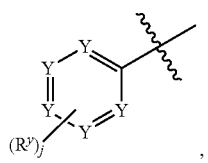

each Y is independently selected from CH, $CR^y$, and N and provided that not all Y are N; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; each j is independently selected from 0, 1, 2, 3, 4, and 5; and $R^6$ is $C_1$-$C_8$ alkyl;

7) $R^5$ is

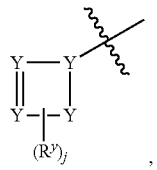

each Y is independently selected from CH, $CR^y$, NH, $NR^y$ and N and provided that not all Y are N; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; j is selected from 0, 1, 2, 3, 4, and 5; and $R^6$ is $C_1$-$C_8$ alkyl;

8) $R^5$ is

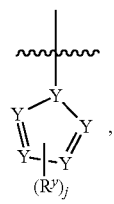

each Y is independently selected from CH, $CR^y$, N, S, and O and not all Y are N; not all Y are O; and not all Y are S; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; j is selected from 0, 1, 2, 3, 4, and 5; and $R^6$ is $C_1$-$C_8$ alkyl;

9) $R^5$ is

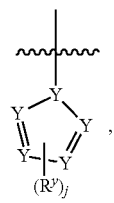

each Y is independently selected from CH, $CR^y$, and N and not all Y are N; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; j is selected from 0, 1, 2, 3, 4, and 5; and $R^6$ is $C_4$-$C_8$ alkyl;

10) $R^5$ is

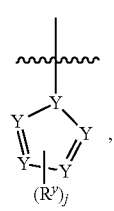

each Y is independently selected from CH, $CR^y$, and S and not all Y are S; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; j is selected from 0, 1, 2, 3, 4, and 5; and $R^6$ is $C_1$-$C_8$ alkyl;

11) $R^5$ is

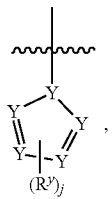

each Y is independently selected from CH, $CR^y$, and O and not all Y are O; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; j is selected from 0, 1, 2, 3, 4, and 5; and $R^6$ is $C_1$-$C_8$ alkyl;

12) $R^5$ is

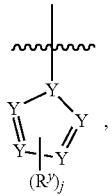

each Y is independently selected from CH, $CR^y$, O and S; and not all Y are O; and not all Y are S; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; j is selected from 0, 1, 2, 3, 4, and 5; and $R^6$ is $C_1$-$C_8$ alkyl;

13) $R^5$ is

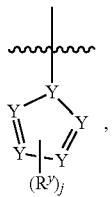

each Y is independently selected from CH, $CR^y$, N and S and not all Y are O; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; j is selected from 0, 1, 2, 3, 4, and 5; and $R^6$ is $C_1$-$C_8$ alkyl;

14) $R^5$ is

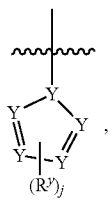

each Y is independently selected from CH, $CR^y$, N and O and not all Y are O; each $R^y$ is independently selected from halogen, OH, $OR^6$, $NH_2$, $NHR^6$, $NR^6R^6$, $C_1$-$C_8$ alkyl, $C_2$-$C_8$ alkenyl, and $C_2$-$C_8$ alkynyl; j is selected from 0, 1, 2, 3, 4, and 5; and $R^6$ is $C_1$-$C_8$ alkyl;

15) $R^5$ is selected from phenyl, 2-pyridinyl, 3-pyridinyl, 4-pyridinyl, 2-pyrimidinyl, 4-pyrimidinyl, 5-pyrimidinyl, 2-pyrazinyl, oxazole, thiazole, and isoxazole;

16) $R^5$ is selected from phenyl, 2-pyridinyl, 3-pyridinyl, 4-pyridinyl, 2-pyrimidinyl, 4-pyrimidinyl, 5-pyrimidinyl, and 2-pyrazinyl.

17) $R^5$ is 4-fluorophenyl;

18) $R^5$ is 4-pyridinyl;

19) $R^5$ is 2-thienyl;

20) $R^5$ is hydrogen;

21) $R^5$ is selected from oxazole, thiazole, and isoxazole;

22) $R^5$ is

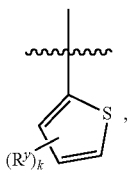

each $R^y$ is independently selected from halogen, $OR^6$, $NHR^6$, $NR^6R^6$, OH, $CF_3$, aromatic ring, $C(O)R^6$, $C_1$-$C_8$ alkyl, $C_2$-$C_8$ alkenyl, and $C_2$-$C_8$ alkynyl, k is selected from 0, 1, 2, or 3; and $R^6$ is $C_1$-$C_8$ alkyl;

23) $R^5$ is selected from hydrogen, deuterium, halogen, OH, $OCH_3$, $CF_3$, $CH_3$, and cyclopropyl;

24) $R^5$ is selected from $OR^6$, wherein $R^6$ is $C_2$-$C_8$ alkyl, $C_2$-$C_8$ alkyl, $C_2$-$C_8$ alkene, $(CH_2)_u$-5-6 membered saturated, unsaturated, or partially unsaturated heterocyclic ring, $(CH_2)_v$—$C_4$-$C_8$ cycloalkyl ring, $(C_1$-$C_8$-alkyl$)_w$-$C_4$-$C_8$cycloalkenyl ring, $(CH_2)_s$-aromatic ring, and $(CH_2)_s$-heteroaromatic and wherein said heterocyclic, cycloalkyl, cycloalkenyl, heteroaromatic, and aromatic ring are unsubstituted or substituted with one or more $R^y$ and said alkene is substituted with one or more $R^T$;

25) $R^5$ is selected from hydrogen, deuterium, halogen, $OCH_3$, $CF_3$, $CH_3$ and cyclopropyl;

26) $R^6$ is $CH_3$;

27) k is 0 or 1;

28) k is 1;

29) k is 0;

30) $R^5$ is

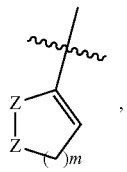

each Z is independently selected from $CH_2$, $CHR^y$, $CR^yR^y$, O, NH, $NR^y$, and S; m is selected from 0, 1, and 2; and each $R^y$ is independently selected from halogen, $OR^6$, $NHR^6$, $NR^6R^6$, OH, $CF_3$, aromatic ring, $C(O)R^6$, $C_1$-$C_8$ alkyl, $C_2$-$C_8$ alkenyl, and $C_2$-$C_8$ alkynyl, and k is selected from 0, 1, 2, or 3; and $R^6$ is $C_1$-$C_8$ alkyl;

31) V is C and taken together $R^{2a}$ and $R^{2b}$ are:

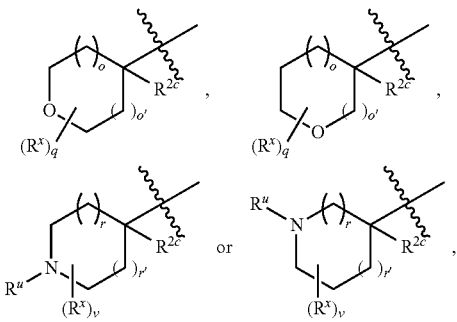

o and o' are each independently selected from 0, 1, and 2; r and r' are each independently selected from 0, 1, and 2; q is selected from 0, 1, 2, 3, 4, 5, 6, 7, and 8; $R^u$ is selected from hydrogen, $C_1$-$C_8$ alkyl, $(C_1$-$C_8$ alkyl$)CF_3$, $(C_1$-$C_8$ alkyl$)OH$, and $C(O)R^{3a}$; $R^{3a}$ is $C_1$-$C_8$ alkyl; v is selected from 0, 1, 2, 3, 4, 5, 6, 7, and 8;

$R^{2c}$ is selected from hydrogen, halogen, OH, $NH_2$, and $C_1$-$C_8$ alkyl; and each $R^x$ is independently selected from $NH_2$, $NHR^3$, $NR^3R^3$, $OR^3$, $(CH_2)_zC_6H_6$, hydroxyl, halogen, $C_1$-$C_8$ alkyl, $(C_1$-$C_8)CF_3$, $(C_1$-$C_8)OH$, $C(O)R^3$ and $(CH_2)_zNHC(O)R^4$ or taken together two $R^x$ attached to the same carbon atom of a cycloalkyl, cycloalkenyl or heterocyclic ring together form =O; or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; each $R^z$ is independently selected from halogen, $C_1$-$C_4$ alkyl, OH, $NH_2$, and $C(O)CH_3$; $R^3$ is selected from $C_1$-$C_8$ alkyl and $O(C_1$-$C_8$ alkyl) and $R^4$ is selected from $C_1$-$C_8$ alkyl and $CF_3$;

32) $R^5$ is

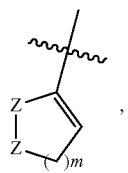

each Z is $CH_2$; and m is selected from 0, 1, and 2;

33) $R^{2a}R^{2b}R^{2c}C$ is

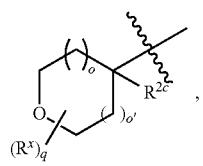

o and o' are each independently selected from 0, 1, and 2; q is selected from 0, 1, 2, 3, 4, 5, 6, 7, and 8; and each R' is independently selected from $NH_2$, $NHR^3$, $NR^3R^3$, $OR^3$, $(CH_2)_zC_6H_6$, hydroxyl, halogen, $C_1$-$C_8$ alkyl, $(C_1$-$C_8)CF_3$, $(C_1$-$C_8)OH$, $C(O)R^3$ and $(CH_2)_zNHC(O)R^4$ or taken together two $R^x$ attached to the same carbon atom of a cycloalkyl, cycloalkenyl or heterocyclic ring together form =O; or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; each $R^z$ is independently selected from halogen, $C_1$-$C_4$ alkyl, OH, $NH_2$, and $C(O)CH_3$; $R^3$ is selected from $C_1$-$C_8$ alkyl and $O(C_1$-$C_8$ alkyl) and $R^4$ is selected from $C_1$-$C_8$ alkyl and $CF_3$;

34) $R^{2a}R^{2b}R^{2c}C$ is

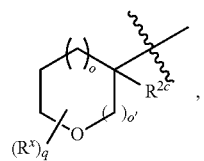

o and o' are each independently selected from 0, 1, and 2; q is selected from 0, 1, 2, 3, 4, 5, 6, 7, and 8; and each $R^x$ is independently selected from $NH_2$, $NHR^3$, $NR^3R^3$, $OR^3$, $(CH_2)_zC_6H_6$, hydroxyl, halogen, $C_1$-$C_8$ alkyl, $(C_1$-$C_8)CF_3$, $(C_1$-$C_8)OH$, $C(O)R^3$ and $(CH_2)_zNHC(O)R^4$ or taken together two $R^x$ attached to the same carbon atom of a cycloalkyl, cycloalkenyl or heterocyclic ring together form =O; or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; each $R^z$ is independently selected from halogen, $C_1$-$C_4$ alkyl, OH, $NH_2$, and $C(O)CH_3$; $R^3$ is selected from $C_1$-$C_8$ alkyl and $O(C_1$-$C_8$ alkyl) and $R^4$ is selected from $C_1$-$C_8$ alkyl and $CF_3$;

35) $R^{2a}R^{2b}R^{2c}C$ is

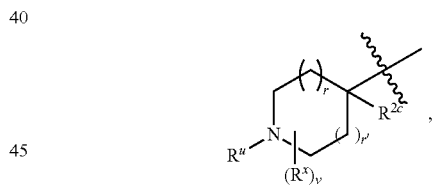

r and r' are each independently selected from 0, 1, and 2; $R^u$ is selected from hydrogen, $C_1$-$C_8$ alkyl, $(C_1$-$C_8)CF_3$, $(C_1$-$C_8)OH$ and $C(O)R^{3a}$; $R^{3a}$ is $C_1$-$C_8$ alkyl; v is selected from 0, 1, 2, 3, 4, 5, 6, 7, and 8; and each $R^x$ is independently selected from $NH_2$, $NHR^3$, $NR^3R^3$, $OR^3$, $(CH_2)_zC_6H_6$, hydroxyl, halogen, $C_1$-$C_8$ alkyl, $(C_1$-$C_8)CF_3$, $(C_1$-$C_8)OH$, $C(O)R^3$ and $(CH_2)_zNHC(O)R^4$ or taken together two $R^x$ attached to the same carbon atom of a cycloalkyl, cycloalkenyl or heterocyclic ring together form =O;

or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; each $R^z$ is independently selected from halogen, $C_1$-$C_4$ alkyl, OH, $NH_2$, and $C(O)CH_3$; $R^3$ is selected from $C_1$-$C_8$ alkyl and $O(C_1$-$C_8$ alkyl) and $R^4$ is selected from $C_1$-$C_8$ alkyl and $CF_3$;

36) $R^{2a}R^{2b}R^{2c}C$ is

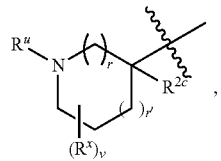

r and r' are each independently selected from 0, 1, and 2; $R^u$ is selected from hydrogen, $C_1$-$C_8$ alkyl, $(C_1$-$C_8)CF_3$, $(C_1$-$C_8)OH$ and $C(O)R^{3a}$; $R^{3a}$ is $C_1$-$C_8$ alkyl; v is selected from 0, 1, 2, 3, 4, 5, 6, 7, and 8; and each $R^x$ is independently selected from $NH_2$, $NHR^3$, $NR^3R^3$, $OR^3$, $(CH_2)_zC_6H_6$, hydroxyl, halogen, $C_1$-$C_8$ alkyl, $(C_1$-$C_8)CF_3$, $(C_1$-$C_8)OH$, $C(O)R^3$ and $(CH_2)_zNHC(O)R^4$ or taken together two $R^x$ attached to the same carbon atom of a cycloalkyl, cycloalkenyl or heterocyclic ring together form $=O$;

or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; each $R^z$ is independently selected from halogen, $C_1$-$C_4$ alkyl, OH, $NH_2$, and $C(O)CH_3$; $R^3$ is selected from $C_1$-$C_8$ alkyl and $O(C_1$-$C_8$ alkyl) and $R^4$ is selected from $C_1$-$C_8$ alkyl and $CF_3$;

37) $R^{2a}R^{2b}R^{2c}C$ is

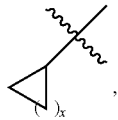

and x is selected from 1, 2, 3, and 4;
38) $R^{2a}R^{2b}R^{2c}C$ is

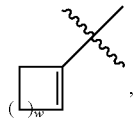

w is selected from 1, 2, and 3;
39) U is O and t is 1;
40) $R^{2a}R^{2b}R^{2c}V(CH_2)_tU$ is

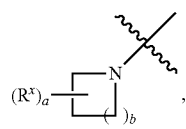

wherein b is selected from 0, 1, 2, and 3; a is selected from 0, 1, 2, 3, 4, 5, 6, 7, 8, 9, or 10 and each $R^x$ is independently selected from $NH_2$, $NHR^3$, $NR^3R^3$, $OR^3$, $(CH_2)_zC_6H_6$, hydroxyl, halogen, $C_1$-$C_8$ alkyl, $(C_1$-$C_8)CF_3$, $(C_1$-$C_8)OH$, $C(O)R^3$ and $(CH_2)_zNHC(O)R^4$; or taken together two $R^x$ attached to the same carbon atom of a cycloalkyl, cycloalkenyl or heterocyclic ring together form $=O$; or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; each $R^z$ is independently selected from halogen, $C_1$-$C_4$ alkyl, OH, $NH_2$, and $C(O)CH_3$; $R^3$ is selected from $C_1$-$C_8$ alkyl and $O(C_1$-$C_8$ alkyl) and $R^4$ is selected from $C_1$-$C_8$ alkyl and $CF_3$;

41) $R^{2a}R^{2b}R^{2c}V(CH_2)_tU$ is

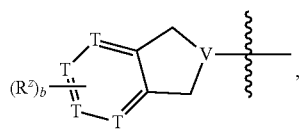

wherein V is N or CH; T is CH, $CR^Z$, or N; each $R^z$ is independently selected from halogen, $C_1$-$C_4$ alkyl, OH, $OR^3$, $CF_3$, $OCF_3$, $OCH_2F$, $OCHF_2$, $NH_2$, $NHR^3$, $NR^3R^3$, and $C(O)CH_3$; b is 0, 1, 2, 3, or 4; and $R^3$ is selected from $C_1$-$C_8$ alkyl and $O(C_1$-$C_8$ alkyl).

42) $R^{2a}R^{2b}R^{2c}V(CH_2)_tU$ is

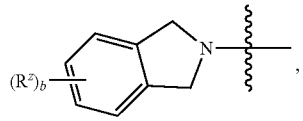

wherein $R^z$ is independently selected from halogen, $C_1$-$C_4$ alkyl, OH, $OR^3$, $CF_3$, $OCF_3$, $OCH_2F$, $OCHF_2$, $NH_2$, $NHR^3$, $NR^3R^3$, and $C(O)CH_3$; b is 0, 1, 2, 3, or 4; and $R^3$ is selected from $C_1$-$C_8$ alkyl and $O(C_1$-$C_8$ alkyl).

43) U is N, t is 1, and $R^{2d}$ is hydrogen, $NH_2$, or $C_1$-$C_8$ alkyl;
44) $R^{2a}R^{2b}R^{2c}V(CH_2)_t$ is

and each $R^x$ is independently selected from $NH_2$, $NHR^3$, $NR^3R^3$, $OR^3$, $(CH_2)_zC_6H_6$, hydroxyl, halogen, $C_1$-$C_8$ alkyl, $(C_1$-$C_8)CF_3$, $(C_1$-$C_8)OH$, $C(O)R^3$ and $(CH_2)_zNHC(O)R^4$ or taken together two $R^x$ attached to the same carbon atom of a cycloalkyl, cycloalkenyl or heterocyclic ring together form $=O$ or taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; each $R^z$ is independently selected from halogen, $C_1$-$C_4$ alkyl, OH, $NH_2$, and $C(O)CH_3$; $R^3$ is selected from $C_1$-$C_8$ alkyl and $O(C_1$-$C_8$ alkyl) and $R^4$ is selected from $C_1$-$C_8$ alkyl and $CF_3$;

45) $R^{2a}R^{2b}R^{2c}C(CH_2)_t$ is

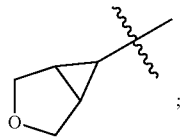 [SMILES: *C1C2COCC12]

46) $R^{2a}R^{2b}R^{2c}C(CH_2)_t$ is cyclohexyl;
47) U is CH=CH (trans);
48) U is CH=CH (cis);
49) U is single bond;
50) t is 0;
51) t is 1;
52) t is 2;
53) taken together two of $R^{2a}$, $R^{2b}$, and $R^{2c}$ form =O and the remaining $R^{2a}$, $R^{2b}$, or $R^{2c}$ is selected from hydrogen, halogen, OH, $NH_2$, and $C_1$-$C_8$ alkyl;
54) $R^{2a}$, $R^{2b}$, and $R^{2c}$ are each independently selected from hydrogen, methyl, and propyl;
55) at least two of $R^{2a}$, $R^{2b}$, and $R^{2c}$ are the same;
56) $R^{2a}$, $R^{2b}$, and $R^{2c}$ are the same;
57) taken together two of $R^{2a}$, $R^{2b}$, and $R^{2c}$ form a saturated heterocyclic ring selected from tetrahydrofuranyl, tetrahydropyranyl, azetidinyl, piperidinyl, azabicyclo[3.1.0]hexyl, 2-oxaspiro[3.3]heptanyl, 2-azaspiro[3.3]heptanyl, 8-oxabicyclo[3.2.1]octanyl, and 8-azabicyclo[3.2.1]octanyl;
58) taken together two of $R^{2a}$, $R^{2b}$, and $R^{2c}$ form a cycloalkyl or cycloalkenyl ring selected from cyclopropyl, cyclobutyl, cyclopentyl, cyclopentenyl, cyclohexyl, and cyclohexenyl;
59) taken together two of $R^{2a}$, $R^{2b}$, and $R^{2c}$ form a ring and the ring is unsubstituted;
60) taken together two of $R^{2a}$, $R^{2b}$, and $R^{2c}$ form a ring and the ring is substituted with one or more $R^x$, wherein each $R^x$ is independently selected from $C(O)R^3$, $(CH_2)_zNHC(O)R^4$ and methyl; $R^3$ is selected from $C_1$-$C_8$ alkyl and $O(C_1$-$C_8$ alkyl) and $R^4$ is selected from $C_1$-$C_8$ alkyl and $CF_3$;
61) taken together two of $R^{2a}$, $R^{2b}$, and $R^{2c}$ form a ring and the ring is substituted with two $R^x$ attached to the same carbon, which taken together to form =O;
62) $R^{2a}$, $R^{2b}$, and $R^{2c}$ are each independently selected from hydrogen, methyl, and fluoro;
63) taken together two of $R^{2a}$, $R^{2b}$, and $R^{2c}$ form a cycloalkyl ring selected from cyclopropyl, cyclobutyl, cyclopentyl, and cyclohexyl;
64) taken together $R^{2a}$ and $R^{2b}$ form a ring and $R^{2c}$ is hydrogen;
65) taken together two of $R^{2a}$, $R^{2b}$, and $R^{2c}$ form a ring and the ring is substituted with one or more $R^x$, wherein each $R^x$ is independently selected from $C(O)R^3$ and methyl;
66) $R^{2a}$, $R^{2b}$, $R^{2c}$, and $R^{2d}$ are each independently selected from hydrogen, methyl, and ethyl;
67) taken together two of $R^{2a}$, $R^{2b}$, and $R^{2c}$ form a saturated heterocyclic ring selected from oxetanyl, piperidinyl, piperidinonyl, azetidinyl, pyrrolidinyl, tetrahydropyranyl, azabicyclo[3.1.0]hexanyl, morpholinyl, piperazinyl, 8-oxa-3-azabicyclo[3.2.1]octanyl, hexahydropyridazinyl, 2-oxa-6-azaspiror[3.3]heptanyl, 2,6-diazaspiro[3.3]heptanyl, 2-oxaspiro[3.3]heptanyl, 2-azaspiroheptanyl, 7-azabicyclo[2.2.1]heptanyl, 8-azabicyclo[3.2.1]octanyl, 8-oxabicyclo[3.2.1]octanyl, pyrazolidinyl, and tetrahydrofuranyl;
68) taken together two of $R^{2a}$, $R^{2b}$, $R^{2c}$ and $R^{2d}$ form a saturated heterocyclic ring selected from oxetanyl, pyrrolidinyl, azetidinyl, piperidinyl, morpholinyl, piperazinyl, azabicyclo[3.1.0]hexyl, azabicyclo[3.2.1]octanyl, hexahydropyridazinyl, 2-oxa-6-azaspiro[3.3]heptanyl, 2,6-diazaspiro[3.3]heptanyl, 7-azabicyclo[2.2.1]heptanyl and pyrazolidinyl;
69) taken together two of $R^{2a}$, $R^{2b}$, and $R^{2c}$ form a cycloalkyl ring selected from cyclopropyl, cyclobutyl, and cyclohexyl;
70) V is C and taken together two of $R^{2a}$, $R^{2b}$, and $R^{2c}$ form an aromatic ring and the remaining $R^{2a}$, $R^{2b}$, or $R^{2c}$ is absent, wherein said aromatic ring is phenyl, provided that U is not a single bond and t is 0;
71) taken together two of $R^{2a}$, $R^{2b}$, and $R^{2c}$ form a ring and the ring is substituted with one or more $R^x$, wherein each $R^x$ is independently selected from halogen, $NH_2$, $C(O)R^3$, $(CH_2)_zNHC(O)R^4$ and methyl;
72) taken together two of $R^{2a}$, $R^{2b}$, and $R^{2c}$ form a ring and the ring is substituted with one or more $R^x$, further wherein taken together two $R^x$ form a $C_3$-$C_8$ cycloalkyl ring, $C_4$-$C_8$ cycloalkenyl ring or 3 to 8 membered saturated or partially unsaturated heterocyclic ring, further wherein said cycloalkyl, cycloalkenyl, and heterocyclic ring are optionally substituted with one or more $R^z$; and each $R^z$ is independently selected from halogen, $C_1$-$C_4$ alkyl, OH, $NH_2$, and $C(O)CH_3$;
73) $R^{2a}$, $R^{2b}$, $R^{2c}$ and $R^{2d}$ are each independently selected from hydrogen and $NH_2$;
74) taken together two of $R^{2a}$, $R^{2b}$, and $R^{2c}$ form a ring and the ring is substituted with one or more $R^x$, wherein each $R^x$ is independently selected from $C(O)R^3$ and methyl;
75) $R^{2d}$ and one of $R^{2a}$ or $R^{2b}$ are selected from hydrogen and $NH_2$;
76) $R^{2d}$ and one of $R^{2a}$ or $R^{2b}$ are both hydrogen;
77) $R^3$ or $R^4$ is methyl;
78) $R^3$ is methyl;
79) $R^3$ is ethyl;
80) $R^4$ is methyl;
81) z is 0;
82) z is 1;
83) $R^5$ is selected from hydrogen, thiophenyl, $(CH_2)_s$phenyl, $(CH_2)_s$heteroaryl, pyridinyl, $C_2$alkenyl, cyclohexenyl, pyrazinyl, and pyrimidinyl;
84) $R^5$ is selected from hydrogen, thiophenyl, $(CH_2)_s$phenyl, pyridinyl, $C_2$alkenyl, cyclohexenyl, pyrazinyl, and pyrimidinyl;
85) $R^5$ is selected from 5-pyridinyl, 4-pyridinyl, 3-pyridinyl, and 4-F phenyl;
86) $R^5$ is selected from 4-pyridinyl, 3-pyridinyl, and 4-F phenyl;
87) $R^5$ is 4-pyridinyl;
88) $R^5$ is 3-pyridinyl;
89) $R^5$ is 4-F phenyl;
90) $R^5$ is 5-pyridinyl;
91) $R^5$ is an unsubstituted ring;
92) $R^5$ is a ring substituted with one or more $R^y$, wherein each $R^y$ is independently selected from $C(O)R^6$, halogen and methyl;
93) $R^5$ is selected from hydrogen, thiopheneyl, cyclopentenyl, and phenyl;
94) $R^5$ is a ring substituted with one or more $R^y$, wherein each $R^y$ is independently selected from fluoro and chloro;
95) $R^5$ is selected from hydrogen, thiopheneyl, cyclopropyl, cyclopentyl cyclopentenyl, cyclohexenyl, phenyl, pyridinyl, $C_2$alkenyl, and pyrazinyl;

96) R⁵ is a ring substituted with one or more $R^y$, wherein each $R^y$ is independently selected from halogen and methyl;
97) $R^5$ is selected from hydrogen and thiopheneyl;
98) $R^5$ is unsubstituted thiopheneyl;
99) $R^5$ is thiopheneyl substituted with one or more $R^y$, wherein each $R^y$ is independently selected from $C(O)R^6$, halogen or methyl;
100) $R^6$ is methyl or ethyl;
101) s is 0;
102) s is 1;
103) s is 2;
104) V is C;
105) V is C and taken together $R^{2a}$ and $R^{2b}$ form a saturated heterocyclic ring:

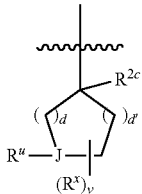

and $R^{2c}$ is selected from hydrogen, halogen, OH, $NH_2$, and $C_1$-$C_8$ alkyl, further wherein J is selected from N, O, C, and S; when J is N or C, $R^u$ is selected from hydrogen, $C_1$-$C_8$ alkyl, $(C_1$-$C_8)CF_3$, $(C_1$-$C_8)OH$, $C(O)R^{3a}$ and when J is O or S, $R^u$ is absent; $R^{3a}$ is $C_1$-$C_8$ alkyl; $R^x$ is selected from $NH_2$, $NHR^3$, $NR^3R^3$, hydroxyl, halogen, $C_1$-$C_8$ alkyl, $C(O)R^3$, $OR^3$, $(CH_2)_zC_6H_6$, and $(CH_2)_zNHC(O)R^4$; $R^3$ is $C_1$-$C_8$ alkyl; $R^4$ is $C_1$-$C_8$ alkyl; v is independently selected from 0, 1, 2, 3, 4, 5, 6, 7, and 8, and z is 0, 1, 2, or 3; d and d' are each independently selected from 0, 1, 2, and 3; or taken together two $R^x$ attached to the same carbon atom of the ring together form =O; or taken together two $R^x$ form a $C_3$-$C_8$ cycloalkyl ring, $C_4$-$C_8$ cycloalkenyl ring, or 3 to 8 membered saturated or partially unsaturated heterocyclic ring, further wherein said cycloalkyl, cycloalkenyl, and heterocyclic ring are optionally substituted with one or more $R^z$; and each $R^z$ is independently selected from halogen, $C_1$-$C_4$ alkyl, OH, $NH_2$, and $C(O)CH_3$;
106) V is C and taken together $R^{2a}$ and $R^{2b}$ form a 6-membered saturated heterocyclic ring selected from:

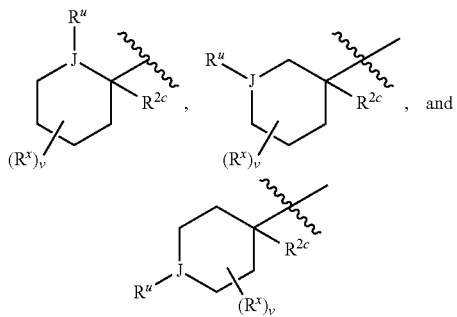

and $R^{2c}$ is selected from hydrogen, halogen, OH, $NH_2$, and $C_1$-$C_8$ alkyl, further wherein J is selected from N, O, C, and S; when J is N or C, $R^u$ is selected from hydrogen, $C_1$-$C_8$ alkyl, $(C_1$-$C_8)CF_3$, $(C_1$-$C_8)OH$, $C(O)R^{3a}$ and when J is O or S, $R^u$ is absent; $R^{3a}$ is $C_1$-$C_8$ alkyl; $R^x$ is selected from $NH_2$, $NHR^3$, $NR^3R^3$, hydroxyl, halogen, $C_1$-$C_8$ alkyl, $C(O)R^3$, $OR^3$, $(CH_2)_zC_6H_6$, and $(CH_2)_zNHC(O)R^4$; $R^3$ is $C_1$-$C_8$ alkyl; $R^4$ is $C_1$-$C_8$ alkyl; v is selected from 0, 1, 2, 3, 4, 5, 6, 7, and 8, and z is 0, 1, 2, or 3; or taken together two $R^x$ attached to the same carbon atom of the ring together form =O; or taken together two $R^x$ form a $C_3$-$C_8$ cycloalkyl ring, $C_4$-$C_8$ cycloalkenyl ring, or 3 to 8 membered saturated or partially unsaturated heterocyclic ring, further wherein said cycloalkyl, cycloalkenyl, and heterocyclic ring are optionally substituted with one or more $R^z$; and each $R^z$ is independently selected from halogen, $C_1$-$C_4$ alkyl, OH, $NH_2$, and $C(O)CH_3$;
107) V is C and taken together $R^{2a}$ and $R^{2b}$ form a 5-membered saturated heterocyclic ring selected from:

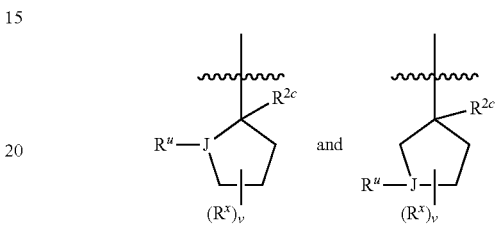

and $R^{2c}$ is selected from hydrogen, halogen, OH, $NH_2$, and $C_1$-$C_8$ alkyl, further wherein J is selected from N, O, C, and S; when J is N or C, $R^u$ is selected from hydrogen, $C_1$-$C_8$ alkyl, $(C_1$-$C_8)CF_3$, $(C_1$-$C_8)OH$, $C(O)R^{3a}$ and when J is O or S, $R^u$ is absent; $R^{3a}$ is $C_1$-$C_8$ alkyl; $R^x$ is selected from $NH_2$, $NHR^3$, $NR^3R^3$, hydroxyl, halogen, $C_1$-$C_8$ alkyl, $C(O)R^3$, $OR^3$, $(CH_2)_zC_6H_6$, and $(CH_2)_zNHC(O)R^4$; $R^3$ is $C_1$-$C_8$ alkyl; $R^4$ is $C_1$-$C_8$ alkyl; v is selected from 0, 1, 2, 3, 4, 5, 6, 7, and 8, and z is 0, 1, 2, or 3;
or taken together two $R^x$ attached to the same carbon atom of the ring together form =O;
or taken together two $R^x$ form a $C_3$-$C_8$ cycloalkyl ring, $C_4$-$C_8$ cycloalkenyl ring, or 3 to 8 membered saturated or partially unsaturated heterocyclic ring, further wherein said cycloalkyl, cycloalkenyl, and heterocyclic ring are optionally substituted with one or more $R^z$; and each $R^z$ is independently selected from halogen, $C_1$-$C_4$ alkyl, OH, $NH_2$, and $C(O)CH_3$;
108) V is C and taken together $R^{2a}$ and $R^{2b}$ form a 4-membered saturated heterocyclic ring selected from:

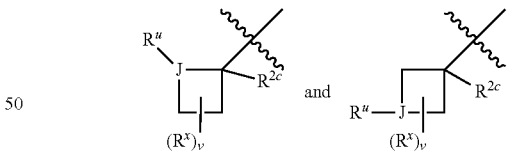

and $R^{2c}$ is selected from hydrogen, halogen, OH, $NH_2$, and $C_1$-$C_8$ alkyl, further wherein J is selected from N, O, C, and S; when J is N or C, $R^u$ is selected from hydrogen, $C_1$-$C_8$ alkyl, $(C_1$-$C_8)CF_3$, $(C_1$-$C_8)OH$, $C(O)R^{3a}$ and when J is O or S, $R^u$ is absent; $R^{3a}$ is $C_1$-$C_8$ alkyl; $R^x$ is selected from $NH_2$, $NHR^3$, $NR^3R^3$, hydroxyl, halogen, $C_1$-$C_8$ alkyl, $C(O)R^3$, $OR^3$, $(CH_2)_zC_6H_6$, and $(CH_2)_zNHC(O)R^4$; $R^3$ is $C_1$-$C_8$ alkyl; $R^4$ is $C_1$-$C_8$ alkyl; v is selected from 0, 1, 2, 3, 4, 5, 6, 7, and 8, and z is 0, 1, 2, or 3; or taken together two $R^x$ attached to the same carbon atom of the ring together form =O; or taken together two $R^x$ form a $C_3$-$C_8$ cycloalkyl ring, $C_4$-$C_8$ cycloalkenyl ring, or 3 to 8 membered saturated or partially unsaturated heterocyclic ring, further wherein said cycloalkyl, cycloalkenyl, and heterocyclic ring are optionally substituted with one or more $R^z$; and each $R^z$ is independently selected from halogen, $C_1$-$C_4$ alkyl, OH, $NH_2$, and $C(O)CH_3$;

109) U is a single bond, t is 0, and V is C;

110) V is C and taken together $R^{2a}$ and $R^{2b}$ form a partially unsaturated bicyclic ring selected from:

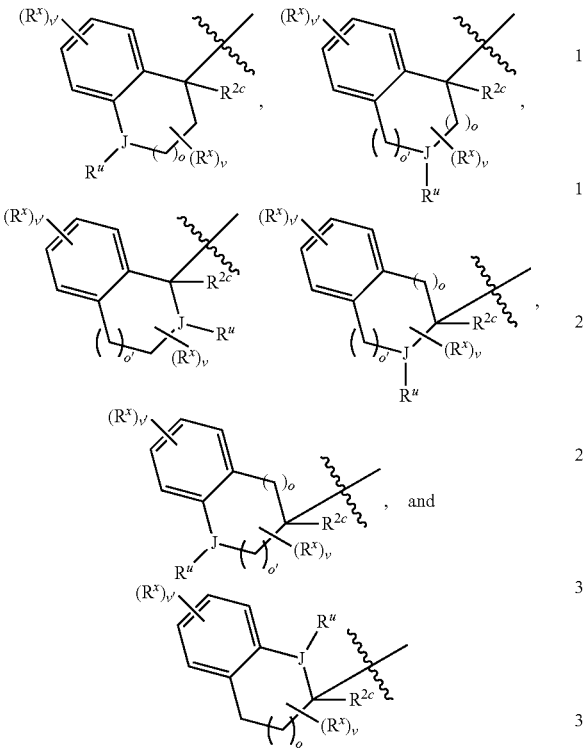

and $R^{2c}$ is selected from hydrogen, halogen, OH, $NH_2$, and $C_1$-$C_8$ alkyl, further wherein J is selected from N, O, C, and S; when J is N or C, $R^u$ is selected from hydrogen, $C_1$-$C_8$ alkyl, $(C_1$-$C_8)CF_3$, $(C_1$-$C_8)OH$, $C(O)R^{3a}$ and when J is O or S, $R^u$ is absent; $R^{3a}$ is $C_1$-$C_8$ alkyl; $R^x$ is selected from NH, $NHR^3$, $NR^3R^3$, hydroxyl, halogen, $C_1$-$C_8$ alkyl, $C(O)R^3$, $OR^3$, $(CH_2)_zC_6H_6$, and $(CH_2)_zNHC(O)R^4$, $R^3$ is $C_1$-$C_8$ alkyl; $R^4$ is $C_1$-$C_8$ alkyl, v is selected from 0, 1, 2, 3, 4, 5, 6, 7, and 8; v' is selected from 0, 1, 2, 3, and 4; o and o' are each independently selected from 0, 1, 2, and 3; and z is 0, 1, 2, or 3; or taken together two $R^x$ attached to the same carbon atom of the ring together form =O; or taken together two $R^x$ form a $C_3$-$C_8$ cycloalkyl ring, $C_4$-$C_8$ cycloalkenyl ring, or 3 to 8 membered saturated or partially unsaturated heterocyclic ring, further wherein said cycloalkyl, cycloalkenyl, and heterocyclic ring are optionally substituted with one or more $R^z$; and each $R^z$ is independently selected from halogen, $C_1$-$C_4$ alkyl, OH, $NH_2$, and $C(O)CH_3$;

111) V is C and taken together $R^{2a}$ and $R^{2b}$ form a saturated bicyclic ring selected from:

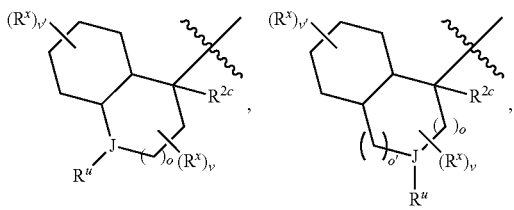

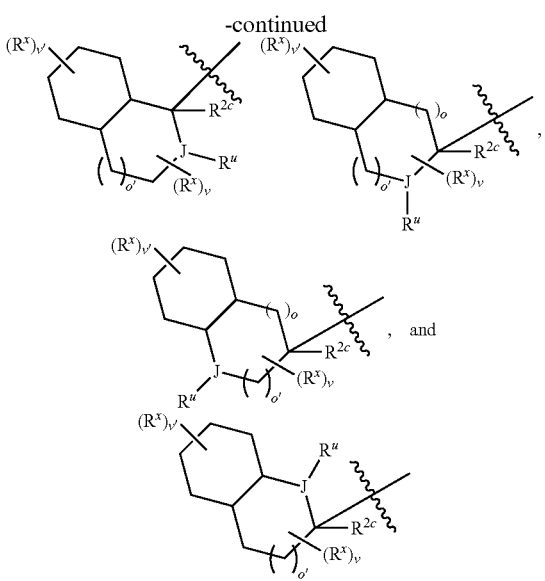

and $R^{2c}$ is selected from hydrogen, halogen, OH, $NH_2$, and $C_1$-$C_8$ alkyl, further wherein J is selected from N, O, C, and S; when J is N or C, $R^u$ is selected from hydrogen, $C_1$-$C_8$ alkyl, $(C_1$-$C_8)CF_3$, $(C_1$-$C_8)OH$, $C(O)R^{3a}$ and when J is O or S, $R^u$ is absent; $R^{3a}$ is $C_1$-$C_8$ alkyl; $R^x$ is selected from NH, $NHR^3$, $NR^3R^3$, hydroxyl, halogen, $C_1$-$C_8$ alkyl, $C(O)R^3$, $OR^3$, $(CH_2)_zC_6H_6$, and $(CH_2)_zNHC(O)R^4$, $R^3$ is $C_1$-$C_8$ alkyl; $R^4$ is $C_1$-$C_8$ alkyl, v is selected from 0, 1, 2, 3, 4, 5, 6, 7, and 8; v' is selected from 0, 1, 2, 3, and 4; o and o' are each independently selected from 0, 1, 2, and 3; and z is 0, 1, 2, or 3; or taken together two $R^x$ attached to the same carbon atom of the ring together form =O; or taken together two $R^x$ form a $C_3$-$C_8$ cycloalkyl ring, $C_4$-$C_8$ cycloalkenyl ring, or 3 to 8 membered saturated or partially unsaturated heterocyclic ring, further wherein said cycloalkyl, cycloalkenyl, and heterocyclic ring are optionally substituted with one or more $R^z$; and each $R^z$ is independently selected from halogen, $C_1$-$C_4$ alkyl, OH, $NH_2$, and $C(O)CH_3$;

112) taken together $R^{2a}$ and $R^{2b}$ form a 10-membered ring system selected from:

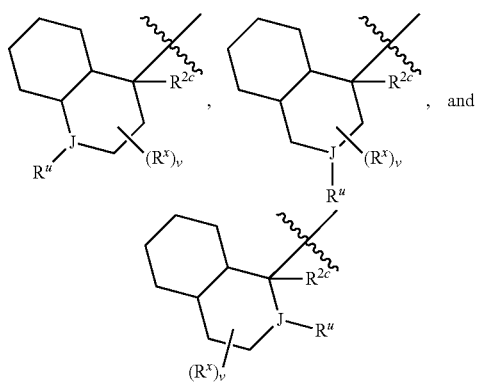

and $R^{2c}$ is selected from hydrogen, halogen, OH, $NH_2$, and $C_1$-$C_8$ alkyl, further wherein J is selected from N, O, C, and S; when J is N or C, $R^u$ is selected from hydrogen, $C_1$-$C_8$ alkyl, $(C_1$-$C_8)CF_3$, $(C_1$-$C_8)OH$, $C(O)R^{3a}$ and when J is O or S, $R^u$ is absent; $R^{3a}$ is $C_1$-$C_8$ alkyl; $R^x$ is selected from NH, $NHR^3$, $NR^3R^3$, hydroxyl, halogen, $C_1$-$C_8$ alkyl, $C(O)R^3$, OR³, (CH₂)$_z$C₆H₆, and (CH₂)$_z$NHC(O)R⁴, R³ is C₁-C₈ alkyl; R⁴ is C₁-C₈ alkyl; v is selected from 0, 1, 2, 3, 4, 5, 6, 7, and 8, and z is 0, 1, 2, or 3; or taken together two R$^x$ attached to the same carbon atom of the ring together form =O; or taken together two R$^x$ form a C₃-C₈ cycloalkyl ring, C₄-C₈ cycloalkenyl ring, or 3 to 8 membered saturated or partially unsaturated heterocyclic ring, further wherein said cycloalkyl, cycloalkenyl, and heterocyclic ring are optionally substituted with one or more R$^z$; and each R$^z$ is independently selected from halogen, C₁-C₄ alkyl, OH, NH₂, and C(O)CH₃;

113) taken together two of R$^{2a}$, R$^{2b}$, and R$^{2c}$ form a C₃-C₈ cycloalkyl ring, C₄-C₈ cycloalkenyl ring, or a 3 to 8 membered saturated or partially unsaturated heterocyclic ring, further wherein said cycloalkyl, cycloalkenyl, and heterocyclic ring are optionally substituted with one or more R$^z$; and each R$^z$ is independently selected from halogen, C₁-C₄ alkyl, OH, NH₂, and C(O)CH₃; or taken together two of R$^{2a}$, R$^{2b}$, and R$^{2c}$ form an aromatic or heteroaromatic ring and the remaining R$^{2a}$, R$^{2b}$, or R$^{2c}$ is absent, further wherein said aromatic or heteroaromatic ring is substituted with one or more R$^x$;

114) V is C and taken together two of R$^{2a}$, R$^{2b}$, and R$^{2c}$ form a ring selected from:

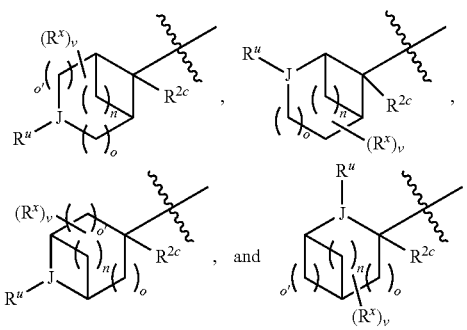

and R$^{2c}$ is selected from hydrogen, halogen, OH, NH₂, and C₁-C₈ alkyl, further wherein J is selected from N, O, C, and S; when J is N or C, R$^u$ is selected from hydrogen, C₁-C₈ alkyl, (C₁-C₈)CF₃, (C₁-C₈)OH, C(O)R$^{3a}$ and when J is O or S, R$^u$ is absent; R$^{3a}$ is C₁-C₈ alkyl; R$^x$ is selected from NH, NHR³, NR³R³, hydroxyl, halogen, C₁-C₈ alkyl, C(O)R³, OR³, (CH₂)$_z$C₆H₆, and (CH₂)$_z$NHC(O)R⁴, R³ is C₁-C₈ alkyl; R⁴ is C₁-C₈ alkyl; n is selected from 0, 1, 2, and 3; v is selected from 0, 1, 2, 3, 4, 5, 6, 7, and 8; and o and o' are each independently selected from 0, 1, 2, and 3;

115) X is selected from hydrogen, deuterium, fluorine, and chlorine;
116) X is hydrogen and J is NH₂;
117) one X is F and the remaining X are hydrogen;
118) the moiety

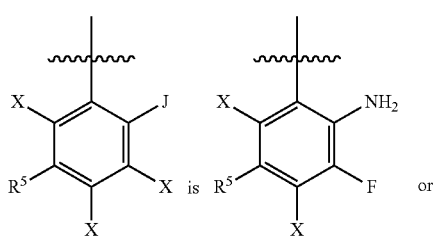

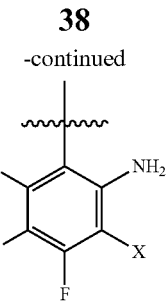

119) the moiety

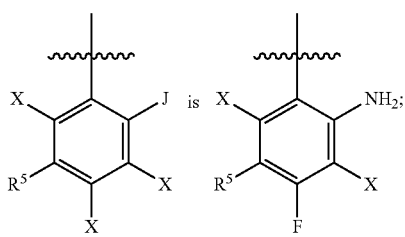

120) R$^{2a}$R$^{2b}$R$^{2c}$V(CH₂)$_t$U is

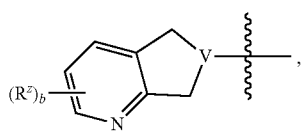

wherein V is N or CH; each R$^z$ is independently selected from halogen, C₁-C₄ alkyl, OH, OR³, CF₃, OCF₃, OCH₂F, OCHF₂, NH₂, NHR³, NR³R³, and C(O)CH₃; b is 0, 1, 2, 3, or 4; and R³ is selected from C₁-C₈ alkyl and O(C₁-C₈ alkyl);

121) R$^{2a}$R$^{2b}$R$^{2c}$V(CH₂)$_t$U is

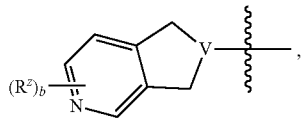

wherein V is N or CH; each R$^z$ is independently selected from halogen, C₁-C₄ alkyl, OH, OR³, CF₃, OCF₃, OCH₂F, OCHF₂, NH₂, NHR³, NR³R³, and C(O)CH₃; b is 0, 1, 2, 3, or 4; and R³ is selected from C₁-C₈ alkyl and O(C₁-C₈ alkyl);

122) R$^{2a}$R$^{2b}$R$^{2c}$V(CH₂)$_t$U is

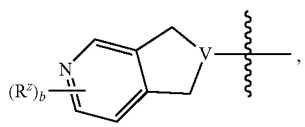

wherein V is N or CH; each R$^z$ is independently selected from halogen, C₁-C₄ alkyl, OH, OR³, CF₃, OCF₃, OCH₂F, OCHF₂, NH₂, NHR³, NR³R³, and C(O)CH₃; b is 0, 1, 2, 3, or 4; and R³ is selected from C₁-C₈ alkyl and O(C₁-C₈ alkyl);

123) V is N;
124) the moiety:

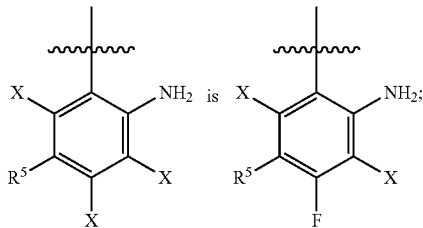

125) any compound exemplified;
126) the compound is a pharmaceutically acceptable salt;
127) the compound is a hydrate;
128) the compound is a solvate; and
129) the compound is a prodrug.

It will be understood that the above classes may be combined to form additional classes, as for example the combination of selections of two or more substituents forming additional classes. Illustrative examples of combinations of the classes above forming additional classes are:
200) the combination of any of classes 31), or 33)-38) with classes 39), 43), and 109);
201) the combination of any of classes 31), or 33)-38) with classes 47)-49);
202) the combination of the combination of 201) with classes 50)-52);
203) the combination of any of classes 40)-42), 70), or 120)-122) with with any of classes 118) or 119);
204) the combination of any of classes 53)-69), 71)-72) or 112)-113) with any of classes 39), 43), and 109);
205) the combination of the combination of 204) with any of classes 123) or 104);
206) the combination of any of classes 53)-69), 71)-72), or 112)-113) with any of classes 47)-49);
207) the combination of the combination of 206) with with classes 50)-52);
208) the combination of the combination of 207) with any of classes 123) or 104);
209) the combination of any of classes of 105)-108), 110)-111), or 114) with any of classes 39), 43), and 109);
210) the combination of any of classes of 105)-108), 110)-111), or 114) with any of classes 47)-49);
211) the combination of the combination of 210) with any of classes 50)-52);
212) the combination of any of classes 73)-76) and class 123);
213) the combination of the combination of 212) with any of classes 50)-52);
214) the combination of any of classes 44)-46) with any of classes 47)-49);
215) the combination of any of the combinations of 200), 202), 203), 205), 208), 209), 211), 213), or 214) with any of classes 118)-119) and 124);
216) the combination of any of the combinations of 200), 202), 203), 205), 208), 209), 211), 213), or 214) with class 116);
217) the combination of any of classes 40)-42), 70), or 120)-122) with with class 116)
218) the combination of any of the combinations of 203) or 215)-217) with 1)-25), 30), 32), and 83)-99).

The above classes and combinations apply to formulae I, Ia, IIa, IIIa, IVa, Va, Ib, Ibb, Ibbb, IIb, IIIb, IVb, and Vb. It is also noted that compounds of formulae Ia, IIa, IIIa, IVa, Va, Ib, Ibb, Ibbb, IIb, IIIb, IVb, and Vb are subsets of compounds of formula I. Features described herein for compounds of formula I apply equally to compounds of formulae Ia, IIa, IIIa, IVa, Va, Ib, Ibb, Ibbb, IIb, IIIb, IVb, and Vb.

In one aspect of the invention, for formula I, Ia and Ib, the compound is not N-(2-amino-5-(thiophen-2-yl)phenyl)acetamide. In one aspect of the invention, for a compound of formulae I or Ia, when $R^5$ is thiopheneyl and X is H, then U—$(CH_2)_t$—$VR^{2a}R^{2b}R^{2c}$ is not $CH_3$. In one aspect of the invention, for a compound of formulae I or Ia, U—$(CH_2)_t$—$VR^{2a}R^{2b}R^{2c}$ is not $CH_3$. In one aspect of the invention, for formula Ib, when $R^5$ is thiopheneyl, then $R^{2a}R^{2b}R^{2c}(CH_2)_t$ is not $CH_3$. In one aspect of the invention, for formula Ib, $R^{2a}R^{2b}R^{2c}(CH_2)_t$ is not $CH_3$.

In one aspect of the invention, for a compound of formula I or Ia, when U is a single bond, t is 0, V is C, then two of $R^{2a}$, $R^{2b}$, and $R^{2c}$ do not form a partially unsaturated heterocylic ring. In one aspect of the invention, for a compound of formula I or Ia, when U is single bond, t is 0, V is C, then two of $R^{2a}$, $R^{2b}$, and $R^{2c}$ do not form a pyridinone, 2,3,4,9-tetrahydrocarbazole, benzoimidazole, or 1,2,3,4-tetrahydroquinoline ring. In one aspect of the invention, for a compound of formula Ib, when t is 0 then two of $R^{2a}$, $R^{2b}$, and $R^{2c}$ do not form a partially unsaturated heterocylic ring. In one aspect, of the invention for a compound of formula Ib, when t is 0, then two of $R^{2a}$, $R^{2b}$, and $R^{2c}$ do not form a pyridinone, 2,3,4,9-tetrahydrocarbazole, benzoimidazole, or 1,2,3,4-tetrahydroquinoline ring.

In one aspect of the invention, for a compound of formula I or Ia, when U is a single bond, t is 0, V is C, and two of $R^{2a}$, $R^{2b}$, and $R^{2c}$ form a piperidine ring, then $R^x$ is not benzyl, benzoyl, or benzodioxole. In one aspect of the invention, for a compound of formula Ib, when t is 0 and two of $R^{2a}$, $R^{2b}$, and $R^{2c}$ form a piperidine ring, then $R^x$ is not benzyl, benzoyl, or benzodioxole.

In one aspect of the invention, for a compound of formula I or Ia, when U is a single bond, t is 0, V is N, and two of $R^{2a}$, $R^{2b}$, and $R^{2c}$ form a piperazine ring, then $R^x$ is not benzyl or benzodioxole and when U is $NR^{2d}$ and taken together $R^{2d}$ with one of $R^{2a}$, $R^{2b}$, and $R^{2c}$ form a piperazine ring, then $R^x$ is not benzyl or benzodioxole. In one aspect of the invention for a compound of formula IIIa or IIIb, when one of $R^{2a}$, $R^{2b}$, and $R^{2c}$ taken together with $R^{2d}$ forms a piperazine ring, then $R^x$ is not benzyl or benzodioxole.

In one aspect, the invention does not include a compound having the moiety:

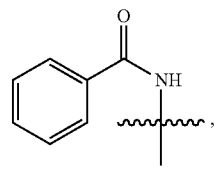 [SMILES: *NC(=O)c1ccccc1]

wherein the phenyl ring is unsubstituted or substituted.

In one aspect of the invention, the compound is not 1-methylpiperidin-2-yl)methyl (2-amino-5-(thiophen-2-yl)phenyl)carbamate, 1-(2-amino-5-(thiophen-2-yl)phenyl)-3-phenylurea, 1-(2-amino-5-(thiophen-2-yl)phenyl)-3-cyclohexylurea, 1-(2-amino-5-(thiophen-2-yl)phenyl)-3-(pyrrolidin-3-yl)urea, phenyl (2-amino-5-(thiophen-2-yl)phenyl)carbamate, N-(2-amino-5-(pyrimidin-5-yl)phenyl) cyclohexanecarboxamide, N-(2-amino-5-phenethylphenyl)

cyclohexanecarboxamide, and N-(2-amino-5-(thiophen-2-yl)phenyl)-2-propylpentanamide.

In addition to those compounds presented in the examples, the following compounds further illustrate the scope of the present invention:

TABLE 1

| Cmpd No. | structure |
|---|---|
| 1 | 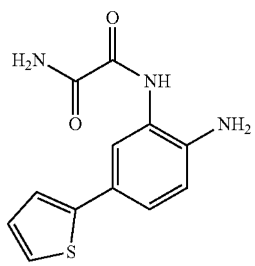 [SMILES: NC(=O)C(=O)Nc1cc(-c2cccs2)ccc1N] |
| 2 | 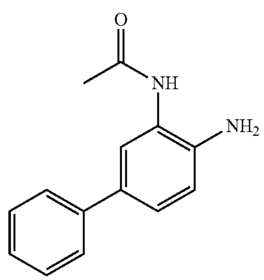 [SMILES: CC(=O)Nc1cc(-c2ccccc2)ccc1N] |
| 3 | 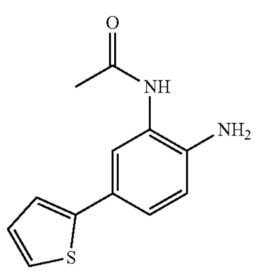 [SMILES: CC(=O)Nc1cc(-c2cccs2)ccc1N] |
| 4 | 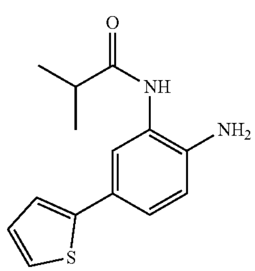 [SMILES: CC(C)C(=O)Nc1cc(-c2cccs2)ccc1N] |
| 5 | 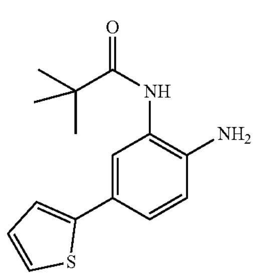 [SMILES: CC(C)(C)C(=O)Nc1cc(-c2cccs2)ccc1N] |

TABLE 1-continued

| Cmpd No. | structure |
|---|---|
| 6 | 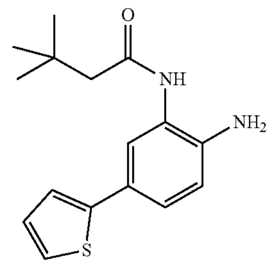 [SMILES: CC(C)(C)CC(=O)Nc1cc(-c2cccs2)ccc1N] |
| 8 | 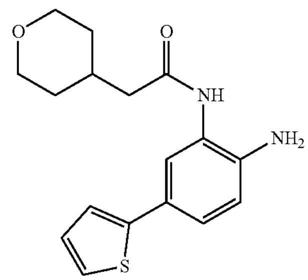 [SMILES: Nc1ccc(-c2cccs2)cc1NC(=O)CC1CCOCC1] |
| 9 | 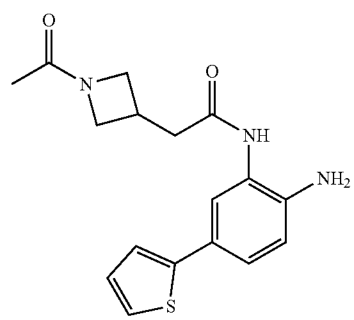 [SMILES: CC(=O)N1CC(CC(=O)Nc2cc(-c3cccs3)ccc2N)C1] |
| 10 | 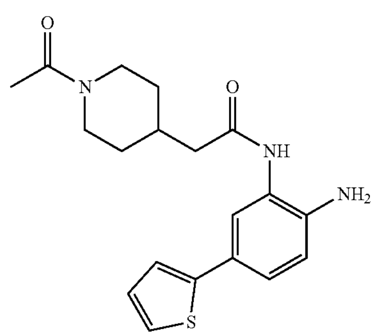 [SMILES: CC(=O)N1CCC(CC(=O)Nc2cc(-c3cccs3)ccc2N)CC1] |
| 11 | 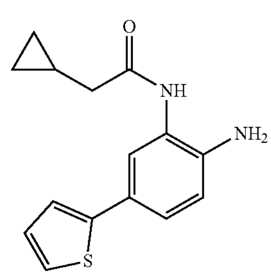 [SMILES: Nc1ccc(-c2cccs2)cc1NC(=O)CC1CC1] |

TABLE 1-continued
| Cmpd No. | structure |
|---|---|
| 12 | 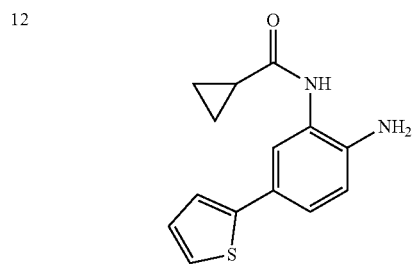 |
| 13 | 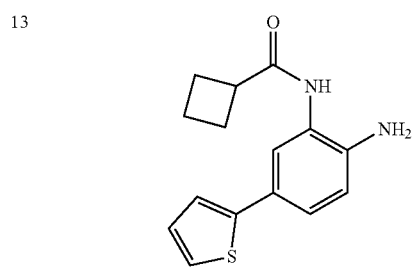 |
| 14 | 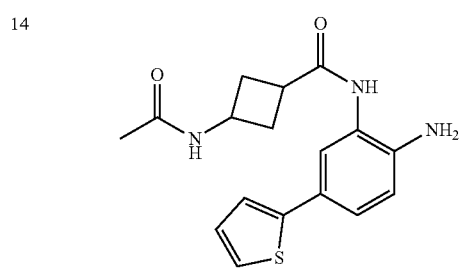 |
| 15 | 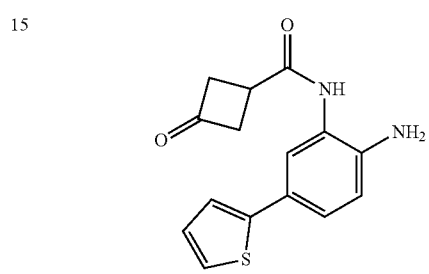 |
| 16 | 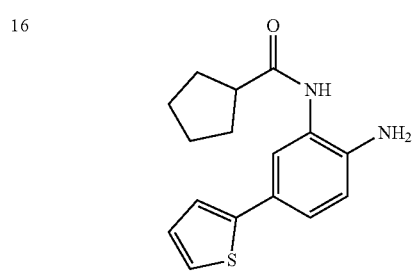 |
| 17 | 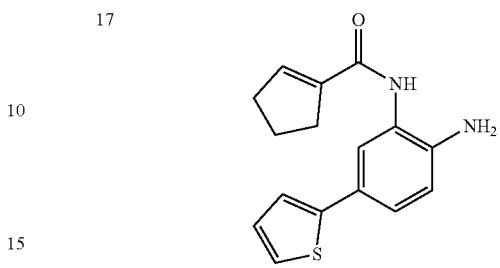 |
| 18 | 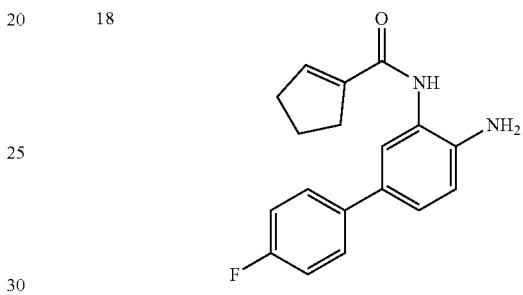 |
| 19 | 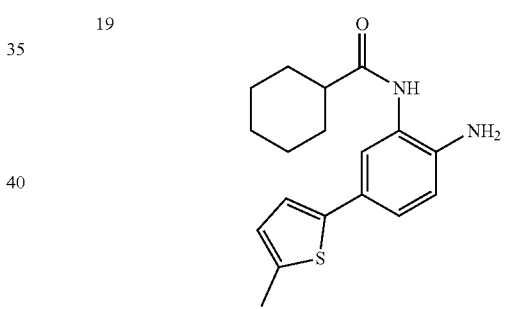 |
| 20 | 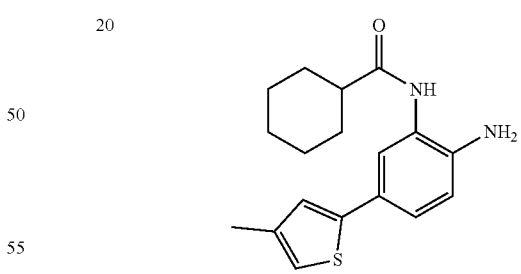 |
| 21 | 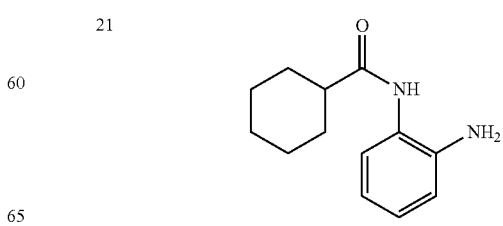 |

TABLE 1-continued
| Cmpd No. | structure |
|---|---|
| 22 | 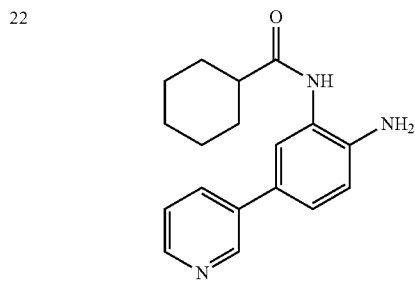 |
| 23 | 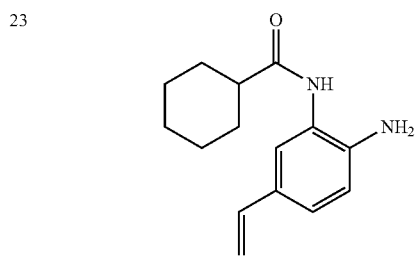 |
| 24 | 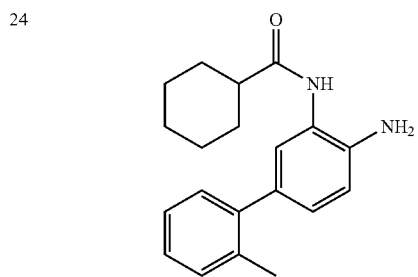 |
| 25 | 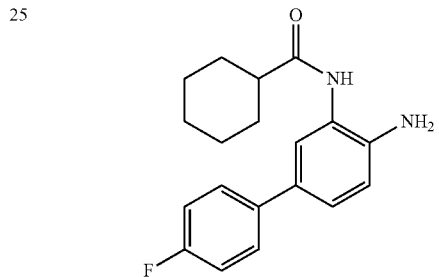 |
| 26 | 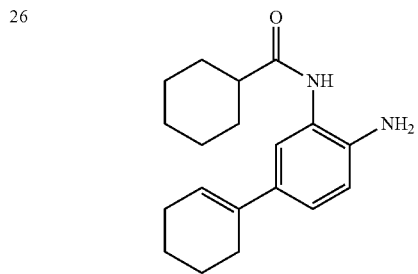 |
| 27 | 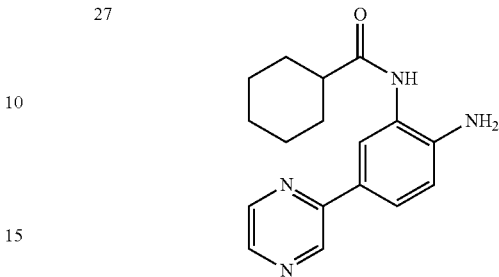 |
| 30 |  |
| 31 | 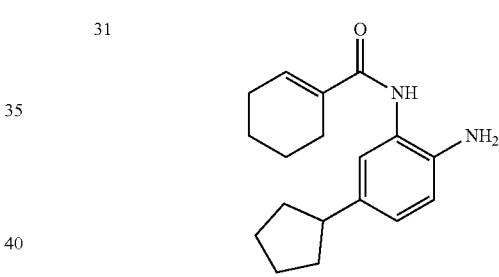 |
| 32 | 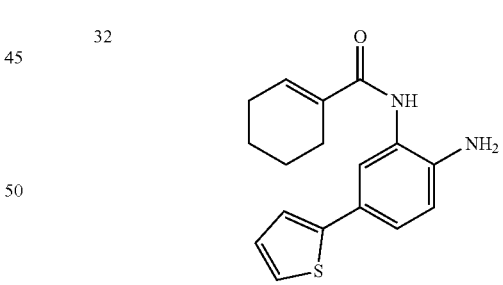 |
| 33 | 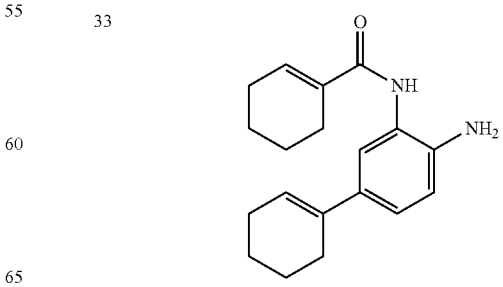 |

TABLE 1-continued

| Cmpd No. | structure |
|---|---|
| 34 | 1-methylpiperidine-4-carboxamide linked to 2-amino-5-(thiophen-2-yl)phenyl |
| 35 | 1-acetylpiperidine-4-carboxamide linked to 2-amino-5-(thiophen-2-yl)phenyl |
| 36 | 1-acetylpiperidine-4-carboxamide linked to 2-aminophenyl |
| 37 | 1-acetylpiperidine-4-carboxamide linked to 2-amino-5-(cyclohex-1-en-1-yl)phenyl |
| 38 | 1-acetylpiperidine-4-carboxamide linked to 2-amino-5-(cyclopent-1-en-1-yl)phenyl |
| 39 | 1-acetylpiperidine-4-carboxamide linked to 2-amino-5-(4-fluorophenyl)phenyl |
| 40 | 1-methyl-2-oxopiperidine-4-carboxamide linked to 2-amino-5-(thiophen-2-yl)phenyl |
| 41 | 1-methyl-6-oxopiperidine-4-carboxamide linked to 2-amino-5-(cyclohex-1-en-1-yl)phenyl |
| 42 | 1-acetylazetidine-3-carboxamide linked to 2-amino-5-(thiophen-2-yl)phenyl |
| 43 | azetidine-3-carboxamide linked to 2-amino-5-(thiophen-2-yl)phenyl |
| 44 | tetrahydrofuran-3-carboxamide linked to 2-amino-5-(thiophen-2-yl)phenyl |

TABLE 1-continued
| Cmpd No. | structure |
|---|---|
| 45 | 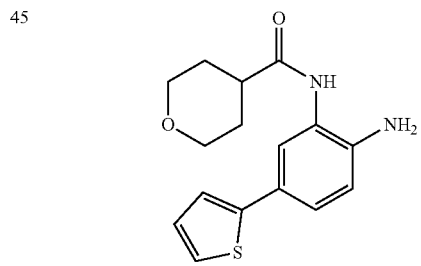 |
| 46 | 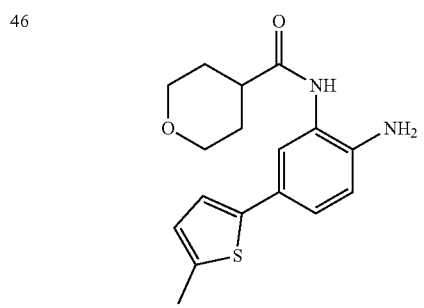 |
| 47 | 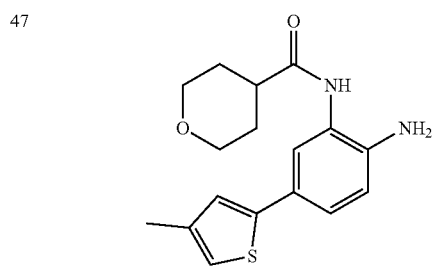 |
| 48 | 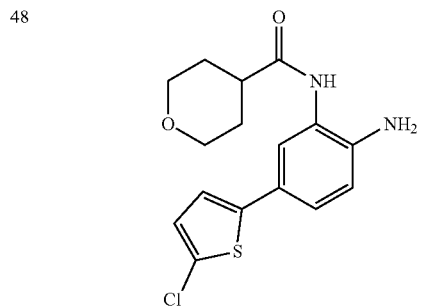 |
| 49 | 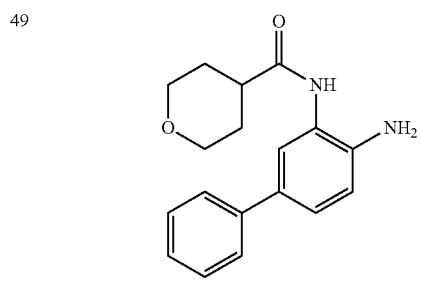 |
| 50 | 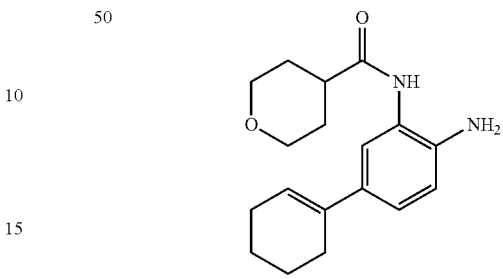 |
| 51 | 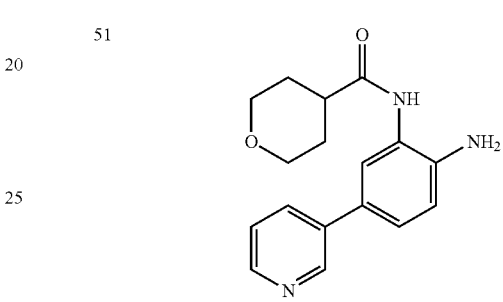 |
| 52 | 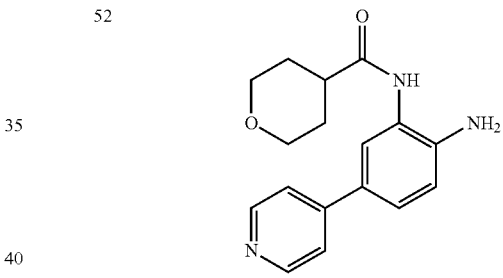 |
| 53 | 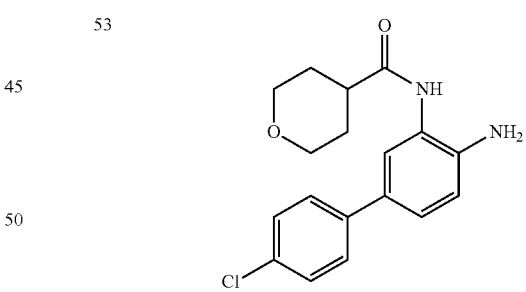 |
| 54 | 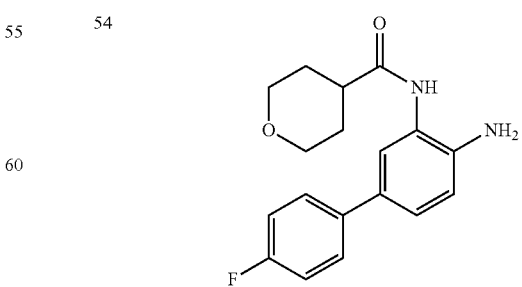 |

TABLE 1-continued
| Cmpd No. | structure |
|---|---|
| 55 | 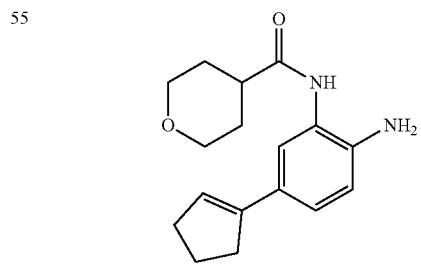 |
| 56 | 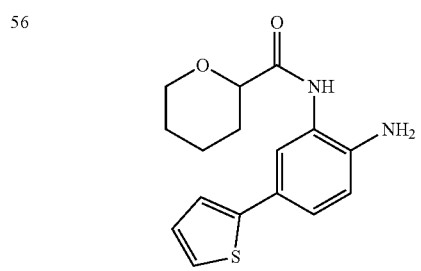 |
| 57 | 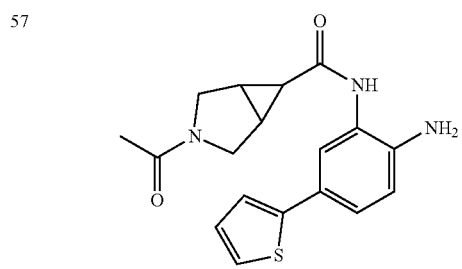 |
| 58 | 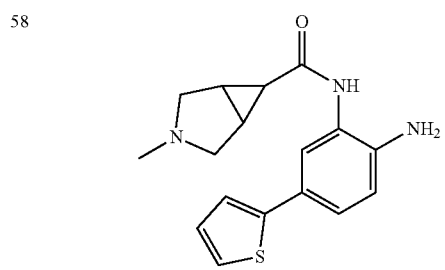 |
| 59 | 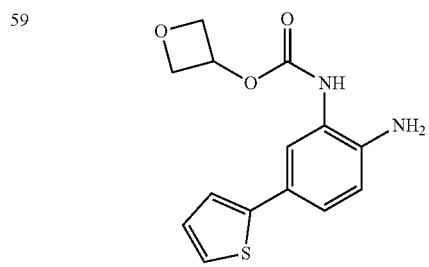 |
| 60 | 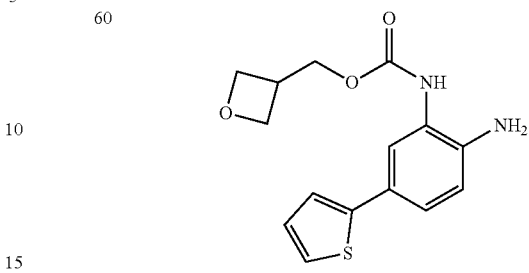 |
| 61 | 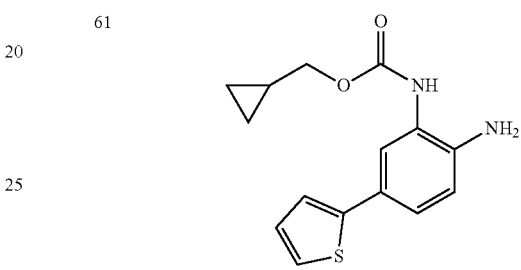 |
| 62 | 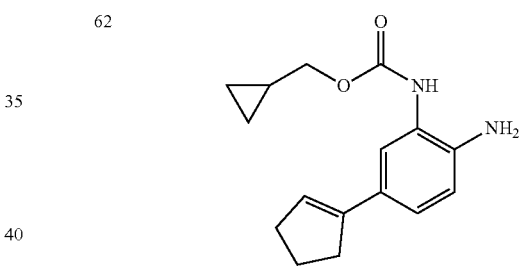 |
| 63 | 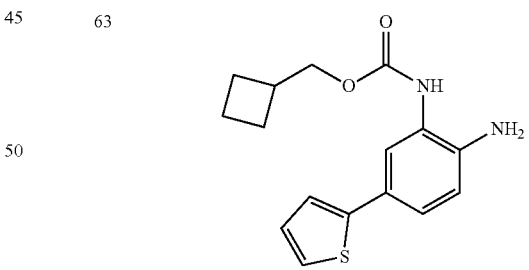 |
| 64 | 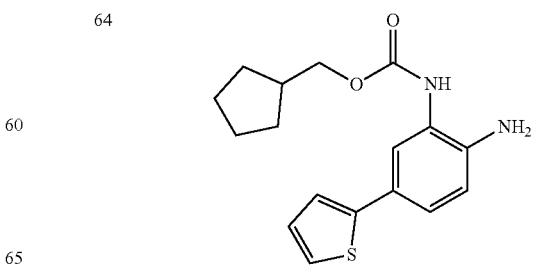 |

TABLE 1-continued

| Cmpd No. | structure |
|---|---|
| 65 | 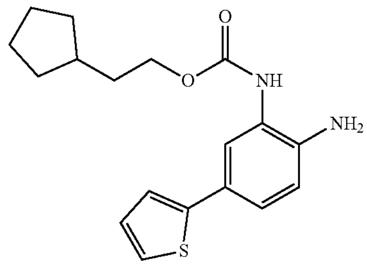 [SMILES: Nc1ccc(-c2cccs2)cc1NC(=O)OCCC1CCCC1] |
| 66 | 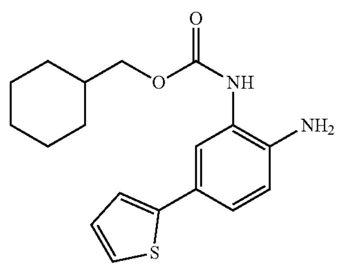 [SMILES: Nc1ccc(-c2cccs2)cc1NC(=O)OCC1CCCCC1] |
| 67 | 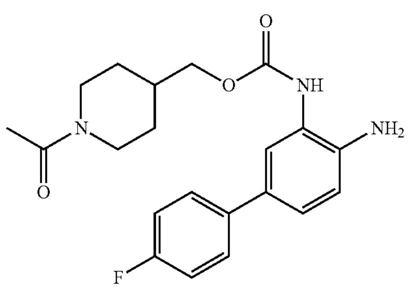 [SMILES: CC(=O)N1CCC(COC(=O)Nc2cc(-c3ccc(F)cc3)ccc2N)CC1] |
| 68 | 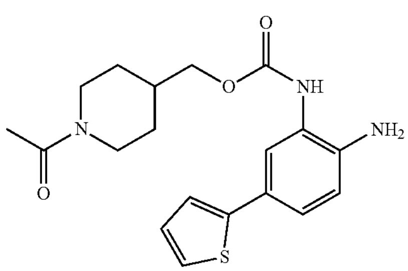 [SMILES: CC(=O)N1CCC(COC(=O)Nc2cc(-c3cccs3)ccc2N)CC1] |
| 69 | 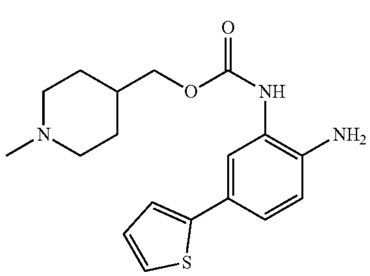 [SMILES: CN1CCC(COC(=O)Nc2cc(-c3cccs3)ccc2N)CC1] |
| 70 | |
| 72 | |
| 73 | |
| 74 | |
| 75 | |

TABLE 1-continued

| Cmpd No. | structure |
|---|---|
| 76 | propyl N-(2-amino-5-(thiophen-2-yl)phenyl)carbamate |
| 77 | 2,2-difluoropropyl N-(2-amino-5-(thiophen-2-yl)phenyl)carbamate |
| 78 | isopropyl N-(2-amino-5-(thiophen-2-yl)phenyl)carbamate |
| 79 | isobutyl N-(2-amino-5-(thiophen-2-yl)phenyl)carbamate |
| 80 | isobutyl N-(2-amino-5-(cyclopenten-1-yl)phenyl)carbamate |
| 81 | ethyl N-(2-amino-5-(thiophen-2-yl)phenyl)carbamate |
| 82 | propyl N-(2-amino-5-(cyclopenten-1-yl)phenyl)carbamate |
| 83 | cyclohexyl N-(2-amino-5-(thiophen-2-yl)phenyl)carbamate |
| 85 | benzyl N-(2-amino-5-(thiophen-2-yl)phenyl)carbamate |
| 86 | pyridin-3-ylmethyl N-(2-amino-5-(thiophen-2-yl)phenyl)carbamate |

TABLE 1-continued

| Cmpd No. | structure |
|---|---|
| 87 | (pyridin-2-yl)methyl (2-amino-5-(thiophen-2-yl)phenyl)carbamate |
| 88 | (pyridin-4-yl)methyl (2-amino-5-(thiophen-2-yl)phenyl)carbamate |
| 89 | (piperidin-4-yl)methyl (2-amino-5-(thiophen-2-yl)phenyl)carbamate |
| 90 | (piperidin-4-yl)methyl (6-amino-4'-fluoro-[1,1'-biphenyl]-3-yl)carbamate |
| 91 | (tetrahydro-2H-pyran-4-yl)methyl (2-amino-5-(thiophen-2-yl)phenyl)carbamate |
| 92 | 3-(2-amino-5-(thiophen-2-yl)phenyl)-1,1-dimethylurea |
| 93 | 3-(2-amino-5-(cyclopent-1-en-1-yl)phenyl)-1-methyl-1-propylurea |
| 94 | 3-(2-amino-5-(thiophen-2-yl)phenyl)-1-methyl-1-propylurea |
| 95 | 3-(2-amino-5-(thiophen-2-yl)phenyl)-1-methyl-1-(oxetan-3-yl)urea |
| 96 | 1-(2-amino-5-(thiophen-2-yl)phenyl)-3-propylurea |

TABLE 1-continued
| Cmpd No. | structure |
|---|---|
| 97 | 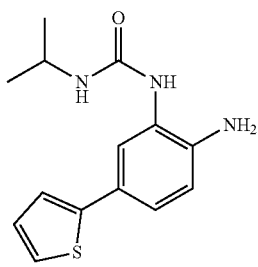 [SMILES: CC(C)NC(=O)Nc1cc(-c2cccs2)ccc1N] |
| 98 | 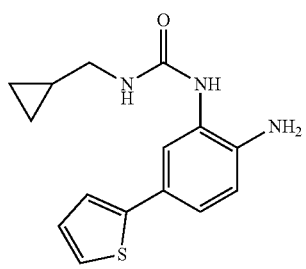 [SMILES: Nc1ccc(-c2cccs2)cc1NC(=O)NCC1CC1] |
| 100 | 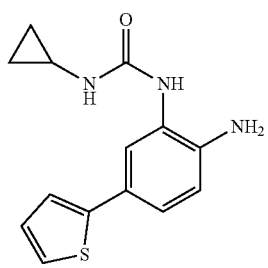 [SMILES: Nc1ccc(-c2cccs2)cc1NC(=O)NC1CC1] |
| 103 | 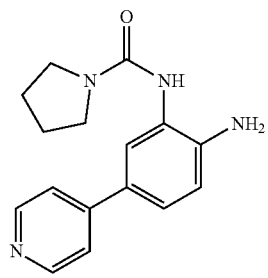 [SMILES: Nc1ccc(-c2ccncc2)cc1NC(=O)N1CCCC1] |
| 104 | 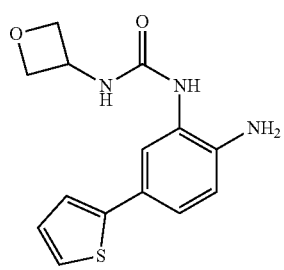 [SMILES: Nc1ccc(-c2cccs2)cc1NC(=O)NC1COC1] |
TABLE 1-continued
| Cmpd No. | structure |
|---|---|
| 105 | 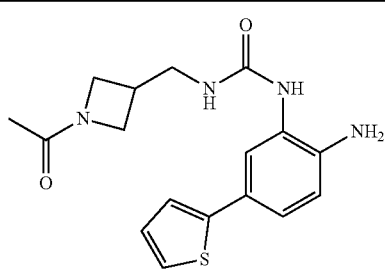 |
| 106 | 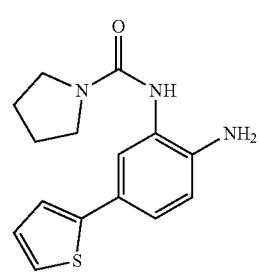 [SMILES: Nc1ccc(-c2cccs2)cc1NC(=O)N1CCCC1] |
| 107 | 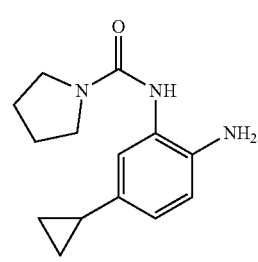 [SMILES: Nc1ccc(C2CC2)cc1NC(=O)N1CCCC1] |
| 108 | 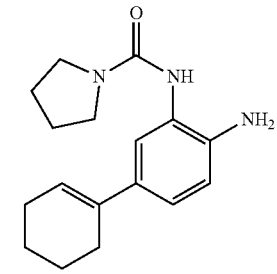 [SMILES: Nc1ccc(C2=CCCCC2)cc1NC(=O)N1CCCC1] |
| 109 | 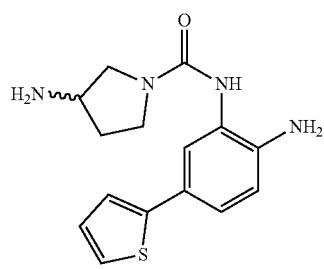 [SMILES: Nc1ccc(-c2cccs2)cc1NC(=O)N1CCC(N)C1] |

TABLE 1-continued

| Cmpd No. | structure |
|---|---|
| 110 | 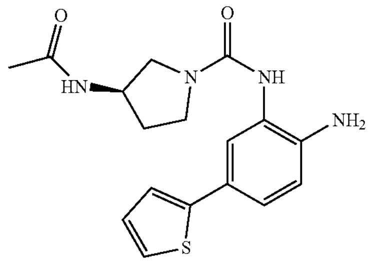 [SMILES: CC(=O)N[C@@H]1CCN(C(=O)Nc2cc(-c3cccs3)ccc2N)C1] |
| 111 | 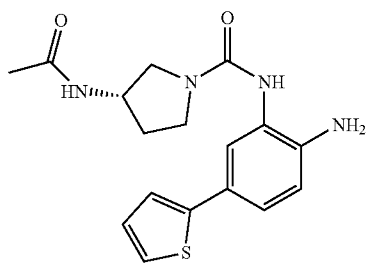 [SMILES: CC(=O)N[C@H]1CCN(C(=O)Nc2cc(-c3cccs3)ccc2N)C1] |
| 112 | 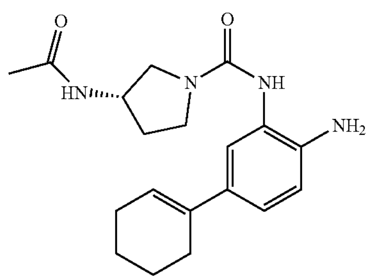 [SMILES: CC(=O)N[C@H]1CCN(C(=O)Nc2cc(C3=CCCCC3)ccc2N)C1] |
| 113 | 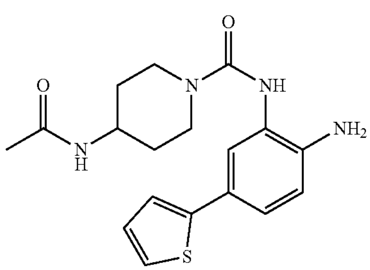 [SMILES: CC(=O)NC1CCN(C(=O)Nc2cc(-c3cccs3)ccc2N)CC1] |
| 114 | 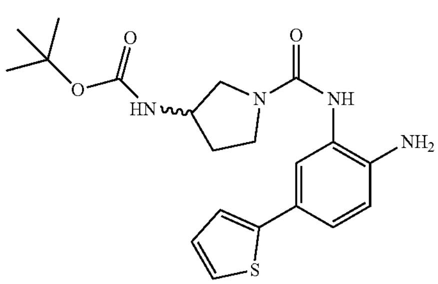 [SMILES: CC(C)(C)OC(=O)NC1CCN(C(=O)Nc2cc(-c3cccs3)ccc2N)C1] |
| 115 | |
| 116 | |
| 117 | |
| 118 | |
| 119 | |

TABLE 1-continued

| Cmpd No. | structure |
|---|---|
| 120 | (pyrrolidine-1-carboxamide on 2-amino-5-vinylphenyl) |
| 121 | (pyrrolidine-1-carboxamide on 2-amino-5-(pyridin-3-yl)phenyl) |
| 122 | (3-fluoropyrrolidine-1-carboxamide on 2-amino-5-(thiophen-2-yl)phenyl) |
| 123 | ((2S)-2-methylpyrrolidine-1-carboxamide on 2-amino-5-(thiophen-2-yl)phenyl) |
| 124 | (piperidine-1-carboxamide on 2-amino-5-(thiophen-2-yl)phenyl) |
| 125 | (3,3-difluoropiperidine-1-carboxamide on 2-amino-5-(thiophen-2-yl)phenyl) |
| 126 | (4,4-difluoropiperidine-1-carboxamide on 2-amino-5-(thiophen-2-yl)phenyl) |
| 127 | (4,4-difluoropiperidine-1-carboxamide on 2-amino-5-cyclopentylphenyl) |
| 128 | (morpholine-4-carboxamide on 2-amino-5-(thiophen-2-yl)phenyl) |
| 129 | (4-acetylpiperazine-1-carboxamide on 2-amino-5-(thiophen-2-yl)phenyl) |

TABLE 1-continued

| Cmpd No. | structure |
|---|---|
| 130 | 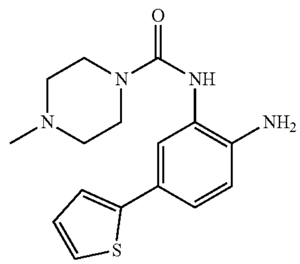 [SMILES: CN1CCN(C(=O)Nc2cc(-c3cccs3)ccc2N)CC1] |
| 131 | 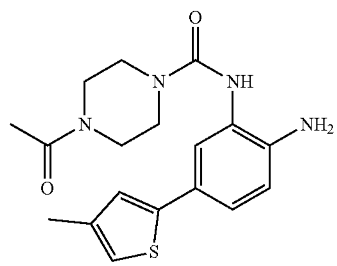 [SMILES: CC(=O)N1CCN(C(=O)Nc2cc(-c3cc(C)cs3)ccc2N)CC1] |
| 132 | 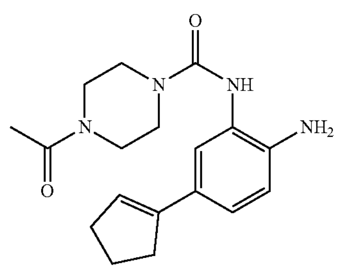 [SMILES: CC(=O)N1CCN(C(=O)Nc2cc(C3=CCCC3)ccc2N)CC1] |
| 133 | 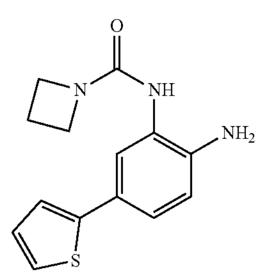 [SMILES: Nc1ccc(-c2cccs2)cc1NC(=O)N1CCC1] |
| 134 | 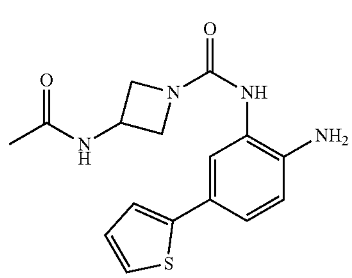 [SMILES: CC(=O)NC1CN(C(=O)Nc2cc(-c3cccs3)ccc2N)C1] |
| 135 | |
| 136 | |
| 137 | |
| 138 | |
| 139 | |

TABLE 1-continued

| Cmpd No. | structure |
|---|---|
| 140 | 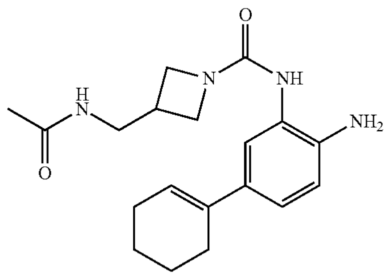 [SMILES: CC(=O)NCC1CN(C(=O)Nc2cc(C3=CCCCC3)ccc2N)C1] |
| 141 | 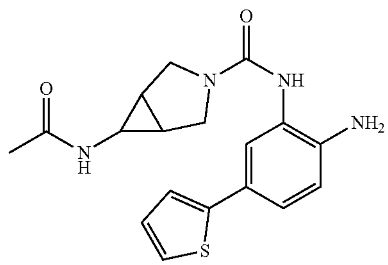 [SMILES: CC(=O)NC1C2CN(C(=O)Nc3cc(-c4cccs4)ccc3N)CC21] |
| 142 | 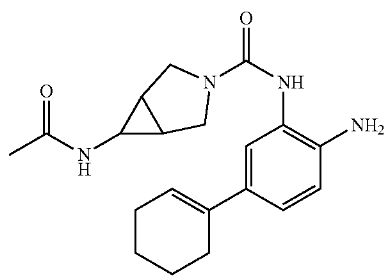 [SMILES: CC(=O)NC1C2CN(C(=O)Nc3cc(C4=CCCCC4)ccc3N)CC21] |
| 143 | 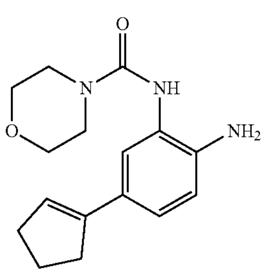 [SMILES: Nc1ccc(C2=CCCC2)cc1NC(=O)N1CCOCC1] |
| 144 | 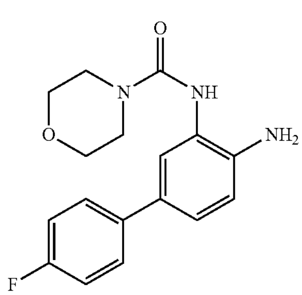 [SMILES: Nc1ccc(-c2ccc(F)cc2)cc1NC(=O)N1CCOCC1] |
| 145 | |
| 146 | |
| 147 | |
| 152 | |
| 153 | |

TABLE 1-continued

| Cmpd No. | structure |
|---|---|
| 154 | 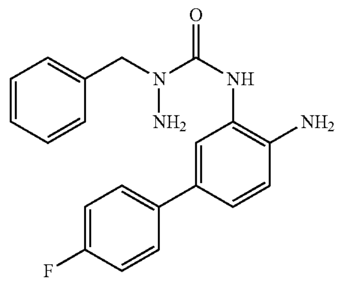 [SMILES: Nc1ccc(-c2ccc(F)cc2)cc1NC(=O)N(N)Cc1ccccc1] |
| 155 | 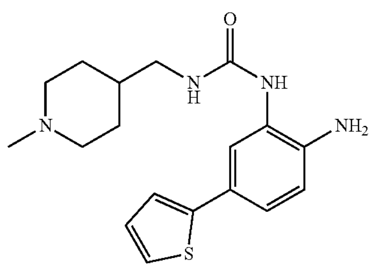 [SMILES: CN1CCC(CNC(=O)Nc2cc(-c3cccs3)ccc2N)CC1] |
| 156 | 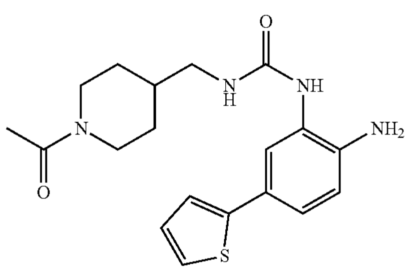 [SMILES: CC(=O)N1CCC(CNC(=O)Nc2cc(-c3cccs3)ccc2N)CC1] |
| 157 | 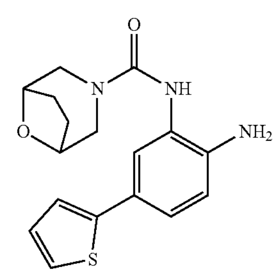 [SMILES: Nc1ccc(-c2cccs2)cc1NC(=O)N1CC2CCC(C1)O2] |
| 158 | 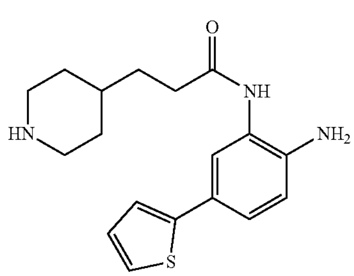 [SMILES: Nc1ccc(-c2cccs2)cc1NC(=O)CCC1CCNCC1] |
| 159 | |
| 160 | |
| 161 | |
| 162 | |
| 163 | |

TABLE 1-continued
| Cmpd No. | structure |
|---|---|
| 164 | 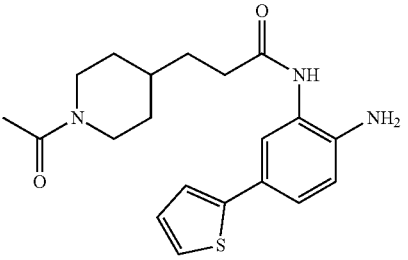 |
| 165 | 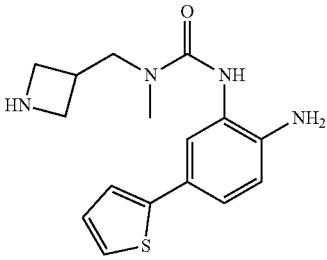 [SMILES: CN(CC1CNC1)C(=O)Nc1cc(-c2cccs2)ccc1N] |
| 166 | 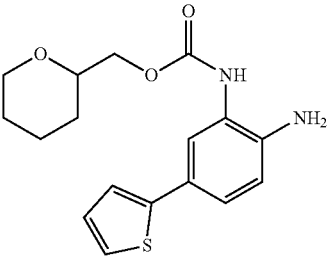 [SMILES: Nc1ccc(-c2cccs2)cc1NC(=O)OCC1CCCCO1] |
| 167 | 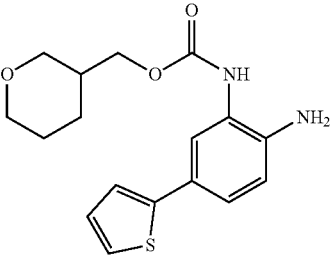 [SMILES: Nc1ccc(-c2cccs2)cc1NC(=O)OCC1CCCOC1] |
| 168 | 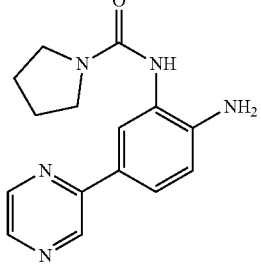 |
| 169 | 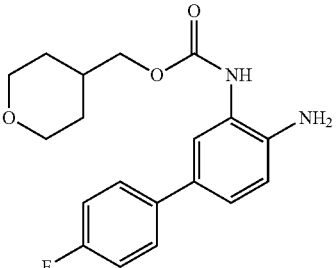 |
| 170 | 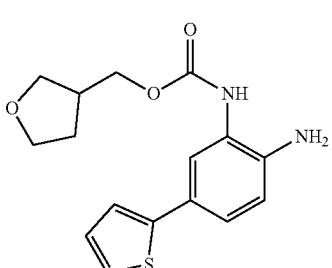 |
| 171 | 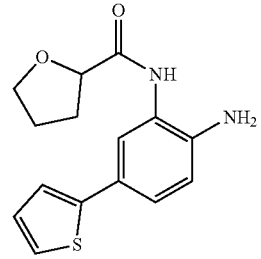 [SMILES: Nc1ccc(-c2cccs2)cc1NC(=O)C1CCCO1] |
| 172 | 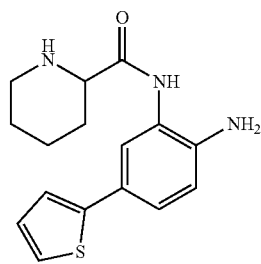 [SMILES: Nc1ccc(-c2cccs2)cc1NC(=O)C1CCCCN1] |
| 173 | |

TABLE 1-continued
| Cmpd No. | structure |
|---|---|
| 174 | 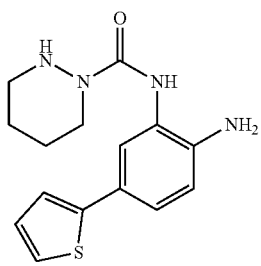 [SMILES: Nc1ccc(-c2cccs2)cc1NC(=O)N1CCCCN1] |
| 175 | 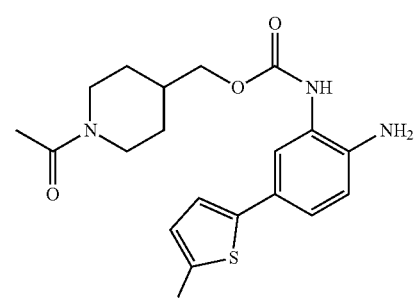 |
| 176 | 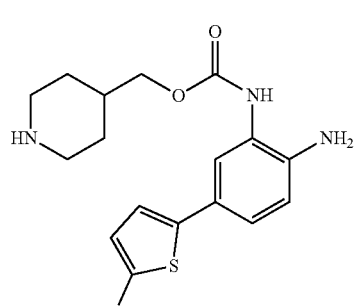 |
| 177 | 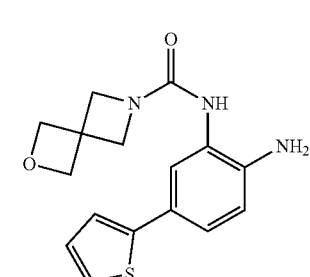 |
| 178 | 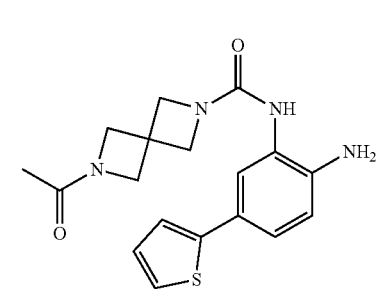 [SMILES: CC(=O)N1CC2(C1)CN(C(=O)Nc1cc(-c3cccs3)ccc1N)C2] |
| 179 | 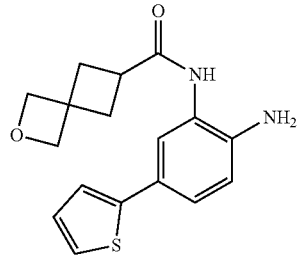 [SMILES: Nc1ccc(-c2cccs2)cc1NC(=O)C1CC2(COC2)C1] |
| 180 | 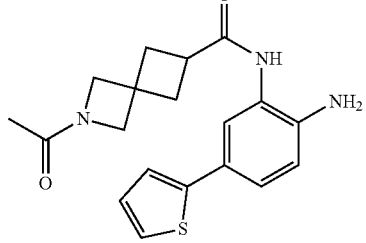 |
| 181 | 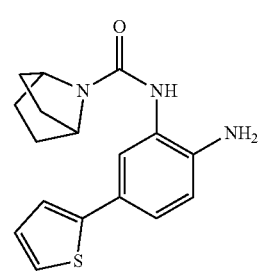 [SMILES: Nc1ccc(-c2cccs2)cc1NC(=O)N1C2CCC1CC2] |
| 182 | 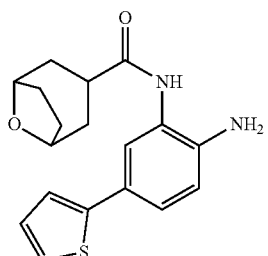 |
| 183 | 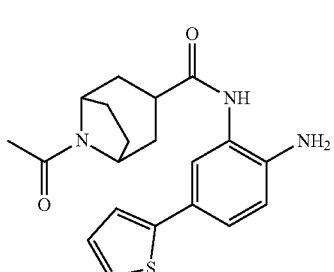 |

TABLE 1-continued

| Cmpd No. | structure |
|---|---|
| 185 | 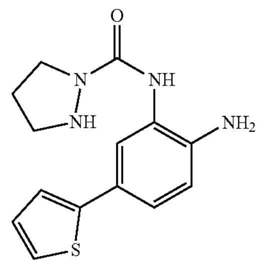 [SMILES: Nc1ccc(-c2cccs2)cc1NC(=O)N1CCCN1] |
| 186 | 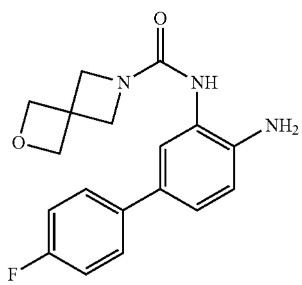 [SMILES: Nc1ccc(-c2ccc(F)cc2)cc1NC(=O)N1CC2(COC2)C1] |
| 187 | 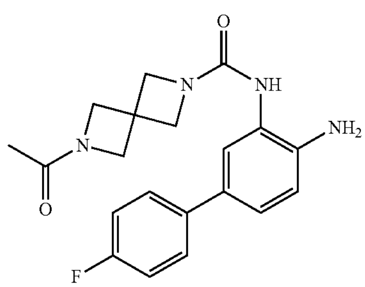 [SMILES: CC(=O)N1CC2(C1)CN(C(=O)Nc1cc(-c3ccc(F)cc3)ccc1N)C2] |
| 188 | 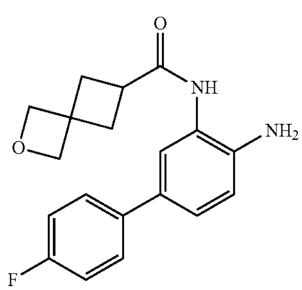 [SMILES: Nc1ccc(-c2ccc(F)cc2)cc1NC(=O)C1CC2(COC2)C1] |
| 189 | 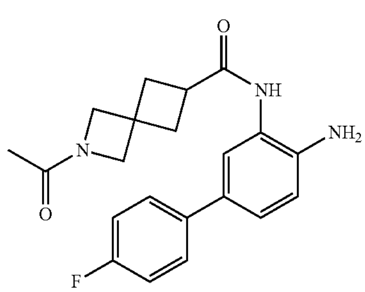 [SMILES: CC(=O)N1CC2(CC(C(=O)Nc3cc(-c4ccc(F)cc4)ccc3N)C2)C1] |
| 190 | |
| 191 | |
| 192 | |
| 193 | |
| 194 | |

TABLE 1-continued

| Cmpd No. | structure |
|---|---|
| 200 | 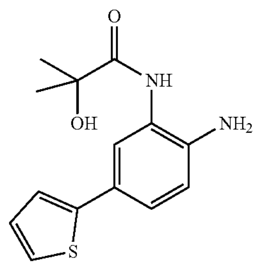 [SMILES: CC(C)(O)C(=O)Nc1cc(-c2cccs2)ccc1N] |
| 195 | 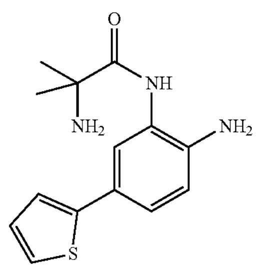 [SMILES: CC(C)(N)C(=O)Nc1cc(-c2cccs2)ccc1N] |
| 196 | 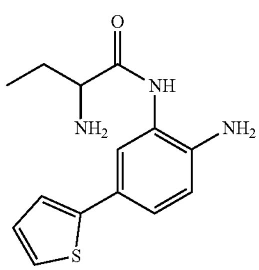 [SMILES: CCC(N)C(=O)Nc1cc(-c2cccs2)ccc1N] |
| 197 | 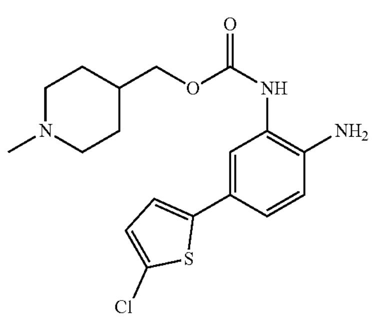 [SMILES: CN1CCC(COC(=O)Nc2cc(-c3ccc(Cl)s3)ccc2N)CC1] |
| 198 | 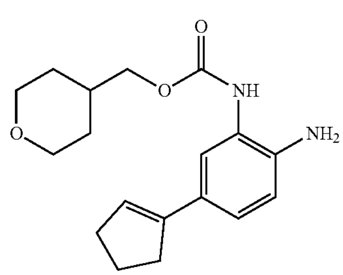 [SMILES: Nc1ccc(C2=CCCC2)cc1NC(=O)OCC1CCOCC1] |

TABLE 1-continued

| Cmpd No. | structure |
|---|---|
| 199 | 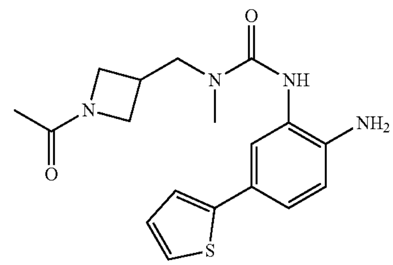 [SMILES: CC(=O)N1CC(CN(C)C(=O)Nc2cc(-c3cccs3)ccc2N)C1] |
| 201 | 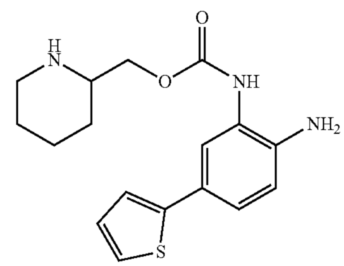 [SMILES: Nc1ccc(-c2cccs2)cc1NC(=O)OCC1CCCCN1] |
| 202 | 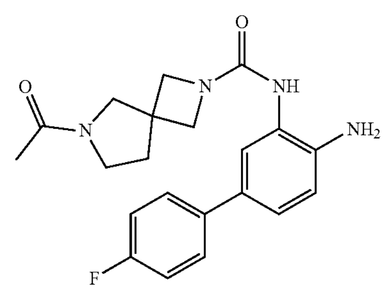 [SMILES: CC(=O)N1CCC2(C1)CN(C(=O)Nc1cc(-c3ccc(F)cc3)ccc1N)C2] |
| 203 | 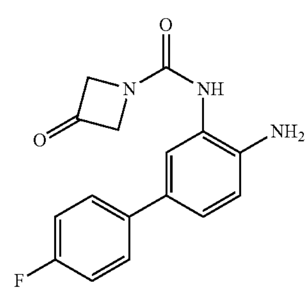 [SMILES: Nc1ccc(-c2ccc(F)cc2)cc1NC(=O)N1CC(=O)C1] |
| 204 | 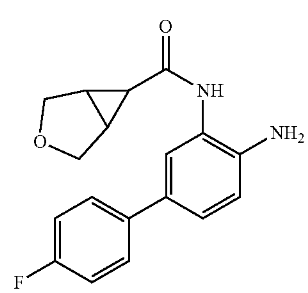 [SMILES: Nc1ccc(-c2ccc(F)cc2)cc1NC(=O)C1C2COCC21] |

TABLE 1-continued

| Cmpd No. | structure |
|---|---|
| 205 | 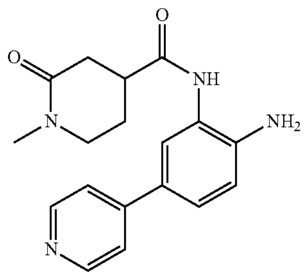 [SMILES: CN1CCC(C(=O)Nc2cc(-c3ccncc3)ccc2N)CC1=O] |
| 206 | 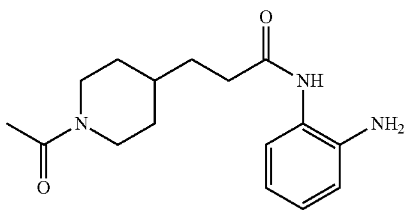 [SMILES: CC(=O)N1CCC(CCC(=O)Nc2ccccc2N)CC1] |
| 207 | 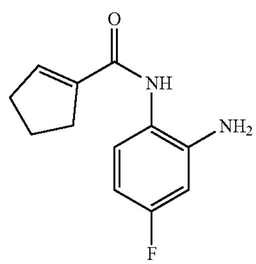 [SMILES: Nc1cc(F)ccc1NC(=O)C1=CCCC1] |
| 208 | 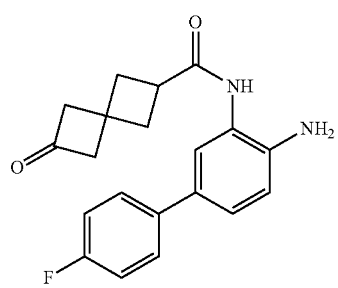 [SMILES: Nc1ccc(-c2ccc(F)cc2)cc1NC(=O)C1CC2(CC(=O)C2)C1] |
| 209 | 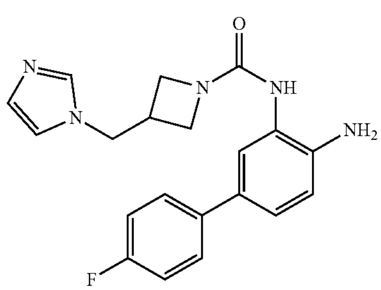 [SMILES: Nc1ccc(-c2ccc(F)cc2)cc1NC(=O)N1CC(Cn2ccnc2)C1] |
| 210 | |
| 211 | |
| 212 | |
| 213 | |
| 214 | |

TABLE 1-continued
| Cmpd No. | structure |
|---|---|
| 215 | 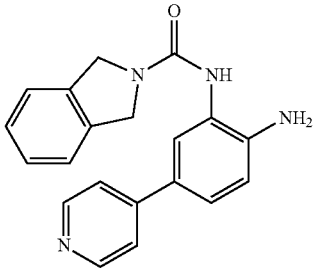 [SMILES: Nc1ccc(-c2ccncc2)cc1NC(=O)N1Cc2ccccc2C1] |
| 216 | 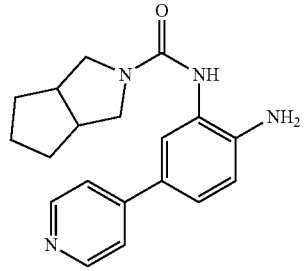 [SMILES: Nc1ccc(-c2ccncc2)cc1NC(=O)N1CC2CCCC2C1] |
| 217 | 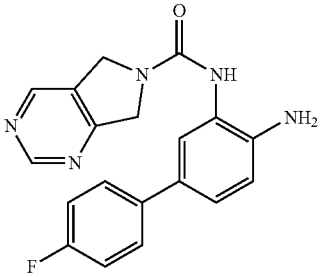 [SMILES: Nc1ccc(-c2ccc(F)cc2)cc1NC(=O)N1Cc2cncnc2C1] |
| 218 | 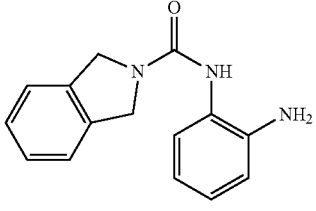 [SMILES: Nc1ccccc1NC(=O)N1Cc2ccccc2C1] |
| 219 | 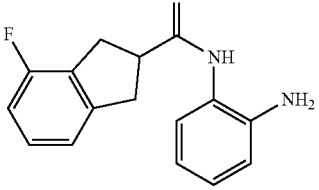 |
| 220 | 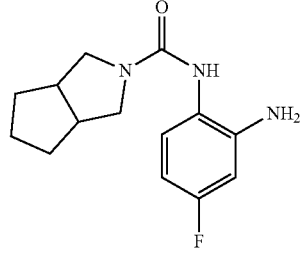 [SMILES: Nc1cc(F)ccc1NC(=O)N1CC2CCCC2C1] |
| 221 | 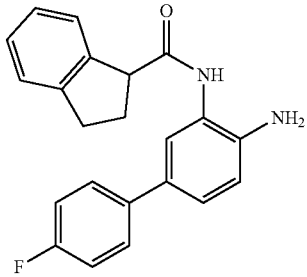 [SMILES: Nc1ccc(-c2ccc(F)cc2)cc1NC(=O)C1CCc2ccccc21] |
| 222 | 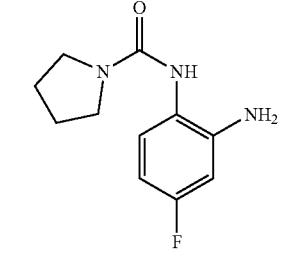 [SMILES: Nc1cc(F)ccc1NC(=O)N1CCCC1] |
| 223 | 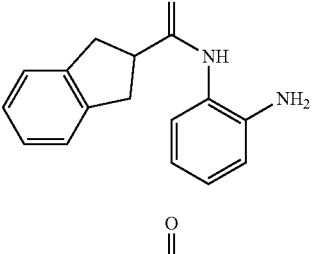 |
| 224 | 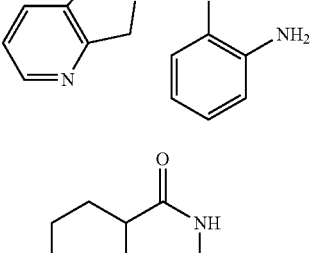 |
| 225 | 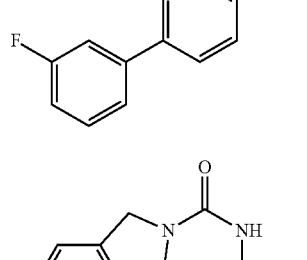 |
| 226 | 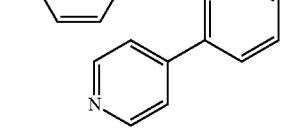 |

TABLE 1-continued

| Cmpd No. | structure |
|---|---|
| 227 | 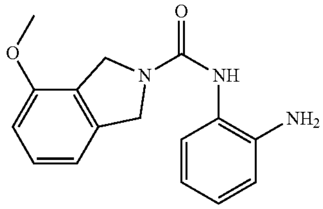 [SMILES: COc1cccc2c1CN(C(=O)Nc1ccccc1N)C2] |
| 228 | 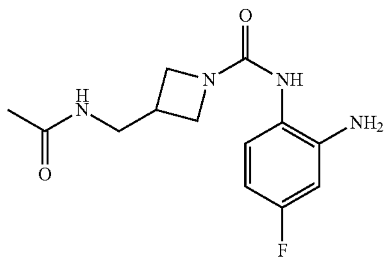 [SMILES: CC(=O)NCC1CN(C(=O)Nc2ccc(F)cc2N)C1] |
| 229 | 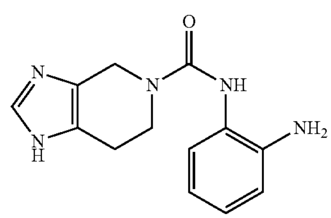 [SMILES: Nc1ccccc1NC(=O)N1CCc2[nH]cnc2C1] |
| 230 | 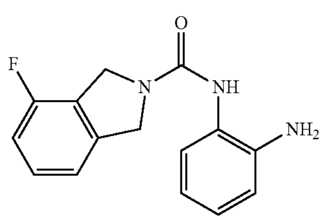 [SMILES: Nc1ccccc1NC(=O)N1Cc2cccc(F)c2C1] |
| 231 | 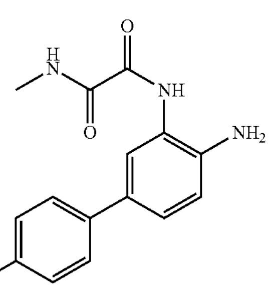 |
| 232 | 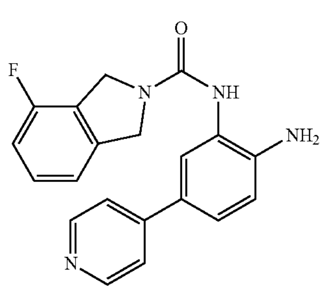 [SMILES: Nc1ccc(-c2ccncc2)cc1NC(=O)N1Cc2cccc(F)c2C1] |
| 233 | 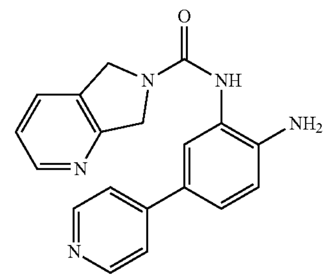 [SMILES: Nc1ccc(-c2ccncc2)cc1NC(=O)N1Cc2cccnc2C1] |
| 234 | 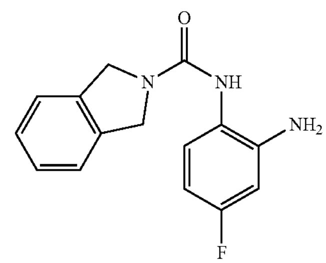 [SMILES: Nc1cc(F)ccc1NC(=O)N1Cc2ccccc2C1] |
| 235 | 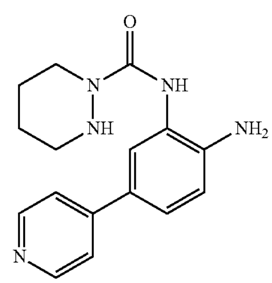 [SMILES: Nc1ccc(-c2ccncc2)cc1NC(=O)N1CCCCN1] |
| 236 | 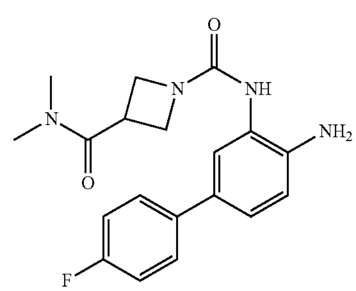 [SMILES: CN(C)C(=O)C1CN(C(=O)Nc2cc(-c3ccc(F)cc3)ccc2N)C1] |
| 237 | 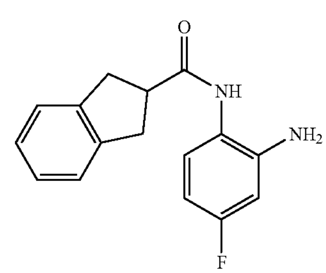 [SMILES: Nc1cc(F)ccc1NC(=O)C1Cc2ccccc2C1] |

TABLE 1-continued
| Cmpd No. | structure |
|---|---|
| 238 | 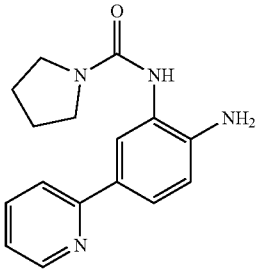 [SMILES: Nc1ccc(-c2ccccn2)cc1NC(=O)N1CCCC1] |
| 239 | 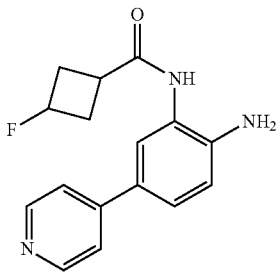 [SMILES: Nc1ccc(-c2ccncc2)cc1NC(=O)C1CC(F)C1] |
| 240 | 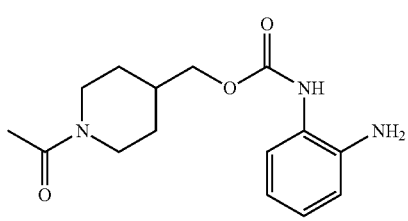 [SMILES: CC(=O)N1CCC(COC(=O)Nc2ccccc2N)CC1] |
| 241 | 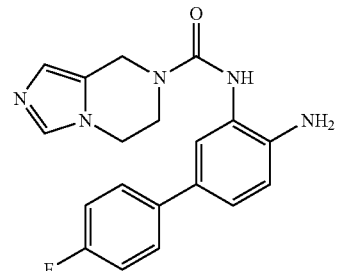 |
| 242 | 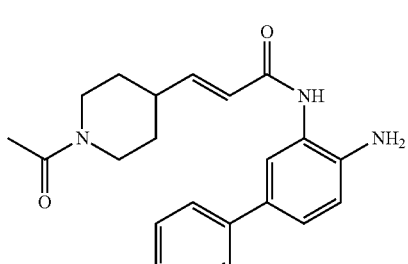 |
| 243 | 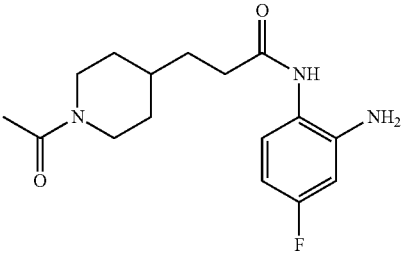 [SMILES: CC(=O)N1CCC(CCC(=O)Nc2ccc(F)cc2N)CC1] |
| 244 | 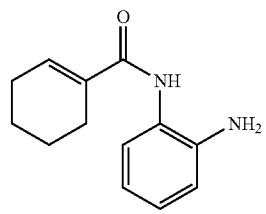 [SMILES: Nc1ccccc1NC(=O)C1=CCCCC1] |
| 245 | 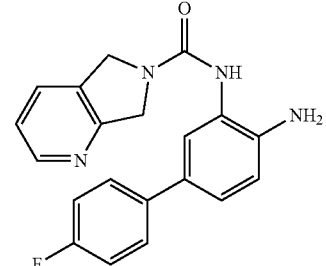 |
| 246 | 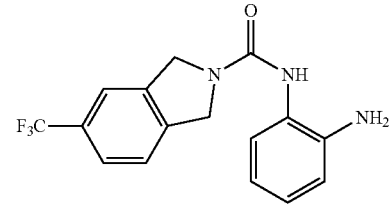 [SMILES: Nc1ccccc1NC(=O)N1Cc2ccc(C(F)(F)F)cc2C1] |
| 247 | 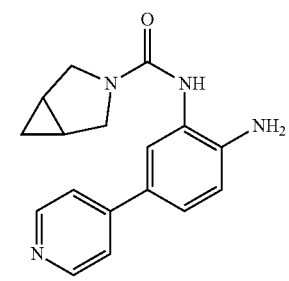 [SMILES: Nc1ccc(-c2ccncc2)cc1NC(=O)N1CC2CC2C1] |
In one aspect, the subject to be administered compounds of this invention is human.
Compounds of the invention can be prepared according to methods known in the art. The schemes below depict general routes for the preparation of compounds of the invention.

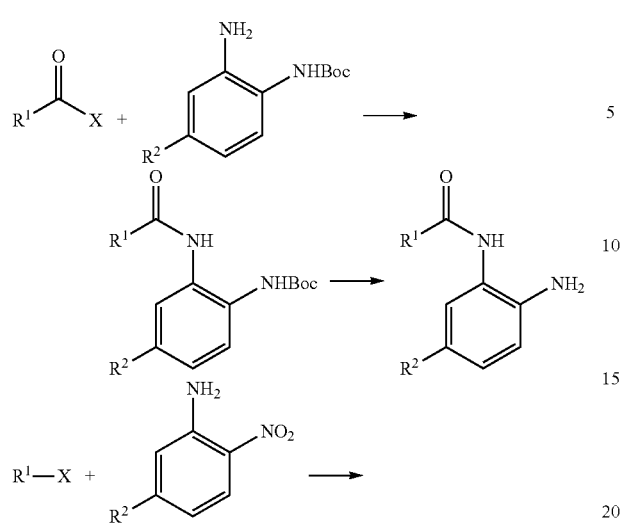
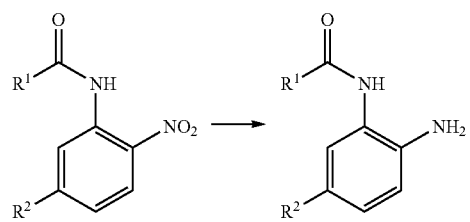
More specifically, compounds of the formula (A) can be prepared according to procedures similar to those depicted in retro-synthesic Schemes 1A-3A.
Scheme 1A
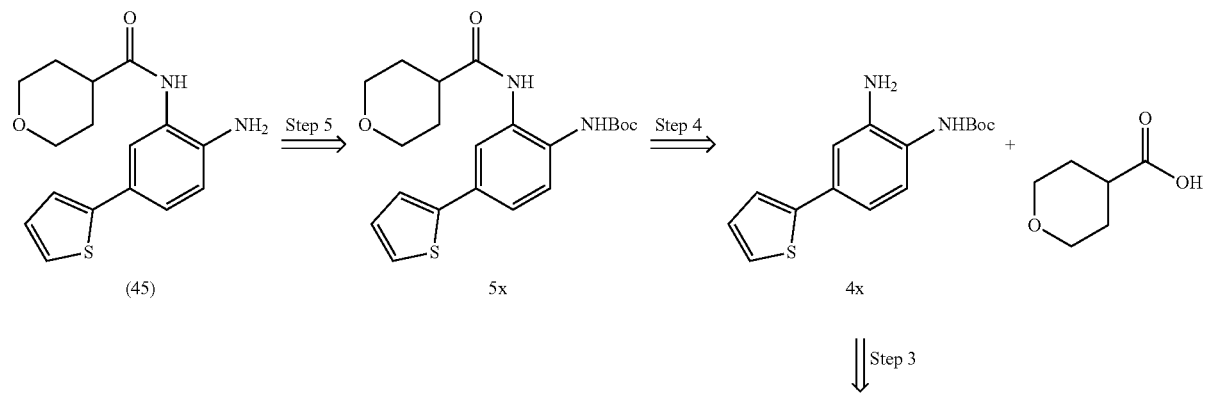
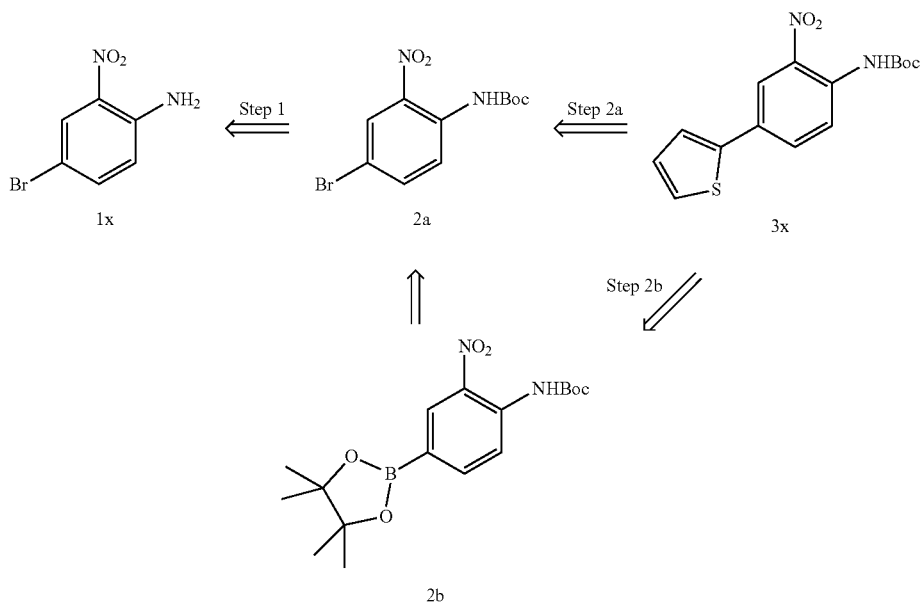

In Scheme 1A, Step 1 is the aniline Boc protection of compound 1x to form compound 2a using sodium hydride and di-tert-butyl dicarbonate. Step 2(a or b) is a Suzuki reaction of compound 2(a or b) with the appropriate boronic acid, or pinacol boronate or bromo coupling partner to form compound 3x. Compound 3x is then reduced under hydrogen atmosphere using palladium on carbon in Step 3. Alternatively, the reduction can also be carried out using ferric chloride and hydrazine hydrate. Step 4 is the amide coupling of compound 4x with a carboxylic acid using HATU in the presence of Hünigs base. Alternatively, compound 4x can be coupled with an acyl chloride in the presence of triethylamine. Finally, Step 5 is the removal of the Boc protecting group in the presence of trifluoroacetic acid or hydrochloric acid to afford a compound of the invention e.g., compound (45).

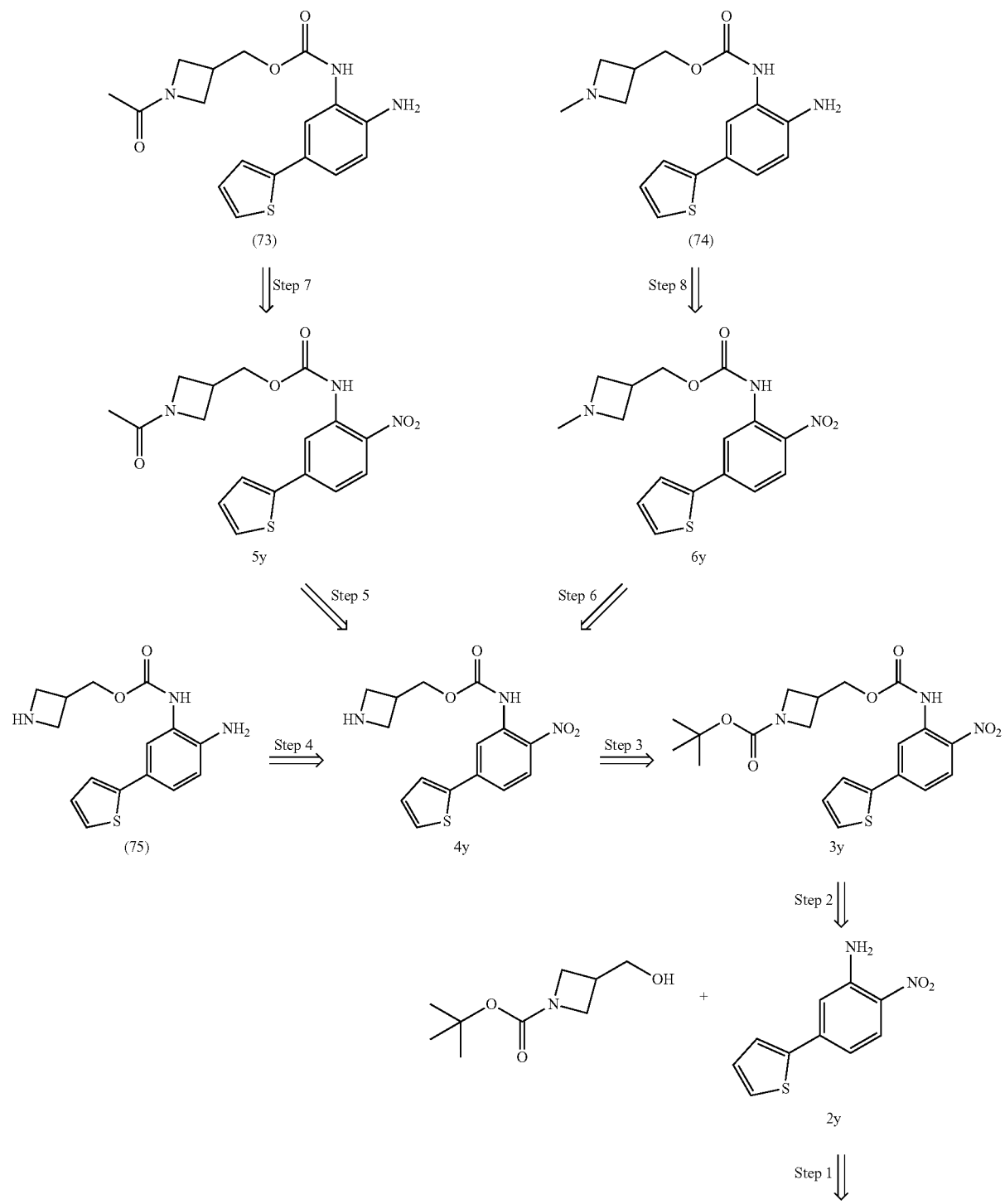

Scheme 2A

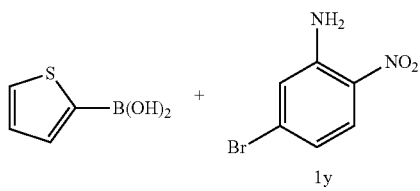

In Scheme 2A, Step 1 is a Suzuki reaction of compound 1y with a boronic acid or pinacol borate group to form compound 2y. In step 2, compound 2y is then coupled to an alcohol using triphosgene to form compound 3y. Alternatively, the coupling can be done using a chloroformate in the presence of triethylamine. Step 3 is the removal of the Boc protecting group to afford compound 4y. Compound 4y can then be reduced under hydrogen atmosphere using palladium on carbon to yield compound (75) in Step 4. Alternatively, the nitro group reduction can be carried out using zinc and ammonium formate. Compound 4y can also be reductively aminated using aqueous formaldehyde and sodium cyanoborohydride to afford compound 6y. Compound 4y can also be acetylated using acetic anhydride in the presence of triethylamine to afford compound 5y. The nitro group is reduced to afford a compound of the invention e.g., compound (73) in step 7 and e.g., compound (74) in step 8.

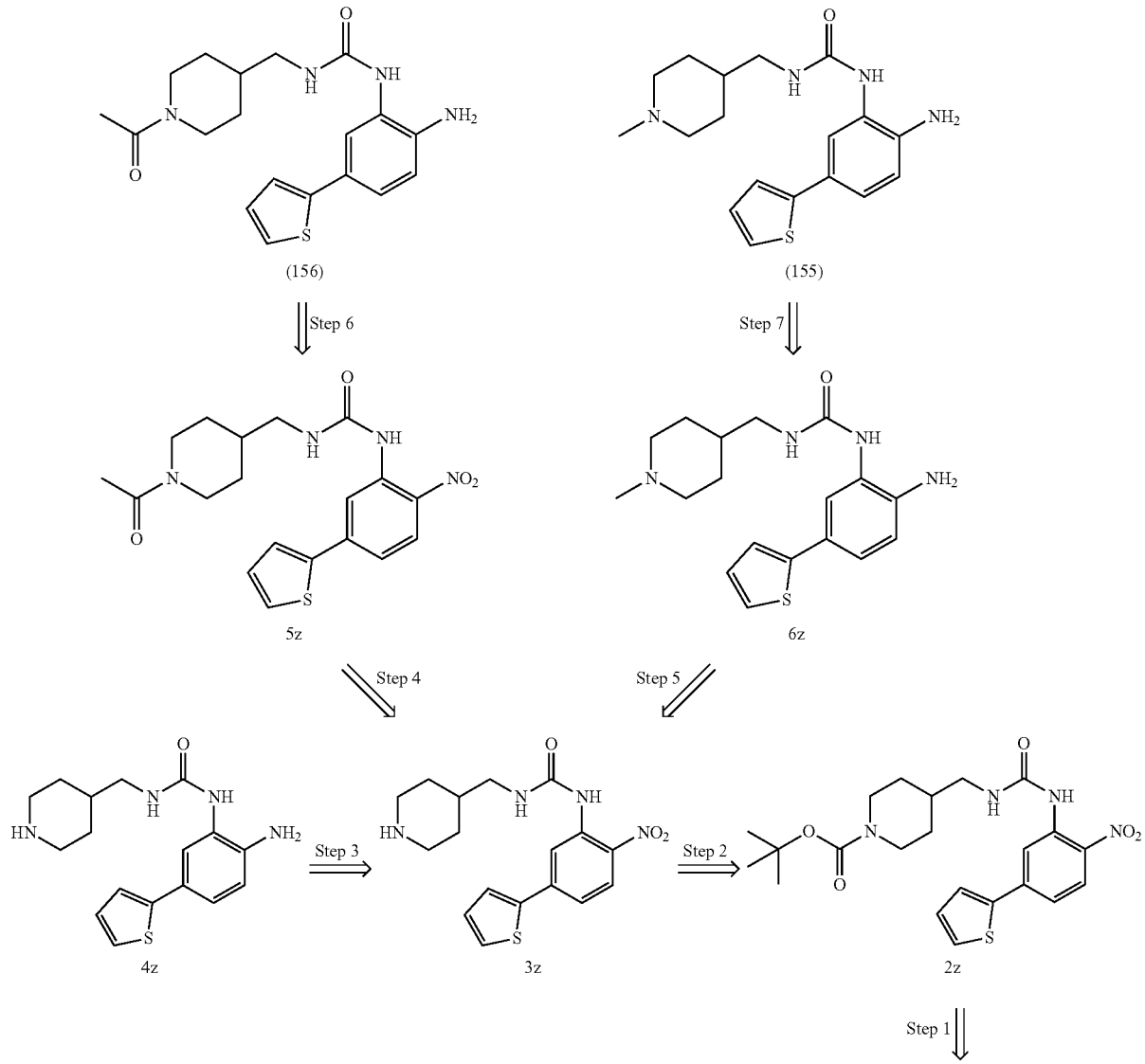

Scheme 3A

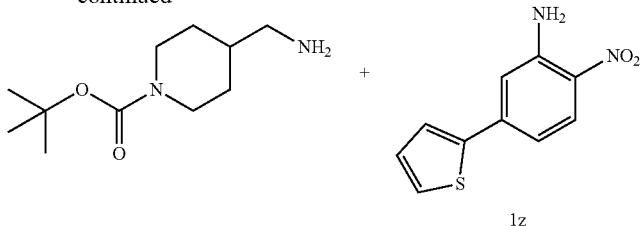

1z

In Scheme 3A, in step 1, compound 1z is coupled to an amine using triphosgene to form compound 2z. Alternatively, the coupling can be done using a readily available isocyanate or a carbamic chloride in the presence of triethylamine. Step 2 is the removal of the Boc protecting group to afford compound 3z. Compound 3z can then be reduced under hydrogen atmosphere using palladium on carbon to yield compound 4z in Step 3. Alternatively, the nitro group reduction can be carried out using zinc and ammonium formate. Compound 3z can also be reductively aminated using aqueous formaldehyde and sodium cyanoborohydride to afford compound 6z. Compound 3z can also be acetylated using acetic anhydride in the presence of triethylamine to afford compound 5z. The nitro group is in turn reduced to afford a compound of the invention e.g., compound (156) in step 6 and compound (155) in step 7.

Selected Methods of the Invention

Compounds of the invention are inhibitors of class I histone deacetylases (HDAC) and are useful for promoting cognitive function and enhancing learning and memory formation. As a result, these compounds are useful in treating, alleviating, and/or preventing various conditions, including e.g., neurological disorders, memory and cognitive function disorders/impairments, extinction learning disorders, fungal diseases, inflammatory diseases, hematological diseases, and neoplastic diseases in humans and animals.

Inhibition of Histone Deacetylase

The compounds of the present invention are useful in a variety of applications for human and animal health. The compounds of the invention are histone deacetylase (HDAC) inhibitors. A histone deacetylase inhibitor as used herein is a compound that inhibits, reduces, or otherwise modulates the activity of histone deacetylase. HDACs catalyze the removal of acetyl groups from lysine residues on proteins, including histones. HDAC inhibitors also show diverse biological functions including effecting gene expression, cell differentiation, cell cycle progression, growth arrest, and/or apoptosis. (J. Med. Chem. 2003, 46:5097 and Curr. Med. Chem. 2003, 10:2343). In various embodiments, the compounds of the invention reduce HDAC activity by at least about 50%, at least about 75%, or at least about 90% or more. In further embodiments, HDAC activity is reduced by at least about 95% or at least about 99% or more.

One aspect of the invention provides a method of inhibiting histone deacetylase in a cell, comprising contacting a cell in which inhibition of histone deacetylase is desired with an inhibition effective amount of a compound of the invention or a composition thereof. Because compounds of the invention inhibit histone deacetylase(s), they are useful research tools for in vitro study of the role of histone deacetylase in biological processes. Accordingly, in one aspect of the invention, the step of contacting the cell is performed in vitro.

The term an "inhibiting effective amount" is meant to denote a dosage sufficient to cause inhibition of activity of one or more histone deacetylase in a cell, which cell can be in a multicellular organism. The multicellular organism can be a plant, a fungus, or an animal, preferably a mammal, more preferably a human. The fungus may be infecting a plant or a mammal, preferably a human, and could therefore be located in and/or on the plant or mammal. If the histone deacetylase is in a multicellular organism, the method according to this aspect of the invention comprises administering to the organism a compound or composition of the invention. Measurement of the effect of a compound of the invention on the enzymatic activity of a histone deacetylase is achieved using known methodologies. For example, Bradner, J. et al. Nature Chemical Biology, Vol. 6, March 2010, 238-243.

The potential of HDAC inhibitors is tremendous, but the development of clinical compounds will likely require the design of isoform selective compounds to minimize side effect issues e.g., fatigue, anorexia, hematological and GI-toxicity. Isoform specific HDAC inhibitors provide advantages by reducing toxicities associated with inhibition of other HDACs. Specific HDAC inhibitors provide a higher therapeutic index, resulting in better tolerance by patients during chronic or long term treatment. While several HDAC inhibitors are now in the clinic, most of these do not show significant selectivity for individual HDAC isoforms.

HDACs are classified into four classes depending on sequence identity, domain, organization, and function. Compounds of the invention are predominately inhibitors of class I histone deacetylases. Class I enzymes (HDACs 1, 2, 3, and 8) range in size from 42-55 kDa, and are homologs of yeast Rpd3. They are ubiquitously expressed, predominantly nuclear and mainly function as transcriptional corepressors.

In some other embodiments, the compound reduces the activity of fewer than all histone deacetylases in the cell. In certain embodiments, the compound reduces the activity of one histone deacetylase (e.g., HDAC1) or a sub-group of histone deacetylases (e.g., HDAC1, HDAC2, and HDAC3) to a greater extent than other histone deacetylases. Where the compound preferentially reduces the activity of a sub-group of histone deacetylases, the reduction in activity of each member of the sub-group may be the same or different.

In certain embodiments, the present invention relates to the aforementioned compound, wherein the compounds of the invention are selective HDAC class 1 inhibitors. In one aspect, a compound is a HDAC2 inhibitor. The compound may be a selective HDAC2 inhibitor. In other embodiments, the compound is a non-selective inhibitor of HDAC2. In another aspect, the compound is a HDAC1 inhibitor. The compound may be a selective HDAC1 inhibitor. In other embodiments, the compound is a non-selective inhibitor of HDAC1. In one aspect, a compound is a HDAC3 inhibitor.

The compound may be a selective HDAC3 inhibitor. In other embodiments, the compound is a non-selective inhibitor of HDAC3.

In yet another embodiment, a compound is a HDAC1/HDAC2 selective inhibitor. In another embodiment, the compound is a HDAC1/HDAC2/HDAC3 selective inhibitor.

In one embodiment, a compound selective for HDAC1 will have at least about 2-fold (e.g., at least about 5-fold, 10-fold, 15-fold, or 20-fold) greater activity to inhibit HDAC1 as compared to one or more other HDACs (e.g., one or more HDACs of class I or II). In one embodiment, a compound selective for HDAC2 will have at least about 2-fold (e.g., at least about 5-fold, 10-fold, 15-fold, or 20-fold) greater activity to inhibit HDAC2 as compared to one or more other HDACs (e.g., one or more HDACs of class I or II). In one embodiment, a compound selective for HDAC3 will have at least about 2-fold (e.g., at least about 5-fold, 10-fold, 15-fold, or 20-fold) greater activity to inhibit HDAC3 as compared to one or more other HDACs (e.g., one or more HDACs of class I or II).

In one embodiment, a compound selectively inhibits at least one class I HDAC enzyme with an $IC_{50}$ value greater than 0.0000001 µM and less than or equal to 0.1 µM, 1 µM, 5 µM, or 30 µM. In another embodiment, a compound selectively inhibits HDAC1 with an $IC_{50}$ value greater than 0.0000001 µM and less than or equal to 0.1 µM, 1 µM, 5 µM, or 30 µM. In another embodiment, a compound selectively inhibits HDAC2 with an $IC_{50}$ value greater than 0.0000001 µM and less than or equal to 0.1 µM, 1 µM, 5 µM, or 30 µM. In another embodiment, a compound selectively inhibits HDAC3 with an $IC_{50}$ value greater than 0.0000001 µM and less than or equal to 0.1 µM, 1 µM, 5 µM, or 30 µM. In one embodiment, a compound selectively inhibits at least two class I HDAC enzymes with $IC_{50}$ values greater than 0.0000001 µM and less than or equal to 0.1 µM, 1 µM, 5 µM, or 30 µM. In one embodiment, a compound selectively inhibits at least three class I HDAC enzymes with $IC_{50}$ values greater than 0.0000001 µM and less than or equal to 0.1 µM, 1 µM, 5 µM, or 30 µM.

Neurological Disorders

In one aspect, the invention provides methods and compositions for treating, alleviating, and/or preventing neurological disorders.

Recent reports have detailed the importance of histone acetylation in central nervous system ("CNS') functions such as neuronal differentiation, memory formation, drug addiction, and depression (Citrome, Psychopharmacol. Bull. 2003, 37, Suppl. 2, 74-88; Johannessen, CNS Drug Rev. 2003, 9, 199-216; Tsankova et al., 2006, Nat. Neurosci. 9, 519-525).

In one aspect, the invention provides methods and compositions for treating, alleviating, and/or preventing neurological disorders. The term "neurological disorder" as used herein includes neurological diseases, neurodegenerative diseases and neuropsychiatric disorders. A neurological disorder is a condition having as a component a central or peripheral nervous system malfunction. Neurological disorders may cause a disturbance in the structure or function of the nervous system resulting from developmental abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems).

As used herein, the term "neurodegenerative disease" implies any disorder that might be reversed, deterred, managed, treated, improved, or eliminated with agents that stimulate the generation of new neurons. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, muscular dystrophy, olivopontocerebellar atrophy, multiple system atrophy, Wilson's disease, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapic, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, restless leg syndrome, vertigo as result of CNS degeneration; pathologies arising with chronic alcohol or drug abuse including, for example, the degeneration of neurons in locus coeruleus and cerebellum, drug-induced movement disorders; pathologies arising with aging including degeneration of cerebellar neurons and cortical neurons leading to cognitive and motor impairments; and pathologies arising with chronic amphetamine abuse to including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurodegenerative diseases affecting sensory neurons include Friedreich's ataxia, diabetes, peripheral neuropathy, and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

In some instances the neurological disorder is a neuropsychiatric disorder, which refers to conditions or disorders that relate to the functioning of the brain and the cognitive processes or behavior. Neuropsychiatric disorders may be further classified based on the type of neurological disturbance affecting the mental faculties. The term "neuropsychiatric disorder," considered here as a subset of "neurological disorders," refers to a disorder which may be generally characterized by one or more breakdowns in the adaptation process. Such disorders are therefore expressed primarily in abnormalities of thought, feeling and/or behavior producing either distress or impairment of function (i.e., impairment of mental function such with dementia or senility). Currently, individuals may be evaluated for various neuropsychiatric disorders using criteria set forth in the most recent version of the American Psychiatric Association's Diagnostic and Statistical Manual of Mental Health (DSM-IV).

One group of neuropsychiatric disorders includes disorders of thinking and cognition, such as schizophrenia and delirium. A second group of neuropsychiatric disorders includes disorders of mood, such as affective disorders and anxiety. A third group of neuropsychiatric disorders includes disorders of social behavior, such as character defects and personality disorders. A fourth group of neuropsychiatric disorders includes disorders of learning, memory, and intelligence, such as mental retardation and dementia. Accordingly, neuropsychiatric disorders encompass schizophrenia, delirium, attention deficit disorder (ADD), schizoaffective disorder, Alzheimer's disease, Rubinstein-Taybi syndrome, depression, mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition.

In one embodiment, the neurological disorder is Alzheimer's disease, Huntington's disease, seizure-induced memory loss, schizophrenia, Rubinstein Taybi syndrome, Rett Syndrome, Fragile X, Lewy body dementia, vascular dementia, ADHD, ADD, dyslexia, bipolar disorder and social, cognitive and learning disorders associated with autism, traumatic head injury, or attention deficit disorder.

In another embodiment, the neurological disorder is an anxiety disorder, conditioned fear response, panic disorder, obsessive compulsive disorder, post-traumatic stress disorder, phobia, social anxiety disorder, or substance dependence recovery.

In some embodiments neurological disorders are treated or prevented by decreasing the amount of DNA damage within the neuronal cell. In some embodiments neurological disorders are treated or prevented by increasing histone deacetylase activity within the neuronal cell. In some embodiments neurological disorders are treated or prevented by decreasing histone acetyl transferase activity within the neuronal cell. In some embodiments neurological disorders are treated or prevented by increasing the activity of class I histone deacetylases.

Enhancing Cognitive Function

In one aspect, the invention provides methods and compositions for promoting cognitive function and enhancing learning and memory formation in both normal subjects as well as those suffering from memory loss and cognitive function disorders/impairments. A normal subject, as used herein, is a subject that has not been diagnosed with a disorder associated with impaired cognitive function. "Cognitive function" refers to mental processes of a subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like.

Memory Disorders/Impairment

Transcription is thought to be a key step for long-term memory processes (Alberini, 2009, Physiol. Rev. 89, 121-145). Transcription is promoted by specific chromatin modifications, such as histone acetylation, which modulate histone-DNA interactions (Kouzarides, 2007, Cell, 128:693-705). Modifying enzymes, such as histone acetyltransferases (HATs) and histone deacetylases (HDACs), regulate the state of acetylation on histone tails. In general, histone acetylation promotes gene expression, whereas histone deacetylation leads to gene silencing. Numerous studies have shown that a potent HAT, cAMP response element-binding protein (CREB)-binding protein (CBP), is necessary for long-lasting forms of synaptic plasticity and long term memory (for review, see Barrett, 2008, Learn Mem 15:460-467).

In contrast, HDACs have been shown to be powerful negative regulators of long-term memory processes. Nonspecific HDAC inhibitors enhance synaptic plasticity as well as long-term memory (Levenson et al., 2004, J. Biol. Chem. 279:40545-40559; Lattal et al., 2007, Behav Neurosci 121:1125-1131; Vecsey et al., 2007, J. Neurosci 27:6128; Bredy, 2008, Learn Mem 15:460-467; Guan et al., 2009, Nature 459:55-60; Malvaez et al., 2010, Biol. Psychiatry 67:36-43; Roozendaal et al., 2010, J. Neurosci. 30:5037-5046). For example, HDAC inhibition can transform a learning event that does not lead to long-term memory into a learning event that does result in significant long-term memory (Stefanko et al., 2009, Proc. Natl. Acad. Sci. USA 106:9447-9452). Furthermore, HDAC inhibition can also generate a form of long-term memory that persists beyond the point at which normal memory fails. HDAC inhibitors have been shown to ameliorate cognitive deficits in genetic models of Alzheimer's disease (Fischer et al., 2007, Nature 447:178-182; Kilgore et al., 2010, Neuropsychopharmacology 35:870-880). These demonstrations suggest that modulating memory via HDAC inhibition have considerable therapeutic potential for many memory and cognitive disorders.

Currently, the role of individual HDACs in long-term memory has been explored in two recent studies. Kilgore et al. 2010, Neuropsychopharmacology 35:870-880 revealed that nonspecific HDAC inhibitors, such as sodium butyrate, inhibit class I HDACs (HDAC1, HDAC2, HDAC3, HDAC8) with little effect on the class IIa HDAC family members (HDAC4, HDAC5, HDAC7, HDAC9). This suggests that inhibition of class I HDACs may be critical for the enhancement of cognition observed in many studies. Indeed, forebrain and neuron specific over expression of HDAC2, but not HDAC1, decreased dendritic spine density, synaptic density, synaptic plasticity and memory formation. (Guan et al., 2009, Nature, 459:55-60). In contrast, HDAC2 knockout mice exhibited increased synaptic density, increased synaptic plasticity and increased dendritic density in neurons. These HDAC2 deficient mice also exhibited enhanced learning and memory in a battery of learning behavioral paradigms. This work demonstrates that HDAC2 is a key regulator of synaptogenesis and synaptic plasticity. Additionally, Guan et al. showed that chronic treatment of mice with SAHA (an HDAC 1, 2, 3, 6, 8 inhibitor) reproduced the effects seen in the HDAC2 deficient mice and recused the cognitive impairment in the HDAC2 overexpression mice. The inhibition of the HDAC2 (selectively or in combination with other class I HDACs) is an attractive target for enhancing cognition and facilitating the learning process through increasing synaptic and dendritic density in neuronal cell populations.

HDAC3 is the most highly expressed class I HDAC throughout the brain, including the hippocampus (Broide et al., 2007, J. Mol. Neurosci. 31:47-58). HDAC3 alters gene expression as part of a large complex that contains corepressors, nuclear receptor corepressor 1 (NCoR) and silencing mediator for retinoid and thyroid-hormone receptors (SMRT), as well as class IIa HDACs, such as HDAC4 (Guenther et al. 2000, Genes Dev. 14:1048-1057; Li et al., 2000, EMBO J. 19:4342-4350) (for review, see Karagianni, 2007, Oncogene 26:5439-5449). NCoR associates with HDAC3 through the deacetylase activation domain (DAD) of NCoR and a single amino acid substitution (Y478A) in the NCoR DAD results in a mutant protein that is unable to associate with or activate HDAC3 (Alenghat et al., 2008, Nature 456:997-1000). In addition, class IIa HDACs may require interaction with HDAC3 for their HDAC activity (Fischle et al., 2002, Mol. Cell 9:45-57). It has been demonstrated that HDAC3 is a critical negative regulator of long-term memory formation. Specifically, focal deletion of HDAC3 as well as selective inhibition of HDAC3 significantly enhanced long-term memory in a persistent manner (McQuown, 2011, 31(2)764-774).

A "memory" as used herein refers to the ability to recover information about past events or knowledge. Memories include short-term memory (also referred to as working or recent memory) and long-term memory. Short-term memories involve recent events, while long-term memories relate to the recall of events of the more distant past. Methods of assessing the ability to recall a memory are known to those of skill in the art and may involve routine cognitive tests. Enhancing or retrieving memories is distinct from learning. However, in some instances in the art learning is referred to as memory. Learning, unlike memory enhancement, refers to the ability to create new memories that had not previously existed. Thus in order to test the ability of a compound to effect the ability of a subject to learn rather than recall old memories, the compound would be administered prior to or at the same time as the memory is created. In order to test the ability of a compound to affect recall of a previously created memory the compound is administered after the memory is created and preferably after the memory is lost.

As used herein "age related memory loss" refers to any of a continuum of conditions characterized by a deterioration of neurological functioning that does not rise to the level of a dementia, as further defined herein and/or as defined by the Diagnostic and Statistical Manual of Mental Disorders: 4th Edition of the American Psychiatric Association (DSM-IV, 1994). Age related memory loss is characterized by objective loss of memory in an older subject compared to his or her younger years, but cognitive test performance that is within normal limits for the subject's age. Age related memory loss subjects score within a normal range on standardized diagnostic tests for dementias, as set forth by the DSM-IV. Moreover, the DSM-IV provides separate diagnostic criteria for a condition termed Age-Related Cognitive Decline. In the context of the present invention, as well as the terms "Age-Associated Memory Impairment" and "Age-Consistent Memory Decline" are understood to be synonymous with the age related memory loss. Age-related memory loss may include decreased brain weight, gyral atrophy, ventricular dilation, and selective loss of neurons within different brain regions. For purposes of some embodiments of the present invention, more progressive forms of memory loss are also included under the definition of age-related memory disorder. Thus persons having greater than age-normal memory loss and cognitive impairment, yet scoring below the diagnostic threshold for frank dementia, may be referred to as having a mild neurocognitive disorder, mild cognitive impairment, late-life forgetfulness, benign senescent forgetfulness, incipient dementia, provisional dementia, and the like. Such subjects may be slightly more susceptible to developing frank dementia in later life (See also US patent application 2006/008517 (Vasogen Ireland limited) which is incorporated by reference). Symptoms associated with age-related memory loss include but are not limited to alterations in biochemical markers associated with the aging brain, such as IL-1 beta, IFN-gamma, p-JNK, p-ERK, reduction in synaptic activity or function, such as synaptic plasticity, evidenced by reduction in long term potentiation, diminution of memory and learning.

As used herein "injury related memory loss" refers to a loss of memory wherein there is damage to the brain, and there may have also been neurological damage. Sources of brain injury include traumatic brain injury such as concussive injuries or penetrating head wounds, brain tumors, alcoholism, Alzheimer's disease, stroke, heart attack and other conditions that deprive the brain of oxygen, meningitis, AIDS, viral encephalitis, and hydrocephalus.

Methods for enhancing memories can include reestablishing access to memories as well as recapturing memories. The term re-establishing access as used herein refers to increasing retrieval of a memory. Although Applicants are not bound by a mechanism of action, it is believed that the compounds of the invention are effective in increasing retrieval of memories by re-establishing a synaptic network. The process of re-establishing a synaptic network may include an increase in the number of active brain synapses and or a reversal of neuronal loss.

Neurogenesis, or the birth of new neuronal cells, was thought to occur only in developing organisms. However, recent research has demonstrated that neurogenesis does indeed continue into and throughout adult life. On going neurogenesis is thought to be an important mechanism underlying neuronal plasticity, enabling organisms to adapt to environmental changes and influencing learning and memory throughout life. In one aspect, the invention includes a method of increasing synaptic density in a subject comprising administering to the subject in need of such increase a compound of the invention or a pharmaceutically acceptable salt, hydrate, solvate, or prodrug thereof. In one aspect, the invention includes a method of increasing synaptic plasticity in a subject comprising administering to the subject in need of such increase a compound of the invention or a pharmaceutically acceptable salt, hydrate, solvate, or prodrug thereof. In one aspect, the invention includes a method of increasing dendritic density in neurons in a subject comprising administering to the subject in need of such increase a compound of the invention or a pharmaceutically acceptable salt, hydrate, solvate, or prodrug thereof.

The invention provides methods for enhancing memory in a subject having a memory disorder. Examples of types of memory disorders include Alzheimer's disease, absent-minded professor, absent-mindedness, amnesia, anterograde amnesia, blackout (alcohol-related amnesia), bromism, childhood amnesia, false memory syndrome, fugue state, hyperthymesia, Korsakoff's syndrome, lacunar amnesia, memory distrust syndrome, memory loss, post-traumatic amnesia, prosopamnesia, psychogenic amnesia, repressed memory, retrograde amnesia, Ribot's Law, selective memory loss, sywald skeid, source amnesia, source-monitoring error, the seven sins of memory, tip of the tongue, transient epileptic amnesia, transient global amnesia, and twilight sleep.

In one embodiment, Alzheimer's disease is the memory disorder. Such methods optionally involve administering the inhibitor and monitoring the subject to identify recapture of a memory that was previously lost. Subjects may be monitored by routine tests known in the art.

In other embodiments the alzheimer's subject is one that has late stage Alzheimer's disease. Many of the drugs suggested for treating Alzheimer's disease are designed to treat the early stages of the disease by preventing plaque buildup. The compounds of the invention are useful for treating both early stages and late stages of dementia because they actually improve memory and cognition rather than preventing only plaque accumulation.

Cognitive Function Disorders/Impairment

The invention relates to methods of treating, alleviating, and/or preventing cognitive function disorders/impairments.

Impaired cognitive function refers to cognitive function that is not as robust as that observed in an age-matched normal subject and includes states in which cognitive function is reduced. In some cases, cognitive function is reduced by about 5%, about 10%, about 30%, or more, compared to cognitive function measured in an age-matched normal subject. Cognitive function may be promoted to any detectable degree, but in humans preferably is promoted sufficiently to allow an impaired subject to carry out daily activities of normal life.

In some embodiments, the cognitive function disorders or impairments are associated with, but not limited to, Alzheimer's disease, Huntington's disease, seizure induced memory loss, schizophrenia, Rubinstein Taybi syndrome, Rett Syndrome, Fragile X, Lewey body dementia, Vascular dementia, bipolar disorder and social, cognitive and learning disorders associated with autism, attention deficit hyperactivity disorder (ADHD), dyselexia, learning disorders, traumatic head injury, stroke induced cognitive and motor impairment, traumatic brain injury, neurodegeneration and neuronal loss mediated cognitive impairment, and attention deficit disorder.

In some embodiments, the cognitive function disorders or impairments are associated with, but not limited to, anxiety disorders, conditioned fear response, panic disorders, obsessive compulsive disorders, post-traumatic stress disorder, phobias, social anxiety disorders, substance dependence recovery or Age Associated Memory Impairment (AAMI), and Age Related Cognitive Decline (ARCD).

In some embodiments, the invention relates to methods of treating, alleviating, and/or preventing vascular dementia. Vascular dementia, also referred to as "multi-infarct dementia", refers to a group of syndromes caused by different mechanisms all resulting in vascular lesions in the brain. The main subtypes of vascular dementia are, for example vascular mild cognitive impairment, multi-infarct dementia, vascular dementia due to a strategic single infarct (affecting the thalamus, the anterior cerebral artery, the parietal lobes or the cingulate gyms), vascular dementia due to hemorrhagic lesions, small vessel disease (including, e.g. vascular dementia due to lacunar lesions and Binswanger disease), and mixed Alzheimer's Disease with vascular dementia.

In some embodiments, the invention relates to treating, alleviating, and/or preventing Huntington's Disease. Huntington's Disease is a neurological disease which results in cognitive decline associated with inexorable progression to death. Cognitive symptoms associated with Huntington's Disease include loss of intellectual speed, attention, and short term memory and/or behavioral symptoms.

Cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology." Neurotoxicol Teratol 1996; 18(4):499-504), Stroop Test, Trail Making, Wechsler Digit Span, or the CogState computerized cognitive test (see also Dehaene et al. "Reward-dependent learning in neuronal networks for planning and decision making." Brain Res. 2000; 126:21729; Iverson et al. "Interpreting change on the WAIS-III/WMS-III in clinical samples." Arch Clin Neuropsychol. 2001; 16(2):183-91; and Weaver et al. "Mild memory impairment in healthy older adults is distinct from normal aging." Cogn. 2006; 60(2):146-55). The methods of the invention may be used to promote cognitive function in a normal subject or to treat, alleviate and/or prevent a subject from having a cognitive dysfunction. A normal subject, as used herein, is a subject that has not been diagnosed with a disorder associated with impaired cognitive function.

Extinction Learning Disorders

In one aspect, the invention relates to methods of treating, alleviating, and/or preventing extinction learning disorders e.g., a fear extinction deficit.

It has been demonstrated that administration of the HDAC inhibitors sodium butyrate or trichostatin A facilitates fear extinction in mice and this enhancement mirrors that caused by commonly used behavioral manipulation and is consistent with other studies demonstrating a role for the hippocampus in the extinction of contextual fear (Lattal, et al., 2007, Behav. Neurosci. 121, 5, 1125-1131).

Compounds of the invention can be used to facilitate the psychological process of extinction learning and thus are useful for treating, alleviating, and/or preventing neuropsychiatric disorders and other related disorders. Unlike traditional anti-anxiety drugs that are administered on a chronic basis and address physiological symptoms of anxiety, the compounds of the invention can be used on a chronic or acute basis in conjunction with a second therapy e.g., psychotherapy.

In one aspect, the present invention is directed to methods for treating, alleviating, and/or preventing a subject from having a neuropsychiatric disorder. The methods comprise subjecting the subject to one or more sessions of a combination therapy protocol, where the combination therapy protocol comprises an acute administration of a therapeutically effective amount of a compound of the invention that enhances learning or conditioning in combination with a session of psychotherapy. By "acute administration" is intended a single exposure of the subject to the therapeutically effective amount of the compound that enhances learning or conditioning. In one aspect, the exposure to the compound occurs within about 24 hours prior to initiating the session of psychotherapy, preferably within about 12 hours, and more preferably within about 6 hours prior to initiating the session of psychotherapy. A full course of treatment for the neuropsychiatric disorder entails at least one session of this combination therapy protocol.

For purposes of the present invention, a subject may have a single disorder, or may have a constellation of disorders that are to be treated, alleviated, and/or prevented by the methods described herein.

The neuropsychiatric disorders contemplated in the present invention include, but are not limited to, fear and anxiety disorders, addictive disorders including substance-abuse disorders, and mood disorders. Within the fear and anxiety disorder category, the invention encompasses the treatment or prevention of panic disorder, specific phobia, post-traumatic stress disorder (PTSD), obsessive-compulsive disorder, and movement disorders such as Tourette's syndrome. The disorders contemplated herein are defined in, for example, the DSM-IV (Diagnostic and Statistical Manual of Mental Disorders (4th ed., American Psychiatric Association, Washington D.C., 1994)), which is herein incorporated by reference.

Anxiety-related disorders relate to those disorders characterized by fear, anxiety, addiction, and the like. Patients with anxiety-related disorders can have a single such disorder, or can have a constellation of disorders. The anxiety-related disorders contemplated in the present invention include, but are not limited to, anxiety disorders, addictive disorders including substance-abuse disorders, mood disorders (e.g., depression and/or bipolar disorder), movement disorders such as Tourette's syndrome, psychogenic erectile dysfunction (impotence resulting from a man's inability to obtain or maintain an erection of his penis), insomnia (e.g. chronic insomnia), and eating disorders (e.g. anorexia).

Anxiety disorders include, but are not limited to, panic disorder, agoraphobia, social phobia, specific phobia, PTSD, obsessive-compulsive disorder, and generalized anxiety disorder. The disorders contemplated herein are defined in, for example, the DSM-IV (Diagnostic and Statistical Manual of Mental Disorders (4th ed., American Psychiatric Association, Washington D.C., 1994)).

Movement disorders are neurological conditions that affect the speed, fluency, quality, and ease of movement. Representative movement disorders include but are not limited to ataxia, chorea, myoclonus, dystonia, Parkinson's disease, restless leg syndrome, tics, and Tourette's syndrome. Movement disorders typically occur as a result of damage or disease in the basal ganglia region of the brain. Movement disorders can result from age-related changes, medications, genetic disorders, metabolic disorders, disease, stroke, or injury. Recovery of movement after stroke or injury may be facilitated when treated according to the methods of the invention.

Addictive disorders are disorders characterized by addiction to an activity or substance, and include, for example, alcohol addiction, drug addiction, and gambling addiction.

Depression refers to the clinical condition known as major depressive disorder, and is characterized by a state of intense sadness, melancholia, or despair that has advanced to the point of being disruptive to an individual's social functioning and/or activities of daily living. Depression is alleviated if either (or both) the severity or frequency of a symptom of the depression is reduced. However, a subject can be treated for depression in accordance with the methods of the invention irrespective of whether the treatment actually was successful in alleviating the depression.

Insomnia is defined herein as the inability to fall asleep or to stay asleep for a sufficient amount of time during regular sleeping hours. It includes acute insomnia, which occurs in either a transient or short term form, and chronic insomnia. It also includes initial insomnia, defined as difficulty in falling asleep; middle insomnia, defined as awakening in the middle of the night followed by eventually falling back to sleep, but with difficulty; and terminal insomnia, defined as awakening before one's usual waking time and being unable to return to sleep.

As defined by the National Institute of Mental Health, Autism Spectrum Disorders (ASD), also widely known as Pervasive Developmental Disorders (PDDs), cause severe and pervasive impairment in thinking, feeling, language, and the ability to relate to others. These disorders are usually first diagnosed in early childhood and range from a severe form, called autistic disorder, through pervasive development disorder not otherwise specified (PDD-NOS), to a much milder form, Asperger syndrome. They also include two rare disorders, Rett syndrome and childhood disintegrative disorder.

Attention-Deficit Hyperactivity Disorder (ADHD) is one of the most common mental disorders that develop in children. Children with ADHD typically have impaired functioning in multiple settings, including home, school, and in relationships with peers. Symptoms of ADHD include impulsiveness, hyperactivity, and inattention.

Typical treatments encompassed by the present invention include combination therapies. For instance, the combination therapy may be a pharmacotherapy (i.e., a compound of the invention) and a behavioral therapy. Behavioral therapy comprises, but is not limited to, electroconvulsive seizure therapy, exercise, group therapy, talk therapy, or conditioning. In another embodiment, the behavioral therapy is cognitive-behavioral therapy. Examples of behavioral therapy that may be used in the ongoing methods are described, for example, in Cognitive-Behavioral Therapies by K. Dobson, ed., Guilford Publications, Inc., 2002; The new Handbook of Cognitive Therapy: Basics and Beyond by Judith S. S. Beck, Guilford Publications, Inc. 1995 herein incorporated by reference in their entireties. Any pharmaceutical active ingredient that is recognized by the skilled artisan as being a pharmacologic agent that enhances learning or conditioning can be used in the methods of the invention. For example, one such class of pharmaceutical active ingredients contemplated herein comprises compounds that increase the level of norepinephrine in the brain. Such compounds include those acting as norepinephrine reuptake inhibitors, for example tomoxetine, reboxetine, duloxetine, venlafaxine, and milnacipran, and those compounds that cause release of norepinephrine, for example amphetamine, dextroamphetamine, pemoline, and methylphenidate. Another class of such pharmaceutical active ingredients is those compounds that increase the level of acetylcholine in the brain, including, for example, compounds that block its breakdown. Examples of such compounds include, but are not limited to, donepezil HCl or Aricept™ and tacrine, which inhibit cholinesterase activity.

Methods of the invention also encompass the use in combination with a compound of the invention of any type of psychotherapy that is suitable for the particular psychiatric disorder for which the subject is undergoing treatment. Suitable methods of psychotherapy include exposure based psychotherapy, cognitive psychotherapy, and psychodynamically oriented psychotherapy. Methods of the invention also encompass exposing the subject to cognitive behavioral therapy (CBT), behavioral exposure treatments, virtual reality exposure (VRE) or cognitive remediation therapy.

Methods of the invention also encompass extinction training. The goal of extinction training is to pair a stimulus that previously provoked a deleterious, unwanted response with a new learning that will not lead to a negative outcome, thereby generating in a subject a new, more appropriate response to the stimulus to compete with and ideally replace the previous undesirable response. Extinction training frequently exposes a subject to a stimulus or situation in the absence of an aversive consequence, e.g., a subject that has deleterious, high anxiety responses to a given stimulus or situation is exposed to that stimulus or situation in the absence of an aversive consequence. A typical goal of extinction training is to produce new learning in the subject that results from the pairing of the original stimulus or situation with a non-deleterious outcome, thereby generating, in subsequent exposures to the stimulus, a more appropriate response in place of the unwanted response. An extinction learning event refers to a completed stimulus/response extinction training cycle.

One form of extinction training entails psychotherapy. For example, the methods of the invention contemplate treating, alleviating, and/or preventing anxiety disorders by: (i) administering psychotherapy to treat, alleviate, and/or prevent an anxiety-related disorder in a suitable human subject, and (ii) administering a therapeutically effective dose a compound of the invention to said subject on an achronic, post-training, pre-sleep basis. Suitable methods of psychotherapy include but are not limited to exposure-based psychotherapy, cognitive psychotherapy, and psychodynamically oriented psychotherapy.

One method of psychotherapy that is specifically contemplated is the use of virtual reality (VR) exposure therapy to treat, alleviate, and/or prevent an anxiety disorder using the methods of the invention.

Another method of psychotherapy that is particularly beneficial when utilized in combination with a compound or composition of the present invention is cognitive behavioral therapy ("CBT"). CBT is a form of psychotherapy that combines cognitive therapy and behavior therapy, and emphasizes the critical role of thinking in causing people to act and feel as they do. Therefore, if an individual is experiencing unwanted feelings and behaviors, CBT teaches that it is important to identify the thinking that is causing the undesirable feelings and/or behaviors and to learn how to replace this deleterious thinking with thoughts that lead to more desirable reactions. CBT is widely used to help people who are experiencing a range of mental health difficulties, some of which do not conveniently fit definitions of a particular medical affliction. CBT has been used to treat anxiety disorders, mood disorders, addictive disorders, eating disorders, insomnia, chronic pain, schizophrenia, fibromyalgia, ADHD, and autism spectrum disorders, among others. Post-extinction training pre-sleep administration of a compound of the invention, subsequent to CBT treatment, can be used to augment the effectiveness of the CBT treatment for these medical conditions.

In one embodiment, subjects suffering from social anxiety disorder undergo weekly cognitive behavioral therapy sessions to treat the affliction. After each therapy session, subjects are administered a therapeutically effective formulation of compounds of the invention on a post-extinction training pre-sleep basis. Relative to subjects treated only via cognitive behavioral therapy, or to subjects treated via cognitive behavioral therapy and a placebo, anxiety associated with social anxiety disorder is expected to be reduced to a greater extent in subjects treated with a combination of cognitive behavioral therapy and achronic administration of a compound of the invention on a post-extinction training pre-sleep basis.

In another embodiment of the invention, a compound of the invention is administered after extinction training only if the extinction training yields positive results on that day. For example, a subject undergoing cognitive behavioral therapy for PTSD is administered a compound of the invention on a post-extinction training only if the cognitive behavioral therapy was deemed to be successful, as determined by the subject and/or therapist. In one aspect, the compound is administered on a post-extinction, pre-sleep basis. In another aspect, a subject undergoing cognitive behavioral therapy for PTSD is administered a compound of the invention on a pre-extinction training. In one aspect, the compound is administered on a pre-extinction, pre-sleep basis. This method may also be useful when applied to treatment of autism spectrum disorders or attention-deficit hyperactivity disorder.

In another embodiment of the invention, subjects afflicted with anxiety disorders such as PTSD receive extinction training using Eye Movement Desensitization and Reprocessing (EMDR), and subsequently are administered a therapeutically effective dose of a compound of the invention on a post-extinction training pre-sleep basis. Another form of extinction training is provided by biofeedback, which is particularly useful in enabling subjects to learn to control physiological processes that normally occur involuntarily, such as blood pressure, heart rate, muscle tension, and skin temperature. As used herein, "biofeedback" refers to a technique in which subjects are trained to improve their health by using signals from their own bodies to control their own physiological responses.

In one embodiment of the invention, a subject suffering from chronic pain undergoes biofeedback sessions to help alleviate the pain. Upon the conclusion of each session wherein the subject has made progress in learning/developing responses that reduce the chronic pain, the subject is administered a compound of the invention on a post-extinction training pre-sleep basis in order to consolidate the desired learning.

In another embodiment, a subject suffering from phantom limb syndrome undergoes thermal biofeedback sessions to reduce and hopefully eliminate the symptoms. After each session, the subject is administered a therapeutically effective formulation of a compound of the invention on a post-extinction training pre-sleep basis.

In another embodiment, extinction training can be provided by physical therapy, or virtual reality physical therapy such as virtual reality gait therapy. For example, a stroke victim re-learning how to walk can undergo virtual reality gait therapy, and then be administered a compound of the invention on an achronic, post-extinction training pre-sleep basis.

Another form of extinction training can be provided by pharmacotherapy. For example, a man afflicted with erectile dysfunction can have an extinction learning event based on a positive sexual outcome, including instances wherein the positive sexual outcome was achieved with the pharmacological assistance of a PDE-5 inhibitor such as sildenafil, tadalafil, vardenafil, and/or udenafil. By administering a compound of the invention on a post-extinction training pre-sleep basis to a subject with erectile dysfunction, following a successful sexual outcome wherein the subject utilized sildenafil, the heightened confidence and reduced sexual performance anxiety resulting from a successful outcome can be consolidated in said subject's psyche, thereby facilitating extinction of any deleterious performance anxiety associated with sexual intercourse.

Extinction training does not always require intervention of a trained specialist. Individuals can carry out extinction training on themselves.

Fungal Diseases or Infections

In some aspects, the invention relates to a method for treating, alleviating, and/or preventing a fungal disease or infection comprising administering to a subject a compound of the invention. The invention provides a method for treating, alleviating, and/or preventing a hospital-acquired fungal infections that attack immunocompromised patients including those with HIV and cancer. In one embodiment, the invention provides a method for treating, alleviating, and/or preventing a fungal disease in a subject not suffering from cancer.

Inflammatory Disease

In some aspects, the invention relates to a method for treating, alleviating, and/or preventing an inflammatory disease, including but not limited to stroke, rheumatoid arthritis, lupus erythematosus, ulcerative colitis and traumatic brain injuries (Leoni et al., PNAS, 99(5); 2995-3000 (2002); Suuronen et al. J. Neurochem. 87; 407-416 (2003) and Drug Discovery Today, 10: 197-204 (2005).

Neoplastic Diseases

In some aspects, the invention relates to methods of selectively inducing terminal differentiation, and arresting cell growth and/or apoptosis of neoplastic cells, thereby inhibiting proliferation of such cells. The compounds of the present invention are useful in treating, alleviating, and/or preventing cancer in a subject.

The term "cancer" refers to any cancer caused by the proliferation of neoplastic cells, such as solid tumors, neoplasms, carcinomas, sarcomas, leukemias, lymphomas and the like. In particular, cancers that may be treated, alleviated and/or prevented by the compounds of the invention include, but are not limited to: cardiac cancer, lung cancer, gastrointestinal cancer, genitourinary tract cancer, liver cancer, nervous system cancer, gynecological cancer, hematologic cancer, skin cancer, and adrenal gland cancer.

In some embodiments, the compounds of the invention relate to treating, alleviating, or preventing cardiac cancers selected from sarcoma (angiosarcoma, fibrosarcoma, rhabdomyosarcoma, liposarcoma), myxoma, rhabdomyoma, fibroma, lipoma and teratoma.

In some embodiments, the compounds of the invention relate to treating, alleviating, or preventing lung cancer selected from bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, and mesothelioma.

In some embodiments, the compounds of the invention relate to treating, alleviating or preventing gastrointestinal cancer selected from esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), and large bowel (adenocarcinoma, tubular adenoma, villous adenoma, hamartoma, leiomyoma).

In some embodiments, the compounds of the invention relate to treating, alleviating, and/or preventing genitourinary tract cancer selected from kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

In some embodiments, the compounds of the invention relate to treating, alleviating, and/or preventing liver cancer selected from hepatoma (hepatocellular carcinoma), cholangiocarcinoma, hepatoblastoma, angiosarcoma, hepatocellular adenoma, and hemangioma.

In some embodiments, the compounds of the invention relate to treating, alleviating, and/or preventing bone cancer selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors.

In some embodiments, the compounds of the invention relate to treating, alleviating, and/or preventing nervous system cancer selected from skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), and spinal cord (neurofibroma, meningioma, glioma, sarcoma).

In some embodiments, the compounds of the invention relate to treating, alleviating, and/or preventing gynecological cancer selected from uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

In some embodiments, the compounds of the invention relate to treating, alleviating, and/or preventing skin cancer selected from malignant melanoma, basal cell carcinoma, squamous cell carcinoma, Karposi's sarcoma, moles dysplastic nevi, lipoma, angioma, dermatofibroma, keloids, and psoriasis.

In some embodiments, the compounds of the invention relate to methods of treating, alleviating, and/or preventing adrenal gland cancer selected from neuroblastoma.

In some embodiments, the instant compounds are useful in the treatment, alleviation, and/or preventing of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

Hematologic Diseases

In some aspects, the invention relates to methods of treating, alleviating, or preventing hematolical diseases. Hematologic diseases include abnormal growth of blood cells which can lead to dysplastic changes in blood cells and hematologic malignancies such as various leukemias. Examples of hematologic diseases include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chormosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Sickle cell disease is attributable to homozygous inheritance of a single amino acid substitution in the β-globin gene that leads to polymerization of deoxygenated hemoglobin, deformation of red blood cells, microvascular occlusion, hemolysis, and consequent disease manifestations, including pain, strokes, and pulmonary complications (Bunn H F, 1997, J. Med. 337:762-769). Abundant biochemical, epidemiological, and clinical evidence have shown that a high level of γ globin, the fetal form of β globin, inhibits the aberrant polymerization of sickle hemoglobin and ameliorates the disease phenotype. The only Food and Drug Administration (FDA)-approved drug for sickle cell disease, hydroxyurea, causes significant induction of fetal hemoglobin, decreased disease severity, and benefits overall mortality (Letvin et al., 1984, N Engl J Med 310:869-873; Platt O S, et al., 1984, J Clin Invest 74:652-656; Charache S, et al., 1995, N Engl J. Med 332: 317-1322; Steinberg M H, et al., 2003, JAMA 289:1645-1651). Nevertheless, hydroxyurea has bone marrow-suppressive effects and is ineffective in a significant portion of patients (Charache S, et al.; Steinberg M H, et al., 2003; Steinberg M H, 1999, N Engl J. Med 340:1021-1030). A drug that induces fetal hemoglobin more substantially with less myelosuppression would be expected to have greater therapeutic utility in sickle cell disease.

Transcriptional regulation of the human globin gene locus has been investigated intensively. Gamma-globin gene expression is influenced by transcription factors (GATA-1, EKLF, NF-E4p22, Ikaros) and chromatin modifying enzymes [SWI/SNF complex, HATs, and histone deacetylase (HDACs)] as part of multiprotein complexes, and a unique, dynamic chromatin structure termed the β-globin active chromatin hub (βACH) (8-11). Polymorphisms in BCL11A, a transcriptional repressor, alter baseline fetal hemoglobin levels, and a multiprotein complex containing BCL11a binds to the β-globin locus, resulting in repression of γ-globin expression (Menzel S, et al., 2007, Nat Genet 39:1197-1199; Lettre G, et al., 2008, Proc Natl Acad Sci USA 105:11869-11874;

Sankaran V G, et al., 2008, Science 322:1839-1842; Uda M, et al., 2008, Proc NATL Acad Sci USA 105:1620-1625; Sankaran V G, et al., 2009, Nature 460:1093-1097). Despite this granularity, discrete targets amenable to ligand discovery efforts have not been identified and functionally validated.

The induction of fetal hemoglobin is a validated strategy to improve symptoms and complications of sickle cell disease. The development of targeted therapies has been limited by the absence of discrete druggable targets. Bradner et al., 2010, PNAS, 107:28, 12617-12622 has developed a unique bead-based strategy for the identification of inducers of fetal hemoglobin transcripts in primary human erythroid cells, which includes a small-molecule screen of bioactive compounds that have been identified to have remarkable class-associated activity among histone deacetylase (HDAC) inhibitors. Using a chemical genetic strategy combining focused libraries of biased chemical probes and reverse genetics by RNA interference, Bradner et al. identified HDAC1 and HDAC2 as molecular targets mediating fetal hemoglobin induction. Isoform-selective inhibitors of HDAC1 and HDAC2 are targets for the treatment of sickle cell disease.

Formulations

The compounds of the invention may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli, Bacillus* calmatte-guerin, *Shigella, Lactobacillus*); Live viral vectors (e.g., *Vaccinia*, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below.

The term an "effective amount" of a compound of the invention refers to the amount necessary or sufficient to realize a desired biologic effect. For example, an effective amount of a compound of the invention is that amount sufficient to treat a condition. In another aspect, an effective amount of a compound is that amount sufficient to alleviate a condition. In another aspect, an effective amount of a compound is that amount sufficient to prevent a condition. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the condition being treated, the particular compounds being administered the size of the subject, or the severity of the condition.

The compounds of the invention may be administered by any route known, such as, for example, orally, transdermally, intravenously, cutaneously, subcutaneously, nasally, intramuscularly, intraperitoneally, intracranially, and intracerebroventricularly.

In certain embodiments, compounds of the invention are administered at dosage levels greater than about 0.001 mg/kg, such as greater than about 0.01 mg/kg or greater than about 0.1 mg/kg. For example, the dosage level may be from about 0.001 mg/kg to about 50 mg/kg such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can also be administered to a subject.

In one embodiment, the compound of the invention is administered once-daily, twice-daily, or three-times daily. In one embodiment, the compound of the invention is administered continuously (i.e., every day) or intermittently (e.g., 3-5 days a week). In another embodiment, administration could be on an intermittent schedule.

Further, administration less frequently than daily, such as, for example, every other day may be chosen. In additional embodiments, administration with at least 2 days between doses may be chosen. By way of example only, dosing may be every third day, bi-weekly or weekly. As another example, a single, acute dose may be administered. Alternatively, compounds of the invention can be administered on a non-regular basis e.g., whenever symptoms begin. For any compound described herein the effective amount can be initially determined from animal models.

Toxicity and efficacy of the compounds of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage of the compounds of the invention for use in humans. The dosage of such agents lies preferably within a range of circulating concentrations that include the ED50 with little or no toxicity. The dosage may vary within this range depending upon the dosage form employed and the route of administration utilized. For any compound used in the method of the invention, the effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Multiple doses of the compounds of the invention are also contemplated.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of one or more compounds of the invention can be administered to a subject by any mode that delivers the compound(s) to the desired surface, e.g., mucosal, systemic. Administering the pharmaceutical composition of the present invention may be accomplished by any means known to the skilled artisan. Compounds of the invention may be administered orally, transdermally, intravenously, cutaneously, subcutaneously, nasally, intramuscularly, intraperitoneally, intracranially, or intracerebroventricularly.

For oral administration, one or more compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of one or more compounds of the invention. The compound(s) may be chemically modified so that oral delivery of the derivative is efficacious. Generally, the chemical modification contemplated is the attachment of at least one moiety to the compound itself, where said moiety permits (a) inhibition of proteolysis; and (b) uptake into the blood stream from the stomach or intestine. Also desired is the increase in overall stability of the compound(s) and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4: 185-189. Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The compound of the invention can be included in the formulation as fine multiparticulates in the form of granules or pellets of particle size about 1 mm. The formulation of the material for capsule administration could also be as a powder, lightly compressed plugs or even as tablets. The compound of the invention could be prepared by compression.

Colorants and flavoring agents may all be included. For example, the compound of the invention may be formulated (such as by liposome or microsphere encapsulation) and then further contained within an edible product, such as a refrigerated beverage containing colorants and flavoring agents.

One may dilute or increase the volume of compound delivered with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants is the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the compound of the invention to prevent sticking during the formulation process. Lubricants may be used as a layer between the compound and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compound into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds of the invention. The compound is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63: 135-144 (leuprolide acetate); Braquet et al., 1989, Journal of Cardiovascular Pharmacology, 13(suppl. 5): 143-146 (endothelin-1); Hubbard et al., 1989, Annals of Internal Medicine, Vol. IJJ, pp. 206-212 (al-antitrypsin); Smith et al., 1989, J. Clin. Invest. 84: 1 145-1 146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified compound may also be prepared in different formulations depending on the type of chemical modification or the type of device employed. Formulations suitable for use with a nebulizer, either jet or ultrasonic, will typically comprise compound dissolved in water at a concentration of about 0.1 to 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound and may also include a bulking agent, such as lactose, sorbitol, sucrose, or mannitol in amounts which facilitate dispersal of the powder from the device, e.g., 50 to 90% by weight of the formulation. The compound should most advantageously be prepared in particulate form with an average particle size of less than 10 mm (or microns), most preferably 0.5 to 5 mm, for most effective delivery to the distal lung.

Nasal delivery of a compound of the invention is also contemplated. Nasal delivery allows the passage of a compound of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compound, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions.

Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249: 1527-1533, 1990, which is incorporated herein by reference.

The compounds of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a compound of the invention optionally included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the invention, and with each other, in a manner such that there is no interaction which would substantially impair the desired pharmaceutical efficiency.

The compounds of the invention may be delivered to the brain using a formulation capable of delivering a compound across the blood brain barrier. One obstacle to delivering compounds to the brain is the physiology and structure of the brain. The blood-brain barrier is made up of specialized capillaries lined with a single layer of endothelial cells. The region between cells is sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipohilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. The compounds described herein may be modified by covalent attachment to a lipophilic carrier or co-formulation with a lipophilic carrier. Others are known to those of skill in the art.

The compounds of the invention may be delivered with other methods for enhancing memory retrieval or treating other symptoms or causes of disorders associated with the memory loss. For instance, environmental enrichment (EE) has been used for enhancing memories. EE involves creating a stimulating environment around a subject. Other therapeutics may also be combined to treat the underlying disorder or to enhance memory.

Combination Therapies

The invention includes combination therapies including the methods of treating, alleviating, and/or preventing conditions described herein. Combination therapy includes administering one or more compounds of the invention in combination with one or more pharmaceutically active ingredients or exposing the subject to cognitive behavioral therapy (CBT), psychotherapy, behavioral exposure treatments, virtual reality exposure (VRE) or cognitive remediation therapy.

In one aspect, the combination therapy is for a method of treating, alleviating, or preventing a neurological disorder. In one aspect, the combination therapy is for methods of treating, alleviating, or preventing Alzheimer's disease. The combination therapies comprise the administration of an effective amount of one or more (e.g. one) compounds of the invention and the administration of an effective amount of one or more (e.g., one) other pharmaceutically active ingredients (e.g., drugs). The compounds of the invention and the other pharmaceutically active ingredients can be administered separately (i.e., each is in its own separate dosage form), or the compounds of the invention can be combined with the other pharmaceutically active ingredients in the same dosage form.

Pharmaceutically active ingredients that are useful in combination therapies of the invention include e.g., BACE inhibitors (beta secretase inhibitors), muscarinic antagonists, cholinesterase inhibitors (e.g., acetyl- and/or butyrylchlolinesterase inhibitors); gamma secretase inhibitors; gamma secretase modulators; HMG-CoA reductase inhibitors; nonsteroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; GABA inverse agonists; inhibitors of amyloid aggregation; glycogen synthase kinase beta inhibitors; tau kinase inhibitors (e.g., GSK3beta inhibitors, cdk5 inhibitors, ERK inhibitors), promoters of alpha secretase activity; PDE-10 inhibitors and cholesterol absorption inhibitors. Further examples of pharmaceutically active ingredients that are useful for combination therapies of the invention are (+)-2,3-dihydro-5,6-dimethoxy-2-[[1-(phenylmethyl)-4-piperidinyl]methy-1]-1H-inden-1-one hydrochloride, i.e., donepezil hydrochloride, available as the Aricept™ brand of donepezil hydrochloride, Exelon (rivastigmine), Cognex (tacrine), anti-Abeta vaccine (active immunization), amyloid precursor protein (APP) ligands, agents that upregulate insulin degrading enzyme and/or neprilysin, cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe, fibrates (for example, clofibrate, Clofibride, Etofibrate, Aluminium Clofibrate), LXR agonists, LRP mimics, 5-HT6 receptor antagonists, nicotinic receptor agonists, H3 receptor antagonists, other histone deacetylase inhibitors, hsp90 inhibitors, muscarinic receptor agonists, 5-HT6 receptor antagonists mGluR1 or mGluR5 positive allosteric modulators or agonists, mGluR2/3 antagonists, anti-inflammatory agents that can reduce neuroinflammation, prostaglandin EP2 receptor antagonists, PAI-1 inhibitors and agents that can induce Abeta efflux such as gelsolin.

Examples of combination therapies of the compounds of the invention with other pharmaceutically active ingredients include combinations with: anti-Alzheimer's agents, beta-secretase inhibitors, gamma-secretase inhibitors, HMG-CoA reductase inhibitors, NSAID's including ibuprofen, N-methyl-D-aspartate (NMDA) receptor antagonists, such as memantine, cholinesterase inhibitors such as galantamine, rivastigmine, donepezil, and tacrine, vitamin E, CB-I receptor antagonists or CB-I receptor inverse agonists, antibiotics such as doxycycline and rifampin, anti-amyloid antibodies, or other pharmaceutically active ingredients that affect receptors or enzymes that either increase the efficacy, safety, convenience, or reduce unwanted side effects or toxicity of the compounds of the invention. The compounds of the invention may also be delivered in a cocktail of multiple HDAC inhibitors. Combination therapies of the invention may be in either unit dose or kit form.

The compounds of the invention are also useful in combination with known pharmaceutically active ingredients such as anti-cancer agents. Combinations of the presently disclosed compounds with other anti-cancer or chemotherapeutic agents are within the scope of the invention. Examples of such agents can be found in Cancer Principles and Practice of Oncology by V. T. Devita and S. Hellman (editors), 6.sup.th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The compounds of the invention are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Additional combination therapies are discussed herein under the extinction learning section.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention. Compounds of the invention can be evaluated using a variety of methods known in the art. For example, the following methods can be used to evaluate compounds of the invention: the inhibition of HDAC activity can be determined using a trypsin-coupled protocol and/or a non-trypsin-coupled Caliper protocol (Schultz, B. E. Biochemistry, 2004, 43, 11083 and U.S. patent application Ser. No. 61/628,562 entitled "Fluorescent Substrates for Determining Lysine Deacetylase Activity" filed Nov. 2, 2011); the inhibition of HDAC activity can be determined in cells e.g., imaging of primary neuronal culture; learning tests such as behavioral tests e.g., fear-conditioning can be performed as described in Fischer et al., Neuron 48, 825-838 (2005); the ability of the compounds to reinstate learning behavior and to recover access to long-term memories can be tested in CK-p25 Tg mice that have developed synaptic and neuronal loss (Cruz, J., et al., Curr. Opin. Neurobiol. 14, 390-394 (2004); Fisher, A. et al., Neuron 48, 471-83 (2003); Cruz, J. et al., Neuron 40, 471-83 (2003)); the effect of compounds on plasticity factors in CK-p25 Tg mice with severe neurodegeneration can be determined by looking at hiippocampal neuronal loss, for example, by comparing images showing hippocampal NeuN and MAP-2 staining and using immunoblots from the hippocampus and cortex of all groups; one or more specific acetylation marks elicited by the compounds can be determined which are relevant to the treatment of disease (e.g., Rubinstein Taybi); mass spectrometry can be used to identify changes in histone acetylation and methylation states induced in neurons by treatment with the compounds; the identification of gene expression changes upon treatment with compounds of the invention in neurons can be determined using RNA for transcript profile analysis on Illumina microarrays; and the ability of the compounds to selectively inhibit HDACs1/2 to effect unique conformational changes in the enzymes induced by assembly into these multi-protein complexes can be evaluated by immunoprecipitating HDAC2 complexes from mouse forebrain and by determining the presence and activity of complex members (e.g., CoREST, mSin3a, and Mta3) using in vitro assays.

The following Examples are illustrative and should not be interpreted in any way so as to limit the scope of the invention.

EXAMPLES

Example 1: Preparation of Compounds of the Invention

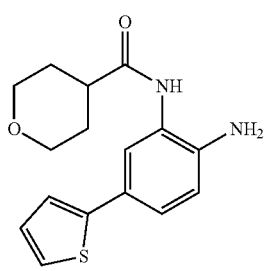

(45)

121

Synthesis of N-(2-amino-5-(thiophen-2-yl)phenyl) tetrahydro-2H-pyran-4-carboxamide (45)

Scheme 1

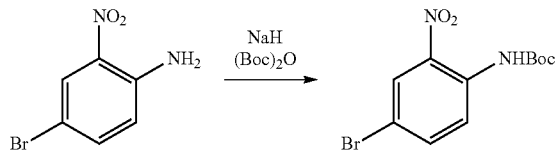

To a solution of 4-bromo-2-nitroaniline (1, 10.0 g, 46.1 mmol, 1.0 eq.) in DMF (50 mL) at 0° C. was added sodium hydride (1.8 g, 73.7 mmol, 1.6 eq.) slowly. After 30 minutes, a solution of di-tert-butyl dicarbonate (12.1 g, 55.3 mmol, 1.2 eq.) in DMF (50 mL) was added dropwise. The reaction mixture was then stirred for 16 h at room temperature. The reaction was quenched with water. The product was extracted with methyl tertiary butyl ether. The organic layer was washed with water and brine. The combined organic layers were dried over anhydrous sodium sulfate, filtered and concentrated in vacuo. The product was purified by column chromatography (silica gel, 0-20% EtOAc/hexanes) to give tert-butyl (4-bromo-2-nitrophenyl)carbamate (7.5 g, 51% yield) as yellow solid.

Scheme 2

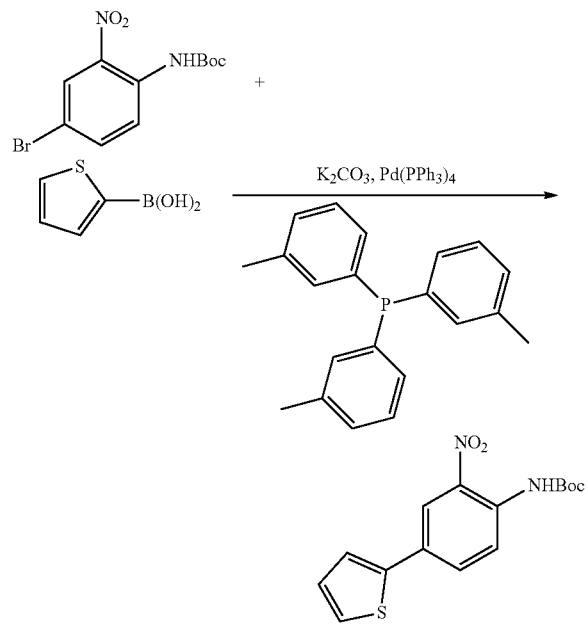

A mixture of tert-butyl (4-bromo-2-nitrophenyl)carbamate (6.0 g, 18.92 mmol, 1.0 eq.), thiophen-2-ylboronic acid (3.2 g, 24.6 mmol, 1.3 eq.), potassium carbonate (7.84 g, 56.8 mmol, 3.0 eq.) and tetrakis(triphenylphosphine)palladium(O) (1.53 g, 1.32 mmol, 0.07 eq.), tri-tolylphosphine in DME/H2O (105 mL) was first degassed then heated to 90° C. for 20 h. The reaction was then filtered through Celite. The product was extracted with ethyl acetate. The combined organic layers were washed with water and brine, dried over anhydrous Na$_2$SO$_4$, filtered and concentrated under reduced pressure. The crude product was purified by flash column chromatography (silica gel, 2% EtOAc/hexanes) to obtain pure tert-butyl (2-nitro-4-(thiophen-2-yl)phenyl)carbamate (4.42 g, 73% yield).

Scheme 3

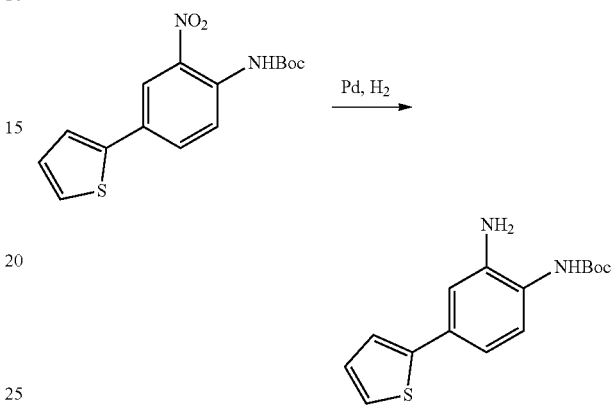

To a solution of tert-butyl (2-nitro-4-(thiophen-2-yl)phenyl)carbamate (2 g, 6.2 mmol, 1.0 eq.) in ethanol (20 mL) and methanol (20 mL) was added 10% Pd/C (0.66 g, 0.1 eq.). The reaction mixture was stirred 12 h under a hydrogen atmosphere. The reaction was filtered and the filtrate was concentrated under reduced pressure to give tert-butyl (2-amino-4-(thiophen-2-yl)phenyl)carbamate (1.25 g, 69% yield) as an off-white solid.

Scheme 4

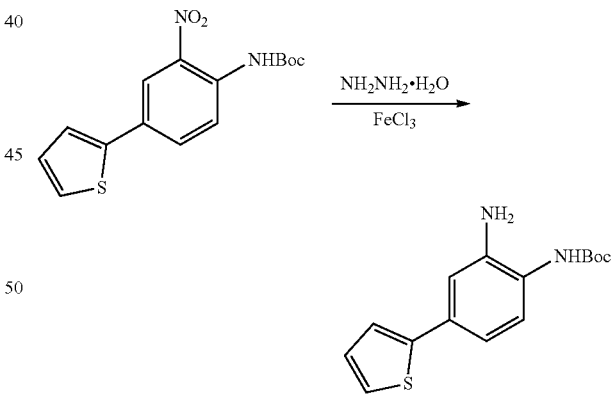

To a solution of tert-butyl (2-nitro-4-(thiophen-2-yl)phenyl)carbamate (1.6 g, 4.99 mmol, 1 eq.) in methanol (20 mL) was added hydrazine hydrate (14 mL) and ferric chloride (0.05 g, 0.3 mmol, 0.06 eq.). The resulting mixture was warmed to 60° C. and stirred for 2 h. The reaction was then filtered through Celite, the solids were washed with MeOH. The filtrate was concentrated under reduced pressure. Water was added to the residue and the suspension was stirred for 1 h. The obtained solid was filtered, washed with hexanes then dried to yield tert-butyl (2-amino-4-(thiophen-2-yl)phenyl)carbamate (1.2 g, 83% yield).

Scheme 5

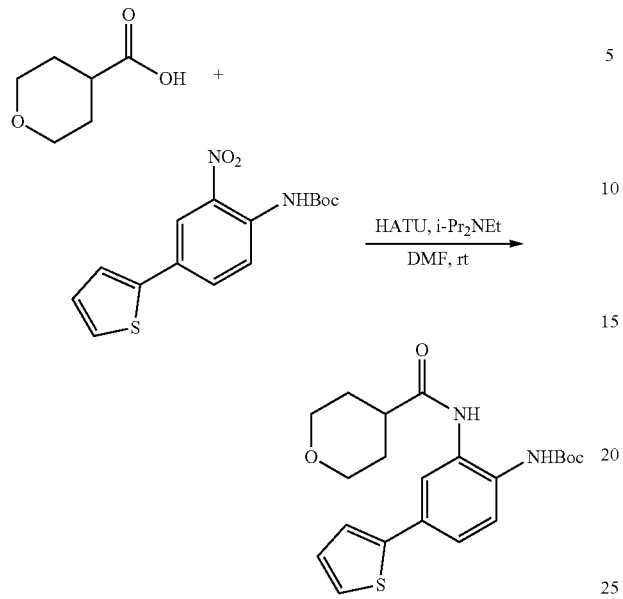

A solution of tert-butyl (2-amino-4-(thiophen-2-yl)phenyl)carbamate (1.2 g, 4.13 mmol, 1.0 eq.), tetrahydro-2H-pyran-4-carboxylic acid (0.65 g, 4.96 mmol, 1.2 eq.), HATU (3.14 g, 8.27 mmol, 2.0 eq.) and Hünigs base (1.80 mL, 10.33 mmol, 2.5 eq.) in DMF (15 mL) was stirred for 18 h at room temperature. The reaction mixture was diluted with water. The solid was isolated by filtration and washed with hexanes to afford tert-butyl (2-(tetrahydro-2H-pyran-4-carboxamido)-4-(thiophen-2-yl)phenyl)carbamate (1.3 g, 78% yield).

Scheme 6

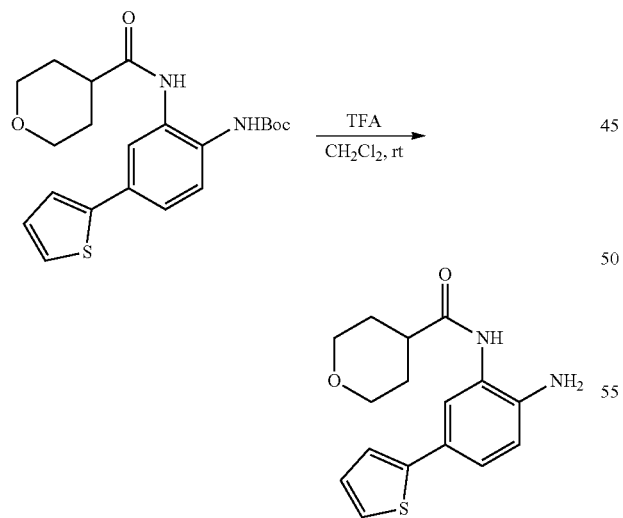

To a stirred solution of tert-butyl (2-(tetrahydro-2H-pyran-4-carboxamido)-4-(thiophen-2-yl)phenyl)carbamate in dichloromethane (20 mL) was added trifluoroacetic acid (7 mL) at room temperature. The reaction mixture was stirred at room temperature for 2 h. the solvents were then removed under reduced pressure. A saturated aqueous solution of sodium bicarbonate was added. The product was extracted with EtOAc, washed with water and brine, dried, filtered and concentrated under reduced pressure. The crude product was purified by column chromatography (silica gel, MeOH/CH$_2$Cl$_2$) to afford N-(2-amino-5-(thiophen-2-yl)phenyl)tetrahydro-2H-pyran-4-carboxamide as a beige solid (1.1 g, 86% yield). ESI+ MS: m/z 303 ([M+H]$^+$), 1H NMR (500 MHz, d$^6$-DMSO): δ 9.12 (s, 1H), 7.51 (d, J=2.0 Hz, 1H), 7.34 (d, J=5.0 Hz, 1H), 7.24-7.18 (m, 2H), 7.03 (dd, J=5.5; 3.5 Hz, 1H), 6.75 (d, J=8.5 Hz, 1H), 5.05 (s, 1H), 3.91 (dd, J=11.0; 2.0 Hz, 2H), 3.36 (dt, J=11.0; 2.0 Hz, 2H), 2.68-2.62 (m, 1H), 1.80-1.64 (m, 4H).

One skilled in the art will recognize that other compounds described below were prepared in a similar manner to the procedures described above.

(30)

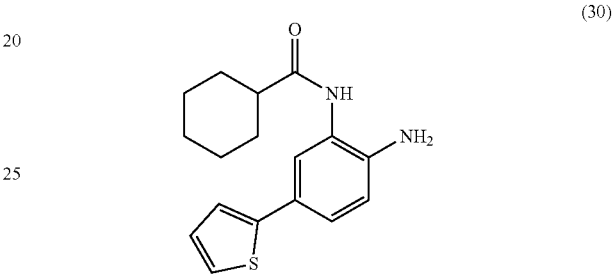

N-(2-amino-5-(thiophen-2-yl)phenyl)cyclohexanecarboxamide (30) was prepared by substituting tetrahydro-2H-pyran-4-carboxylic acid in Scheme 5 with cyclohexane carboxylic acid. ESI+ MS: m/z 301 ([M+H]$^+$), 1H NMR (500 MHz, d$^6$-DMSO): δ 9.06 (s, 1H), 7.51 (d, J=1.0 Hz, 1H), 7.34 (d, J=5.5 Hz, 1H), 7.26-7.14 (m, 2H), 7.04 (t, J=7.04 Hz, 1H), 6.75 (d, J=8.5 Hz, 1H), 5.06 (s, 2H), 2.39 (t, J=11.5 Hz, 1H), 1.84 (d, J=12.0 Hz, 2H), 1.76 (d, J=12.0 Hz, 2H), 1.66 (d, J=12.0 Hz, 1H), 1.43 (q, J=11.5 Hz, 2H), 1.10-1.35 (m, 3H).

(8)

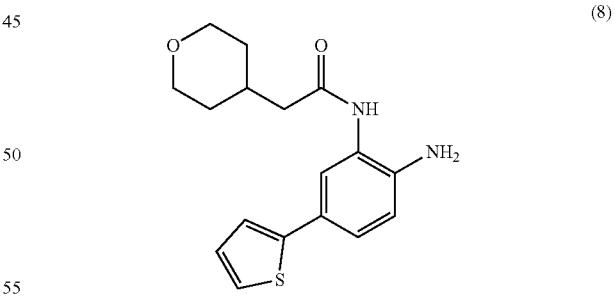

N-(2-amino-5-(thiophen-2-yl)phenyl)-2-(tetrahydro-2H-pyran-4-yl)acetamide (8) was prepared by substituting tetrahydro-2H-pyran-4-carboxylic acid in Scheme 5 with 2-(tetrahydro-2H-pyran-4-yl)acetic acid. ESI+ MS: m/z 316 ([M]$^+$), 1H NMR (500 MHz, d$^6$-DMSO): δ 9.21 (s, 1H), 7.50 (d, J=2.0 Hz, 1H), 7.26-7.18 (m, 2H), 7.04 (dd, J=4.0, 5.0 Hz, 1H), 6.76 (d, J=8.0 Hz, 1H), 5.20 (bs, 2H), 3.84 (dd, J=11.0, 3.0 Hz, 2H), 3.81 (t, J=11.0 Hz, 2H), 2.29 (d, J=7.0 Hz, 2H), 2.05-1.95 (m, 1H), 1.63 (d, J=11.0 Hz, 2H), 1.35-1.20 (m, 2H).

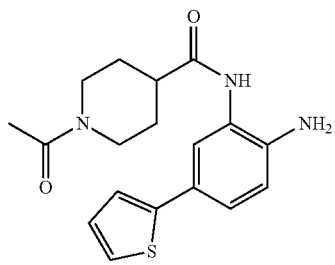
(35)

1-acetyl-N-(2-amino-5-(thiophen-2-yl)phenyl)piperidine-4-carboxamide (35) was prepared by substituting tetrahydro-2H-pyran-4-carboxylic acid in Scheme 5 with 1-acetylpiperidine-4-carboxylic acid. ESI+ MS: m/z 316 ([M]+), 1H NMR (500 MHz, d6-DMSO): δ 9.19 (s, 1H), 7.50 (d, J=1.5 Hz, 1H), 7.34 (d, J=4.5 Hz, 1H), 7.24-7.18 (m, 2H), 7.04 (dd, J=4.0, 5.5 Hz, 1H), 6.75 (d, J=8.5 Hz, 1H), 5.06 (s, 2H), 4.35 (d, J=13.0 Hz, 1H), 3.79 (d, J=13.5 Hz, 2H), 3.01 (t, J=11.5 Hz, 1H), 2.60-2.50 (m, 1H), 2.29 (d, J=7.0 Hz, 2H), 2.05-1.95 (m, 4H), 1.80-1.65 (m, 2H), 1.25-1.10 (m, 1H), 1.10-1.00 (m, 1H).

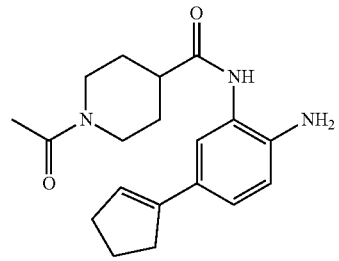
(38)

1-acetyl-N-(2-amino-5-(cyclopent-1-en-1-yl)phenyl)piperidine-4-carboxamide (38) was prepared by substituting tetrahydro-2H-pyran-4-carboxylic acid in Scheme 5 with 1-acetylpiperidine-4-carboxylic acid and by substituting thiophen-2-ylboronic acid in Scheme 2 with cyclopent-1-en-1-ylboronic acid. ESI+ MS: m/z 328 ([M+H]+), 1H NMR (500 MHz, d6-DMSO): δ 9.12 (s, 1H), 7.24 (s, 1H), 7.05 (d, J=8.0 Hz, 1H), 6.67 (d, J=8.0 Hz, 1H), 5.92 (bs, 1H), 4.88 (s, 2H), 4.39 (d, J=13.0 Hz, 1H), 4.12-4.05 (m, 1H), 3.86 (d, J=14.0 Hz, 1H), 3.06 (t, J=12.5 Hz, 1H), 2.65-2.40 (m, 5H), 2.01 (s, 3H), 1.95-1.78 (m, 4H), 1.65-1.52 (m, 1H), 1.50-1.38 (m, 1H).

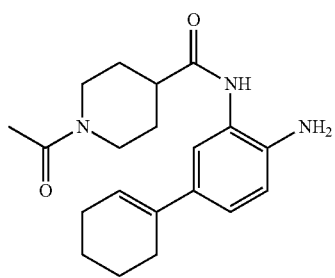
(37)

1-acetyl-N-(4-amino-2',3',4',5'-tetrahydro-[1,1'-biphenyl]-3-yl)piperidine-4-carboxamide (37) was prepared by substituting tetrahydro-2H-pyran-4-carboxylic acid in Scheme 5 with 1-acetylpiperidine-4-carboxylic acid and by substituting thiophen-2-ylboronic acid with cyclohex-1-en-1-ylboronic acid in Scheme 2. ESI+ MS: m/z 342 ([M+H]+), 1H NMR (500 MHz, d6-DMSO): δ 9.08 (s, 1H), 7.22 (d, J=2.0 Hz, 1H), 6.97 (dd, J=2.0, 8.0 Hz, 1H), 6.66 (d, J=8.0 Hz, 1H), 5.91 (bs, 1H), 4.80 (s, 2H), 4.39 (d, J=13.0 Hz, 1H), 3.86 (d, J=14.0 Hz, 1H), 3.06 (t, J=12.5 Hz, 1H), 2.66-2.54 (m, 2H), 2.33-2.30 (m, 2H), 2.16-2.10 (m, 2H), 2.01 (s, 3H), 1.86-1.78 (m, 2H), 1.72-1.66 (m, 2H), 1.64-1.54 (m, 3H), 1.50-1.40 (m, 1H).

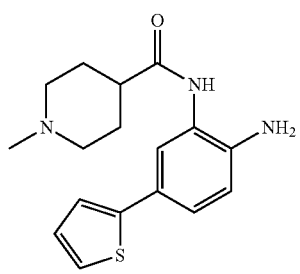
(34)

N-(2-amino-5-(thiophen-2-yl)phenyl)-1-methylpiperidine-4-carboxamide (34) was prepared by substituting tetrahydro-2H-pyran-4-carboxylic acid in Scheme 5 with 1-methylpiperidine-4-carboxylic acid. ESI+ MS: m/z 316 ([M+H]+), 1H NMR (500 MHz, d6-DMSO): δ 9.12 (s, 1H), 7.51 (s, 1H), 7.34 (d, J=5.0 Hz, 1H), 7.24-7.18 (m, 2H), 7.04 (t, J=4.0 Hz, 1H), 6.75 (t, J=8.5 Hz, 1H), 5.06 (bs, 2H), 2.82 (d, J=11.0 Hz, 2H), 2.35-2.25 (m, 1H), 1.80-1.60 (m, 6H).

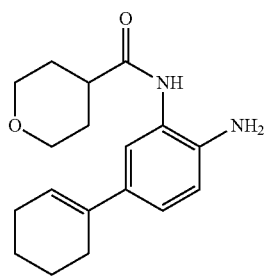
(50)

N-(4-amino-2',3',4',5'-tetrahydro-[1,1'-biphenyl]-3-yl)tetrahydro-2H-pyran-4-carboxamide (59) was prepared by substituting thiophen-2-ylboronic acid in Scheme 2 with cyclohex-1-en-1-ylboronic acid. ESI+ MS: m/z 301 ([M+H]+).

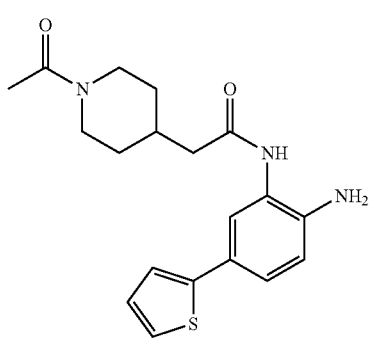
(10)

2-(1-acetylpiperidin-4-yl)-N-(2-amino-5-(thiophen-2-yl)phenyl)acetamide (10) was prepared by substituting tetrahydro-2H-pyran-4-carboxylic acid in Scheme 5 with 2-(1-acetylpiperidin-4-yl)acetic acid. ESI+ MS: m/z 316 ([M]+), 1H NMR (500 MHz, d6-DMSO): δ 9.19 (s, 1H), 7.50 (d, J=1.5 Hz, 1H), 7.34 (d, J=4.5 Hz, 1H), 7.24-7.18 (m, 2H), 7.04 (dd, J=4.0, 5.5 Hz, 1H), 6.75 (d, J=8.5 Hz, 1H), 5.06 (s, 2H), 4.35 (d, J=13.0 Hz, 1H), 3.79 (d, J=13.5 Hz, 2H), 3.01 (t, J=11.5 Hz, 1H), 2.60-2.50 (m, 1H), 2.29 (d, J=7.0 Hz, 2H), 2.05-1.95 (m, 4H), 1.80-1.65 (m, 2H), 1.25-1.10 (m, 1H), 1.10-1.00 (m, 1H).

7.35 (dd, J=5, 1 Hz, 1H), 7.26 (dd, J=8; 2 Hz, 1H), 7.22 (dd, J=4 Hz; 1.5 Hz, 1H), 7.04 (dd, J=5; 4.5 Hz, 1H), 6.78 (d, J=8.5 Hz, 1H), 6.73-6.68 (m, 1H), 5.06 (s, 2H), 2.61-2.57 (m, 2H), 2.51-2.48 (m, 2H), 1.93-1.90 (m, 2H).

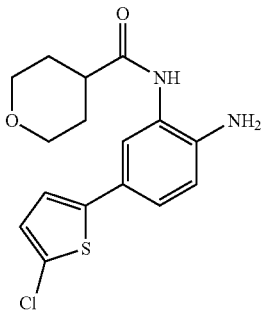

(48)

N-(2-amino-5-(5-chlorothiophen-2-yl)phenyl)tetrahydro-2H-pyran-4-carboxamide (48) was prepared by substituting thiophen-2-ylboronic acid in Scheme 2 with (5-chlorothiophen-2-yl)boronic acid. ESI+ MS: m/z 337 ([M+H]$^+$), 1H NMR (300 MHz, d$^6$-DMSO): δ 9.15 (s, 1H), 7.46 (d, J=3.0 Hz, 1H), 7.18 (dd, J=3.0, 9.0 Hz, 1H), 7.09-7.03 (m, 2H), 6.76 (d, J=9.0 Hz, 1H), 5.17 (bs, 2H), 3.88-3.82 (m, 2H), 3.42-3.24 (m, 2H), 2.66-2.46 (m, 1H), 1.80-1.60 (m, 4H).

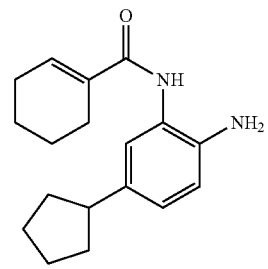

(31)

N-(2-amino-5-cyclopentylphenyl)cyclohex-1-enecarboxamide (31) was prepared by substituting tetrahydro-2H-pyran-4-carboxylic acid in Scheme 5 with cyclohex-1-enecarboxylic acid and by substituting thiophen-2-ylboronic acid in Scheme 2 with cyclopentylboronic acid. ESI+ MS: m/z 285 ([M+H]$^+$), 1H NMR (500 MHz, d$^6$-DMSO): δ 8.94 (s, 1H), 6.98 (d, J=1.5 Hz, 1H), 6.81 (dd, J=1.5, 8.5 Hz, 1H), 6.70-6.64 (m, 2H), 4.56 (s, 2H), 2.85-2.75 (m, 1H), 2.30-2.24 (m, 2H), 2.20-2.12 (m, 2H), 1.96-1.88 (m, 2H), 1.76-1.66 (m, 2H), 1.66-1.52 (m, 6H), 1.48-1.38 (m, 2H).

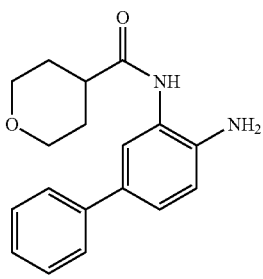

(49)

N-(4-amino-[1,1'-biphenyl]-3-yl)tetrahydro-2H-pyran-4-carboxamide (49) was prepared by substituting thiophen-2-ylboronic acid in Scheme 2 with phenylboronic acid. ESI+ MS: m/z 296.9 ([M+H]$^+$).

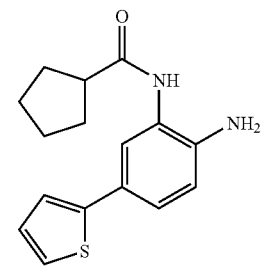

(16)

N-(2-amino-5-(thiophen-2-yl)phenyl)cyclopentanecarboxamide (16) was prepared by substituting tetrahydro-2H-pyran-4-carboxylic acid in Scheme 5 with cyclopentanecarboxylic acid. ESI+ MS: m/z 287 ([M+H]$^+$), 1H NMR (500 MHz, d$^6$-DMSO): δ 9.15 (s, 1H), 7.52 (s, 1H), 7.35 (d, J=4 Hz, 1H), 7.18-7.26 (m, 2H), 7.04 (t, J=4 Hz, 1H), 6.75 (d, J=8.5 Hz, 1H), 5.06 (s, 2H), 2.84 (q, J=7.5 Hz, 1H), 1.95-1.65 (m, 2H), 1.65-1.30 (m, 4H), 1.30-1.50 (m, 2H).

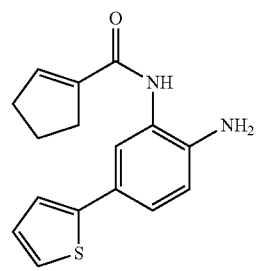

(17)

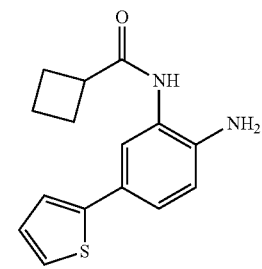

(13)

N-(2-amino-5-(thiophen-2-yl)phenyl)cyclopent-1-enecarboxamide (17) was prepared by substituting tetrahydro-2H-pyran-4-carboxylic acid in Scheme 5 with cyclopent-1-enecarboxylic acid. ESI+ MS: m/z 285 ([M+H]$^+$), 1H NMR (500 MHz, d$^6$-DMSO): δ 9.12 (s, 1H), 7.40 (d, J=2 Hz, 1H), N-(2-amino-5-(thiophen-2-yl)phenyl)cyclobutanecarboxamide (13) was prepared by substituting tetrahydro-2H-pyran-4-carboxylic acid in Scheme 5 with cyclobutanecarboxylic acid. ESI+ MS: m/z 273 ([M+H]⁺), 1H NMR (500 MHz, d⁶-DMSO): δ 9.01 (s, 1H), 7.52 (s, 1H), 7.35 (d, J=4.0 Hz, 1H), 7.18-7.25 (m, 2H), 7.04 (t, J=5.0 Hz, 1H), 6.75 (d, J=8.5 Hz, 1H), 5.06 (s, 2H), 3.27 (q, J=8.0 Hz, 1H), 2.25 (q, J=9.0 Hz, 2H), 2.30-2.15 (m, 2H), 2.10-1.80 (m, 1H), 1.80-1.55 (m, 1H).

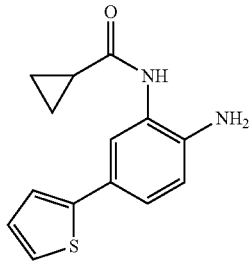

(12)

N-(2-amino-5-(thiophen-2-yl)phenyl)cyclopropanecarboxamide (12) was prepared by substituting tetrahydro-2H-pyran-4-carboxylic acid in Scheme 5 with cyclopropanecarboxylic acid. ESI+ MS: m/z 259 ([M+H]⁺), 1H NMR (500 MHz, d⁶-DMSO): δ 9.46 (s, 1H), 7.56 (s, 1H), 7.34 (d, J=4.5 Hz, 1H), 7.25-7.16 (m, 2H), 7.04 (t, J=3.5 Hz, 1H), 6.75 (d, J=9 Hz, 1H), 5.09 (s, 2H), 1.84 (d, J=4.5 Hz, 1H), 0.80 (t, J=3 Hz, 4H).

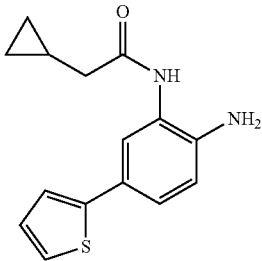

(11)

N-(2-amino-5-(thiophen-2-yl)phenyl)-2-cyclopropylacetamide (11) was prepared by substituting tetrahydro-2H-pyran-4-carboxylic acid in Scheme 5 with 2-cyclopropylacetic acid. ESI+ MS: m/z 273 ([M+H]⁺), 1H NMR (500 MHz, d⁶-DMSO): δ 8.84 (s, 1H), 7.30 (d, J=2.5 Hz, 1H), 7.12 (dd, J=1.0, 6.0 Hz, 1H), 7.25-7.19 (m, 2H), 6.81 (dd, J=4.5, 6.5 Hz, 1H), 6.52 (d, J=10.5 Hz, 1H), 4.86 (bs, 2H), 2.02 (d, J=9.0 Hz, 2H), 1.13-1.03 (m, 1H), 0.52-0.46 (m, 2H), 0.25-0.18 (m, 2H).

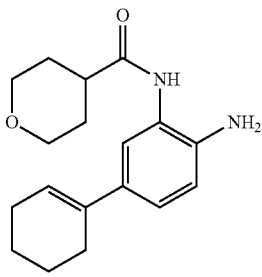

(50)

N-(4-amino-2',3',4',5'-tetrahydro-[1,1'-biphenyl]-3-yl)tetrahydro-2H-pyran-4-carboxamide (50) was prepared by substituting thiophen-2-ylboronic acid in Scheme 2 with cyclohex-1-en-1-ylboronic acid. ESI+ MS: m/z 301 ([M+H]⁺), 1H NMR (500 MHz, d⁶-DMSO): δ 9.04 (s, 1H), 7.23 (d, J=2.0 Hz, 1H), 6.97 (dd, J=2.0, 8.0 Hz, 1H), 6.65 (d, J=8.0 Hz, 1H), 5.91 (bs, 1H), 4.80 (s, 2H), 3.94-3.86 (m, 2H), 3.40-3.30 (m, 2H), 2.66-2.56 (m, 1H), 2.30-2.22 (m, 2H), 2.15-2.09 (m, 2H), 1.75-1.60 (m, 6H), 1.60-1.53 (m, 2H).

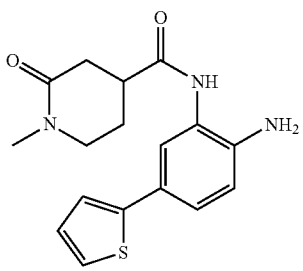

(40)

N-(2-amino-5-(thiophen-2-yl)phenyl)-1-methyl-2-oxopiperidine-4-carboxamide (40) was prepared by substituting tetrahydro-2H-pyran-4-carboxylic acid in Scheme 5 with 1-methyl-2-oxopiperidine-4-carboxylic acid. ESI+ MS: m/z 330 ([M+H]⁺), 1H NMR (500 MHz, d⁶-DMSO): δ 9.22 (s, 1H), 7.49 (s, 1H), 7.34 (d, J=5.0 Hz, 1H), 7.26-7.18 (m, 2H), 7.04 (t, J=5.0 Hz, 1H), 6.75 (d, J=8.5 Hz, 1H), 5.08 (s, 2H), 2.98-2.90 (m, 1H), 2.50-2.35 (m, 3H), 2.13-2.05 (m, 1H), 1.92-1.82 (m, 1H).

(41)

N-(4-amino-2',3',4',5'-tetrahydro-[1,1'-biphenyl]-3-yl)-1-methyl-2-oxopiperidine-4-carboxamide (41) was prepared by substituting tetrahydro-2H-pyran-4-carboxylic acid in Scheme 5 with 1-methyl-2-oxopiperidine-4-carboxylic acid and by substituting thiophen-2-ylboronic acid in Scheme 2 with cyclohex-1-en-1-ylboronic acid. ESI+ MS: m/z 328 ([M+H]⁺), 1H NMR (500 MHz, d⁶-DMSO): δ 9.14 (s, 1H), 7.23 (s, 1H), 6.98 (d, J=6.5 Hz, 1H), 6.66 (d, J=6.5 Hz, 1H), 5.91 (bs, 1H), 4.83 (s, 2H), 3.34-3.26 (m, 2H), 2.96-2.86 (m, 1H), 2.82 (s, 3H), 2.44-2.32 (m, 2H), 2.30-2.22 (m, 2H), 2.16-2.02 (m, 3H), 1.92-1.80 (m, 1H), 1.72-1.64 (m, 2H), 1.60-1.52 (m, 2H).

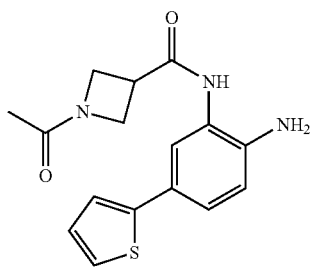

(42)

1-acetyl-N-(2-amino-5-(thiophen-2-yl)phenyl)azetidine-3-carboxamide (42) was prepared by substituting tetrahydro-2H-pyran-4-carboxylic acid in Scheme 5 with 1-acetylazetidine-3-carboxylic acid. ESI+ MS: m/z 316 ([M+H]$^+$), 1H NMR (500 MHz, d$^6$-DMSO): δ 9.29 (s, 1H), 7.51 (d, J=2.0 Hz, 1H), 7.35 (d, J=4.5 Hz, 1H), 7.24 (d, J=2.5, 8.5 Hz, 1H), 7.21 (d, J=3.0 Hz, 1H), 7.04 (dd, J=3.5, 5.0 Hz, 1H), 6.75 (d, J=8.5 Hz, 1H), 5.15 (bs, 2H), 4.30-4.20 (m, 2H), 4.06-3.90 (m, 2H), 3.60-3.50 (m, 1H), 1.78 (s, 3H).

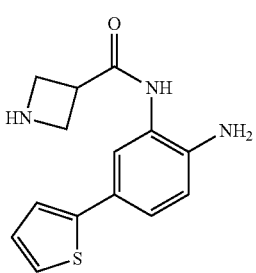

(43)

N-(2-amino-5-(thiophen-2-yl)phenyl)azetidine-3-carboxamide (43) was prepared by substituting tetrahydro-2H-pyran-4-carboxylic acid in Scheme 5 with 1-(tert-butoxycarbonyl)azetidine-3-carboxylic acid. ESI+ MS: m/z 274 ([M+H]$^+$), 1H NMR (500 MHz, d$^6$-DMSO): δ 9.30 (s, 1H), 7.54 (s, 1H), 7.34 (d, J=5.0 Hz, 1H), 7.24-7.18 (m, 2H), 7.05-7.02 (m, 1H), 6.74 (d, J=8.5 Hz, 1H), 5.13 (s, 2H), 3.80-3.60 (m, 4H).

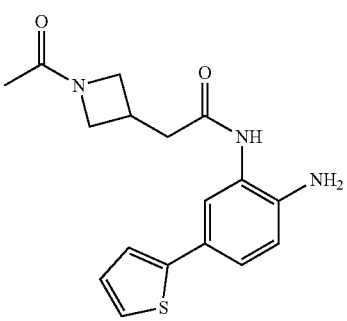

(9)

2-(1-acetylazetidin-3-yl)-N-(2-amino-5-(thiophen-2-yl)phenyl)acetamide (9) was prepared by substituting tetrahydro-2H-pyran-4-carboxylic acid in Scheme 5 with 2-(1-acetylazetidin-3-yl)acetic acid. ESI+ MS: m/z 330 ([M+H]$^+$), 1H NMR (500 MHz, d$^6$-DMSO): δ 9.19 (s, 1H), 7.49 (d, J=2.0 Hz, 1H), 7.34 (d, J=5.0 Hz, 1H), 7.22 (dd, J=2.0, 8.0 Hz, 1H), 7.19 (d, J=3.0 Hz, 1H), 7.03 (t, J=5.0 Hz, 1H), 6.74 (d, J=8.0 Hz, 1H), 5.09 (s, 2H), 4.24 (t, J=8.5 Hz, 1H), 3.95 (t, J=9.5 Hz, 1H), 3.86 (dd, J=6.0, 8.5 Hz, 1H), 3.57 (dd, J=6.0, 9.5 Hz, 1H), 2.96-2.86 (m, 1H), 2.70 (d, J=7.5 Hz, 2H), 1.74 (s, 3H).

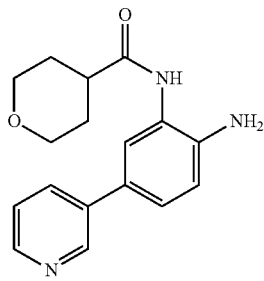

(51)

N-(2-amino-5-(pyridin-3-yl)phenyl)tetrahydro-2H-pyran-4-carboxamide (51) was prepared by substituting thiophen-2-ylboronic acid in Scheme 2 with pyridin-3-ylboronic acid. ESI+ MS: m/z 298 ([M+H]$^+$), 1H NMR (500 MHz, d$^6$-DMSO): δ 9.15 (s, 1H), δ 8.75 (s, 1H), δ 8.44 (d, J=4.0 Hz, 1H), δ 7.89 (d, J=8.5 Hz, 1H), δ 7.59 (d, J=1.5, 1H), δ 7.39 (dd, J=7.5; 4.5 Hz, 1H), δ 7.31 (dd, J=8.0; 1.5 Hz, 1H), δ 6.84 (d, J=8.5 Hz, 1H), δ 5.11 (s, 2H), δ 3.92 (d, J=9.5 Hz, 2H), δ 3.37 (t, J=9.5 Hz, 2H), δ 2.70-2.61 (m, 1H), δ 1.80-1.63 (m, 4H)

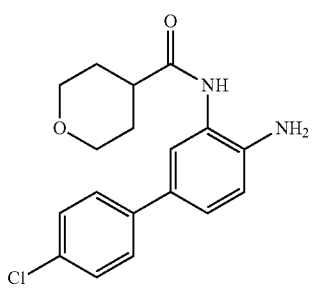

(53)

N-(4-amino-4'-chloro-[1,1'-biphenyl]-3-yl)tetrahydro-2H-pyran-4-carboxamide (53) was prepared by substituting thiophen-2-ylboronic acid in Scheme 2 with (4-chlorophenyl)boronic acid. ESI+ MS: m/z 331 ([M+H]$^+$), 1H NMR (500 MHz, d$^6$-DMSO): δ 9.12 (s, 1H), 7.55 (s, 1H), 7.53 (d, J=9.0 Hz, 2H), 7.42 (d, J=9.0 Hz, 2H), 7.25 (dd, J=8.5 Hz; 1 Hz, 1H), 6.80 (d, J=8.0 Hz, 1H), 5.07 (s, 2H), 3.91 (d, J=10.5 Hz, 2H), 3.40-3.31 (m, 2H), 2.70-2.62 (m, 1H), 1.77-1.63 (m, 4H).

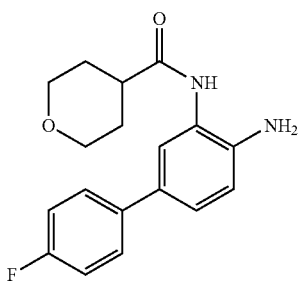

(54)

N-(4-amino-4'-fluoro-[1,1'-biphenyl]-3-yl)tetrahydro-2H-pyran-4-carboxamide (54) was prepared by substituting thiophen-2-ylboronic acid in Scheme 2 with (4-fluorophenyl)boronic acid. ESI+ MS: m/z 331 ([M+H]$^+$), 1H NMR (500 MHz, d⁶-DMSO): δ 9.12 (s, 1H), 7.55 (s, 1H), 7.53 (d, J=9.0 Hz, 2H), 7.42 (d, J=9.0 Hz, 2H), 7.25 (dd, J=8.5 Hz; 1 Hz, 1H), 6.80 (d, J=8.0 Hz, 1H), 5.07 (s, 2H), 3.91 (d, J=10.5 Hz, 2H), 3.40-3.31 (m, 2H), 2.70-2.62 (m, 1H), 1.77-1.63 (m, 4H).

(55)

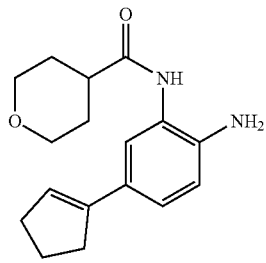

N-(2-amino-5-(cyclopent-1-en-1-yl)phenyl)tetrahydro-2H-pyran-4-carboxamide (55) was prepared by substituting thiophen-2-ylboronic acid in Scheme 2 with cyclopent-1-en-1-ylboronic acid. ESI+ MS: m/z 287 ([M+H]⁺), 1H NMR (500 MHz, d⁶-DMSO): δ 9.09 (s, 1H), 7.25 (d, J=2.0 Hz, 1H), 7.05 (dd, J=2.0, 9.0 Hz, 1H), 6.68 (d, J=8.0 Hz, 1H), 5.93 (s, 1H), 4.92 (bs, 2H), 3.94-3.86 (m, 2H), 3.42-3.20 (m, 2H), 2.66-2.58 (m, 1H), 2.58-2.50 (m, 2H), 2.46-2.40 (m, 2H), 1.91 (quintet, J=7.5 Hz, 2H), 1.80-1.60 (m, 4H)

(44)

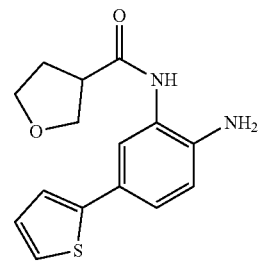

N-(2-amino-5-(thiophen-2-yl)phenyl)tetrahydrofuran-3-carboxamide (44) was prepared by substituting tetrahydro-2H-pyran-4-carboxylic acid in Scheme 5 with tetrahydrofuran-3-carboxylic acid. ESI+ MS: m/z 289 ([M+H]⁺), 1H NMR (500 MHz, d⁶-DMSO): δ 9.27 (s, 1H), 7.50 (s, 1H), 7.35 (d, J=5.0 Hz, 1H), 7.25-7.18 (m, 2H), 7.04 (t, J=4.5 Hz, 1H), 6.76 (d, J=8.0 Hz, 1H), 5.11 (s, 2H), 3.96 (t, J=8 Hz, 1H), 3.82-3.68 (m, 3H), 3.25-3.15 (m, 1H), 2.10 (q, J=7.5 Hz, 2H)

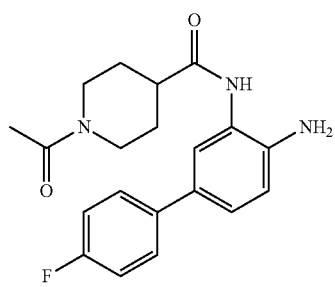 [SMILES: CC(=O)N1CCC(C(=O)Nc2cc(-c3ccc(F)cc3)ccc2N)CC1]

1-acetyl-N-(4-amino-4'-fluoro-[1,1'-biphenyl]-3-yl)piperidine-4-carboxamide (39) was prepared by substituting tetrahydro-2H-pyran-4-carboxylic acid in Scheme 5 with 1-acetylpiperidine-4-carboxylic acid and by substituting thiophen-2-ylboronic acid in Scheme 2 with (4-fluorophenyl)boronic acid. ESI+ MS: m/z 356 ([M+H]⁺), 1H NMR (500 MHz, d⁶-DMSO): δ 9.16 (s, 1H), 7.58-7.46 (m, 3H), 7.28-7.16 (m, 3H), 6.80 (d, J=8 Hz, 1H), 5.00 (s, 2H), 4.40 (d, J=12.5 Hz, 1H), 3.87 (d, J=13.5 Hz, 1H), 3.08 (t, J=12.5 Hz, 1H), 2.70-2.55 (m, 2H), 2.01 (s, 3H), 1.86 (t, J=13.5 Hz, 2H), 1.68-1.55 (m, 1H), 1.55-1.40 (m, 1H)

(52)

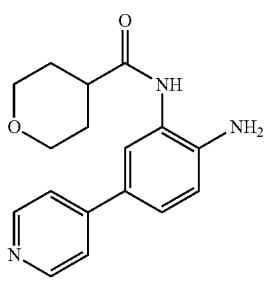

N-(2-amino-5-(pyridin-4-yl)phenyl)tetrahydro-2H-pyran-4-carboxamide (52) was prepared by substituting thiophen-2-ylboronic acid in Scheme 2 with pyridin-4-ylboronic acid. ESI+ MS: m/z 298 ([M+H]⁺), 1H NMR (500 MHz, d⁶-DMSO): δ 9.13 (s, 1H), 8.50 (d, J=5 Hz, 2H), 7.71 (d, J=1.5 Hz, 1H), 7.53 (d, J=5.5 Hz, 2H), 7.42 (dd, J=8.5; 2 Hz, 1H), 6.83 (d, J=8.5 Hz, 1H), 5.27 (s, 2H), 3.92 (d, J=9 Hz, 2H), 3.37 (dt, J=10.5 Hz; 1.5 Hz, 2H), 2.70-2.62 (m, 1H), 1.80-1.64 (m 4H)

(32)

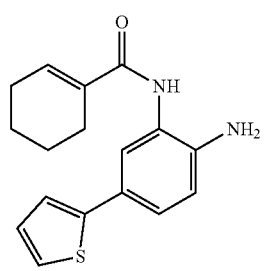

N-(2-amino-5-(thiophen-2-yl)phenyl)cyclohex-1-enecarboxamide (32) was prepared by substituting tetrahydro-2H-pyran-4-carboxylic acid in Scheme 5 with cyclohex-1-enecarboxylic acid. ESI+ MS: m/z 299 ([M+H]⁺), 1H NMR (500 MHz, d⁶-DMSO): δ 9.01 (s, 1H), 7.40 (s, 1H), 7.34 (d, J=4.5 Hz, 1H), 7.28-7.18 (m, 2H), 7.04 (t, J=4.0 Hz, 1H), 6.77 (d, J=8.0 Hz, 1H), 6.72 (bs, 1H), 5.01 (s, 2H), 2.32-2.26 (m, 2H), 2.22-2.14 (m, 2H), 1.66-1.55 (m, 4H).

(33)

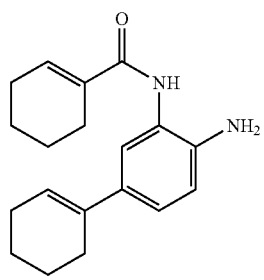

N-(4-amino-2',3',4',5'-tetrahydro-[1,1'-biphenyl]-3-yl)cyclohex-1-enecarboxamide (33) was prepared by substituting tetrahydro-2H-pyran-4-carboxylic acid in Scheme 5 with cyclohex-1-enecarboxylic acid and by substituting thiophen-2-ylboronic acid in Scheme 2 with cyclohex-1-en-1-ylboronic acid.

ESI+ MS: m/z 297 ([M+H]⁺), 1H NMR (500 MHz, d⁶-DMSO): δ 8.95 (s, 1H), 7.16 (s, 1H), 7.01 (d, J=8.0 Hz, 1H), 6.73-6.66 (m, 2H), 5.93 (s, 1H), 4.92 (bs, 2H), 2.30-2.22 (m, 4H), 2.20-2.10 (m, 4H), 1.72-1.54 (m, 8H).

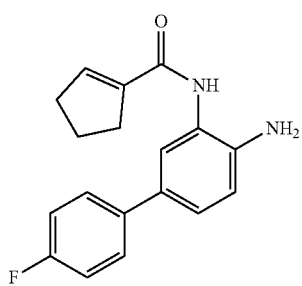

(18)

N-(4-amino-4'-fluoro-[1,1'-biphenyl]-3-yl)cyclopent-1-enecarboxamide (18) was prepared by substituting tetrahydro-2H-pyran-4-carboxylic acid in Scheme 5 with cyclopent-1-enecarboxylic acid and by substituting thiophen-2-ylboronic acid in Scheme 2 with (4-fluorophenyl)boronic acid.

ESI+ MS: m/z 297 ([M+H]⁺), 1H NMR (500 MHz, d⁶-DMSO): δ 9.09 (s, 1H), 7.54 (dd, J=8.5; 5.5 Hz, 2H), 7.41 (d, J=2 Hz, 1H), 7.25 (dd, J=8; 2 Hz, 1H), 7.19 (t, J=12.5 Hz, 2H), 6.82 (d, J=8 Hz, 1H), 6.69 (s, 1H), 4.98 (s, 2H), 2.62-2.54 (m, 2H), 2.54-2.43 (m, 2H), 1.91 (q, J=7.5 Hz, 2H).

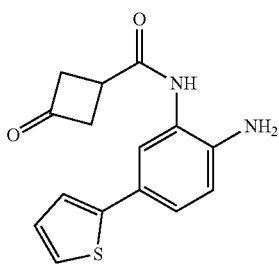

(15)

N-(2-amino-5-(thiophen-2-yl)phenyl)-3-oxocyclobutanecarboxamide (15) was prepared by substituting tetrahydro-2H-pyran-4-carboxylic acid in Scheme 5 with 3-oxocyclobutanecarboxylic acid. ESI+ MS: m/z 287 ([M+H]⁺), 1H NMR (500 MHz, d⁶-DMSO): δ 9.44 (s, 1H), 7.54 (d, J=2.0 Hz, 1H), 7.34 (d, J=4.0 Hz, 1H), 7.25-7.20 (m, 2H), 7.04 (dd, J=4.0, 5.5 Hz, 1H), 6.76 (d, J=8.5 Hz, 1H), 5.13 (s, 2H), 3.43-3.35 (m, 1H), 3.32-3.27 (m, 4H).

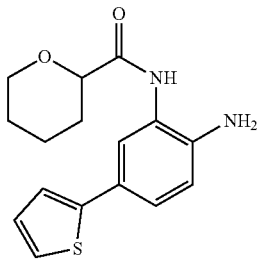

(56)

N-(2-amino-5-(thiophen-2-yl)phenyl)tetrahydro-2H-pyran-2-carboxamide (56) was prepared by substituting tetrahydro-2H-pyran-4-carboxylic acid in Scheme 5 with tetrahydro-2H-pyran-2-carboxylic acid. ESI+ MS: m/z 303 ([M+H]⁺), 1H NMR (500 MHz, d⁶-DMSO): δ 8.97 (s, 1H), 7.51 (s, 1H), 7.35 (d, J=4.5 Hz, 1H), 7.24-7.20 (m, 2H), 7.04 (t, J=4.5 Hz, 1H), 6.78 (d, J=8.5 Hz, 1H), 4.97 (s, 2H), 4.04-3.94 (dd, J=11.5 Hz, 2H), 3.54-3.51 (m, 1H), 1.95-1.84 (m, 2H), 1.54-1.49 (m, 4H).

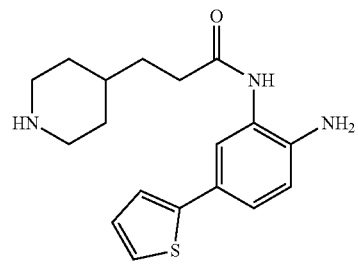

(158)

N-(2-amino-5-(thiophen-2-yl)phenyl)-3-(piperidin-4-yl)propanamide (158) was prepared by substituting tetrahydro-2H-pyran-4-carboxylic acid in Scheme 5 with 3-(1-(tert-butoxycarbonyl)piperidin-4-yl)propanoic acid. ESI+ MS: m/z 330 ([M+H]⁺). 1H NMR (500 MHz, d⁶-DMSO): δ 9.14 (s, 1H), 7.49 (s, 1H), 7.34 (d, J=5.0 Hz, 1H), 7.22-7.18 (m, 2H), 7.04-7.03 (m, 1H), 6.74 (d, J=8.5 Hz, 1H), 5.06 (s, 2H), 3.06 (d, J=12.0 Hz, 2H), 2.60 (t, J=11.0 Hz, 2H), 2.36 (t, J=8.0 Hz, 2H), 1.71 (d, J=12.0 Hz, 2H), 1.57-1.52 (m, 2H), 1.46-1.42 (m, 1H), 1.16-1.11 (m, 4H).

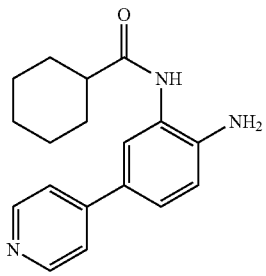

(163)

N-(2-amino-5-(pyridin-4-yl)phenyl)cyclohexanecarboxamide (163) was prepared by substituting tetrahydro-2H-pyran-4-carboxylic acid in Scheme 5 with cyclohexane carboxylic acid and by substituting thiophen-2-ylboronic acid in Scheme 2 with pyridin-4-ylboronic acid. ESI+ MS: m/z 296 ([M]⁺); 1H NMR (500 MHz, d⁶-DMSO): δ 9.07 (s, 1H), 8.50 (d, J=5.5 Hz, 2H), 7.71 (s, 1H), 7.53 (d, J=5.5 Hz, 2H), 7.41-7.39 (m, 1H), 6.82 (d, J=8.5 Hz, 1H), 5.24 (s, 2H), 2.40 (t, J=12.0 Hz, 1H), 1.87-1.64 (m, 5H), 1.46-1.39 (m, 2H), 1.32-1.18 (m, 3H).

2-methylpropanoic acid. ESI+ MS: m/z 277 ([M+H]⁺); 1H NMR (500 MHz, d⁶-DMSO): δ 9.04 (s, 1H), 7.61 (s, 1H), 7.35 (d, J=4.5 Hz, 1H), 7.24-7.21 (m, 2H), 7.05-7.03 (m, 1H), 6.79 (d, J=8.0 Hz, 1H), 5.64 (s, 1H), 4.97 (s, 2H), 1.37 (s, 6H).

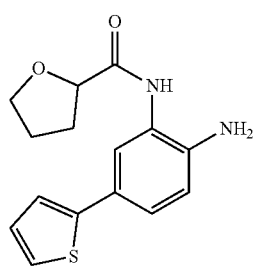

(171)

N-(2-amino-5-(thiophen-2-yl)phenyl)tetrahydrofuran-2-carboxamide (171) was prepared by substituting tetrahydro-2H-pyran-4-carboxylic acid in Scheme 5 with tetrahydrofuran-2-carboxylic acid. ESI+ MS: m/z 289 ([M]⁺); 1H NMR (500 MHz, d⁶-DMSO): δ 9.15 (s, 1H), 7.50 (s, 1H), 7.35 (d, J=5.0 Hz, 1H), 7.25-7.22 (m, 2H), 7.04 (t, J=4.5 Hz, 1H), 6.75 (d, J=8.5 Hz, 1H), 5.00 (s, 2H), 4.44-4.41 (m, 1H), 4.01 (q, J=7.0 Hz, 1H), 3.83 (q, J=7.0 Hz, 1H), 2.22-2.18 (m, 1H), 2.03-1.98 (m, 1H), 1.92-1.85 (m, 2H).

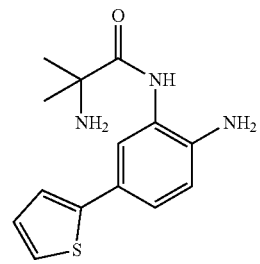

(195)

2-Amino-N-(2-amino-5-(thiophen-2-yl)phenyl)-2-methylpropanamide (195) was prepared by substituting tetrahydro-2H-pyran-4-carboxylic acid in Scheme 5 with 2-((tert-butoxycarbonyl)amino)-2-methylpropanoic acid. ESI+ MS: m/z 276 ([M+H]⁺); 1H NMR (500 MHz, d⁶-DMSO): δ 7.67 (s, 1H), 7.35 (d, J=4.5 Hz, 1H), 7.22-7.20 (m, 2H), 7.04 (t, J=4.0 Hz, 1H), 6.79 (d, J=8.5 Hz, 1H), 4.98 (s, 2H), 1.31 (s, 6H).

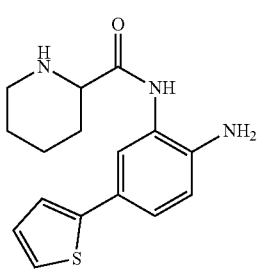

(173)

N-(2-amino-5-(thiophen-2-yl)phenyl)piperidine-2-carboxamide (173) was prepared by substituting tetrahydro-2H-pyran-4-carboxylic acid in Scheme 5 with 1-(tert-butoxycarbonyl)piperidine-2-carboxylic acid. ESI+ MS: m/z 302 ([M]⁺); 1H NMR (500 MHz, d⁶-DMSO): δ 8.86 (bs, 1H), 7.55 (s, 1H), 7.35 (d, J=4.5 Hz, 1H), 7.23-7.19 (m, 2H), 7.05-7.03 (m, 1H), 6.76 (d, J=8.0 Hz, 1H), 5.05 (s, 2H), 3.23 (d, J=6.5 Hz, 1H), 2.99 (d, J=11.5 Hz, 1H), 2.57 (t, J=11.0 Hz, 1H), 1.85-1.78 (m, 2H), 1.52-1.34 (m, 4H).

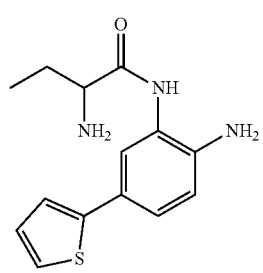

(196)

2-Amino-N-(2-amino-5-(thiophen-2-yl)phenyl)butanamide (196) was prepared by substituting tetrahydro-2H-pyran-4-carboxylic acid in Scheme 5 with 2-((tert-butoxycarbonyl)amino)butanoic acid. ESI+ MS: m/z 276 ([M+H]⁺); 1H NMR (500 MHz, d⁶-DMSO): δ 9.59 (s, 1H), 7.34 (d, J=5.0 Hz, 1H), 7.23-7.19 (m, 2H), 7.04 (t, J=4.0 Hz, 1H), 6.77 (d, J=8.5 Hz, 1H), 5.04 (s, 2H), 3.30-3.27 (m, 2H), 1.74-. 167 (m, 1H), 1.55-1.49 (m, 1H), 0.94 (t, J=7.0 Hz, 3H).

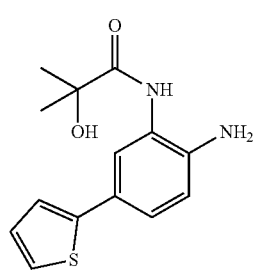

(200)

N-(2-amino-5-(thiophen-2-yl)phenyl)-2-hydroxy-2-methylpropanamide (200) was prepared by substituting tetrahydro-2H-pyran-4-carboxylic acid in Scheme 5 with 2-hydroxy-

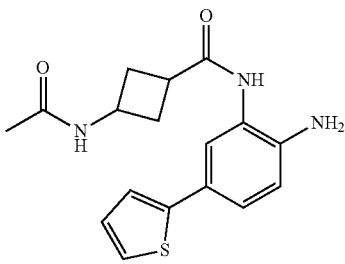

(14)

3-Acetamido-N-(2-amino-5-(thiophen-2-yl)phenyl)cyclobutanecarboxamide (14) was prepared by substituting tetrahydro-2H-pyran-4-carboxylic acid in Scheme 5 with 3-acetamidocyclobutanecarboxylic acid. ESI+ MS: m/z 330

([M+H]+), 1H NMR (500 MHz, d6-DMSO): δ 9.10 (s, 1H), 8.16 (d, J=7.5 Hz, 1H), 7.5 (s, 1H), 7.32 (d, J=5.0 Hz, 1H), 7.21-7.18 (m, 2H), 7.02 (t, J=4.0 Hz, 1H), 6.73 (d, J=8.5 Hz, 1H), 5.05 (s, 2H), 4.15 (q, J=9.0 Hz, 1H), 2.91-2.88 (m, 1H), 2.38-2.35 (m, 2H), 2.10 (q, J=10.0 Hz, 2H), 1.75 (s, 3H).

(21)

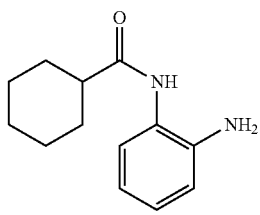

N-(2-aminophenyl)cyclohexanecarboxamide (21) was prepared by substituting tetrahydro-2H-pyran-4-carboxylic acid in Scheme 5 with cyclohexanecarboxylic acid and by substituting tert-butyl (2-amino-4-(thiophen-2-yl)phenyl) carbamate in Scheme 5 with tert-butyl (2-aminophenyl) carbamate. ESI+ MS: m/z 319 ([M+H]+), 1H NMR (300 MHz, d6-DMSO): δ 9.02 (s, 1H), 7.15 (d, J=9 Hz, 1H), 6.89 (t, J=6 Hz, 1H), 6.71 (d, J=6 Hz, 1H), 6.54 (t, J=6 Hz, 1H), 4.79 (bs, 2H), 1.87-1.72 (m, 4H), 1.45-1.38 (m, 2H), 1.33-1.18 (m, 4H).

(36)

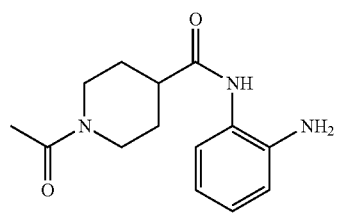

1-Acetyl-N-(2-aminophenyl)piperidine-4-carboxamide (36) was prepared by substituting tetrahydro-2H-pyran-4-carboxylic acid in Scheme 5 with piperidine-1,4-dicarboxylic acid and by substituting tert-butyl (2-amino-4-(thiophen-2-yl)phenyl)carbamate in Scheme 5 with tert-butyl (2-aminophenyl)carbamate. ESI+ MS: m/z 262 ([M+H]+), 1H NMR (500 MHz, d6-DMSO): δ 9.12 (s, 1H), 7.15 (d, J=6 Hz, 1H), 6.90 (t, J=9 Hz, 1H), 6.72 (d, J=9 Hz, 1H), 6.54 (t, J=9 Hz, 1H), 4.82 (bs, 2H), 4.49-4.60 (m, 2H), 3.90-3.75 (m, 2H), 3.30-3.00 (m, 2H), 2.40-2.30 (m, 1H), 2.01 (s, 3H), 1.70-1.65 (m, 2H).

(19)

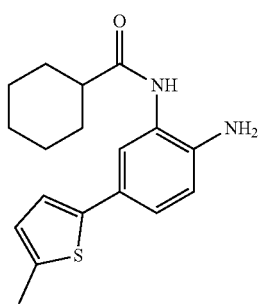

N-(2-amino-5-(5-methylthiophen-2-yl)phenyl)cyclohexanecarboxamide (19) was prepared by substituting tetrahydro-2H-pyran-4-carboxylic acid in Scheme 5 with cyclohexanecarboxylic acid and by substituting thiophen-2-ylboronic acid in Scheme 2 with 5-methylthiophen-2-ylboronic acid.

ESI+ MS: m/z 315 ([M+H]+), 1H NMR (300 MHz, d6-DMSO): δ 9.07 (s, 1H), 7.44 (d, J=3 Hz, 1H), 7.14 (dd, J=3 Hz, 6 Hz, 1H), 6.98 (d, J=3 Hz, 1H), 6.75-6.64 (m, 2H0, 5.01 (bs, 1H0, 2.45-2.41 (m, 3H), 1.90-1.71 (m, 4H), 1.70-1.63 (m, 1H), 1.50-1.38 (m, 2H0, 1.37-1.16 (m, 5H).

(46)

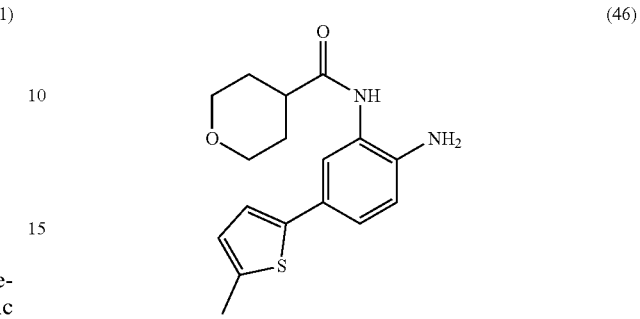

N-(2-amino-5-(5-methylthiophen-2-yl)phenyl)tetrahydro-2H-pyran-4-carboxamide (46) was prepared by substituting thiophen-2-ylboronic acid in Scheme 2 with 5-methylthiophen-2-ylboronic acid. ESI+ MS: m/z 315 ([M+H]+), 1H NMR (500 MHz, d6-DMSO): δ 9.19 (s, 1H0, 7.49 (d, J=3, 1H), 7.20 (dd, J=3 Hz, 9 Hz, 1H), 3.60-6.70 (m, 2H), 5.08 (bs, 2H0, 4.01-3.90 (m, 2H), 3.48-3.44 9m, 1H), 2.78-2.61 (m, 2H), 2.48 (s, 3H), 1.85-1.65 (m, 4H0, 1.32-1.28 (m, 1H).

(20)

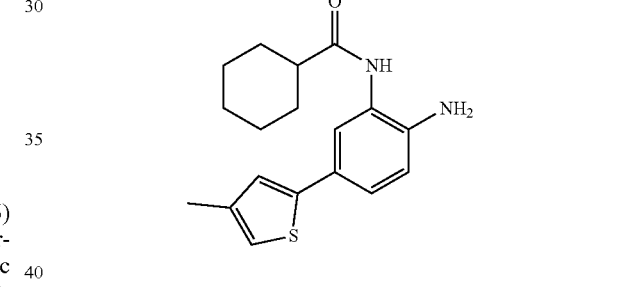

N-(2-amino-5-(4-methylthiophen-2-yl)phenyl)cyclohexanecarboxamide (20) was prepared by substituting tetrahydro-2H-pyran-4-carboxylic acid in Scheme 5 with cyclohexanecarboxylic acid and by substituting thiophen-2-ylboronic acid in Scheme 2 with 4-methylthiophen-2-ylboronic acid. 1H NMR (500 MHz, d6-DMSO): δ 9.06 (s, 1H), 7.49 (d, J=3 Hz, 1h), 7.16 (dd, J=6 Hz, 1H), 7.03 (s, 1H), 6.92 (s, 1H0, 6.74 (d, J=6 Hz, 1H), 5.06 (bs, 2H), 2.20 (s, 3H), 1.90-1.70 (m, 4H), 1.69-1.61 9m, 1H).

(47)

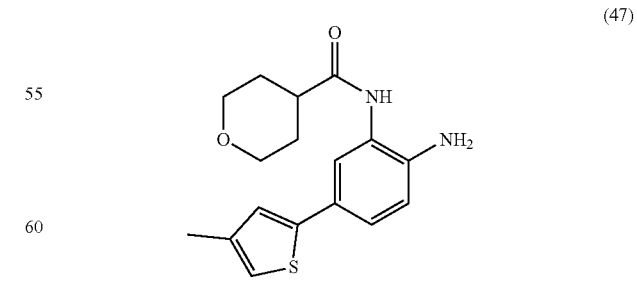

N-(2-amino-5-(4-methylthiophen-2-yl)phenyl)tetrahydro-2H-pyran-4-carboxamide (47) was prepared by substituting thiophen-2-ylboronic acid in Scheme 2 with 4-methylthiophen-2-ylboronic acid. ESI+ MS: m/z XXX ([M+H]+), 1H NMR (300 MHz, d6-DMSO): δ 9.12 (s, 1H), 7.49 (d, J=1 Hz, 1H), 7.18 (dd, J=1 Hz, 9 Hz, 1H0, 7.04 (s, 1H), 6.92 (s, 1h)m, 6.74 (d, J=9 Hz, 1H), 5.07 (s, 2H), 4.00-3.85 (m, 2h), 3.43-3.41 (m, 1H), 2.20 (s, 3h), 1.80-1.60 (m, 5H), 1.24 (bs, 1H).

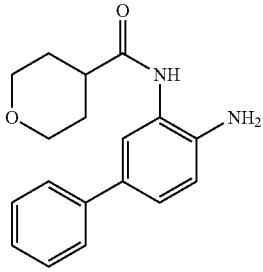

(49)

N-(4-amino-[1,1'-biphenyl]-3-yl)tetrahydro-2H-pyran-4-carboxamide (49) was prepared by substituting thiophen-2-ylboronic acid in Scheme 2 with phenyl boronic acid. ESI+ MS: m/z 297 ([M+H]+), 1H NMR (500 MHz, d6-DMSO): δ 91.5 (s, 1H), 7.60-7.45 (m, 3H), 7.44-7.36 (m, 2H), 7.30-7.20 (m, 2H), 6.81 (d, J=6 Hz, 1H), 5.02 (s, 1H), 3.93 (d, J=9 Hz, 2H), 3.43-3.36 (m, 2H), 1.80-1.60 (m, 4H).

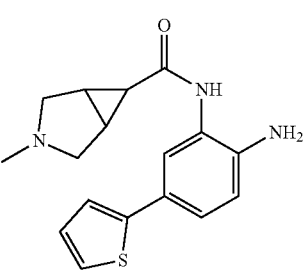

(58)

N-(2-amino-5-(thiophen-2-yl)phenyl)-3-methyl-3-azabicyclo[3.1.0]hexane-6-carboxamide (58) was prepared by substituting tetrahydro-2H-pyran-4-carboxylic acid in Scheme 5 with 3-methyl-3-azabicyclo[3.1.0]hexane-6-carboxylic acid. ESI+ MS: m/z 314 ([M+H]+), 1H NMR (500 MHz, d6-DMSO): δ 9.31 (s, 1H), 7.60 (d, J=1.0 Hz, 1H), 7.33 (d, J=5.0 Hz, 1H), 7.22-7.15 (m, 2H), 7.03 (t, J=4.5 Hz, 1H), 6.73 (d, J=8.5 Hz, 1H), 5.09 (s, 2H), 3.04-2.95 (m, 2H), 2.38-2.20 (m, 6H), 1.90-1.80 (m, 2H).

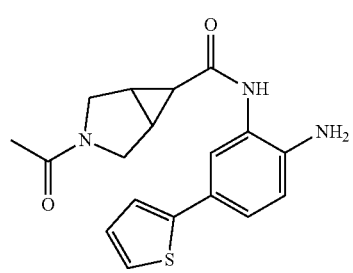

(57)

3-acetyl-N-(2-amino-5-(thiophen-2-yl)phenyl)-3-azabicyclo[3.1.0]hexane-6-carboxamide (57) was prepared by substituting tetrahydro-2H-pyran-4-carboxylic acid in Scheme 5 with 3-acetyl-3-azabicyclo[3.1.0]hexane-6-carboxylic acid. ESI+ MS: m/z 342 ([M+H]+), 1H NMR (500 MHz, d6-DMSO): δ 9.35 (s, 1H), 7.59 (d, J=2.0 Hz, 1H), 7.34 (d, J=5.0 Hz, 1H), 7.24-7.16 (m, 2H), 7.03 (t, J=4.0 Hz, 1H), 6.74 (d, J=8.5 Hz, 1H), 5.11 (s, 2H), 3.75-3.60 (m, 3H), 3.35-3.30 (m, 1H), 2.12-1.98 (m, 2H), 1.93 (s, 3H), 1.71-1.67 (m, 1H).

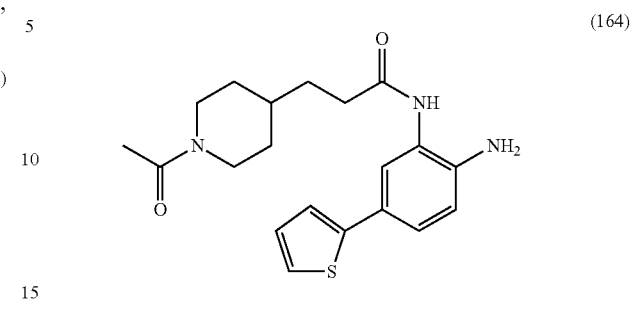

(164)

3-(1-Acetylpiperidin-4-yl)-N-(2-amino-5-(thiophen-2-yl)phenyl)propanamide (164) was prepared by substituting tetrahydro-2H-pyran-4-carboxylic acid in Scheme 5 with 3-(1-acetylpiperidin-4-yl)propanoic acid. ESI+ MS: m/z 372 ([M]+); 1HNMR (500 MHz, d6-DMSO): δ 9.15 (s, 1H), 7.49 (s, 1H), 7.34 (d, J=5.5 Hz, 1H), 7.22-7.19 (m, 2H), 7.03 (t, J=4.5 Hz, 1H), 6.74 (d, J=8.5 Hz, 1H), 5.06 (s, 2H), 4.36 (d, J=13.0 Hz, 1H), 3.79 (d, J=13.0 Hz, 1H), 2.98 (t, J=12.5 Hz, 1H), 2.37 (t, J=7.5 Hz, 2H), 1.97 (s, 3H), 1.71 (t, J=14.0 Hz, 2H), 1.57-1.50 (m, 3H), 1.09-0.93 (m, 2H).

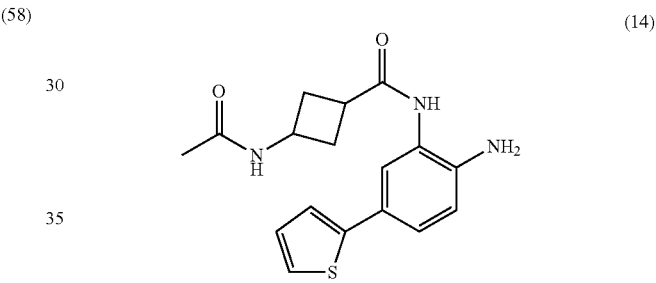

(14)

3-Acetamido-N-(2-amino-5-(thiophen-2-yl)phenyl)cyclobutanecarboxamide (14) was prepared by substituting tetrahydro-2H-pyran-4-carboxylic acid in Scheme 5 with 3-acetamidocyclobutanecarboxylic acid. ESI+ MS: m/z 330 ([M+H]+), 1H NMR (500 MHz, d6-DMSO): δ 9.10 (s, 1H), 8.16 (d, J=7.5 Hz, 1H), 7.5 (s, 1H), 7.32 (d, J=5.0 Hz, 1H), 7.21-7.18 (m, 2H), 7.02 (t, J=4.0 Hz, 1H), 6.73 (d, J=8.5 Hz, 1H), 5.05 (s, 2H), 4.15 (q, J=9.0 Hz, 1H), 2.91-2.88 (m, 1H), 2.38-2.35 (m, 2H), 2.10 (q, J=10.0 Hz, 2H), 1.75 (s, 3H).

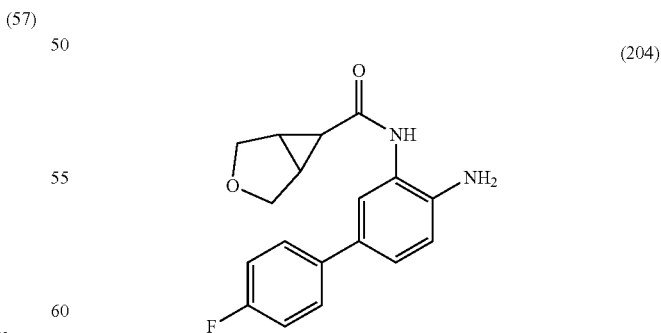

(204)

N-(4-amino-4'-fluoro-[1,1'-biphenyl]-3-yl)-3-oxabicyclo[3.1.0]hexane-6-carboxamide (204) was prepared by substituting tetrahydro-2H-pyran-4-carboxylic acid in Scheme 5 with tert-butyl 3-acetyl-3-azabicyclo[3.1.0]hexane-6-carboxylate and tert-butyl (2-amino-4-(thiophen-2-yl)phenyl)

carbamate in Scheme 5 with tert-butyl (3-amino-4'-fluoro-[1,1'-biphenyl]-4-yl)carbamate. ESI+ MS: m/z 313 ([M+H]$^+$), 1H NMR (500 MHz, d$^6$-DMSO): δ 9.38 (s, 1H), 7.58 (s, 1H), 7.53-7.50 (m, 2H), 7.21-7.18 (m, 3H), 6.79 (d, J=8.5 Hz, 1H), 5.04 (s, 2H), 3.85 (d, J=8.5 Hz, 2H), 3.67 (d, J=8.5 Hz, 2H), 2.08 (s, 2H), 1.77 (m, 1H).

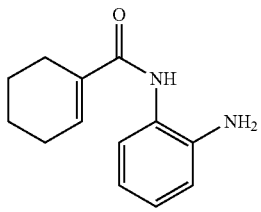

(244)

N-(2-aminophenyl)cyclohex-1-enecarboxamide (244) was prepared by substituting tetrahydro-2H-pyran-4-carboxylic acid in Scheme 5 with cyclohex-1-enecarboxylic acid and tert-butyl (2-amino-4-(thiophen-2-yl)phenyl)carbamate in Scheme 5 with tert-butyl (2-aminophenyl)carbamate. ESI+ MS: m/z 217 ([M+H]$^+$), 1H NMR (400 MHz, d$^6$-DMSO): δ 8.98 (s, 1H), 7.14-7.12 (m, 1H), 6.98-6.94 (m, 1H), 6.79 (dd, J$_{1,2}$=1.2 Hz, J$_{1,3}$=8.0 Hz, 2H), 6.62-6.58 (m, 1H), 4.80 (s, 2H), 2.31 (t, J=2.0 Hz, 2H), 2.22-2.21 (m, 2H), 1.69-1.60 (m, 4H).

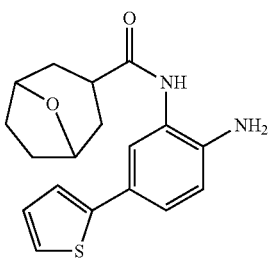

(182)

N-(2-amino-5-(thiophen-2-yl)phenyl)-8-oxabicyclo[3.2.1]octane-3-carboxamide (182) was prepared by substituting tetrahydro-2H-pyran-4-carboxylic acid in Scheme 5 with 8-oxabicyclo[3.2.1]octane-3-carboxylic acid. ESI+ MS: m/z 329 ([M+H]$^+$), 1H NMR (500 MHz, d$^6$-DMSO): δ 9.07 (s, 1H), 7.48 (s, 1H), 7.34 (d, J=5.0 Hz, 1H), 7.22-7.19 (m, 2H), 7.03 (t, J=4.0 Hz, 1H), 6.74 (d, J=8.5 Hz, 1H), 5.04 (s, 2H), 4.34 (bs, 2H), 2.91-2.89 (m, 1H), 1.86-1.76 (m, 6H), 1.62-1.58 (m, 2H).

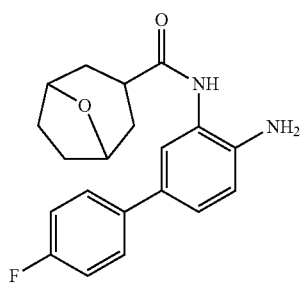

(191)

N-(4-amino-4'-fluoro-[1,1'-biphenyl]-3-yl)-8-oxabicyclo[3.2.1]octane-3-carboxamide (191) was prepared by substituting tetrahydro-2H-pyran-4-carboxylic acid in Scheme 5 with 8-oxabicyclo[3.2.1]octane-3-carboxylic acid and tert-butyl (2-amino-4-(thiophen-2-yl)phenyl)carbamate in Scheme 5 with tert-butyl (3-amino-4'-fluoro-[1,1'-biphenyl]-4-yl)carbamate. ESI+ MS: m/z 341 ([M+H]$^+$), 1H NMR (500 MHz, d$^6$-DMSO): δ 9.05 (s, 1H), 7.53-7.49 (m, 3H), 7.21-7.18 (m, 3H), 6.79 (d, J=8.5 Hz, 1H), 4.98 (s, 2H), 4.34 (s, 2H), 2.90-2.89 (m, 1H), 1.87-1.77 (m, 6H), 1.60 (dd, J=4.5 Hz, J=12.5 Hz, 2H).

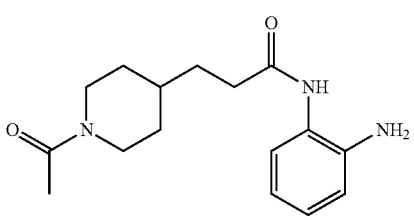

(206)

3-(1-acetylpiperidin-4-yl)-N-(2-aminophenyl)propanamide (206) was prepared by substituting tetrahydro-2H-pyran-4-carboxylic acid in Scheme 5 with 3-(1-(tert-butoxycarbonyl)piperidin-4-yl)propanoic acid and tert-butyl (2-amino-4-(thiophen-2-yl)phenyl)carbamate in Scheme 5 with tert-butyl (2-aminophenyl)carbamate. ESI+ MS: m/z 290 ([M+H]$^+$), 1H NMR (300 MHz, d$^6$-DMSO): δ 9.12 (s, 1H), 7.15 (d, J=9 Hz, 1H), 6.89 (t, J=9 Hz, 1H), 6.72 (t, J=9 Hz, 1H), 4.35 (d, J=45 Hz, 1H), 3.79 (d, J=45 Hz, 1H), 3.01-2.93 (m, 2H), 2.36-2.32 (m, 2H), 1.97 (s, 3H), 1.74-1.66 (m, 2H), 1.57-1.50 (m, 3H), 1.08-0.91 (m, 2H).

(208)

N-(4-amino-4'-fluoro-[1,1'-biphenyl]-3-yl)-6-oxospiro[3.3]heptane-2-carboxamide (208) was prepared by substituting tetrahydro-2H-pyran-4-carboxylic acid in Scheme 5 with 1,6-oxospiro[3.3]heptane-2-carboxylic acid and tert-butyl (2-amino-4-(thiophen-2-yl)phenyl)carbamate in Scheme 5 with tert-butyl (3-amino-4'-fluoro-[1,1'-biphenyl]-4-yl)carbamate. ESI+ MS: m/z 340 ([M+H]$^+$), 1H NMR (500 MHz, d$^6$-DMSO): δ 7.80 (bs, 1H), 7.55-7.51 (m, 2H), 7.37 (d, J=2.5 Hz, 1H), 7.20 (t, J=11.0 Hz, 3H), 6.79 (d, J=10.5 Hz, 1H), 5.15 (bs, 2H), 4.14 (s, 4H), 3.33 (s, 4H).

(214)

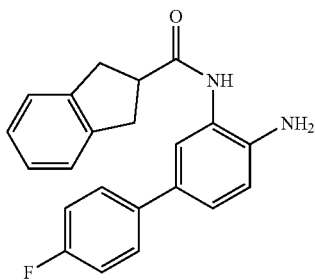

N-(4-amino-4'-fluoro-[1,1'-biphenyl]-3-yl)-2,3-dihydro-1H-indene-2-carboxamide (214) was prepared by substituting tetrahydro-2H-pyran-4-carboxylic acid in Scheme 5 with 2,3-dihydro-1H-indene-2-carboxylic acid and tert-butyl (2-amino-4-(thiophen-2-yl)phenyl)carbamate in Scheme 5 with tert-butyl (3-amino-4'-fluoro-[1,1'-biphenyl]-4-yl)carbamate. ESI+ MS: m/z 346 ([M+H]+), 1H NMR (400 MHz, d6-DMSO): δ 9.30 (s, 1H), 7.54 (dd, $J_{1,2}$=5.6 Hz, $J_{1,3}$=8.4 Hz, 3H), 7.23-7.13 (m, 7H), 6.81 (d, J=8.4 Hz, 1H), 5.04 (s, 2H), 3.52-3.43 (m, 1H), 3.20 (d, J=8.8 Hz, 4H).

(207)

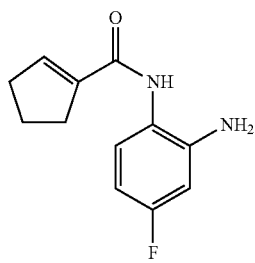

N-(2-amino-4-fluorophenyl)cyclopent-1-enecarboxamide (207) was prepared by substituting tetrahydro-2H-pyran-4-carboxylic acid in Scheme 5 with cyclopent-1-enecarboxylic acid and tert-butyl (2-amino-4-(thiophen-2-yl)phenyl)carbamate in Scheme 5 with tert-butyl 2-amino-5-fluorophenylcarbamate. ESI+ MS: m/z 321 ([M+H]+), 1H NMR (300 MHz, d6-DMSO): δ 8.98 (s, 1H), 7.02 (dd, $J_1$=6 Hz, $J_2$=3 Hz, 1H), 6.66 (bs, 1H), 6.50 (dd, $J_1$=3 Hz, $J_2$=12 Hz, 1H), 6.32 (dt, $J_1$=3 Hz, $J_2$=9 Hz, 1H), 5.13 (s, 2H), 2.59-2.54 (m, 3H), 1.95-1.84 (m, 3H).

(205)

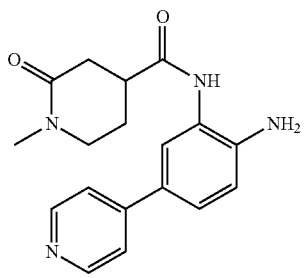

N-(2-amino-5-(pyridin-4-yl)phenyl)-1-methyl-2-oxopiperidine-4-carboxamide (205) was prepared by substituting tetrahydro-2H-pyran-4-carboxylic acid in Scheme 5 with 1-methyl-2-oxopiperidine-4-carboxylic acid and tert-butyl (2-amino-4-(thiophen-2-yl)phenyl)carbamate in Scheme 5 with tert-butyl (2-amino-4-(pyridin-4-yl)phenyl)carbamate. ESI+ MS: m/z 325 ([M+H]+); 1H NMR (500 MHz, d6-DMSO): δ 9.24 (s, 1H), 8.50 (d, J=5.0 Hz, 2H), 7.69 (s, 1H), 7.53 (d, J=5.0 Hz, 2H), 7.43 (d, J=7.5 Hz, 1H), 6.83 (d, J=8.5 Hz, 1H), 5.30 (s, 2H), 3.35 (m, 2H), 2.95 (s, 1H), 2.82 (s, 3H), 2.44-2.41 (m, 2H), 2.09 (m, 1H), 1.89 (m, 1H).

(211)

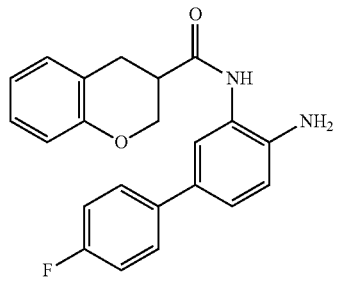

N-(4-amino-4'-fluoro-[1,1'-biphenyl]-3-yl)chroman-3-carboxamide (211) was prepared by substituting tetrahydro-2H-pyran-4-carboxylic acid in Scheme 5 with chroman-3-carboxylic acid and tert-butyl (2-amino-4-(thiophen-2-yl)phenyl)carbamate in Scheme 5 with tert-butyl (3-amino-4'-fluoro-[1,1'-biphenyl]-4-yl)carbamate. ESI+ MS: m/z 363 ([M+H]+); 1H NMR (400 MHz, DMSO-d6): δ 9.41 (s, 1H), 7.53 (dd, J=5.6 Hz, J=8.8 Hz, 3H), 7.25-7.07 (m, 5H), 6.87-6.78 (m, 3H), 5.07 (s, 2H), 4.50 (d, J=10.8 Hz, 1H), 4.00 (t, J=10.0 Hz, 1H), 3.08-2.99 (m, 3H).

(219)

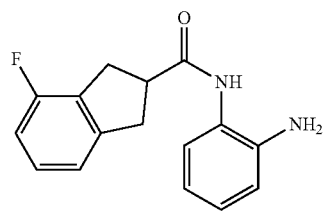

N-(2-aminophenyl)-4-fluoro-2,3-dihydro-1H-indene-2-carboxamide (219) was prepared by substituting tetrahydro-2H-pyran-4-carboxylic acid in Scheme 5 with 4-fluoro-2,3-dihydro-1H-indene-2-carboxylic acid and tert-butyl (2-amino-4-(thiophen-2-yl)phenyl)carbamate in Scheme 2 with tert-butyl (2-aminophenyl)carbamate. ESI+ MS: m/z 271 ([M+H]+); 1H NMR (400 MHz, D6-DMSO-$d_6$): δ 9.26 (s, 1H), 7.22-7.17 (m, 2H), 7.07 (d, J=7.6 Hz, 1H), 6.98-6.88 (m, 2H), 6.73 (dd, J=1.2 Hz, J=8.0 Hz, 1H), 6.56-6.52 (m, 1H), 4.84 (s, 2H), 3.56-3.47 (m, 1H), 3.31-3.11 (m, 4H).

(221)

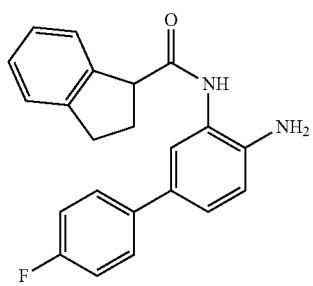

N-(4-amino-4'-fluoro-[1,1'-biphenyl]-3-yl)-2,3-dihydro-1H-indene-1-carboxamide (221) was prepared by substituting tetrahydro-2H-pyran-4-carboxylic acid in Scheme 5 with 2,3-dihydro-1H-indene-1-carboxylic acid and tert-butyl (2-amino-4-(thiophen-2-yl)phenyl)carbamate in Scheme 5 with tert-butyl (3-amino-4'-fluoro-[1,1'-biphenyl]-4-yl)carbamate. ESI+ MS: m/z 347 ([M+H]+); 1H NMR (400 MHz, d6-DMSO): δ 9.61 (s, 1H), 7.55-7.52 (m, 3H), 7.41-7.39 (m, 1H), 7.27-7.18 (m, 6H), 6.86 (d, J=8.0 Hz, 1H), 4.18 (t, J=7.6 Hz, 1H), 3.06-3.03 (m, 1H), 2.92-2.90 (m, 1H), 2.36-2.31 (m, 2H).

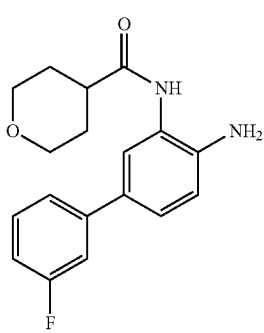

(225)

N-(4-amino-3'-fluoro-[1,1'-biphenyl]-3-yl)tetrahydro-2H-pyran-4-carboxamide (225) was prepared by substituting tert-butyl (2-amino-4-(thiophen-2-yl)phenyl)carbamate in Scheme 5 with tert-butyl (3-amino-3'-fluoro-[1,1'-biphenyl]-4-yl)carbamate. ESI+ MS: m/z 315 ([M+H]+); 1HNMR (400 MHz, d6-DMSO): δ 9.11 (s, 1H), 7.56 (br s, 3H), 7.40-7.26 (m, 4H), 7.02 (t, J=7.6 Hz, 1H), 6.78 (d, J=8.4 Hz, 1H), 5.07 (s, 2H), 3.90 (d, J=11.2 Hz, 2H), 3.37-3.35 (m, 2H), 2.65-2.64 (m, 1H), 1.75-1.65 (m, 4H).

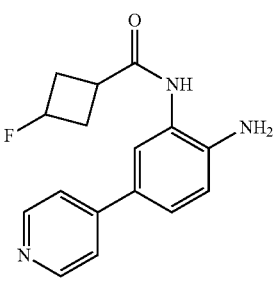

(239)

N-(2-amino-5-(pyridin-4-yl)phenyl)-3-fluorocyclobutanecarboxamide (239) was prepared by substituting tetrahydro-2H-pyran-4-carboxylic acid in Scheme 5 with 3-fluorocyclobutanecarboxylic acid and tert-butyl (2-amino-4-(thiophen-2-yl)phenyl)carbamate in Scheme 5 with tert-butyl (2-amino-4-(pyridin-4-yl)phenyl)carbamate. ESI+ MS: m/z 286 (M+H); 1H NMR (300 MHz, d6-DMSO): δ 9.24 (s, 1H), δ 8.50 (d, J=6 Hz, 2H), δ 7.72 (bs, 1H), δ 7.54 (d, J=6 Hz, 1H), δ 7.43 (d, J=6 Hz, 1H), δ 6.83 (d, J=9 Hz, 1H), δ 5.31 (s, 2H), δ 5.16 (tm, J=69 Hz, 1H), δ 3.35-3.22 (m, 1H), δ 2.62-2.50 (m, 4H).

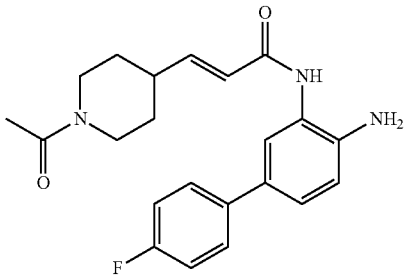

(242)

(E)-3-(1-acetylpiperidin-4-yl)-N-(4-amino-4'-fluoro-[1,1'-biphenyl]-3-yl)acrylamide (242) was prepared by substituting tetrahydro-2H-pyran-4-carboxylic acid in Scheme 5 with (E)-3-(1-acetylpiperidin-4-yl)acrylic acid and tert-butyl (2-amino-4-(thiophen-2-yl)phenyl)carbamate in Scheme 5 with tert-butyl (3-amino-4'-fluoro-[1,1'-biphenyl]-4-yl) carbamate. ESI+ MS: m/z 382 ([M+H]+); 1H NMR (400 MHz, d6-DMSO): δ 9.29 (s, 1H), 7.60-7.51 (m, 3H), 7.23-7.18 (m, 3H), 6.18 (d, J=15.6 Hz, 1H), 5.06 (s, 2H), 4.39 (d, J=13.2 Hz, 1H), 3.84 (d, J=14.0 Hz, 1H), 3.12-3.06 (m, 1H), 2.66-2.49 (m, 2H), 2.00 (s, 3H), 1.76 (t, J=13.6 Hz, 2H), 1.35-1.29 (m, 1H), 1.23-1.15 (m, 1H).

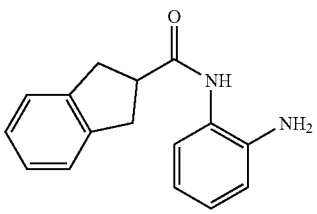

(223)

N-(2-aminophenyl)-2,3-dihydro-1H-indene-2-carboxamide (223) was prepared by substituting tetrahydro-2H-pyran-4-carboxylic acid in Scheme 5 with 2,3-dihydro-1H-indene-2-carboxylic acid and by substituting tert-butyl (2-amino-4-(thiophen-2-yl)phenyl)carbamate in Scheme 5 with tert-butyl (2-aminophenyl)carbamate. ESI+ MS: m/z 253 ([M+H]+), 1H NMR (300 MHz, d6-DMSO): δ 9.26 (s, 1H), 7.24-7.12 (m, 5H), 6.90 (t, J=6 Hz, 1H), 6.73 (d, J=6 Hz, 1H), 6.55 (t, J=6 Hz, 1H), 4.85 (s, 2H), 3.45 (quint, J=9 Hz, 1H), 3.16 (d, J=9 Hz, 4H).

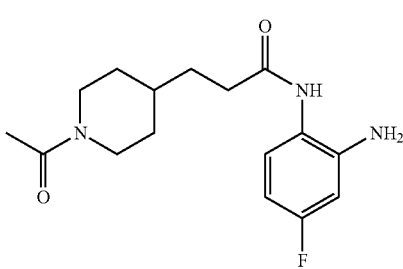

(243)

3-(1-acetylpiperidin-4-yl)-N-(2-amino-4-fluorophenyl)propanamide (243) was prepared by substituting tetrahydro-2H-pyran-4-carboxylic acid in Scheme 5 with 3-(1-acetylpiperidin-4-yl)propanoic acid and by substituting tert-butyl (2-amino-4-(thiophen-2-yl)phenyl)carbamate in Scheme 5 with tert-butyl 2-amino-5-fluorophenylcarbamate. ESI+ MS: m/z 408 ([M+H]$^+$).

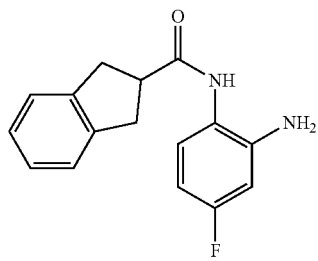

(237)

N-(2-amino-4-fluorophenyl)-2,3-dihydro-1H-indene-2-carboxamide (237) was prepared by substituting tetrahydro-2H-pyran-4-carboxylic acid in Scheme 5 with 2,3-dihydro-1H-indene-2-carboxylic acid and by substituting tert-butyl (2-amino-4-(thiophen-2-yl)phenyl)carbamate in Scheme 5 with tert-butyl 2-amino-5-fluorophenylcarbamate. ESI+ MS: m/z 271 ([M+H]$^+$), 1H NMR (400 MHz, d6-DMSO): δ 9.16 (bs, 1H), 7.21-7.13 (m, 5H), 6.51-6.31 (m, 2H), 5.15 (s, 2H), 3.42-3.40 (m, 1H), 3.31-3.17 (m, 4H).

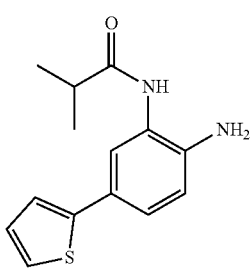

(4)

Synthesis of N-(2-amino-5-(thiophen-2-yl)phenyl)isobutyramide (4)

Scheme 6A

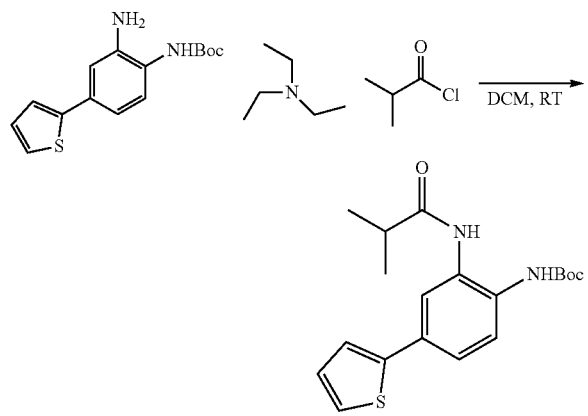

To a solution of tert-butyl (2-amino-4-(thiophen-2-yl)phenyl)carbamate (200 mg, 0.689 mmol) in dichloromethane (4 mL) was added isobutyryl chloride (0.08 mL, 0.76 mmol, 1 equiv.) and TEA (0.23 mL, 1.72 mmol, 2.5 equiv.) at 0° C. The reaction was warmed to room temperature and stirred for 16 h. The reaction was then diluted with dichloromethane and water. The organic layers were washed with water and brine, dried over Na$_2$SO$_4$ and concentrated. The crude material was purified by column chromatography (silica gel, EtOAc/hexanes) to afford tert-butyl (2-isobutyramido-4-(thiophen-2-yl)phenyl)carbamate (0.2 g, 81% yield).

Scheme 7A

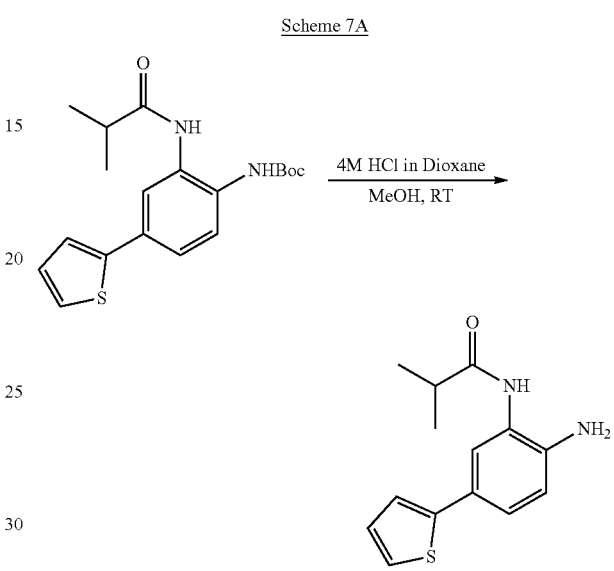

To a stirred solution of tert-butyl (2-isobutyramido-4-(thiophen-2-yl)phenyl)carbamate (0.2 g, 0.52 mmol) in methanol (4 mL) was added 4M HCl in Dioxane (2 mL, 0.53 mmol, 1 equiv.) at 0° C. The reaction was warmed to room temperature and stirred for 2 h. After completion the reaction was concentrated under reduced pressure then basified with a saturated aqueous solution of NaHCO$_3$. The obtained solid was filtered and dried. The crude material was purified by column chromatography (silica gel, MeOH/CH$_2$Cl$_2$) to afford N-(2-amino-5-(thiophen-2-yl)phenyl)isobutyramide (0.05 mg, 36% yield). ESI+ MS: m/z 261 ([M+H]$^+$), 1H NMR (500 MHz, d$^6$-DMSO): δ 9.10 (s, 1H0, 7.5 (s, 1H0, 7.34 (d, J=4.5 Hz, 1H), 7.23-7.19 (m, 2H), 7.05-7.03 (m, 1H0, 6.75 (d, J=8.5 hz, 1H0, 5.03 (s, 2H), 2.67-2.64 (m, 1H), 1.13 (d, J=7 Hz, 6H).

One skilled in the art will recognize that other compounds described below were prepared in a similar manner to the procedures described above.

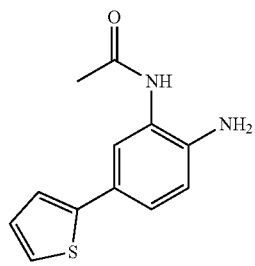

(3)

N-(2-amino-5-(thiophen-2-yl)phenyl)acetamide (3) was prepared by substituting isobutyryl chloride in Scheme 6A with acetyl chloride. ESI+ MS: m/z 233 ([M+H]$^+$), 1H NMR (300 MHz, d$^6$-DMSO): δ 9.23 (s, 1H), 7.51 (d, J=3.0 Hz, 1H), 7.35 (d, J=6.0 Hz, 1H), 7.26-7.16 (m, 2H), 7.05 (dd, J=3.0, 4.0 Hz, 1H), 6.76 (d, J=9.0 Hz, 1H), 5.14 (bs, 2H), 2.08 (s, 3H).

(2)

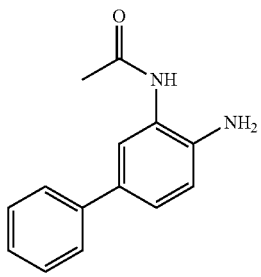

N-(4-amino-[1,1'-biphenyl]-3-yl)acetamide (2) was prepared by substituting isobutyryl chloride in Scheme 6A with acetyl chloride and by substituting tert-butyl (2-amino-4-(thiophen-2-yl)phenyl)carbamate with tert-butyl (3-amino-[1,1'-biphenyl]-4-yl)carbamate. ESI+ MS: m/z 227 ([M+H]$^+$), 1H NMR (500 MHz, d$^6$-DMSO): δ 9.21 (s, 1H), 7.55-7.50 (m, 3H), 7.39 (t, J=7.5 Hz, 2H), 7.27-7.21 (m, 2H), 6.81 (d, J=8.5 Hz, 1H), 5.12 (s, 2H), 2.07 (s, 3H).

(5)

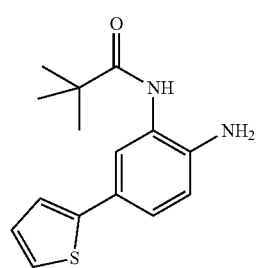

N-(2-amino-5-(thiophen-2-yl)phenyl)pivalamide (5) was prepared by substituting isobutyrylchloride in Scheme 6A with pivaloyl chloride. ESI+ MS: m/z 275 ([M+H]$^+$), 1H NMR (500 MHz, d$^6$-DMSO): δ 8.84 9s, 1H), 7.35-7.32 (m, 1H), 7.30-7.22 9m, 2H), 7.21-7.19 (m, 1H), 7.06-7.01 (m, 1H), 6.78 (d, J=8 Hz, 1H), 4.89 (s, 2H), 1.25 (s, 9H).

(6)

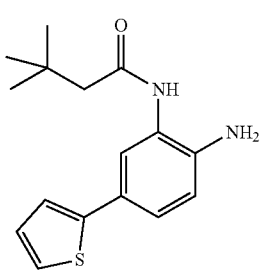

N-(2-amino-5-(thiophen-2-yl)phenyl)-3,3-dimethylbutanamide (6) was prepared by substituting isobutyrylchloride in Scheme 6A with 3,3-dimethylbutanoyl chloride. ESI+ MS: m/z 289 ([M+H]$^+$), 1H NMR (500 MHz, d$^6$-DMSO): δ 9.15 (s, 1H), 7.47-7.46 (m, 1H), 7.36-7.34 (m, 1H), 7.24-7.19 (m, 2H), 7.06-7.03 (m, 1H0, 6.76 (d, J=8 Hz, 1H), 5.04 (s, 2H), 2.22 (s, 2H), 1.05 (s, 9H).

(27)

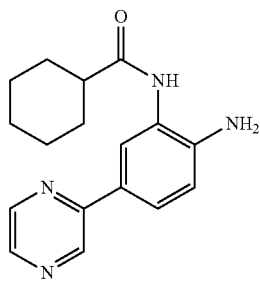

N-(2-amino-5-(pyrazin-2-yl)phenyl)cyclohexanecarboxamide (27) was prepared by substituting isobutyryl chloride in Scheme 6A with cyclohexanecarbonyl chloride and by substituting tert-butyl (2-amino-4-(thiophen-2-yl)phenyl)carbamate with tert-butyl (2-amino-4-(pyrazin-2-yl)phenyl)carbamate. ESI+ MS: m/z 297 ([M+H]$^+$), 1H NMR (500 MHz, d$^6$-DMSO): δ 9.09 (s, 1H), 9.03 (d, J=1.5 Hz, 1H), 8.58-8.55 (m, 1H), 8.41 (d, J=3.0 Hz, 1H), 8.04 (d, J=2.0 Hz, 1H), 7.72 (dd, J=12.5, 2.0 Hz, 1H), 6.82 (d, J=12.5 Hz, 1H), 5.33 (bs, 2H), 2.46-2.35 (m, 1H), 1.90-1.80 (m, 2H), 1.80-1.72 (m, 2H), 1.72-1.60 (m, 2H), 1.50-1.38 (m, 2H), 1.38-1.16 (m, 3H).

(22)

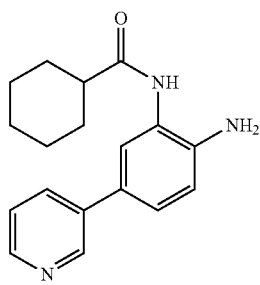

N-(2-amino-5-(pyridin-3-yl)phenyl)cyclohexanecarboxamide (22) was prepared by substituting isobutyryl chloride in Scheme 6A with cyclohexanecarbonyl chloride and by substituting tert-butyl (2-amino-4-(thiophen-2-yl)phenyl)carbamate with tert-butyl (2-amino-4-(pyridin-3-yl)phenyl)carbamate. ESI+ MS: m/z 296 ([M+H]$^+$), 1H NMR (500 MHz, d$^6$-DMSO): δ 9.10 (s, 1H), 8.75 (s, 1H), 8.44 (d, J=3.5 Hz, 1H), 7.89 (d, J=7.5 Hz, 1H), 7.59 (s, 1H), 7.42-7.36 (m, 1H), 7.29 (d, J=8.0 Hz, 1H), 6.83 (d, J=8.0 Hz, 1H), 5.10 (bs, 2H), 2.44-2.36 (m, 1H), 1.88-1.82 (m, 2H), 1.79-1.74 (m, 2H), 1.68-1.64 (m, 1H), 1.50-1.39 (m, 2H), 1.31-1.20 (m, 3H).

(26)

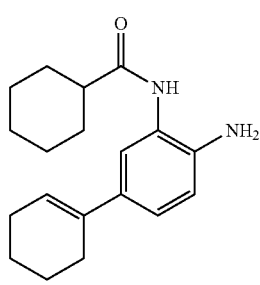

N-(4-amino-2',3',4',5'-tetrahydro-[1,1'-biphenyl]-3-yl)cyclohexanecarboxamide (26) was prepared by substituting isobutyryl chloride in Scheme 6A with cyclohexanecarbonyl chloride and by substituting tert-butyl (2-amino-4-(thiophen-2-yl)phenyl)carbamate in Scheme 6A with tert-butyl (3-amino-2',3',4',5'-tetrahydro-[1,1'-biphenyl]-4-yl)carbamate. ESI+ MS: m/z 299 ([M+H]⁺), 1H NMR (500 MHz, d⁶-DMSO): δ 8.98 (s, 1H), 7.29 (s, 1H), 6.96 (d, J=8.5 Hz, 1H), 6.65 (d, J=8.5 Hz, 1H), 5.90 (bs, 1H), 4.77 (s, 2H), 2.40-2.32 (m, 1H), 2.30-2.22 (m, 2H), 2.16-2.08 (m, 2H), 1.86-1.73 (m, 4H), 1.72-1.61 (m, 3H), 1.60-1.54 (m, 2H), 1.46-1.36 (m, 2H), 1.34-1.14 (m, 3H).

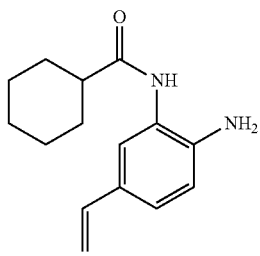

(23)

N-(2-amino-5-vinylphenyl)cyclohexanecarboxamide (23) was prepared by substituting isobutyryl chloride in Scheme 6A with cyclohexanecarbonyl chloride and by substituting tert-butyl (2-amino-4-(thiophen-2-yl)phenyl)carbamate in Scheme 6A with tert-butyl (2-amino-4-vinylphenyl)carbamate. ESI+ MS: m/z 245 ([M+H]⁺), 1H NMR (500 MHz, d⁶-DMSO): δ 7.28 (d, J=1.5 Hz, 1H), 7.03 (dd, J=2 Hz, 8.5 Hz, 1H), 6.67 (d, J=8.5 Hz, 1H), 6.56-6.49 (m, 1H), 5.46 (d, J=17 Hz, 1H), 4.98-4.94 (m, 3H), 2.40-2.33 (m, 1H), 1.80 (d, J=13 Hz, 2H), 1.77-1.73 (m, 2H), 1.65 (d, J=12 Hz, 1H), 1.45-1.36 (m, 2H), 1.31-1.18 (m, 3H).

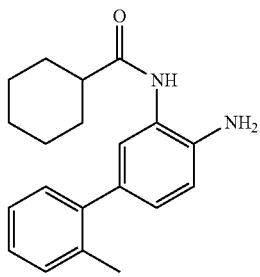

(24)

N-(4-amino-2'-methyl-[1,1'-biphenyl]-3-yl)cyclohexanecarboxamide (24) was prepared by substituting isobutyryl chloride in Scheme 6A with cyclohexanecarbonyl chloride and by substituting tert-butyl (2-amino-4-(thiophen-2-yl)phenyl)carbamate in Scheme 6A with tert-butyl (3-amino-2'-methyl-[1,1'-biphenyl]-4-yl)carbamate. ESI+ MS: m/z 309 ([M+H]⁺), 1H NMR (500 MHz, d⁶-DMSO): δ 9.06 (s, 1H), 7.24-7.18 (m, 1H), 7.14-7.12 (m, 1H), 6.90-6.88 (m, 1H), 6.78 (d, J=8 Hz, 1H), 4.92 (s, 2H), 2.52-2.50 (m, 1H), 2.25 (s, 3H), 1.83 (d, J=12.5 Hz, 2H), 1.76 (d, J=11 Hz, 2H), 1.67-1.64 (m, 1H), 1.46-1.37 (m, 2H), 1.31-1.18 (m, 3H).

(25)

N-(4-amino-4'-fluoro-[1,1'-biphenyl]-3-yl)cyclohexanecarboxamide (25) was prepared by substituting isobutyryl chloride in Scheme 6A with cyclohexanecarbonyl chloride and by substituting tert-butyl (2-amino-4-(thiophen-2-yl)phenyl)carbamate in Scheme 6A with tert-butyl (3-amino-4'-fluoro-[1,1'-biphenyl]-4-yl)carbamate. ESI+ MS: m/z 313 ([M+H]+), 1H NMR (500 MHz, d6-DMSO): δ 9.05 (s, 1H), 7.53-7.51 (m, 3H), 7.21-7.20 (m, 3H), 6.79 (d, J=8.5 Hz, 1H), 4.97 (s, 2H), 2.39 (t, J=11.0 Hz, 1H), 1.85-1.75 (m, 4H), 1.65 (d, J=11.0 Hz, 2H), 1.46-1.39 (m, 2H), 1.33-1.17 (m, 2H).

Example 2

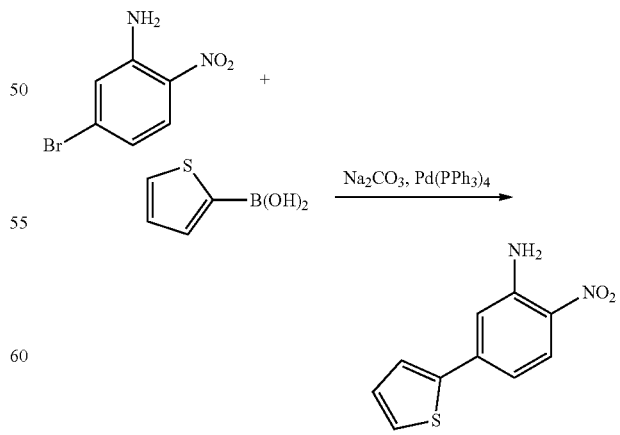

Synthesis of propyl azetidin-3-ylmethyl (2-amino-5-(thiophen-2-yl)phenyl)carbamate (75)

Scheme 7

To a stirred solution of 5-bromo-2-nitroaniline (10.3 g, 47.3 mmol, 1 eq.), thiophen-2-ylboronic acid (9.08 g, 70.9 mmol, 1.5 eq.) and tetrakis(triphenylphosphine)palladium(O) (5.46 g, 4.73 mmol, 0.1 eq.) in THF (150 mL) was added a solution of sodium carbonate (7.27 g, 68.6 mmol, 1.45 eq.) in water (15 mL). The resulting mixture was warmed to 90° C. for 18 h. The reaction was then diluted with EtOAc and water and filtered through Celite. The organic layer was separated and dried over sodium sulfate, filtered and concentrated under reduced pressure. The crude product was purified by column chromatography (silica gel, 2% EtOAc/hexanes) to afford 2-nitro-5-(thiophen-2-yl)aniline (12.0 g, 79% yield).

Scheme 8

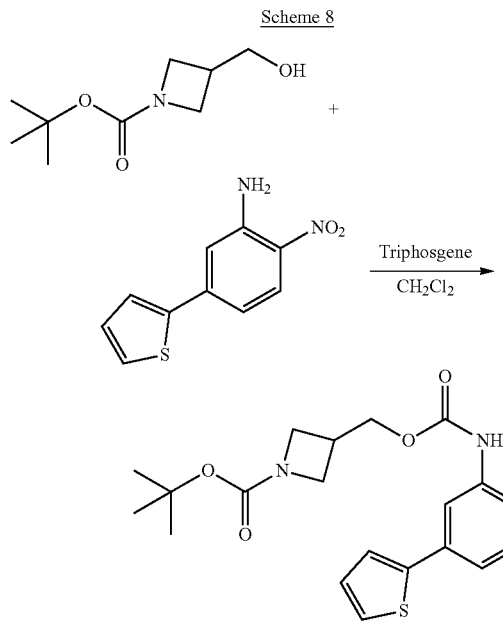

To a solution of 2-nitro-5-(thiophen-2-yl)aniline (0.30 g, 1.36 mmol, 1 eq.) and triphosgene (0.24 g, 0.82 mmol, 0.6 eq.) in dichloromethane (7 mL) at 0° C. was added TEA (0.38 mL, 2.90 mmol, 2 eq.). The reaction was stirred at room temperature for 2 h, then cooled down to 0° C. Tert-butyl 3-(hydroxymethyl)azetidine-1-carboxylate (0.31 g, 1.64 mmol, 1.2 eq.) in dichloromethane (7 mL) and TEA (0.38 mL, 2.90 mmol, 2 eq.) were added at 0° C. The reaction was warmed to room temperature and stirred for 1 h. The reaction was diluted with dichloromethane and washed with citric acid solution then brine. The organic layer was separated, dried over sodium sulfate and concentrated. The crude product was purified by column chromatography (silica gel, 25% EtOAc/hexanes) to obtain tert-butyl 3-((((2-nitro-5-(thiophen-2-yl)phenyl)carbamoyl)oxy)methyl)azetidine-1-carboxylate (0.59 g, 85% yield).

Scheme 9

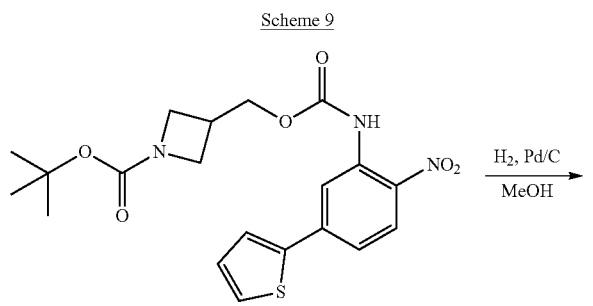

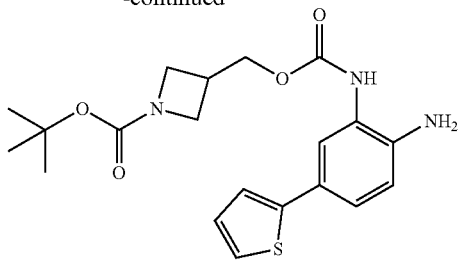

To a stirred solution of tert-butyl 3-((((2-nitro-5-(thiophen-2-yl)phenyl)carbamoyl)oxy)methyl)azetidine-1-carboxylate (0.14 g, 0.32 mmol, 1.0 eq.) in MeOH (10 mL) was added Pd/C (40 mg, 0.38 mmol, 1.2 eq.). The reaction mixture was stirred at room temperature under $H_2$ atmosphere for 1 h. The reaction mixture was then filtered through Celite, the solids washed with methanol. The filtrate was concentrated under reduced pressure to afford pure amine (0.12 g, 89% yield) which was used in the next step without further purification.

Scheme 10

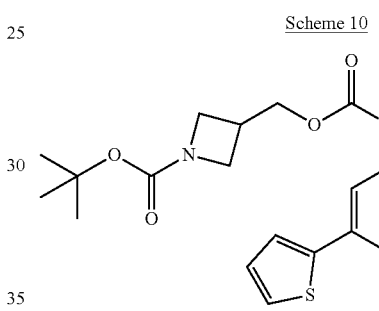

To a solution of tert-butyl 3-((((2-amino-5-(thiophen-2-yl)phenyl)carbamoyl)oxy)methyl)azetidine-1-carboxylate (0.12 g, 0.30 mmol) in dichloromethane (5 mL) was added TFA (1.5 mL) at 0° C. The reaction was then warmed to room temperature and stirred for 2 h. The solvents were then removed under reduced pressure. A saturated solution of sodium bicarbonate was added. The product was extracted with ethyl acetate, washed with water and brine. The combined organic layers were dried over sodium sulfate, filtered and concentrated under reduced pressure. The crude solid was washed with ether to obtain azetidin-3-ylmethyl (2-amino-5-(thiophen-2-yl)phenyl)carbamate (49.6 mg, 55% yield). ESI+ MS: m/z 304 ([M+H]$^+$), 1H NMR (500 MHz, d$^6$-DMSO): δ 8.78 (bs, 1H), 7.53 (bs, 1H), 7.34 (d, J=4.5 Hz, 1H), 7.22-7.16 (m, 2H), 7.04 (dd, J=5.5; 4.0 Hz, 1H), 6.76-6.70 (m, 1H), 5.18 (bs, 2H), 4.23 (d, J=6.0 Hz, 2H), 3.92 (t, J=8.5 Hz, 2H), 3.70-3.64 (m, 2H), 3.08-3.00 (m, 1H).

One skilled in the art will recognize that other compounds described below can be prepared in a similar manner to the procedures described above.

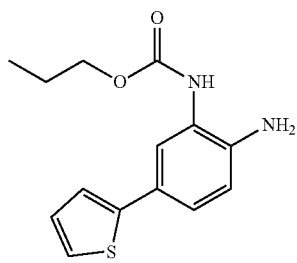

(76)

Propyl (2-amino-5-(thiophen-2-yl)phenyl)carbamate (76) was prepared by substituting tert-butyl 3-(hydroxymethyl)azetidine-1-carboxylate in Scheme 8 with propanol. ESI+ MS: m/z 277 ([M+H]$^+$), 1H NMR (500 MHz, d$^6$-DMSO): δ 8.60 (bs, 1H), 7.52 (bs, 1H), 7.34 (d, J=5.0 Hz, 1H), 7.21-7.16 (m, 2H), 7.05-7.02 (m, 1H), 6.71 (d, J=8.5 Hz, 1H), 5.11 (s, 2H), 4.02 (t, J=7.0 Hz, 2H), 1.68-1.60 (m, 2H), 0.94 (t, J=7.5 Hz, 3H).

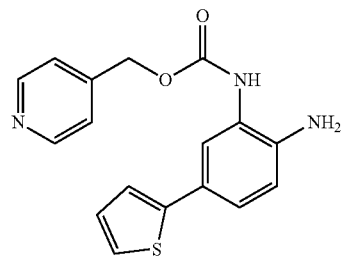

(88)

Pyridin-4-ylmethyl (2-amino-5-(thiophen-2-yl)phenyl)carbamate (88) was prepared by substituting tert-butyl 3-(hydroxymethyl)azetidine-1-carboxylate in Scheme 8 with pyridin-4-ylmethanol. ESI+ MS: m/z 326 ([M+H]$^+$), 1H NMR (500 MHz, d$^6$-DMSO): δ 8.91 (bs, 1H), 8.58 (d, J=4.0 Hz, 2H), 7.53 (bs, 1H), 7.46-7.38 (m, 2H), 7.34 (d, J=5.0 Hz, 1H), 7.24-7.16 (m, 2H), 7.03 (dd, J=4.0, 5.0 Hz, 1H), 6.74 (d, J=8.5 Hz, 1H), 5.20 (s, 2H), 5.18 (s, 2H).

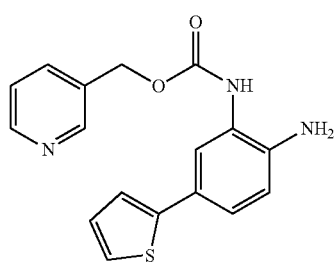

(86)

Pyridin-3-ylmethyl (2-amino-5-(thiophen-2-yl)phenyl)carbamate (86) was prepared by substituting tert-butyl 3-(hydroxymethyl)azetidine-1-carboxylate in Scheme 8 with pyridin-3-ylmethanol. ESI+ MS: m/z 326 ([M+H]$^+$), 1H NMR (500 MHz, d$^6$-DMSO): δ 8.80 (bs, 1H), 8.66 (s, 1H), 8.55 (d, J=3.5 Hz, 1H), 7.80-7.73 (m, 1H), 7.53 (bs, 1H), 7.45-7.40 (m, 1H), 7.34 (d, J=5.0 Hz, 1H), 7.22-7.16 (m, 2H), 7.05-7.00 (m, 1H), 6.72 (d, J=8.0 Hz, 1H), 5.19 (s, 2H), 5.16 (s, 2H).

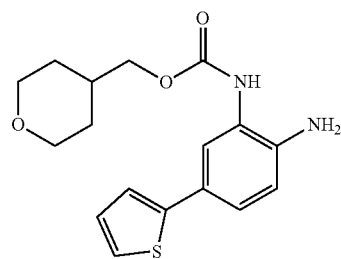

(91)

(Tetrahydro-2H-pyran-4-yl)methyl (2-amino-5-(thiophen-2-yl)phenyl)carbamate (91) was prepared by substituting tert-butyl 3-(hydroxymethyl)azetidine-1-carboxylate in Scheme 8 with (tetrahydro-2H-pyran-4-yl)methanol. ESI+ MS: m/z 333 ([M+H]$^+$), 1H NMR (500 MHz, d$^6$-DMSO): δ 8.61 (bs, 1H), 7.52 (bs, 1H), 7.34 (d, J=5.0 Hz, 1H), 7.20-7.16 (m, 2H), 7.03 (dd, J=3.5, 5.0 Hz, 1H), 6.72 (d, J=8.0 Hz, 1H), 5.12 (s, 2H), 3.94 (d, J=7.0 Hz, 2H), 3.90-3.82 (m, 2H), 3.35-3.28 (m, 2H), 1.95-1.85 (m, 1H), 1.64-1.56 (m, 2H), 1.34-1.20 (m, 2H).

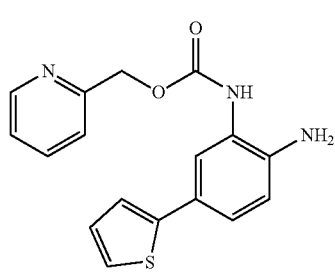

(87)

Pyridin-2-ylmethyl (2-amino-5-(thiophen-2-yl)phenyl)carbamate (87) was prepared by substituting tert-butyl 3-(hydroxymethyl)azetidine-1-carboxylate in Scheme 8 with pyridin-2-ylmethanol. ESI+ MS: m/z 326 ([M+H]$^+$), 1H NMR (500 MHz, d$^6$-DMSO): δ 8.89 (bs, 1H), 8.57 (d, J=4.0 Hz, 1H), 7.84 (t, J=7.5 Hz, 1H), 7.55 (bs, 1H), 7.52-7.44 (m, 1H), 7.38-7.32 (m, 2H), 7.24-7.16 (m, 2H), 7.03 (dd, J=3.5, 5.0 Hz, 1H), 6.73 (d, J=8.5 Hz, 1H), 5.21 (s, 2H), 5.19 (s, 2H).

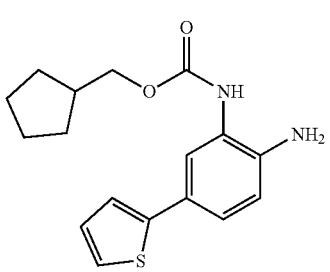

(64)

Cyclopentylmethyl (2-amino-5-(thiophen-2-yl)phenyl)carbamate (64) was prepared by substituting tert-butyl 3-(hydroxymethyl)azetidine-1-carboxylate in Scheme 8 with cyclopentylmethanol. ESI+ MS: m/z 317 ([M+H]$^+$), 1H NMR (500 MHz, d$^6$-DMSO): δ 8.60 (s, 1H), 7.52 (s, 1H), 7.34 (d, J=5 Hz, 1H), 7.23-7.12 (m, 2H), 7.03 (dt, J=4.5; 1 Hz, 1H), 6.72 (d, J=8 Hz, 1H), 5.11 (s, 2H), 3.96 (d, J=7 Hz, 2H), 2.21 (sept, J=7.5 Hz, 1H), 1.8-1.65 (m, 2H), 1.65-1.40 (m, 4H), 1.40-1.15 (m, 2H).

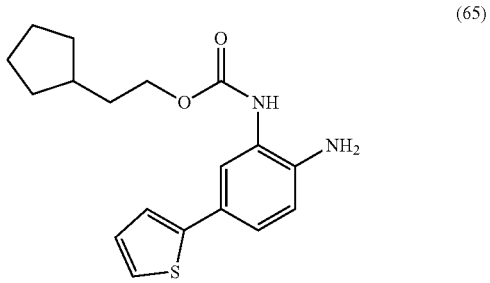 [SMILES: Nc1ccc(-c2cccs2)cc1NC(=O)OCCC1CCCC1]

(65)

2-Cyclopentylethyl (2-amino-5-(thiophen-2-yl)phenyl)carbamate (65) was prepared by substituting tert-butyl 3-(hydroxymethyl)azetidine-1-carboxylate in Scheme 8 with cyclopentylethanol. ESI+ MS: m/z 331 ([M+H]$^+$), 1H NMR (500 MHz, d$^6$-DMSO): δ 8.59 (s, 1H), 7.52 (s, 1H), 7.34 (d, J=5 Hz, 1H), 7.23-7.13 (m, 2H), 7.04 (dt, J=4; 1.5 Hz, 1H), 6.72 (d, J=8 Hz, 1H), 5.11 (s, 2H), 4.08 (t, J=6.5 Hz, 2H), 1.87 (t, J=7 Hz, 1H), 1.81-1.70 (m, 2H), 1.70-1.53 (m, 4H), 1.53-1.40 (m, 2H), 1.20-1.05 (m, 2H).

(60)

Oxetan-3-ylmethyl (2-amino-5-(thiophen-2-yl)phenyl)carbamate (60) was prepared by substituting tert-butyl 3-(hydroxymethyl)azetidine-1-carboxylate in Scheme 8 with oxetan-3-ylmethanol. ESI+ MS: m/z 305 ([M+H]$^+$), 1H NMR (500 MHz, d$^6$-DMSO): δ 8.70 (bs, 1H), 7.51 (bs, 1H), 7.33 (d, J=5.0 Hz, 1H), 7.19-7.17 (m, 2H), 7.03 (t, J=5.0 Hz, 1H), 6.71 (d, J=8.0 Hz, 1H), 5.12 (s, 2H), 4.67 (t, J=7.0 Hz, 2H), 4.40 (t, J=6.0 Hz, 2H), 4.29 (d, J=7.0 Hz, 2H), 3.21 (m, 1H).

(63)

Cyclobutylmethyl (2-amino-5-(thiophen-2-yl)phenyl)carbamate (63) was prepared by substituting tert-butyl 3-(hydroxymethyl)azetidine-1-carboxylate in Scheme 8 with cyclobutylmethanol. ESI+ MS: m/z 303 ([M+H]$^+$), 1H NMR (500 MHz, d$^6$-DMSO): δ 8.62 (bs, 1H), 7.52 (bs, 1H), 7.33 (d, J=5.0 Hz, 1H), 7.19-7.16 (m, 2H), 7.04-7.02 (m, 1H), 6.71 (d, J=8.0 Hz, 1H), 5.10 (s, 2H), 4.05 (d, J=6.5 Hz, 2H), 2.64-2.58 (m, 1H), 2.03 (m, 2H), 1.91-1.76 (m, 4H).

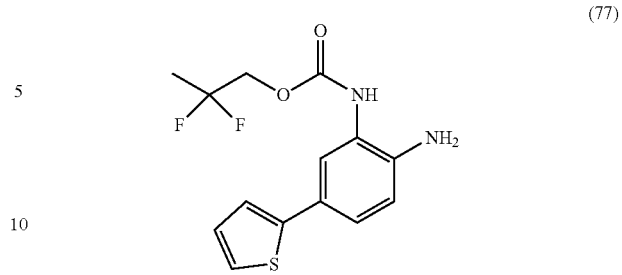

(77)

2,2-Difluoropropyl (2-amino-5-(thiophen-2-yl)phenyl)carbamate (77) was prepared by substituting tert-butyl 3-(hydroxymethyl)azetidine-1-carboxylate in Scheme 8 with 2,2-difluoropropan-1-ol. ESI+ MS: m/z 313 ([M+H]$^+$), 1H NMR (500 MHz, d$^6$-DMSO): δ 8.96 (bs, 1H), 7.49 (bs, 1H), 7.35 (d, J=5.0 Hz, 1H), 7.22-7.19 (m, 2H), 7.04-7.02 (m, 1H), 6.73 (d, J=8.5 Hz, 1H), 5.15 (s, 2H), 4.36 (t, J=13.5 Hz, 2H), 1.69 (t, J=19.0 Hz, 3H).

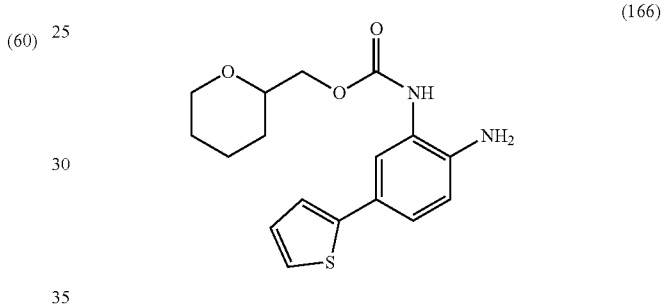

(166)

(Tetrahydro-2H-pyran-2-yl)methyl (2-amino-5-(thiophen-2-yl)phenyl)carbamate (166) was prepared by substituting tert-butyl 3-(hydroxymethyl)azetidine-1-carboxylate in Scheme 8 with (tetrahydro-2H-pyran-2-yl)methanol. ESI+ MS: m/z 333 ([M+H]+), 1HNMR (500 MHz, d$^6$-DMSO): δ 8.73 (bs, 1H), 7.53 (bs, 1H), 7.33 (d, J=5.0 Hz, 1H), 7.18-7.16 (m, 2H), 7.03 (t, J=4.5 Hz, 1H), 6.71 (d, J=8.0 Hz, 1H), 5.11 (bs, 2H), 4.03-3.97 (m, 2H), 3.88 (d, J=10.5 Hz, 1H), 3.53 (m, 1H), 3.36 (m, 1H), 1.79 (m, 1H), 1.58 (d, J=13 Hz, 1H), 1.47 (bs, 3H), 1.26-1.24 (m, 1H).

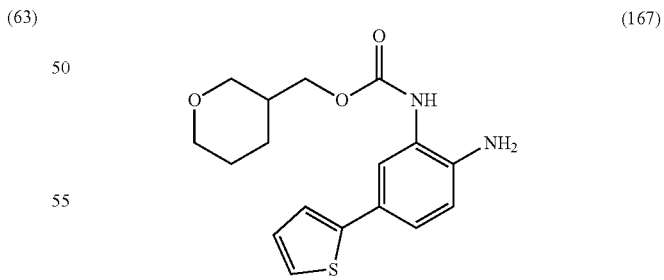

(167)

(Tetrahydro-2H-pyran-3-yl)methyl (2-amino-5-(thiophen-2-yl)phenyl)carbamate (167) was prepared by substituting tert-butyl 3-(hydroxymethyl)azetidine-1-carboxylate in Scheme 8 with (tetrahydro-2H-pyran-3-yl)methanol. ESI+ MS: m/z 333 ([M+H]+), 1HNMR (500 MHz, d$^6$-DMSO): δ 8.62 (bs, 1H), 7.50 (bs, 1H), 7.33 (d, J=5.0 Hz, 1H), 7.19-7.17 (m, 2H), 7.04-7.02 (m, 1H), 6.71 (d, J=8.0 Hz, 1H), 5.11 (s, 2H), 4.01-3.82 (m, 3H), 3.73-3.72 (m, 1H), 3.34 (m, 1H), 3.21 (t, J=9.5 Hz, 1H), 1.88-1.77 (m, 2H), 1.57-1.48 (m, 2H), 1.30-1.23 (m, 1H).

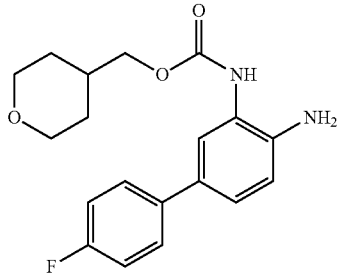
(169)

(Tetrahydro-2H-pyran-4-yl)methyl (4-amino-4'-fluoro-[1,1'-biphenyl]-3-yl)carbamate (169) was prepared by substituting tert-butyl 3-(hydroxymethyl)azetidine-1-carboxylate in Scheme 8 with (tetrahydro-2H-pyran-4-yl)methanol and by substituting thiophen-2-ylboronic acid in Scheme 7 with (4-fluorophenyl)boronic acid. ESI+ MS: m/z 345 ([M+H]+), 1HNMR (500 MHz, d$^6$-DMSO): δ 8.61 (bs, 1H), 7.52-7.50 (m, 3H), 7.20-7.15 (m, 3H), 6.75 (d, J=8.5 Hz, 1H), 5.04 (s, 2H), 3.93-3.84 (m, 4H), 3.29 (t, J=9.0 Hz, 2H), 1.88 (m, 1H), 1.63-1.58 (m, 2H), 1.30-1.26 (m, 2H).

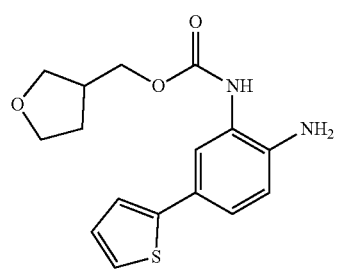
(170)

(Tetrahydrofuran-3-yl)methyl (2-amino-5-(thiophen-2-yl)phenyl)carbamate (170) was prepared by substituting tert-butyl 3-(hydroxymethyl)azetidine-1-carboxylate in Scheme 8 with (tetrahydrofuran-3-yl)methanol. ESI+ MS: m/z 319 ([M+H]+), 1HNMR (500 MHz, d$^6$-DMSO): δ 8.65 (bs, 1H), 7.50 (bs, 1H), 7.33 (d, J=5.0 Hz, 1H), 7.19-7.17 (m, 2H), 7.04-7.02 (m, 1H), 6.72 (d, J=8.0 Hz, 1H), 5.12 (s, 2H), 4.08-3.95 (m, 2H), 3.76-3.73 (m, 2H), 3.66-3.61 (m, 1H), 3.61-3.48 (m, 1H), 2.56-2.53 (m, 1H), 1.99-1.96 (m, 1H), 1.64-1.59 (m, 1H).

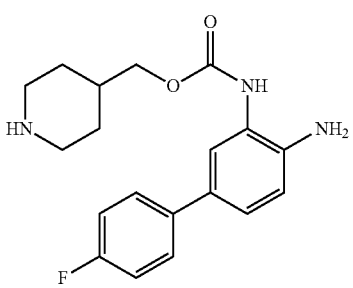
(90)

Piperidin-4-ylmethyl (4-amino-4'-fluoro-[1,1'-biphenyl]-3-yl)carbamate (90) was prepared by substituting tert-butyl 3-(hydroxymethyl)azetidine-1-carboxylate in Scheme 8 with tert-butyl 4-(hydroxymethyl)piperidine-1-carboxylate and by substituting thiophen-2-ylboronic acid in Scheme 7 with (4-fluorophenyl) boronic acid. ESI+ MS: m/z 344 ([M+H]$^+$), 1H NMR (500 MHz, d$^6$-DMSO): δ 8.62 (s, 1H), 7.58-7.46 (m, 3H), 7.24-7.12 (m, 3H), 6.76 (d, J=7.5 Hz, 1H), 5.05 (s, 2H), 3.91 (d, J=6.5 Hz, 2H), 3.31 (s, 1H), 2.98 (d, J=11.5 Hz, 2H), 2.60-2.30 (m, 2H), 1.80-1.55 9m, 3H), 1.20-1.05 (m, 2H).

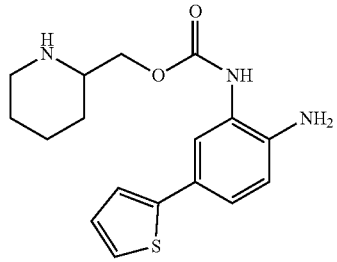
(201)

Piperidin-2-ylmethyl (2-amino-5-(thiophen-2-yl)phenyl)carbamate (201) was prepared by substituting tert-butyl 3-(hydroxymethyl)azetidine-1-carboxylate in Scheme 8 with tert-butyl 2-(hydroxymethyl)piperidine-1-carboxylate. ESI+ MS: m/z 332 ([M+H]$^+$), 1H NMR (500 MHz, d$^6$-DMSO): δ 8.60 (bs, 1H), 7.52 (bs, 1H), 7.33 (d, J=5.0 Hz, 1H), 7.21-7.16 (m, 2H), 7.04-7.02 (m, 1H), 6.72 (d, J=8.0 Hz, 1H), 5.14 (s, 2H), 3.94-3.87 (m, 2H), 2.95 (d, J=11.0 Hz, 1H), 2.73 (bs, 1H), 2.53 (s, 1H), 1.74 (bs, 1H), 1.61-1.50 (m, 2H), 1.33-1.23 (m, 2H), 1.09-1.05 (m, 1H).

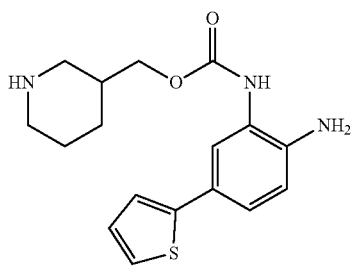
(153)

Piperidin-3-ylmethyl (2-amino-5-(thiophen-2-yl)phenyl)carbamate (153) was prepared by substituting tert-butyl 3-(hydroxymethyl)azetidine-1-carboxylate in Scheme 8 with tert-butyl 3-(hydroxymethyl)piperidine-1-carboxylate. ESI+ MS: m/z 362 ([M+H]+), 1HNMR (500 MHz, d$^6$-DMSO): δ ESI+ MS: m/z 332 ([M+H]$^+$); 1H NMR (500 MHz, d$^6$-DMSO): δ 8.69 (bs, 1H), 7.51 (bs, 1H), 7.34 (d, J=5.0 Hz, 1H), 7.19-7.18 (m, 2H), 7.03 (d, J=4.5 Hz, 1H), 6.72 (d, J=8.5 Hz, 1H), 5.15 (bs, 2H), 4.03-3.93 (m, 2H), 3.31-3.16 (m, 3H), 2.73-2.50 (m, 2H), 2.06 (bs, 1H), 1.78 (d, J=11.0 Hz, 2H), 2.53 (s, 1H), 1.61-1.59 (m, 1H), 1.27-1.23 (m, 1H).

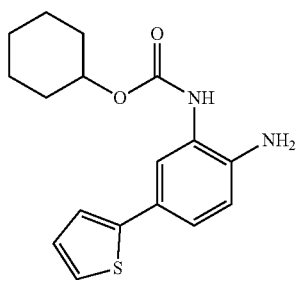

(83)

cyclohexyl (2-amino-5-(thiophen-2-yl)phenyl)carbamate (83) was prepared by substituting tert-butyl 3-(hydroxymethyl)azetidine-1-carboxylate in Scheme 8 with cyclohexanol. ESI+ MS: m/z 317 ([M+H]+).

Alternatively, the nitro group reduction can be carried out using zinc and ammonium formate as described in the scheme below:

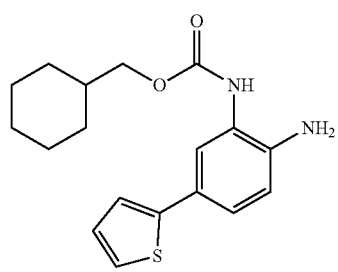

(66)

Synthesis of Cyclohexylmethyl (2-amino-5-(thiophen-2-yl)phenyl)carbamate (66)

Scheme 11

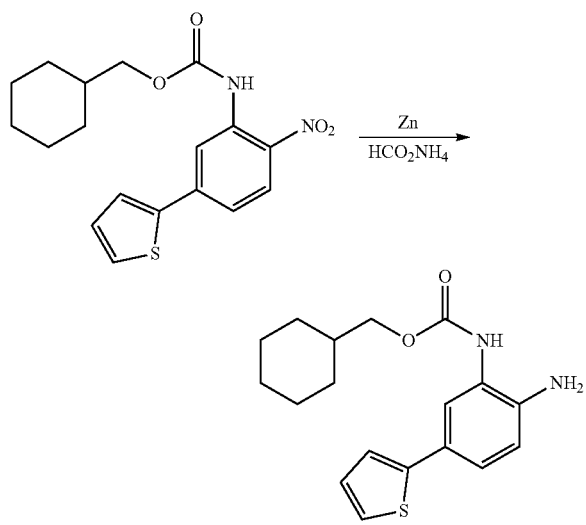

To a stirred solution of cyclohexylmethyl (2-nitro-5-(thiophen-2-yl)phenyl)carbamate (0.09 g, 0.25 mmol, 1.0 equiv.) in methanol (5 mL) and THF (5 mL) were added Zn (0.08 mg, 1.25 mmol, 5.0 equiv.) and HCOONH$_4$ (0.13 mmol, 2.0 mmol, 8.0 equiv.) at room temperature. The reaction mixture was stirred at room temperature for 4 h then filtered through celite and concentrated under reduced pressure. The crude residue was diluted with ethyl acetate, washed with water and brine. The combined organic layers were dried over sodium sulfate, filtered and concentrated. The crude residue was purified by column chromatography (silica gel, 30% EtOAc/hexanes) to afford cyclohexylmethyl (2-amino-5-(thiophen-2-yl)phenyl)carbamate (0.08 g, 100% yield). ESI+ MS: m/z 331 ([M+H]+), 1H NMR (500 MHz, d$^6$-DMSO): δ 8.58 (bs, 1H), 7.52 (bs, 1H), 7.33 (d, J=4.5 Hz, 1H), 7.22-7.14 (m, 2H), 7.03 (dd, J=3.5, 5.0 Hz, 1H), 6.72 (d, J=8.0 Hz, 1H), 5.11 (s, 2H), 3.89 (d, J=6.5 Hz, 2H), 1.80-1.38 (m, 6H), 1.25-1.03 (m, 3H), 1.03-0.92 (m, 2H).

One skilled in the art will recognize that other compounds described below were prepared in a similar manner to the procedures described above.

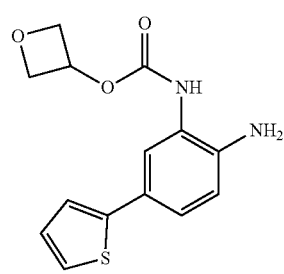

(59)

Oxetan-3-yl(2-amino-5-(thiophen-2-yl)phenyl)carbamate (59) was prepared by substituting tert-butyl 3-(hydroxymethyl)azetidine-1-carboxylate in Scheme 8 with oxetan-3-ol. ESI+ MS: m/z 291 ([M+H]+), 1H NMR (500 MHz, d$^6$-DMSO): δ 8.88 (bs, 1H), 7.49 (bs, 1H), 7.32 (d, J=5.0 Hz, 1H), 7.22-7.16 (m, 2H), 7.03 (dd, J=3.5, 4.5 Hz, 1H), 6.72 (d, J=8.5 Hz, 1H), 5.44-5.38 (m, 1H), 5.16 (s, 2H), 4.08 (t, J=6.5 Hz, 2H), 4.60-4.54 (m, 2H).

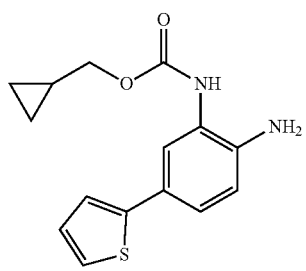

(61)

Cyclopropylmethyl (2-amino-5-(thiophen-2-yl)phenyl)carbamate (61) was prepared by substituting tert-butyl 3-(hydroxymethyl)azetidine-1-carboxylate in Scheme 8 with cyclopropylmethanol. ESI+ MS: m/z 288 ([M+H]+), 1H NMR (500 MHz, d$^6$-DMSO): δ 8.67 (bs, 1H), 7.54 (bs, 1H), 7.34 (d, J=5.0 Hz, 1H), 7.20-7.15 (m, 2H), 7.03 (dd, J=4.0, 5.0 Hz, 1H), 6.71 (d, J=9.0 Hz, 1H), 5.12 (s, 2H), 3.91 (d, J=7.0 Hz, 2H), 1.20-1.12 (m, 1H), 0.52-0.50 (m, 2H), 0.35-0.28 (m, 2H).

(79)

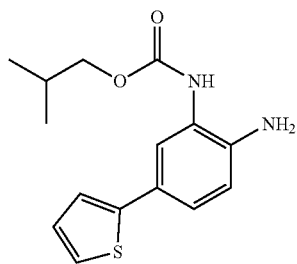

Isobutyl (2-amino-5-(thiophen-2-yl)phenyl)carbamate (79) was prepared by substituting tert-butyl 3-(hydroxymethyl) azetidine-1-carboxylate in Scheme 8 with 2-methylpropan-1-ol. ESI+ MS: m/z 291 ([M+H]$^+$), 1H NMR (500 MHz, d$^6$-DMSO): δ 8.60 (bs, 1H), 7.52 (bs, 1H), 7.34 (d, J=5.0 Hz, 1H), 7.20-7.15 (m, 2H), 7.03 (dd, J=3.5, 5.0 Hz, 1H), 6.72 (d, J=9.0 Hz, 1H), 5.11 (s, 2H), 3.86 (d, J=6.5 Hz, 2H), 1.92 (sept, J=7.0 Hz, 1H), 0.93 (d, J=6.5 Hz, 6H).

(89)

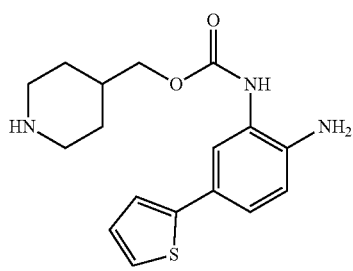

Piperidin-4-ylmethyl (2-amino-5-(thiophen-2-yl)phenyl)carbamate (89) was prepared by substituting tert-butyl 3-(hydroxymethyl)azetidine-1-carboxylate in Scheme 8 with tert-butyl 4-(hydroxymethyl)piperidine-1-carboxylate. ESI+ MS: m/z 332 ([M+H]$^+$), 1H NMR (500 MHz, d$^6$-DMSO): δ 8.59 (bs, 1H), 7.52 (bs, 1H), 7.34 (d, J=5.0 Hz, 1H), 7.21-7.16 (m, 2H), 7.04 (t, J=4.0 Hz, 1H), 6.72 (d, J=8 Hz, 1H), 5.11 (bs, 2H), 3.90 (d, J=6.5 Hz, 2H), 2.95 (d, J=11.5 Hz, 2H), 2.50-2.40 (m, 2H), 1.80-1.65 (m, 1H), 1.63 (d, J=12.5 Hz, 2H), 1.20-1.05 (m, 2H).

(176)

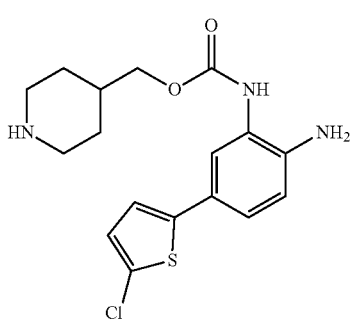

Piperidin-4-ylmethyl (2-amino-5-(5-chlorothiophen-2-yl) phenyl)carbamate (179) was prepared by substituting tert-butyl 3-(hydroxymethyl)azetidine-1-carboxylate in Scheme 8 with tert-butyl 4-(hydroxymethyl)piperidine-1-carboxylate and by substituting thiophen-2-ylboronic acid in Scheme 7 with 5-chloro-thiophen-2-ylboronic acid. ESI+ MS: m/z 366 ([M+H]+), 1H NMR (500 MHz, d$^6$-DMSO): δ 8.61 (bs, 1H), 7.46 (bs, 1H), 7.13-7.11 (m, 1H), 7.05-7.02 (m, 2H), 6.71 (d, J=8.0 Hz, 1H), 5.20 (s, 2H), 3.93-3.89 (m, 2H), 2.95 (d, J=11.0 Hz, 2H), 2.50-2.44 (m, 2H), 1.71-1.61 (m, 3H), 1.16-1.08 (m, 2H).

Alternatively, other substituted nitroanilines can be prepared according to the scheme described below:

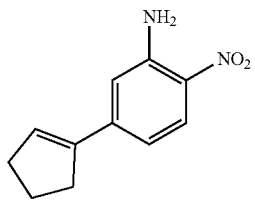 [SMILES: Nc1cc(C2=CCCC2)ccc1[N+](=O)[O-]]

Synthesis of 5-(cyclopent-1-en-1-yl)-2-nitroaniline

Scheme 12

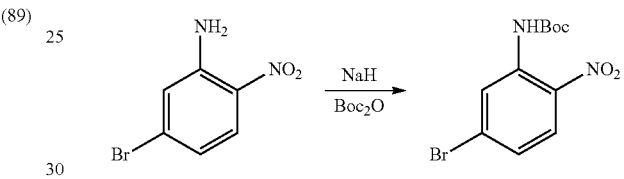

To a solution of 5-bromo-2-nitroaniline (35.0 g, 161 mmol, 1.0 equiv.) in DMF (4 L) was slowly added sodium hydride (4.64 g, 194 mmol, 1.2 equiv.) followed by the dropwise addition of a solution of (Boc)$_2$O (42.2 g, 194 mmol, 1.2 equiv.) in DMF (100 mL) at room temperature. The reaction mixture was stirred for 4 h at room temperature, then quenched with water. The product was extracted with ethyl acetate. The combined organic layers were washed with water, dried with sodium sulfate and concentrated under reduced pressure. The crude residue was purified by column chromatography (silica gel, 1% EtOAc/hexanes) to give tert-butyl (5-bromo-2-nitrophenyl)carbamate (26.6 g, 52% yield).

Scheme 13

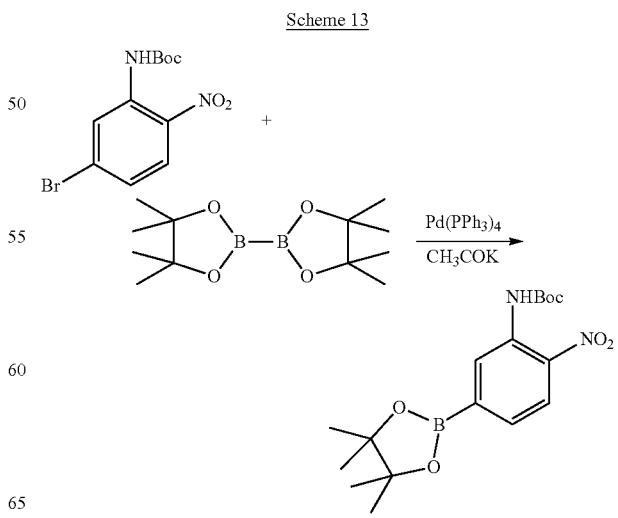

A mixture of tert-butyl (5-bromo-2-nitrophenyl)carbamate (17.0 g, 53.6 mmol, 1.0 equiv.), bis(pinacolato)diboron (20.4 g, 80.0 mmol, 1.5 equiv.), potassium acetate (174 g, 1.8 mol, 33 equiv.) and Pd(PPh₃)₄ (61.9 g, 53.6 mmol, 1.0 equiv.) in toluene (240 mL) was degassed then heated to 110° C. After vigorously stirring for 3 h, the solution was diluted with water, filtered through celite, washed with ethyl acetate. The organic layer was separated, dried with magnesium sulfate and concentrated under reduced pressure. The crude residue was purified by flash column chromatography (silica gel, 20% EtOAc/hexanes) to give tert-butyl (2-nitro-5-(4,4,5,5-tetramethyl-1,3,2-dioxaborolan-2-yl)phenyl)carbamate (16 g, 82% yield).

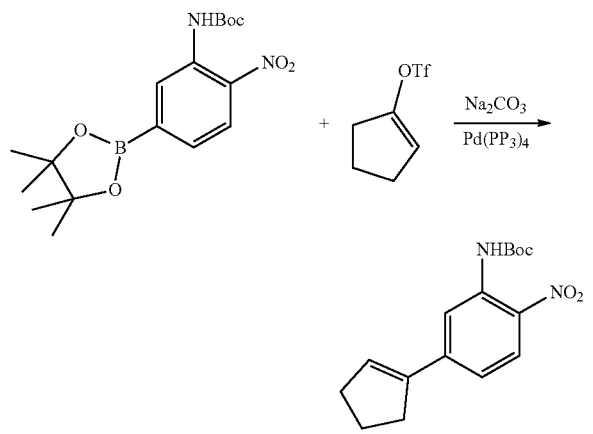

Scheme 14

To a solution of tert-butyl (2-nitro-5-(4,4,5,5-tetramethyl-1,3,2-dioxaborolan-2-yl)phenyl)carbamate (16 g, 43.9 mmol, 1.0 equiv.) in 1,4-dioxane (320 mL) were added cyclopent-1-en-1-yl trifluoromethanesulfonate (11.4 g, 52.7 mmol, 1.2 equiv.), Pd (PPh₃)₄ (2.54 g, 2.2 mmol, 0.05 equiv.) and a solution of Na₂CO₃ (5.6 g, 52.7 mmol, 1.2 equiv.) in water (160 mL) at room temperature. The reaction was then heated to 110° C. and stirred for 4 h. The reaction mixture was filtered through celite then concentrated under reduced pressure. The crude residue was purified by column chromatography (silica gel, 2% EtOAc/hexanes) to give tert-butyl (5-(cyclopent-1-en-1-yl)-2-nitrophenyl)carbamate (4.3 g, 32% yield).

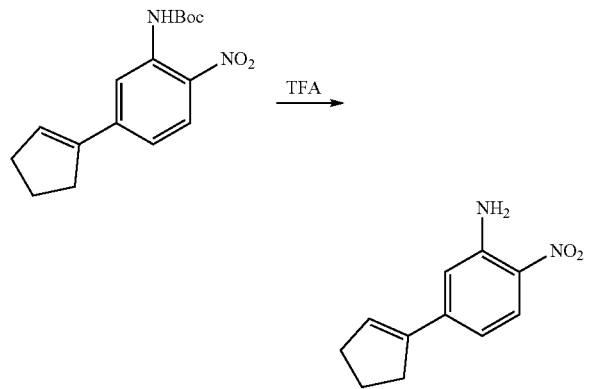

Scheme 15

A solution of tert-butyl (5-(cyclopent-1-en-1-yl)-2-nitrophenyl)carbamate (4.3 g, 14.13 mmol, 1.0 equiv.) in dichloromethane (50 mL) was added TFA (10 mL) at room temperature. The reaction mixture was stirred at room temperature for 2 h. The reaction was then evaporated under reduced pressure. The crude residue was quenched with a saturated solution of sodium bicarbonate. The product was extracted with ethyl acetate, washed with water and brine, dried, filtered and concentrated under reduced pressure. The crude residue was purified by column chromatography (silica gel, 60% EtOAc/hexanes) to give 5-(cyclopent-1-en-1-yl)-2-nitroaniline (2.5 g, 87% yield).

One skilled in the art will recognize that other compounds described below were prepared in a similar manner to the previously described procedures using other substituted nitroanilines.

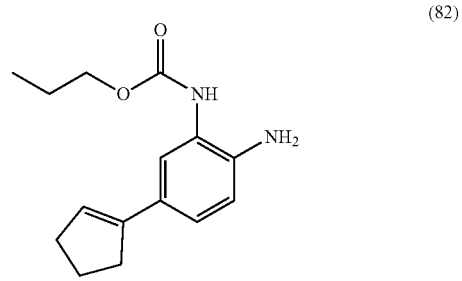 [SMILES: CCCOC(=O)Nc1cc(C2=CCCC2)ccc1N]

(82)

Propyl (2-amino-5-(cyclopent-1-en-1-yl)phenyl)carbamate (82) was prepared by substituting tert-butyl 3-(hydroxymethyl)azetidine-1-carboxylate in Scheme 8 with propanol and by substituting 2-ntro-5-(thiophen-2-yl)aniline in Scheme 8 with 5-(cyclopenten-1-yl)nitroaniline. ESI+ MS: m/z 261 ([M+H]⁺), 1H NMR (500 MHz, d⁶-DMSO): δ 8.51 (bs, 1H), 7.28 (bs, 1H), 7.01 (dd, J=1.5, 8.0 Hz, 1H), 6.64 (d, J=8.5 Hz, 1H), 5.91 (s, 1H), 4.93 (s, 2H), 4.00 (t, J=6.5 Hz, 2H), 2.56-2.54 (m, 2H), 2.45-2.40 (m, 2H), 1.94-1.90 (m, 2H), 1.65-1.60 (m, 2H), 0.93 (t, J=7.5 Hz, 3H).

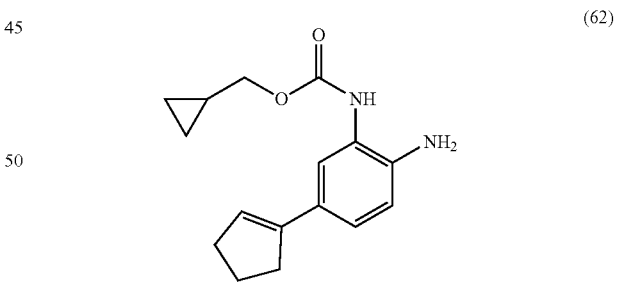

(62)

Cyclopropylmethyl (2-amino-5-(cyclopent-1-en-1-yl)phenyl)carbamate (62) was prepared by substituting tert-butyl 3-(hydroxymethyl)azetidine-1-carboxylate in Scheme 8 with cyclopropylmethanol and by substituting 2-ntro-5-(thiophen-2-yl)aniline in Scheme 8 with 5-(cyclopenten-1-yl)nitroaniline. ESI+ MS: m/z 273 ([M+H]⁺), 1H NMR (500 MHz, d⁶-DMSO): δ 8.58 (bs, 1H), 7.31 (bs, 1H), 7.00 (dd, J=2.0, 8.5 Hz, 1H), 6.64 (d, J=8.0 Hz, 1H), 5.91 (s, 1H), 4.94 (s, 2H), 3.89 (d, J=7.5 Hz, 2H), 2.58-2.50 (m, 2H), 2.47-2.40 (m, 2H), 1.94-1.87 (m, 2H), 1.20-1.08 (m, 1H), 0.56-0.51 (m, 2H), 0.32-0.27 (m, 2H).

(80)

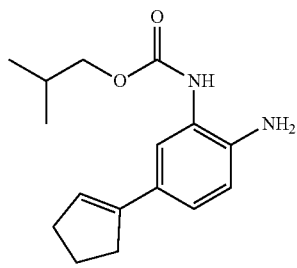

isobutyl (2-amino-5-(cyclopent-1-en-1-yl)phenyl)carbamate (80) was prepared by substituting tert-butyl 3-(hydroxymethyl)azetidine-1-carboxylate in Scheme 8 with 2-methylpropan-1-ol and by substituting 2-ntro-5-(thiophen-2-yl)aniline in Scheme 8 with 5-(cyclopenten-1-yl)nitroaniline. ESI+ MS: m/z 275 ([M+H]$^+$), 1H NMR (500 MHz, d$^6$-DMSO): δ 8.51 (bs, 1H), 7.28 (bs, 1H), 7.01 (dd, J=1.5, 8.0 Hz, 1H), 6.64 (d, J=8.5 Hz, 1H), 5.91 (s, 1H), 4.93 (s, 2H), 3.83 (d, J=6.0 Hz, 2H), 2.56-2.50 (m, 2H), 2.46-2.40 (m, 2H), 1.95-1.85 (m, 3H), 0.92 (d, J=6.5 Hz, 6H).

(198)

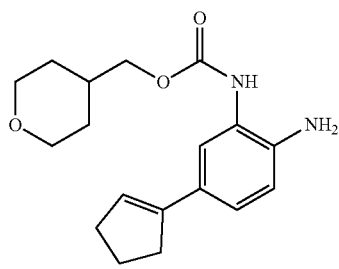

(Tetrahydro-2H-pyran-4-yl) methyl (2-amino-5-(cyclopent-1-en-1-yl)phenyl) carbamate (198) was prepared by substituting tert-butyl 3-(hydroxymethyl)azetidine-1-carboxylate in Scheme 8 with (tetrahydro-2H-pyran-4-yl)methanol and by substituting 2-ntro-5-(thiophen-2-yl)aniline in Scheme 8 with 5-(cyclopenten-1-yl)nitroaniline. ESI+ MS: m/z 317 ([M+H]+), 1HNMR (500 MHz, d$^6$-DMSO): δ 8.52 (bs, 1H), 7.27 (bs, 1H), 7.01 (d, J=7.5 Hz, 1H), 6.64 (d, J=8.5 Hz, 1H), 5.91 (s, 1H), 4.93 (s, 2H), 3.92-3.84 (m, 5H), 2.53-2.42 (m, 5H), 1.92-1.89 (m, 3H), 1.59 (d, J=11.5 Hz, 2H), 1.28-1.25 (m, 2H).

Alternatively, carbamates can be formed according to the scheme below:

(81)

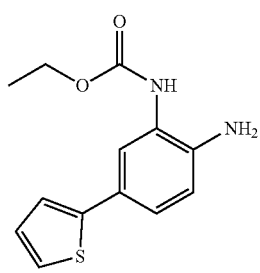

Synthesis of ethyl (2-amino-5-(thiophen-2-yl)phenyl)carbamate (81)

Scheme 16

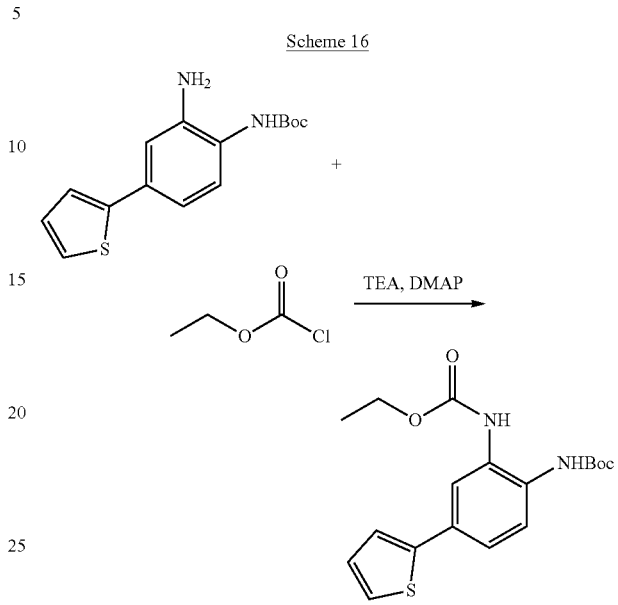

To a solution of tert-butyl (2-amino-4-(thiophen-2-yl)phenyl)carbamate (0.20 g, 0.69 mmol, 1.0 equiv.) in dichloromethane (4 mL) was added ethyl chloroformate (0.08 mL, 0.83 mmol, 1.2 equiv.), TEA (0.19 mL, 1.37 mmol, 2.0 equiv.) and DMAP (8 mg, 0.07 mmol, 0.1 equiv.) at 0° C. The reaction was warmed to room temperature and stirred for 16 h. The reaction was then diluted with dichloromethane and water. The organic layer was separated, washed with water and brine, dried over sodium sulfate, filtered and concentrated under reduced pressure. The crude material was purified on column chromatography (silica gel, 20% EtOAc/hexanes) to give tert-butyl ethyl (4-(thiophen-2-yl)-1,2-phenylene)dicarbamate (0.11 g, 44% yield).

Scheme 17

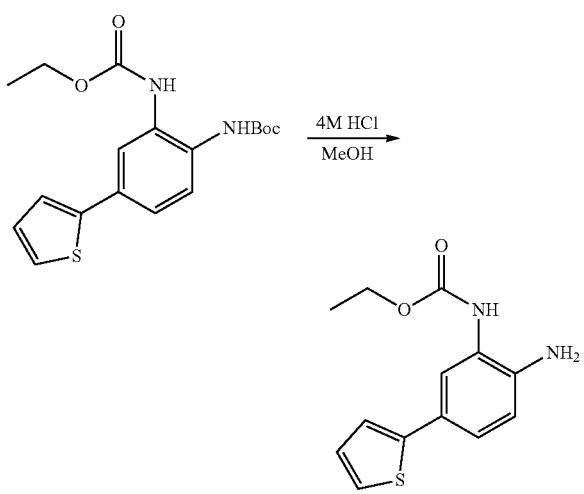

To a stirred solution of tert-butyl ethyl (4-(thiophen-2-yl)-1,2-phenylene)dicarbamate (0.10 g, 0.28 mmol, 1.0 equiv.) in MeOH (2 mL) at 0° C. was added a 4M solution of HCl in dioxane (1.5 mL). The reaction was warmed to room temperature and stirred for 2 h, The reaction was concentrated under reduced pressure. A saturated aqueous solution of sodium bicarbonate was added. The obtained solid was filtered, washed with water and dried. The crude material was purified by column chromatography (silica gel, 15% EtOAc/hexanes) to give ethyl (2-amino-5-(thiophen-2-yl)phenyl)carbamate (0.05 g, 69% yield).

One skilled in the art will recognize that other compounds described below were prepared in a similar manner to the procedures described above.

(78)

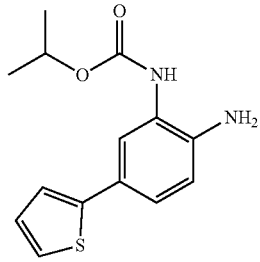

Isopropyl (2-amino-5-(thiophen-2-yl)phenyl)carbamate (78) was prepared by substituting ethyl chloroformate in Scheme 16 with isopropyl chloroformate. ESI+ MS: m/z 277 ([M+H]$^+$), 1H NMR (500 MHz, d$^6$-DMSO): δ 8.59 (bs, 1H), 7.55 (bs, 1H), 7.34 (dd, J=1.0, 5.0 Hz, 1H), 7.21-7.15 (m, 2H), 7.03 (dd, J=4.0, 5.0 Hz, 1H), 6.71 (d, J=8.0 Hz, 1H), 5.12 (s, 2H), 4.88 (sept, J=6.0 Hz, 1H), 1.26 (d, J=6.5 Hz, 6H).

(85)

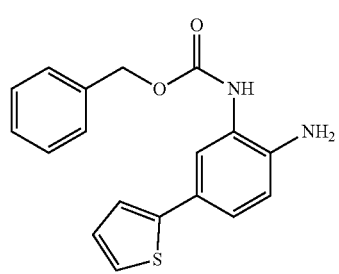

Benzyl (2-amino-5-(thiophen-2-yl)phenyl)carbamate (85) was prepared by substituting ethyl chloroformate in Scheme 16 with benzyl chloroformate. ESI+ MS: m/z 325 ([M+H]$^+$), 1H NMR (500 MHz, d$^6$-DMSO): δ 8.77 (bs, 1H), 7.55 (bs, 1H), 7.46-7.32 (m, 6H), 7.22-7.16 (m, 2H), 7.03 (dd, J=4.0, 5.0 Hz, 1H), 6.72 (d, J=8.0 Hz, 1H), 5.15 (bs, 2H), 5.14 (bs, 2H).

(74)

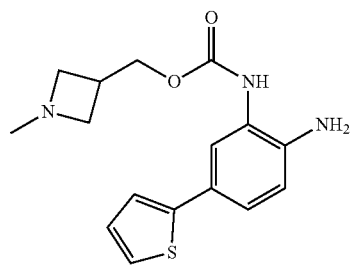

Synthesis of (1-methylazetidin-3-yl)methyl (2-amino-5-(thiophen-2-yl)phenyl) carbamate (74)

Scheme 18

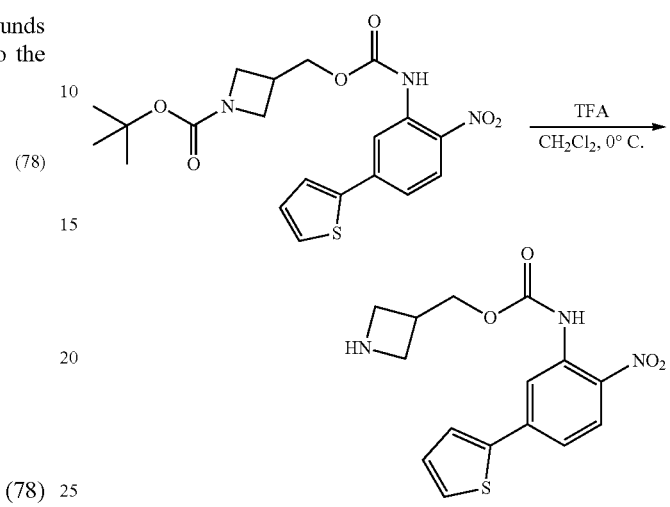

To a solution of tert-butyl 3-((((2-nitro-5-(thiophen-2-yl)phenyl)carbamoyl)oxy)methyl) azetidine-1-carboxylate (0.50 g, 1.15 mmol, 1 eq.) in dichloromethane (10 mL) was added TFA (3 mL) at 0° C. The reaction was stirred at room temperature for 2 h. The reaction was concentrated under reduced pressure. A saturated solution of sodium bicarbonate was added. The obtained solid was filtered and dried under reduced pressure to afford azetidin-3-ylmethyl (2-nitro-5-(thiophen-2-yl)phenyl)carbamate (0.35 g, 91% yield).

Scheme 19

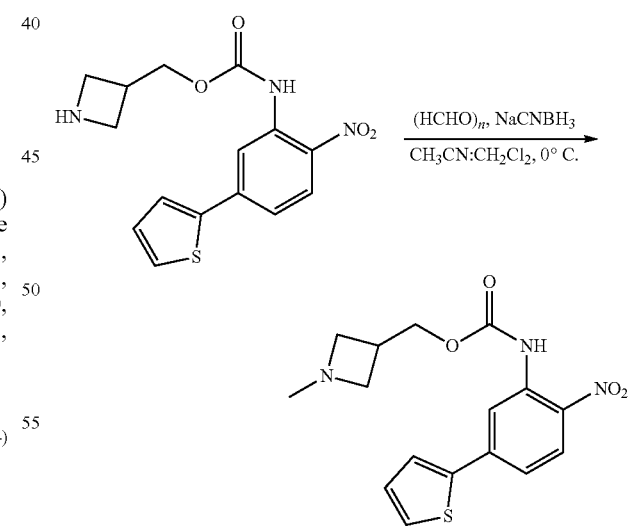

To a stirred solution of azetidin-3-ylmethyl (2-nitro-5-(thiophen-2-yl)phenyl)carbamate (0.09 g, 0.26 mmol, 1.0 eq.) in CH$_3$CN:CH$_2$Cl$_2$ was added aq. formaldehyde (0.77 mmol, 3.0 eq.). The reaction mixture was stirred at room temperature for 30 min then cooled to 0° C. Sodium cyanoborohydride (0.03 g, 0.46 mmol, 1.8 eq.) was added slowly. The reaction was quenched with an aqueous saturated solution of sodium bicarbonate. The product was extracted with ethyl acetate. The combined organic layers were washed with brine, dried over sodium sulfate and concentrated under reduced pressure. The crude product was purified by column chromatography (silica gel, 5% MeOH/CH$_2$Cl$_2$) to obtain (1-methylazetidin-3-yl)methyl (2-nitro-5-(thiophen-2-yl) phenyl)carbamate (0.07 g, 75% yield).

Scheme 20

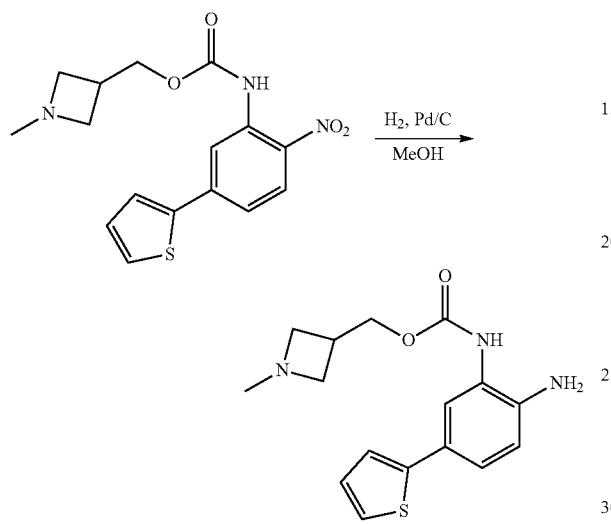

To a stirred solution of (1-methylazetidin-3-yl)methyl (2-nitro-5-(thiophen-2-yl)phenyl)carbamate (0.06 g, 0.16 mmol, 1 eq.) in MeOH (5 mL) was added Pd/C (0.03 g, 0.24 mmol, 1.5 eq). The reaction was stirred at room temperature under H$_2$ atmosphere for 2 h. The reaction mixture was filtered through Celite and concentrated. The crude solid, which was washed with ether and pentane to obtain (1-methylazetidin-3-yl)methyl (2-amino-5-(thiophen-2-yl)phenyl)carbamate (0.03 g, 62% yield) as ash color solid. ESI+ MS: m/z 318 ([M+H]$^+$), 1H NMR (500 MHz, d$^6$-DMSO): δ 8.69 (bs, 1H), 7.50 (bs, 1H), 7.34 (d, J=4.5 Hz, 1H), 7.22-7.16 (m, 2H), 7.06-7.02 (m, 1H), 6.72 (d, J=8.0 Hz, 1H), 5.13 (bs, 2H), 4.19 (d, J=6.5 Hz, 2H), 3.54-3.45 (m, 2H), 3.25-3.15 (m, 2H), 2.82-2.70 (m, 1H), 2.35 (s, 3H).

One skilled in the art will recognize that other compounds described below were prepared in a similar manner to the procedures described above.

(70)

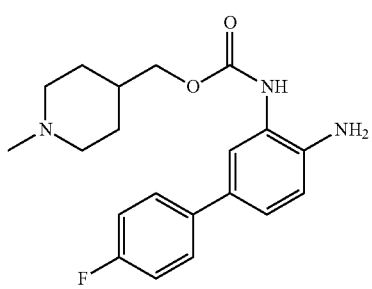

(1-methylpiperidin-4-yl)methyl (4-amino-4'-fluoro-[1,1'-biphenyl]-3-yl)carbamate (70) was prepared by substituting tert-butyl 3-(hydroxymethyl)azetidine-1-carboxylate in Scheme 8 with tert-butyl 4-(hydroxymethyl)piperidine-1-carboxylate and by substituting thiophen-2-ylboronic acid in Scheme 2 with (4-fluorophenyl) boronic acid. ESI+ MS: m/z 358 ([M+H]$^+$), 1H NMR (500 MHz, d$^6$-DMSO): δ 8.60 (bs, 1H), 7.53-7.59 (m, 3H), 7.21-7.16 (m, 3H), 6.76 (d, J=8.0 Hz, 1H), 5.05 (s, 2H), 3.92 (d, J=6.0 Hz, 2H), 2.75 (d, J=11.0 Hz, 2H), 1.82 (t, J=10.5 Hz, 2H), 1.67-1.57 (m, 3H), 1.27-1.21 (m, 2H).

(161)

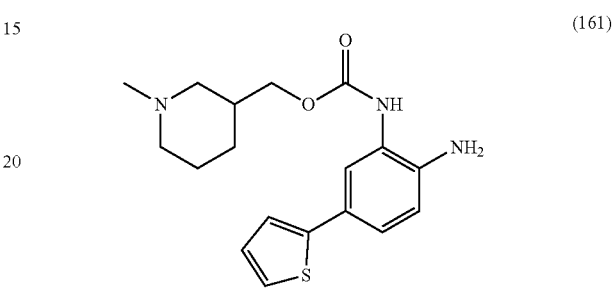

(1-Methylpiperidin-3-yl)methyl (2-amino-5-(thiophen-2-yl) phenyl)carbamate (161) was prepared by substituting tert-butyl 3-(hydroxymethyl)azetidine-1-carboxylate in Scheme 8 with tert-butyl 3-(hydroxymethyl)piperidine-1-carboxylate. ESI+ MS: m/z 346 ([M+H]+), 1H NMR (500 MHz, d$^6$-DMSO): δ 8.61 (s, 1H), 7.51 (s, 1H), 7.34 (s, 1H), 7.19-7.13 (m, 2H), 7.04-7.02 (m, 1H), 6.73-6.68 (m, 1H), 5.12 (s, 2H), 4.03-3.88 (m, 2H), 2.83-2.69 (m, 2H), 2.21 (s, 3H), 1.98-1.90 (m, 3H), 1.65 (brs, 2H), 1.49 (d, J=12.0 Hz, 1H), 1.02 (d, J=10.0 Hz, 1H).

Alternatively, the nitro group reduction can be carried out using zinc and ammonium formate as previously described and one skilled in the art will recognize that other compounds described below can be prepared in a similar manner:

(69)

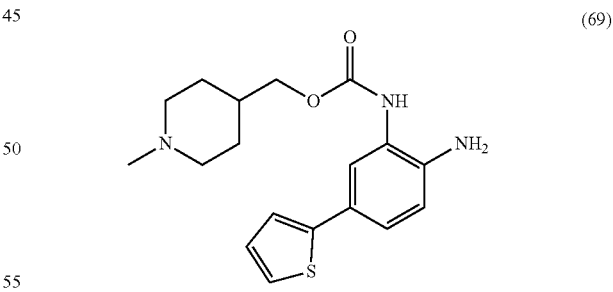

(1-Methylpiperidin-4-yl)methyl (2-amino-5-(thiophen-2-yl) phenyl)carbamate (69) was prepared by substituting tert-butyl 3-(hydroxymethyl)azetidine-1-carboxylate in Scheme 8 with tert-butyl 4-(hydroxymethyl)piperidine-1-carboxylate. ESI+ MS: m/z 346 ([M+H]$^+$), 1H NMR (500 MHz, d$^6$-DMSO): δ 8.60 (bs, 1H), 7.52 (bs, 1H), 7.33 (d, J=4.5 Hz, 1H), 7.22-7.14 (m, 2H), 7.03 (dd, J=4.0, 5.5 Hz, 1H), 5.11 (s, 2H), 3.93 (d, J=6.5 Hz, 2H), 2.76 (d, J=11.5 Hz, 2H), 2.14 (s, 3H), 1.83 (t, J=11.0 Hz, 2H), 1.66 (d, J=12.5 Hz, 2H), 1.63-1.52 (m, 1H), 1.30-1.18 (m, 2H).

175

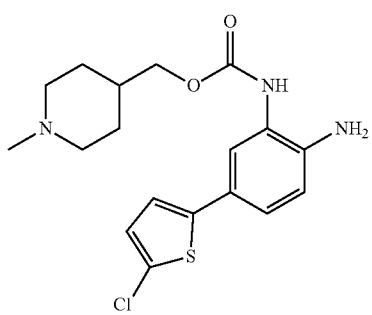
(197)

(1-Methylpiperidin-4-yl)methyl (2-amino-5-(5-chlorothiophen-2-yl)phenyl)carbamate (197) was prepared by substituting tert-butyl 3-(hydroxymethyl)azetidine-1-carboxylate in Scheme 8 with tert-butyl 4-(hydroxymethyl)piperidine-1-carboxylate and thiophen-2-ylboronic acid in Scheme 7 with 5-chlorothiophen-2-ylboronic acid. ESI+ MS: m/z 380 ([M+H]$^+$), 1H NMR (500 MHz, d$^6$-DMSO): δ 8.62 (bs, 1H), 7.46 (bs, 1H), 7.13-7.11 (m, 1H), 7.06-7.03 (m, 2H), 6.71 (d, J=8.0 Hz, 1H), 5.21 (bs, 2H), 3.92 (d, J=6.5 Hz, 2H), 2.75 (d, J=11.5 Hz, 2H), 2.14 (s, 3H), 1.82 (t, J=11.0 Hz, 2H), 1.66-1.57 (m, 3H), 1.27-1.22 (m, 2H).

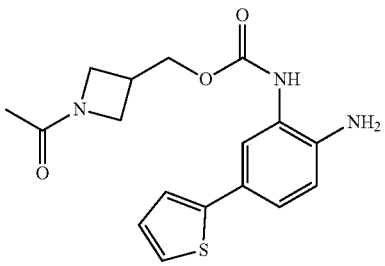
(73)

Synthesis of (1-acetylazetidin-3-yl)methyl (2-amino-5-(thiophen-2-yl)phenyl) Carbamate (73)

Scheme 21

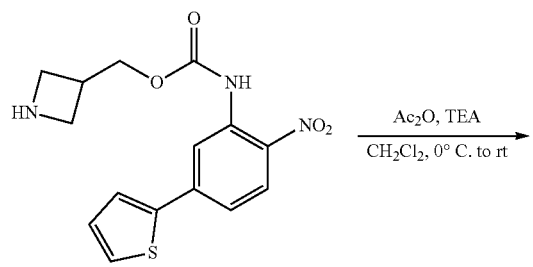

176

-continued

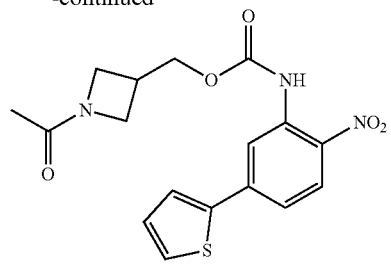

To a solution of azetidin-3-ylmethyl (2-nitro-5-(thiophen-2-yl)phenyl)carbamate (0.35 g, 1.05 mmol, 1 eq.) in dichloromethane (10 mL) was added TEA (0.22 mL, 1.57 mmol, 1.5 eq.) and acetic anhydride (0.11 mL, 1.15 mmol, 1.1 eq.) at 0° C. The reaction was warmed to room temperature and stirred for 1 h. The reaction was diluted with dichloromethane. The organic layer was washed with water and brine. The combined organic layers were dried over sodium sulfate, filtered and concentrated under reduced pressure. The crude material was purified by column chromatography (silica gel, 4% MeOH/CH$_2$Cl$_2$) to obtain (1-acetylazetidin-3-yl)methyl (2-nitro-5-(thiophen-2-yl)phenyl)carbamate (0.31 g, 79% yield).

Scheme 22

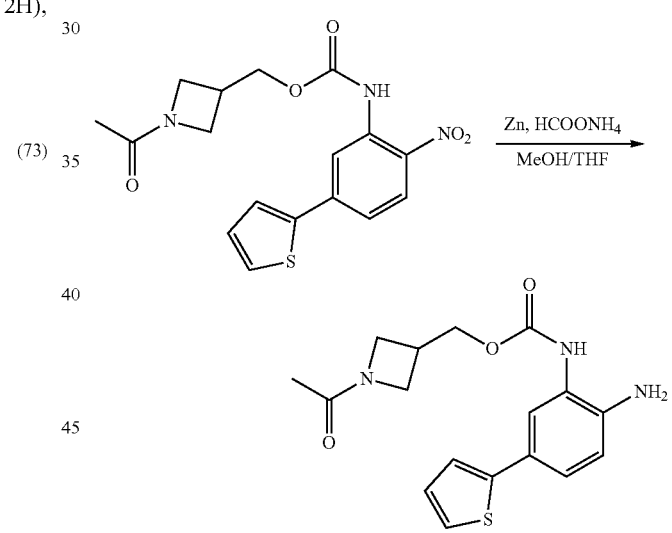

To a solution of (1-acetylazetidin-3-yl)methyl (2-nitro-5-(thiophen-2-yl)phenyl)carbamate (0.15 g, 0.40 mmol, 1 eq.) in MeOH/THF (5 mL/5 mL) was added Zinc powder (0.13 g, 2.00 mmol, 5 eq.) and ammonium formate (0.20 g, 3.20 mmol, 8 eq.). The reaction was stirred at room temperature for 3 h. The reaction was filtered through Celite and the solids washed with MeOH. The filtrate was concentrated under reduced pressure then diluted with water. The obtained solid was filtered and dried. The crude product was purified by column chromatography (silica gel, 5% MeOH/CH$_2$Cl$_2$) to obtain (1-acetylazetidin-3-yl)methyl (2-amino-5-(thiophen-2-yl)phenyl)carbamate (0.030 g, 22% yield). ESI+ MS: m/z 346 ([M+H]$^+$), 1H NMR (500 MHz, d$^6$-DMSO): δ 8.74 (bs, 1H), 7.50 (bs, 1H), 7.34 (d, J=5.0 Hz, 1H), 7.24-7.14 (m, 2H), 7.08-7.01 (m, 1H), 6.72 (d, J=8.0 Hz, 1H), 5.14 (bs, 2H), 4.30-4.10 (m, 3H), 3.95-3.80 (m, 2H), 3.68-3.55 (m, 1H), 2.95-2.85 (m 1H), 1.74 (s, 3H).

One skilled in the art will recognize that other compounds described below can be prepared in a similar manner to the procedures described above.

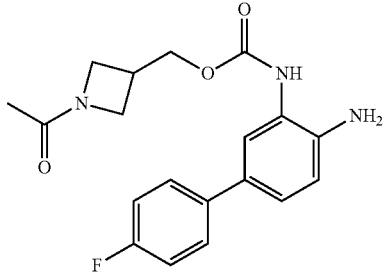

(72)

(1-acetylazetidin-3-yl)methyl (4-amino-4'-fluoro-[1,1'-biphenyl]-3-yl)carbamate (72) was prepared by substituting thiophen-2-ylboronic acid in Scheme 7 with (4-fluorophenyl) boronic acid. ESI+ MS: m/z 358 ([M+H]+), 1H NMR (500 MHz, d6-DMSO): δ 8.74 (s, 1H), 7.60-7.45 (m, 3H), 7.23-7.15 (m, 3H), 6.77 (d, J=8 Hz, 1H), 5.06 (s, 2H), 4.22 (d, J=6.5 Hz, 2H), 4.21-4.12 (m, 1H), 3.94-3.84 (m, 2H), 3.58-3.66 (m, 1H), 2.96-2.84 (m, 1H), 1.73 (s, 3H).

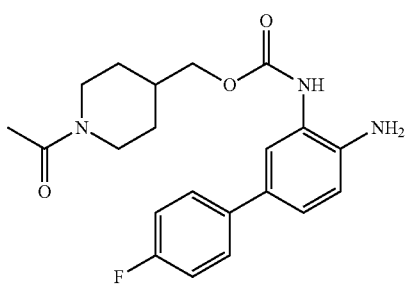

(67)

(1-Acetylpiperidin-4-yl)methyl (4-amino-4'-fluoro-[1,1'-biphenyl]-3-yl)carbamate (67) was prepared by substituting tert-butyl 3-(hydroxymethyl)azetidine-1-carboxylate in Scheme 8 with tert-butyl 4-(hydroxymethyl)piperidine-1-carboxylate and by substituting thiophen-2-ylboronic acid in Scheme 7 with (4-fluorophenyl) boronic acid. ESI+ MS: m/z 386 ([M+H]+), 1H NMR (500 MHz, d6-DMSO): δ 8.64 (s, 1H), 7.58-7.46 (m, 3H), 7.24-7.14 (m, 3H), 6.77 (d, J=8 Hz, 1H), 5.06 (s, 2H), 4.39 (d, J=12 Hz, 1H), 3.95 (d, J=6.5 Hz, 2H), 3.82 (d, J=14 Hz, 1H), 3.02 (t, J=12.5 Hz, 1H), 1.98 (s, 3H), 1.93-1.80 (m, 2H), 1.71 (t, J=14 Hz, 2H), 1.30-1.13 (m, 1H), 1.13-1.00 (m, 1H).

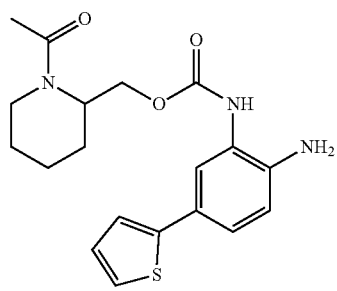

(152)

(1-Acetylpiperidin-2-yl)methyl (2-amino-5-(thiophen-2-yl)phenyl)carbamate (152) was prepared by substituting tert-butyl 3-(hydroxymethyl)azetidine-1-carboxylate in Scheme 8 with tert-butyl 2-(hydroxymethyl)piperidine-1-carboxylate. ESI+ MS: m/z 374 ([M+H]+), 1HNMR (500 MHz, d6-DMSO): δ 8.37 (bs, 1H), 7.43 (bs, 1H), 7.28 (d, J=4.5 Hz, 1H), 7.17-7.14 (m, 2H), 7.02-7.01 (m, 1H), 6.73 (d, J=8.5 Hz, 1H), 4.90 (s, 2H), 4.48 (s, 1H), 4.16 (m, 1H), 2.0 (s, 3H), 1.73 (d, J=7.0 Hz, 1H), 1.64-1.56 (m, 4H), 1.38-1.25 (m, 2H).

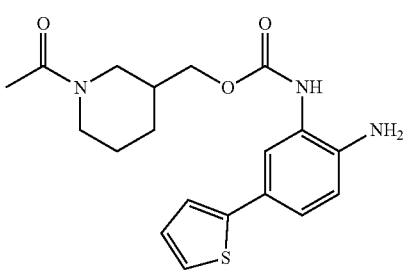

(160)

(1-Acetylpiperidin-3-yl)methyl (2-amino-5-(thiophen-2-yl)phenyl)carbamate (160) was prepared by substituting tert-butyl 3-(hydroxymethyl)azetidine-1-carboxylate in Scheme 8 with tert-butyl 3-(hydroxymethyl)piperidine-1-carboxylate. ESI+ MS: m/z 374 ([M+H]+), 1HNMR (500 MHz, d6-DMSO): δ 8.66 (brs, 1H), 7.50 (brs, 1H), 7.33 (d, J=5.0 Hz, 1H), 7.17 (t, J=3.5 Hz, 2H), 7.03 (d, J=4.0 Hz, 1H), 6.71 (d, J=8.5 Hz, 1H), 5.11 (s, 2H), 4.28 (brs, 1H), 4.05-3.87 (m, 2H), 3.69-3.67 (m, 1H), 3.02-2.97 (m, 1H), 2.72 (brs, 1H), 1.98 (s, 3H), 1.78-1.59 (m, 3H), 1.42-1.40 (m, 1H), 1.29-1.22 (m, 2H).

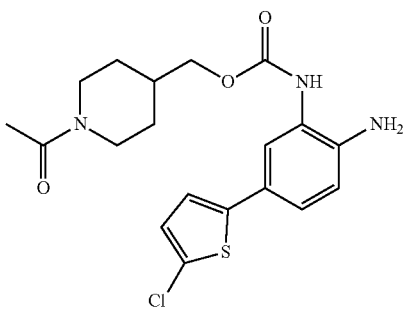

(175)

(1-Acetylpiperidin-4-yl)methyl (2-amino-5-(5-chlorothiophen-2-yl)phenyl)carbamate (175) was prepared by substituting tert-butyl 3-(hydroxymethyl)azetidine-1-carboxylate in Scheme 8 with tert-butyl 4-(hydroxymethyl)piperidine-1-carboxylate and by substituting thiophen-2-ylboronic acid in Scheme 7 with (5-chlorothiophen-2-yl)boronic acid. ESI+ MS: m/z 408 ([M+H]+), 1H NMR (500 MHz, d6-DMSO): δ 8.65 (bs, 1H), 7.46 (bs, 1H), 7.12 (d, J=8.5 Hz, 1H), 7.06-7.03 (m, 2H), 6.71 (d, J=8.0 Hz, 1H), 5.22 (s, 2H), 4.38 (d, J=13.0 Hz, 1H), 3.94 (d, J=6.0 Hz, 2H), 3.82 (d, J=13.5 Hz, 1H), 3.01 (t, J=12.5 Hz, 1H), 1.98 (s, 3H), 1.88 (m, 1H), 1.71 (t, J=14.5 Hz, 2H), 1.28-1.18 (m, 2H), 1.07-1.05 (m, 1H).

Alternatively, the nitro group reduction can be carried out using zinc and ammonium formate as previously described and one skilled in the art will recognize that other compounds described below can be prepared in a similar manner:

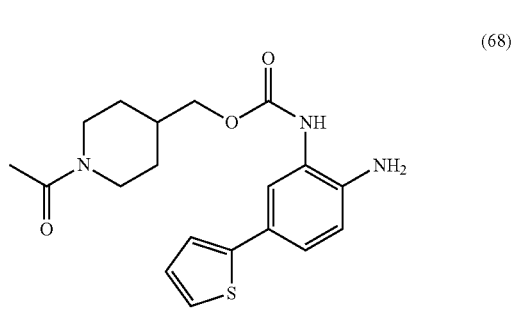 [SMILES: CC(=O)N1CCC(COC(=O)Nc2cc(-c3cccs3)ccc2N)CC1]

(68)

(1-Acetylpiperidin-4-yl)methyl (2-amino-5-(thiophen-2-yl)phenyl)carbamate (68) was prepared by substituting tert-butyl 3-(hydroxymethyl)azetidine-1-carboxylate in Scheme 8 with tert-butyl 4-(hydroxymethyl)piperidine-1-carboxylate. ESI+ MS: m/z 374 ([M+H]$^+$), 1H NMR (500 MHz, d$^6$-DMSO): δ 8.62 (bs, 1H), 7.52 (bs, 1H), 7.34 (d, J=4.5 Hz, 1H), 7.21-7.16 (m, 2H), 7.03 (dd, J=3.5, 5.0 Hz, 1H), 6.72 (d, J=8.5 Hz, 1H), 5.12 (s, 2H), 4.39 (d, J=13.0 Hz, 1H), 3.95 (d, J=6.0 Hz, 2H), 3.82 (d, J=13.5 Hz, 1H), 3.02 (t, J=13.5 Hz, 1H), 1.99 (s, 3H), 1.95-1.85 (m, 1H), 1.72 (t, J=15.0 Hz, 2H), 1.30-1.15 (m, 2H), 1.15-1.02 (m, 1H).

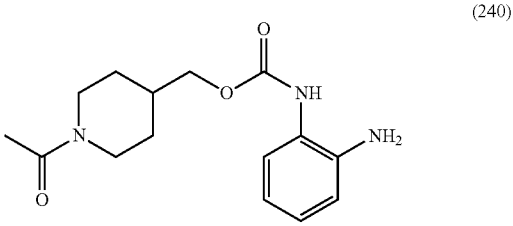 [SMILES: CC(=O)N1CCC(COC(=O)Nc2ccccc2N)CC1]

(240)

(1-acetylpiperidin-4-yl)methyl (2-aminophenyl)carbamate (240) was prepared by substituting tert-butyl 3-(hydroxymethyl)azetidine-1-carboxylate in Scheme 8 with tert-butyl 4-(hydroxymethyl)piperidine-1-carboxylate and 2-nitro-5-(thiophen-2-yl)aniline in Scheme 8 with 2-nitroaniline. ESI+ MS: m/z 292 ([M+H]+); 1H NMR (400 MHz, d6-DMSO): δ 8.51 (bs, 1H), 7.17-7.15 (m, 1H), 6.69-6.67 (m, 1H), 6.54-6.50 (m, 1H), 4.84 (s, 2H), 4.38 (d, J=12.8 Hz, 1H), 3.91 (d, J=6.4 Hz, 2H), 3.82 (d, J=13.6 Hz, 1H), 3.01 (t, J=12.4 Hz, 1H), 2.54-2.50 (m, 1H), 1.98 (s, 3H), 1.87 (bs, 1H), 1.70 (t, J=12.8 Hz, 2H), 1.19-1.04 (m, 2H).

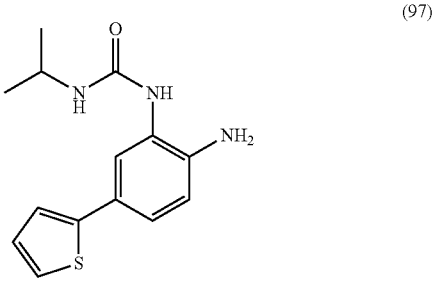 [SMILES: CC(C)NC(=O)Nc1cc(-c2cccs2)ccc1N]

(97)

Synthesis of 1-(2-amino-5-(thiophen-2-yl)phenyl)-3-isopropylurea (97)

Scheme 23

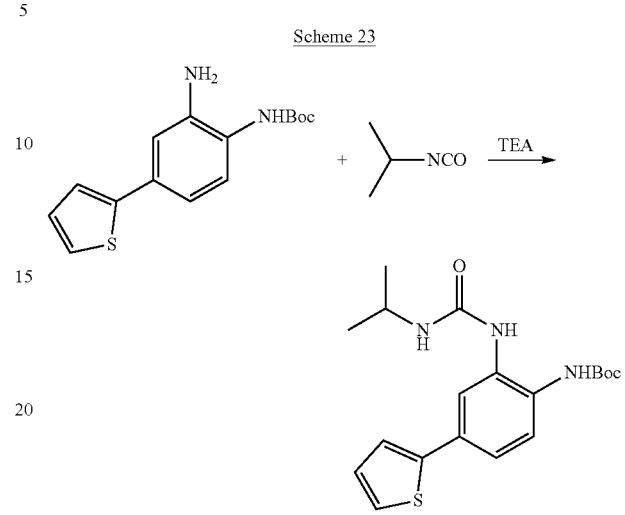

To a solution of tert-butyl (2-amino-4-(thiophen-2-yl)phenyl)carbamate (0.20 g, 0.70 mmol, 1.0 equiv.) in dichloromethane (4 mL) was added isopropyl isocyanate (0.07 mL, 0.83 mmol, 1.2 equiv.) and TEA (0.19 mL, 1.37 mmol) at 0° C. The reaction was stirred at room temperature for 16 h. The reaction was then diluted with dichloromethane and water. The organic layer was separated, washed with water and brine, dried over sodium sulfate, then concentrated under reduced pressure. The crude material was purified by column chromatography (silica gel, 20% EtOAc/hexanes) to give tert-butyl (2-(3-isopropylureido)-4-(thiophen-2-yl)phenyl)carbamate (0.18 g, 70% yield).

Scheme 24

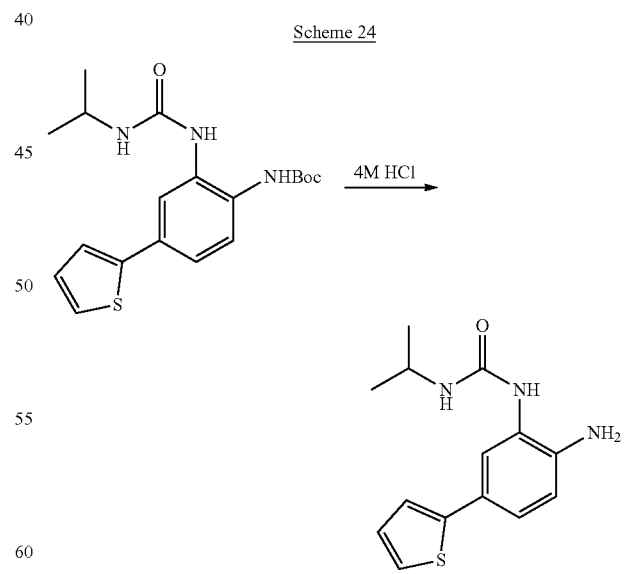

A 4M solution of HCl in dioxane (2 mL) was added to a stirred solution of tert-butyl (2-(3-isopropylureido)-4-(thiophen-2-yl)phenyl)carbamate (0.15 g, 0.40 mmol, 1 equiv.) in methanol (4 mL) at 0° C. The reaction was warmed to room temperature and stirred for 2 h. The reaction was then concentrated under reduced pressure. A saturated aqueous solution of sodium bicarbonate was added. The obtained solid was filtered, washed with water and dried to yield 1-(2-amino-5-(thiophen-2-yl)phenyl)-3-isopropylurea (0.10 g, 91% yield). ESI+ MS: m/z 276 ([M+H]$^+$), 1H NMR (500 MHz, d$^6$-DMSO): δ 7.67 (d, J=2.0 Hz, 1H), 7.47 (s, 1H), 7.33 (d, J=5.0 Hz, 1H), 7.17 (d, J=3.0 Hz, 1H), 7.09 (dd, J=1.5, 8.0 Hz, 1H), 7.05-7.01 (m, 1H), 6.72 (d, J=8.0 Hz, 1H), 6.08 (d, J=8.0 Hz, 1H), 4.87 (s, 2H), 3.76 (sept, J=7.0 Hz, 1H), 1.10 (d, J=7.0 Hz, 6H).

One skilled in the art will recognize that other compounds described below can be prepared in a similar manner to the procedures described above.

(96)

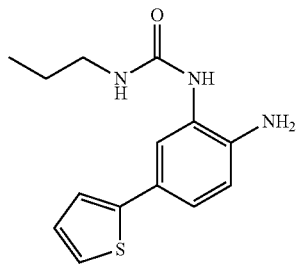

1-(2-Amino-5-(thiophen-2-yl)phenyl)-3-propylurea (96) was prepared by substituting isopropyl isocyanate in Scheme 23 with n-propyl isocyanate. ESI+ MS: m/z 276 ([M+H]$^+$), 1H NMR (500 MHz, d$^6$-DMSO): δ 7.65 (s, 1H), 7.56 (s, 1H), 7.33 (d, J=5.0 Hz, 1H), 7.18 (d, J=3.0 Hz, 1H), 7.10 (dd, J=8.0, 1.5 Hz, 1H), 7.03 (t, J=4.5 Hz, 1H), 6.72 (d, J=8.0 Hz, 1H), 6.21 (t, J=5.5 Hz, 1H), 4.90 (s, 2H), 3.05 (t, J=6.5 Hz, 2H), 1.45 (sext, J=6.5 Hz, 2H), 0.89 (t, J=6.5 Hz, 3H).

(93)

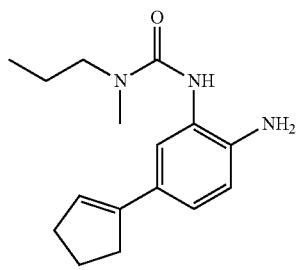

Synthesis of 3-(2-amino-5-(cyclopent-1-en-1-yl)phenyl)-1-methyl-1-propylurea (93)

Scheme 25

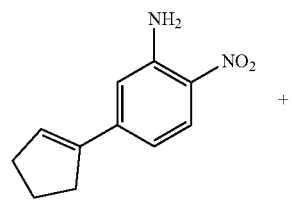

+

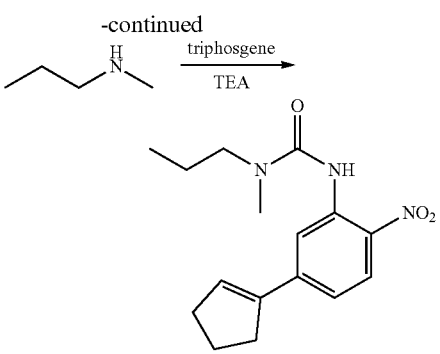

To a solution of 5-(cyclopent-1-en-1-yl)-2-nitroaniline (0.13 g, 0.61 mmol, 1.0 equiv.) in dichloromethane were added triethylamine (0.68 mL, 4.90 mmol, 8.0 equiv.) and triphosgene (0.18 g, 0.61 mmol, 1.0 equiv.) at 0° C. The mixture was warmed to room temperature and stirred for 3 h at room temperature. Triethylamine (0.17 mL, 1.22 mmol, 2.0 equiv.) and N-methylpropan-1-amine (0.07 g, 0.92 mmol, 1.5 equiv.) were added slowly to the reaction mixture. The reaction mixture was slowly warmed to 50° C. and stirred for 2 h. The mixture was diluted with dichloromethane, washed with water and brine, dried over anhydrous magnesium sulfate, filtered, and concentrated under reduced pressure to give crude 3-(5-(cyclopent-1-en-1-yl)-2-nitrophenyl)-1-methyl-1-propylurea (0.14 g, 76% crude yield) which was used in the next step without further purification.

Scheme 26

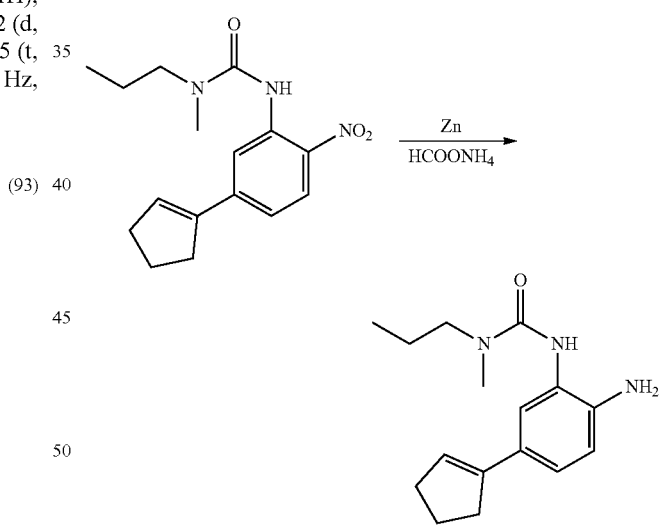

To a stirred solution 3-(5-(cyclopent-1-en-1-yl)-2-nitrophenyl)-1-methyl-1-propylurea (0.17 g, 0.56 mmol, 1.0 equiv.) in MeOH were added Zn (0.18 g, 2.80 mmol, 5.0 equiv.) and HCOONH$_4$ (0.28 d, 4.48 mmol, 8.0 equiv.) at room temperature. The reaction was stirred for 2 h then filtered through celite. The organic layer was concentrated and the crude residue was purified by column chromatography (silica gel, 5% MeOH/CH$_2$Cl$_2$) to afford 3-(2-amino-5-(cyclopent-1-en-1-yl)phenyl)-1-methyl-1-propylurea (0.12 g, 78% yield). ESI+ MS: m/z 274 ([M+H]$^+$), 1H NMR (500 MHz, d$^6$-DMSO): δ 7.61 (s, 1H), 7.08 (d, J=1.5 Hz, 1H), 7.01 (dd, J=8.0, 1.5 Hz, 1H), 6.66 (d, J=8.0 Hz, 1H), 5.94-8.90 (m, 1H), 4.77 (s, 2H), 3.24 (t, J=7.5 Hz, 2H), 2.92

(s, 3H), 2.58-2.52 (m, 2H), 2.46-2.40 (m, 2H), 1.95-1.86 (m, 2H), 1.52 (sext, J=7.5 Hz, 2H), 0.86 (t, J=7.5 Hz, 3H).

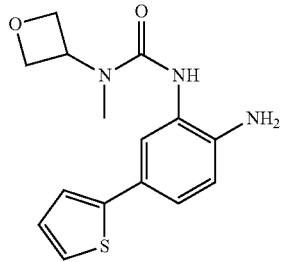

(95)

3-(2-Amino-5-(thiophen-2-yl)phenyl)-1-methyl-1-(oxetan-3-yl)urea (95) was prepared by substituting N-methylpropan-1-amine in Scheme 25 with N-methyloxetan-3-amine and by substituting 5-(cyclopent-1-en-1-yl)-2-nitroaniline with 2-nitro-5-(thiophen-2-yl)aniline. ESI+ MS: m/z 304 ([M+H]$^+$), 1H NMR (500 MHz, d$^6$-DMSO): δ 7.83 (s, 1H), 7.33 (d, J=5.0 Hz, 1H), 7.27 (s, 1H), 7.22-7.16 (m, 2H), 7.03 (t, J=4.5 Hz, 1H), 6.73 (d, J=8.5 Hz, 1H), 5.21 (quintet, J=7.5 Hz, 1H), 4.98 (bs, 2H), 4.70-4.63 (m, 4H), 3.07 (s, 3H).

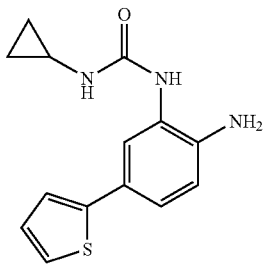

(100)

1-(2-amino-5-(thiophen-2-yl)phenyl)-3-cyclopropylurea (100) was prepared by substituting N-methylpropan-1-amine in Scheme 25 with cyclopropanamine and by substituting 5-(cyclopent-1-en-1-yl)-2-nitroaniline in Scheme 25 with 2-nitro-5-(thiophen-2-yl)aniline. ESI+ MS: m/z 273 ([M]$^+$), 1H NMR (500 MHz, d$^6$-DMSO): δ 7.62 (d, J=2.0 Hz, 1H), 7.50 (s, 1H), 7.33 (d, J=4.5 Hz, 1H), 7.18 (d, J=3.0 Hz, 1H), 7.11 (dd, J=2.0, 8.0 Hz, 1H), 7.03 (dd, J=3.5, 4.5 Hz, 1H), 6.72 (d, J=8.5 Hz, 1H), 6.47 (s, 1H), 4.90 (s, 2H), 2.58-2.50 (m, 1H), 0.65-0.61 (m, 2H), 0.45-0.40 (m, 2H).

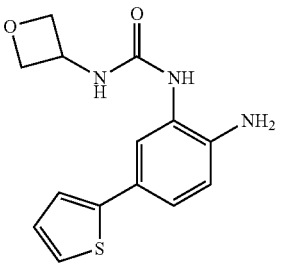

(104)

1-(2-amino-5-(thiophen-2-yl)phenyl)-3-(oxetan-3-yl)urea was prepared by substituting N-methylpropan-1-amine in Scheme 25 with oxetan-3-amine and by substituting 5-(cyclopent-1-en-1-yl)-2-nitroaniline in Scheme 25 with 2-nitro-5-(thiophen-2-yl)aniline. ESI+ MS: m/z 289 ([M]$^+$), 1H NMR (500 MHz, d$^6$-DMSO): δ 7.67 (s, 1H), 7.59 (s, 1H), 7.33 (d, J=4.5 Hz, 1H), 7.18 (d, J=2.5 Hz, 1H), 7.12 (d, J=8.0 Hz, 1H), 7.05-6.96 (m, 2H), 6.73 (d, J=8.0 Hz, 1H), 4.93 (bs, 2H), 4.82-4.70 (m, 3H), 4.47-4.43 (m, 2H).

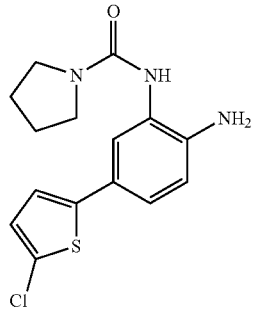

(117)

N-(2-amino-5-(5-chlorothiophen-2-yl)phenyl)pyrrolidine-1-carboxamide (117) was prepared by substituting N-methylpropan-1-amine in Scheme 25 with pyrrolidine and by substituting 5-(cyclopent-1-en-1-yl)-2-nitroaniline in Scheme 25 with 5-(5-chlorothiophen-2-yl)-2-nitroaniline. ESI+ MS: m/z 291 ([M]$^+$), 1H NMR (300 MHz, d$^6$-DMSO): δ 7.49 (s, 1H), 7.28 (d, J=3.0 Hz, 1H), 7.16 (dd, J=3.0, 6.0 Hz, 1H), 7.07-7.02 (m, 2H), 6.73 (d, J=6.0 Hz, 1H), 5.12 (s, 2H), 3.45-3.35 (m, 4H), 1.92-1.80 (m, 4H).

(122)

N-(2-amino-5-(thiophen-2-yl)phenyl)-3-fluoropyrrolidine-1-carboxamide (122) was prepared by substituting N-methylpropan-1-amine in Scheme 25 with 3-fluoropyrrolidine and by substituting 5-(cyclopent-1-en-1-yl)-2-nitroaniline in Scheme 25 with 2-nitro-5-(thiophen-2-yl)aniline. ESI+ MS: m/z 305 ([M]$^+$), 1H NMR (500 MHz, d$^6$-DMSO): δ 7.62 (s, 1H), 7.35 (d, J=1.5 Hz, 1H), 7.35-7.31 (m, 1H), 7.22-7.18 (m, 2H), 7.03 (dd, J=3.5, 5.0 Hz, 1H), 6.74 (d, J=8.0 Hz, 1H), 5.44-5.30 (m, 1H), 5.04 (s, 2H), 3.74-3.50 (m, 3H), 3.48-3.40 (m, 1H), 2.22-2.00 (m, 2H).

(126)

N-(2-amino-5-(thiophen-2-yl)phenyl)-4,4-difluoropiperidine-1-carboxamide (126) was prepared by substituting N-methylpropan-1-amine in Scheme 25 with 4,4-difluoropiperidine and by substituting 5-(cyclopent-1-en-1-yl)-2-nitroaniline in Scheme 25 with 2-nitro-5-(thiophen-2-yl)aniline. ESI+ MS: m/z 338 ([M+H]⁺), 1H NMR (500 MHz, d⁶-DMSO): δ 8.09 (s, 1H), 7.33 (d, J=5.0 Hz, 1H), 7.26 (d, J=2.0 Hz, 1H), 7.24-7.18 (m, 2H), 7.03 (dd, J=3.5, 5.0 Hz, 1H), 6.73 (d, J=8.0 Hz, 1H), 4.98 (s, 2H), 3.57 (t, J=5.5 Hz, 4H), 2.05-1.95 (m, 4H).

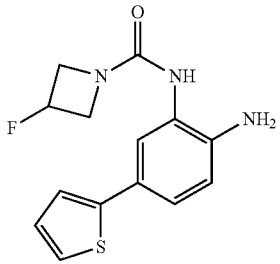

(137)

N-(2-amino-5-(thiophen-2-yl)phenyl)-3-fluoroazetidine-1-carboxamide (137) was prepared by substituting N-methylpropan-1-amine in Scheme 25 with 3-fluoroazetidine and by substituting 5-(cyclopent-1-en-1-yl)-2-nitroaniline in Scheme 25 with 2-nitro-5-(thiophen-2-yl)aniline. ESI+ MS: m/z 291 ([M]⁺), 1H NMR (500 MHz, d⁶-DMSO): δ 7.85 (s, 1H), 7.36-7.32 (m, 2H), 7.22-7.16 (m, 2H), 7.05-7.02 (m, 1H), 6.72 (d, J=8.0 Hz, 1H), 5.47-5.30 (m, 1H), 5.07 (s, 2H), 4.32-4.22 (m, 2H), 4.05-3.95 (m, 2H).

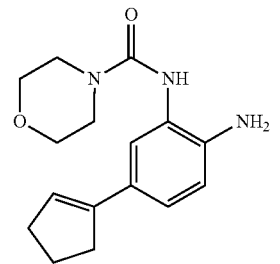

(143)

N-(2-amino-5-(cyclopent-1-en-1-yl)phenyl)morpholine-4-carboxamide (143) was prepared by substituting N-methylpropan-1-amine in Scheme 25 with morpholine. ESI+ MS: m/z 288 ([M+H]⁺), 1H NMR (500 MHz, d⁶-DMSO): δ 7.86 (s, 1H), 7.07 (d, J=1.5 Hz, 1H), 7.03 (dd, J=1.5, 8.0 Hz, 1H), 6.66 (d, J=8.0 Hz, 1H), 5.92 (bs, 1H), 4.81 (s, 2H), 3.60 (t, J=5 Hz, 4H), 3.40 (t, J=5.0 Hz, 4H), 2.58-2.52 (m, 2H), 2.45-2.40 (m, 2H), 1.95-1.88 (m, 2H).

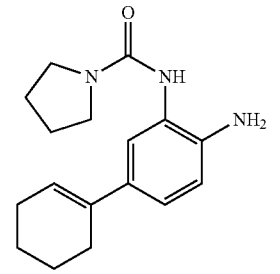

(108)

N-(4-amino-2',3',4',5'-tetrahydro-[1,1'-biphenyl]-3-yl)pyrrolidine-1-carboxamide (108) was prepared by substituting N-methylpropan-1-amine in Scheme 25 with pyrrolidine and by substituting 5-(cyclopent-1-en-1-yl)-2-nitroaniline in Scheme 25 with 4-nitro-2',3',4',5'-tetrahydro-[1,1'-biphenyl]-3-amine. ESI+ MS: m/z 286 ([M+H]⁺), 1H NMR (500 MHz, d⁶-DMSO): δ 7.39 (s, 1H), 7.11 (d, J=2.0 Hz, 1H), 6.93 (dd, J=2.5, 8.0 Hz, 1H), 6.64 (d, J=8.5 Hz, 1H), 5.91 (bs, 1H), 4.77 (s, 2H), 3.37-3.32 (m, 4H), 2.30-2.24 (m, 2H), 2.16-2.10 (m, 2H), 1.88-1.82 (m, 4H), 1.72-1.66 (m, 2H), 1.60-1.54 (m, 2H).

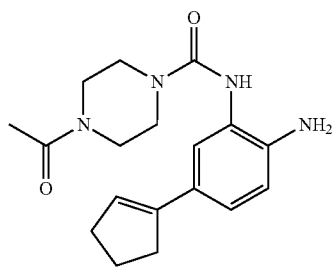

(132)

4-acetyl-N-(2-amino-5-(cyclopent-1-en-1-yl)phenyl)piperazine-1-carboxamide (132) was prepared by substituting N-methylpropan-1-amine in Scheme 25 with 1-(piperazin-1-yl)ethanone. ESI+ MS: m/z 329 ([M+H]⁺), 1H NMR (500 MHz, d⁶-DMSO): δ 7.92 (s, 1H), 7.07 (s, 1H), 7.03 (d, J=8.5 Hz, 1H), 6.66 (d, J=8.5 Hz, 1H), 5.92 (bs, 1H), 4.82 (s, 2H), 3.50-3.44 (m, 6H), 3.44-3.36 (m, 2H), 2.58-2.52 (m, 2H), 2.46-2.40 (m, 2H), 2.03 (s, 3H), 1.96-1.86 (m, 2H).

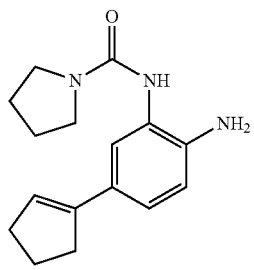

(119)

N-(2-amino-5-(cyclopent-1-en-1-yl)phenyl)pyrrolidine-1-carboxamide (119) was prepared by substituting N-methylpropan-1-amine in Scheme 25 with pyrrolidine. ESI+ MS: m/z 272 ([M+H]⁺), 1H NMR (500 MHz, d⁶-DMSO): δ 7.44 (s, 1H), 7.13 (d, J=1.5 Hz, 1H), 7.01 (dd, J=1.5, 8.0 Hz, 1H), 6.66 (d, J=8.0 Hz, 1H), 5.92 (bs, 1H), 4.87 (s, 2H), 3.40-3.30 (m, 4H), 2.60-2.50 (m, 2H), 2.46-2.40 (m, 2H), 1.95-1.86 (m, 2H), 1.86-1.60 (m, 4H).

Alternatively, the nitro group reduction can be carried out using Pd/C and hydrogen as previously described and one skilled in the art will recognize that other compounds described below can be prepared in a similar manner:

(94)

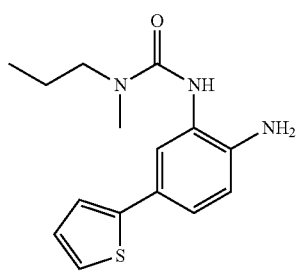

3-(2-amino-5-(thiophen-2-yl)phenyl)-1-methyl-1-propylurea (94) was prepared by substituting 5-(cyclopent-1-en-1-yl)-2-nitroaniline in Scheme 25 with 2-nitro-5-(thiophen-2-yl)aniline. ESI+ MS: m/z 290 ([M+H]$^+$), 1H NMR (500 MHz, d$^6$-DMSO): δ 7.69 (s, 1H), 7.34 (s, 1H), 7.29 (bs, 1H), 7.22-7.16 (m, 2H), 7.04 (t, J=5.0, 1H), 6.74 (d, J=8.5 Hz, 1H), 4.94 (s, 2H), 3.26 (t, J=7.5 Hz, 2H), 2.94 (s, 3H), 1.53 (sext, J=7.5 Hz, 2H), 0.86 (t, J=7.5 Hz, 3H).

(98)

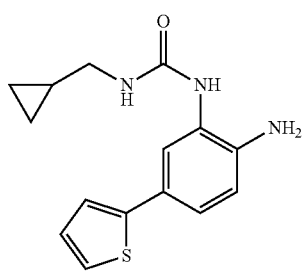

1-(2-Amino-5-(thiophen-2-yl)phenyl)-3-(cyclopropylmethyl)urea (98) was prepared by substituting N-methylpropan-1-amine in Scheme 25 with cyclopropylmethanamine and by substituting 5-(cyclopent-1-en-1-yl)-2-nitroaniline in Scheme 25 with 2-nitro-5-(thiophen-2-yl)aniline. ESI+ MS: m/z 288 ([M+H]$^+$), 1H NMR (500 MHz, d$^6$-DMSO): δ 7.66 (d, J=2.0 Hz, 1H), 7.61 (s, 1H), 7.33 (d, J=4.0 Hz, 1H), 7.17 (d, J=2.5 Hz, 1H), 7.10 (dd, J=2.0, 8.0 Hz, 1H), 7.03 (dd, J=3.5, 4.5 Hz, 1H), 6.72 (d, J=8.5 Hz, 1H), 6.28 (t, J=5.5 Hz, 1H), 4.90 (s, 2H), 2.98 (t, J=5.5 Hz, 2H), 1.00-0.90 (m, 1H), 0.45-0.40 (m, 2H), 0.21-0.16 (m, 2H).

(106)

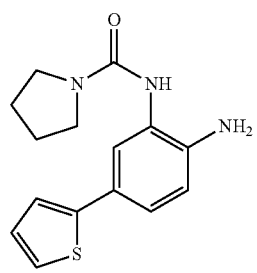

N-(2-Amino-5-(thiophen-2-yl)phenyl)pyrrolidine-1-carboxamide (106) was prepared by substituting N-methylpropan-1-amine in Scheme 25 with pyrrolidine and by substituting 5-(cyclopent-1-en-1-yl)-2-nitroaniline in Scheme 25 with 2-nitro-5-(thiophen-2-yl)aniline. ESI+ MS: m/z 288 ([M+H]$^+$), 1H NMR (500 MHz, d$^6$-DMSO): δ 7.48 (s, 1H), 7.38-7.30 (m, 2H), 7.22-7.16 (m, 2H), 7.03 (dd, J=4.0, 5.0 Hz, 1H), 6.73 (d, J=7.5 Hz, 1H), 5.01 (s, 2H), 3.38 (t, J=6.0 Hz, 4H), 1.86 (t, J=6.0 Hz, 4H).

(115)

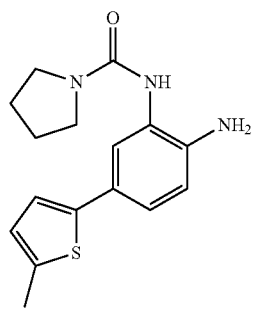

N-(2-amino-5-(5-methylthiophen-2-yl)phenyl)pyrrolidine-1-carboxamide (115) was prepared by substituting N-methylpropan-1-amine in Scheme 25 with pyrrolidine and by substituting 5-cyclopent-1-en-1-yl)-2-nitroaniline in Scheme 25 with 2-nitro-5-(5-methylthiophen-2-yl)aniline. ESI+ MS: m/z 302 ([M+H]$^+$), 1H NMR (300 MHz, d$^6$-DMSO): δ 7.50 (s, 1H), 7.29 (d, J=3.0 Hz, 1H), 7.11 (dd, J=3.0, 9.0 Hz, 1H), 6.97 (d, J=3.0 Hz, 1H), 6.74-6.70 (m, 2H), 4.99 (s, 2H), 3.50-3.30 (m, 4H), 2.42 (s, 3H), 1.90-1.80 (m, 4H).

(116)

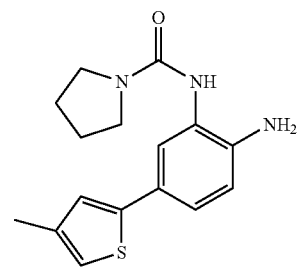

N-(2-amino-5-(4-methylthiophen-2-yl)phenyl)pyrrolidine-1-carboxamide (116) was prepared by substituting N-methylpropan-1-amine in Scheme 25 with pyrrolidine and by substituting 5-(cyclopent-1-en-1-yl)-2-nitroaniline in Scheme 25 with 2-nitro-5-(4-methylthiophen-2-yl)aniline. ESI+ MS: m/z 302 ([M+H]$^+$), 1H NMR (300 MHz, d$^6$-DMSO): δ 7.49 (s, 1H), 7.35-7.31 (m, 1H), 7.16 (dd, J=2.0, 9.0 Hz, 1H), 7.06-7.02 (m, 1H), 6.94-6.90 (m, 1H), 6.73 (d, J=9.0 Hz, 1H), 5.02 (s, 2H), 3.45-3.35 (m, 4H), 2.20 (s, 3H), 1.90-1.80 (m, 4H).

(118)

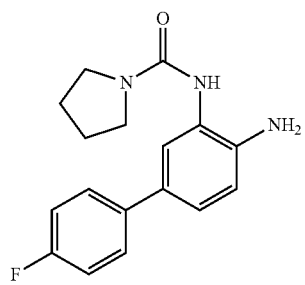

N-(4-amino-4'-fluoro-[1,1'-biphenyl]-3-yl)pyrrolidine-1-carboxamide (118) was prepared by substituting N-methylpropan-1-amine in Scheme 25 with pyrrolidine and by substituting 5-(cyclopent-1-en-1-yl)-2-nitroaniline in Scheme 25 with 4'-fluoro-4-nitro-[1,1'-biphenyl]-3-amine. ESI+ MS: m/z 300 ([M+H]$^+$), 1H NMR (500 MHz, d$^6$-DMSO): δ 7.58-7.50 (m, 2H), 7.48 (s, 1H), 7.38 (d, J=2.5 Hz, 1H), 7.24-7.14 (m, 3H), 6.78 (d, J=8.5 Hz, 1H), 4.97 (s, 2H), 3.38 (t, J=6.5 Hz, 4H), 1.86 (t, J=6.5 Hz, 4H).

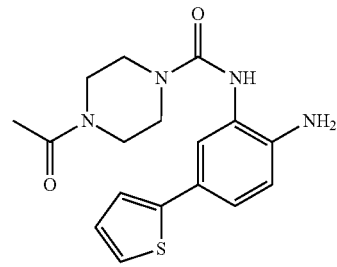

(129)

4-Acetyl-N-(2-amino-5-(thiophen-2-yl)phenyl)piperazine-1-carboxamide (129) was prepared by substituting N-methylpropan-1-amine in Scheme 25 with 1-(piperazin-1-yl)ethanone and by substituting 5-(cyclopent-1-en-1-yl)-2-nitroaniline in Scheme 25 with 2-nitro-5-(thiophen-2-yl)aniline. ESI+ MS: m/z 345 ([M+H]$^+$), 1H NMR (500 MHz, d$^6$-DMSO): δ 7.98 (s, 1H), 7.33 (d, J=5.0 Hz, 1H), 7.28 (d, J=1.5 Hz, 1H), 7.22-7.18 (m, 2H), 7.04 (t, J=4.0 Hz, 1H), 6.74 (d, J=8.5 Hz, 1H), 4.99 (s, 2H), 3.52-3.38 (m, 8H), 2.04 (s, 3H).

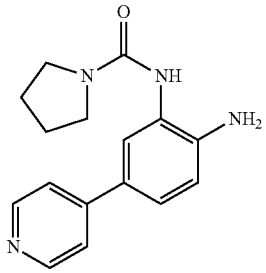

(103)

N-(2-amino-5-(pyridin-4-yl)phenyl)pyrrolidine-1-carboxamide (103) was prepared by substituting N-methylpropan-1-amine in Scheme 25 with pyrrolidine and by substituting 5-(cyclopent-1-en-1-yl)-2-nitroaniline in Scheme 25 with 2-nitro-5-(pyridin-4-yl)aniline. ESI+ MS: m/z 283 ([M+H]+), 1HNMR (500 MHz, d6-DMSO): δ 8.49 (d, J=6.5 Hz, 2H), 7.55-7.53 (m, 3H), 7.50 (s, 1H), 7.38 (dd, J=2.0 Hz, J=8.0 Hz, 1H), 6.81 (d, J=8.0 Hz, 1H), 5.23 (s, 2H), 3.39-3.37 (m, 4H), 1.86 (m, 4H).

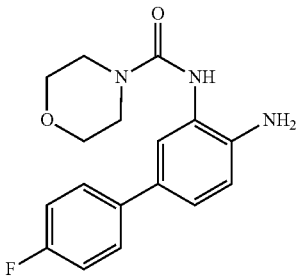

(144)

N-(4-amino-4'-fluoro-[1,1'-biphenyl]-3-yl)morpholine-4-carboxamide (144) was prepared by substituting N-methylpropan-1-amine with morpholine in Scheme 25 and by substituting 5-(cyclopent-1-en-1-yl)-2-nitroaniline in Scheme 25 with 4'-fluoro-4-nitro-[1,1'-biphenyl]-3-amine. ESI+ MS: m/z 316 ([M+H]$^+$), 1H NMR (500 MHz, d$^6$-DMSO): δ 7.92 (s, 1H), 7.58-7.50 (m, 2H), 7.31 (d, J=2 Hz, 1H), 7.24-7.16 (m, 3H), 6.78 (d, J=8.5 Hz, 1H), 4.93 (s, 2H), 3.62 (t, J=5 Hz, 4H), 3.42 (t, J=5 Hz, 4H).

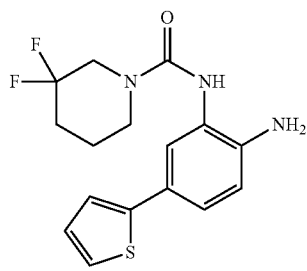

(125)

N-(2-amino-5-(thiophen-2-yl)phenyl)-3,3-difluoropiperidine-1-carboxamide (125) was prepared by substituting N-methylpropan-1-amine in Scheme 25 with 3,3-difluoropiperidine and by substituting 5-(cyclopent-1-en-1-yl)-2-nitroaniline in Scheme 25 with 2-nitro-5-(thiophen-2-yl)aniline. ESI+ MS: m/z 338 ([M+H]$^+$), 1H NMR (500 MHz, d$^6$-DMSO): δ 8.10 (s, 1H), 7.33 (d, J=4.5 Hz, 1H), 7.26-7.18 (m, 3H), 7.03 (dd, J=4.0, 5.0 Hz, 1H), 6.74 (d, J=8.5 Hz, 1H), 4.93 (s, 2H), 3.78 (t, J=12.0 Hz, 2H), 3.49 (t, J=4.5 Hz, 2H), 2.11-2.00 (m, 2H), 1.75-1.66 (m, 2H).

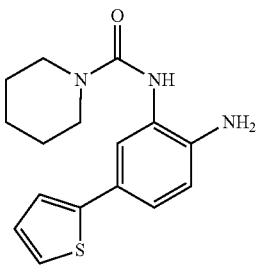

(124)

N-(2-Amino-5-(thiophen-2-yl)phenyl)piperidine-1-carboxamide (124) was prepared by substituting N-methylpropan-1-amine in Scheme 25 with piperidine and by substituting 5-(cyclopent-1-en-1-yl)-2-nitroaniline in Scheme 25 with 2-nitro-5-(thiophen-2-yl)aniline. ESI+ MS: m/z 302 ([M+H]$^+$), 1H NMR (500 MHz, d$^6$-DMSO): δ 7.87 (s, 1H), 7.33

(d, J=4.5 Hz, 1H), 7.27 (d, J=2.0 Hz, 1H), 7.22-7.16 (m, 2H), 7.03 (dd, J=3.5, 5.0 Hz, 1H), 6.73 (d, J=8.0 Hz, 1H), 4.92 (s, 2H), 3.41 (t, J=5.5 Hz, 4H), 1.62-1.54 (m, 2H), 1.54-1.47 (m, 4H).

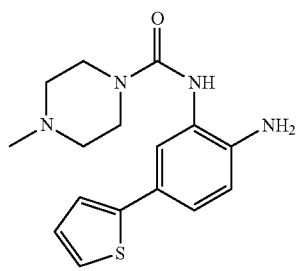

(130)

N-(2-amino-5-(thiophen-2-yl)phenyl)-4-methylpiperazine-1-carboxamide (130) was prepared by substituting N-methylpropan-1-amine in Scheme 25 with 1-methylpiperazine and by substituting 5-(cyclopent-1-en-1-yl)-2-nitroaniline in Scheme 25 with 2-nitro-5-(thiophen-2-yl)aniline. ESI+ MS: m/z 317 ([M+H]$^+$), 1H NMR (500 MHz, d$^6$-DMSO): δ 7.91 (s, 1H), 7.33 (d, J=4.5 Hz, 1H), 7.30-7.25 (m, 1H), 7.23-7.16 (m, 2H), 7.04 (dd, J=3.5, 4.5 Hz, 1H), 6.73 (d, J=8.5 Hz, 1H), 4.95 (s, 2H), 3.46-3.40 (m, 4H), 2.38-2.28 (m, 4H), 2.21 (s, 3H).

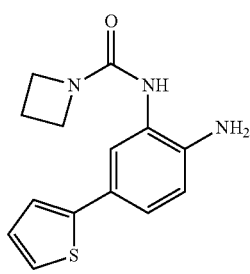

(133)

N-(2-amino-5-(thiophen-2-yl)phenyl)azetidine-1-carboxamide (133) was prepared by substituting N-methylpropan-1-amine in Scheme 25 with azetidine and by substituting 5-(cyclopent-1-en-1-yl)-2-nitroaniline in Scheme 25 with 2-nitro-5-(thiophen-2-yl)aniline. ESI+ MS: m/z 274 ([M+H]$^+$), 1H NMR (500 MHz, d$^6$-DMSO): δ 7.63 (s, 1H), 7.36-7.28 (m, 2H), 7.20-7.16 (m, 2H), 7.03 (dd, J=3.5, 5.0 Hz, 1H), 6.72 (d, J=8.0 Hz, 1H), 5.03 (s, 2H), 3.94 (t, J=7.0 Hz, 4H), 2.18 (quintet, J=7.0 Hz, 2H).

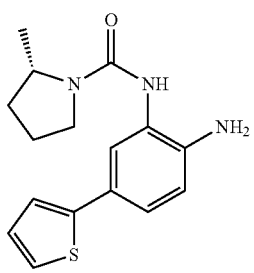

(123)

(S)—N-(2-amino-5-(thiophen-2-yl)phenyl)-2-methylpyrrolidine-1-carboxamide (123) was prepared by substituting N-methylpropan-1-amine in Scheme 25 with (S)-2-methylpyrrolidine and by substituting 5-(cyclopent-1-en-1-yl)-2-nitroaniline in Scheme 25 with 2-nitro-5-(thiophen-2-yl)aniline. ESI+ MS: m/z 302 ([M+H]$^+$), 1H NMR (300 MHz, d$^6$-DMSO): δ 7.49 (s, 1H), 7.38-7.32 (m, 2H), 7.24-7.16 (m, 2H), 7.06-7.02 (m, 1H), 6.74 (d, J=6.0 Hz, 1H), 5.00 (s, 2H), 4.10-3.95 (m, 1H), 3.55-3.42 (m, 1H), 2.02-1.80 (m, 4H), 1.60-1.50 (m, 1H), 1.15 (d, J=9.0 Hz, 3H).

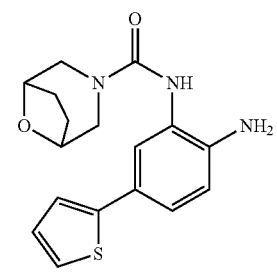

(157)

N-(2-amino-5-(thiophen-2-yl)phenyl)-8-oxa-3-azabicyclo[3.2.1]octane-3-carboxamide (157) was prepared by substituting N-methylpropan-1-amine in Scheme 25 with 8-oxa-3-azabicyclo[3.2.1]octane and by substituting 5-(cyclopent-1-en-1-yl)-2-nitroaniline in Scheme 25 with 2-nitro-5-(thiophen-2-yl)aniline. ESI+ MS: m/z 330 ([M+H]$^+$); 1H NMR (500 MHz, d$^6$-DMSO): δ 7.79 (bs, 1H), 7.33 (d, J=5.0 Hz, 1H), 7.29 (bs, 1H), 7.20-7.18 (m, 2H), 7.03 (t, J=5.0 Hz, 1H), 6.73 (d, J=8.5 Hz, 1H), 4.95 (s, 2H), 4.33 (bs, 2H), 3.69 (d, J=13.0 Hz, 2H), 3.03 (d, J=11.0 Hz, 2H), 1.82-1.76 (m, 4H).

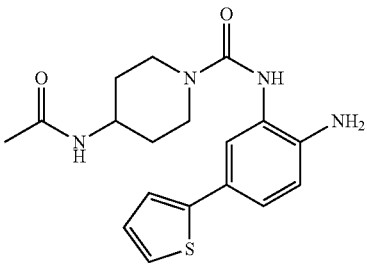

(113)

4-acetamido-N-(2-amino-5-(thiophen-2-yl)phenyl)piperidine-1-carboxamide (113) was prepared by substituting N-methylpropan-1-amine in Scheme 25 with N-(piperidin-4-yl)acetamide and by substituting 5-(cyclopent-1-en-1-yl)-2-nitroaniline in Scheme 25 with 2-nitro-5-(thiophen-2-yl)aniline. ESI+ MS: m/z 359 ([M+H]$^+$), 1H NMR (300 MHz, d$^6$-DMSO): δ 7.98 (s, 1H), 7.86 (d, J=9.0 Hz, 1H), 7.35 (dd, J=1.0, 6.0 Hz, 1H), 7.27 (d, J=3.0 Hz, 1H), 7.23-7.18 (m, 2H), 7.05 (dd, J=3.0, 4.0 Hz, 1H), 6.75 (d, J=9.0 Hz, 1H), 4.95 (s, 2H), 4.08-3.95 (m, 2H), 3.85-3.70 (m, 1H), 3.00-2.86 (m, 2H), 1.81 (s, 3H), 1.81-1.70 (m, 2H), 1.40-1.20 (m, 2H).

(138)

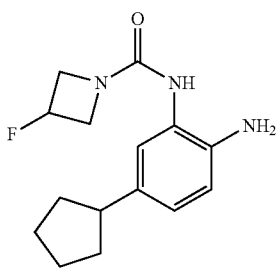

N-(2-amino-5-cyclopentylphenyl)-3-fluoroazetidine-1-carboxamide (138) was prepared by substituting N-methylpropan-1-amine in Scheme 25 with 3-fluoroazetidine and by substituting 5-(cyclopent-1-en-1-yl)-2-nitroaniline in Scheme 25 with 5-cyclopentyl-2-nitroaniline. ESI+ MS: m/z 278 ([M]+), 1H NMR (500 MHz, d6-DMSO): δ 7.78 (s, 1H), 6.90 (d, J=2.0 Hz, 1H), 6.75 (dd, J=2.0, 8.0 Hz, 1H), 6.61 (d, J=8.0 Hz, 1H), 5.46-5.28 (m, 1H), 4.63 (s, 2H), 4.27-4.18 (m, 2H), 3.99-3.91 (m, 2H), 2.83-2.75 (m, 1H), 1.96-1.88 (m, 2H), 1.75-1.66 (m, 2H), 1.65-1.54 (m, 2H), 1.49-1.38 (m, 2H).

(128)

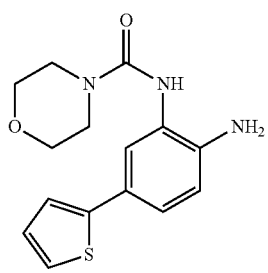

N-(2-amino-5-(thiophen-2-yl)phenyl)morpholine-4-carboxamide (128) was prepared by substituting N-methylpropan-1-amine in Scheme 25 with morpholine and by substituting 5-(cyclopent-1-en-1-yl)-2-nitroaniline in Scheme 25 with 2-nitro-5-(thiophen-2-yl)aniline. ESI+ MS: m/z 304 ([M+H]+), 1H NMR (500 MHz, d6-DMSO): δ 7.92 (s, 1H), 7.33 (d, J=4.5 Hz, 1H), 7.29 (d, J=2.0 Hz, 1H), 7.22-7.18 (m, 2H), 7.03 (dd, J=3.5, 5.0 Hz, 1H), 6.73 (d, J=8.0 Hz, 1H), 4.98 (s, 2H), 3.62 (t, J=5.0 Hz, 4H), 3.42 (t, J=5.0 Hz, 4H).

(127)

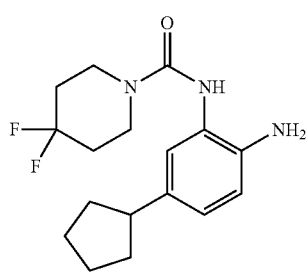

N-(2-amino-5-cyclopentylphenyl)-4,4-difluoropiperidine-1-carboxamide (127) was prepared by substituting N-methylpropan-1-amine in Scheme 25 with 4,4-difluoropiperidine and by substituting 5-(cyclopent-1-en-1-yl)-2-nitroaniline in Scheme 25 with 5-cyclopentyl-2-nitroaniline. ESI+ MS: m/z 324 ([M+H]+), 1H NMR (500 MHz, d6-DMSO): δ 8.03 (s, 1H), 6.84 (d, J=1.5 Hz, 1H), 6.77 (dd, J=1.5, 8.0 Hz, 1H), 6.63 (d, J=8.0 Hz, 1H), 4.53 (s, 2H), 3.54 (t, J=5.5 Hz, 4H), 2.82-2.75 (m, 1H), 2.02-1.88 (m, 6H), 1.75-1.68 (m, 2H), 1.65-1.55 (m, 2H), 1.50-1.38 (m, 2H).

(114)

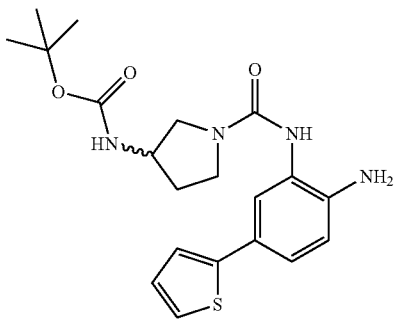

tert-Butyl (1-((2-amino-5-(thiophen-2-yl)phenyl)carbamoyl)pyrrolidin-3-yl)carbamate (114) was prepared by substituting N-methylpropan-1-amine in Scheme 25 with tert-butyl pyrrolidin-3-ylcarbamate and by substituting 5-(cyclopent-1-en-1-yl)-2-nitroaniline in Scheme 25 with 2-nitro-5-(thiophen-2-yl)aniline. ESI+ MS: m/z 403 ([M+H]+), 1H NMR (500 MHz, d6-DMSO): δ 7.53 (s, 1H), 7.33-7.29 (m, 2H), 7.19-7.17 (m, 3H), 7.03-7.02 (m, 1H), 6.72 (d, J=8 Hz, 1H), 5.02 (s, 1H), 4.01-3.95 (m, 1H), 3.63-3.56 (m, 1H), 3.54-3.43 (m, 1H), 3.42-3.35 (m, 1H), 2.23-3.16 (m, 1H), 2.09-1.97 (m, 1H), 1.86-1.75 (m, 1H), 1.40 (s, 9H).

(131)

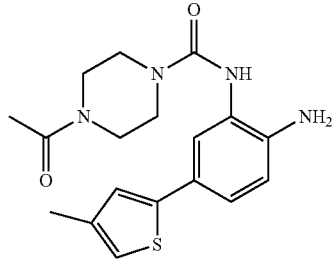

4-Acetyl-N-(2-amino-5-(4-methylthiophen-2-yl)phenyl)piperazine-1-carboxamide (131) was prepared by substituting N-methylpropan-1-amine in Scheme 25 with 1-(piperazin-1-yl)ethanone and by substituting 5-(cyclopent-1-en-1-yl)-2-nitroaniline in Scheme 25 with 5-(4-methylthiophen-2-yl)-2-nitroaniline. ESI+ MS: m/z 359 ([M+H]+), 1H NMR (500 MHz, d6-DMSO): δ 7.99 (s, 1H), 7.25 (d, J=1 Hz, 1H), 7.18 (dd, J=9 Hz, 1 Hz, 1H), 7.04 (s, 1H), 6.91 (s, 1H), 6.73 (d, J=9 Hz, 1H), 5.00 (s, 2H), 3.49 (s, 8H), 2.20 (s, 3H), 2.05 (s, 3H).

(145)

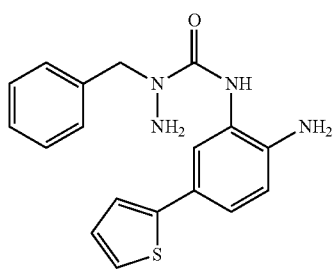

N-(2-amino-5-(thiophen-2-yl)phenyl)-1-benzylhydrazinecarboxamide (145) was prepared by substituting N-methylpropan-1-amine in Scheme 25 with benzylhydrazine and by substituting 5-(cyclopent-1-en-1-yl)-2-nitroaniline in Scheme 25 with 2-nitro-5-(thiophen-2-yl)aniline. ESI+ MS: m/z 339 ([M+H]$^+$), 1H NMR (500 MHz, d$^6$-DMSO): 8.57 (s, 1H), 7.51 (d, J=2.0 Hz, 1H), 7.40-7.26 (m, 6H), 7.20 (d, J=3.0 Hz, 1H), 7.14 (dd, J=2.0, 8.0 Hz, 1H), 7.04 (dd, J=8.0; 5.0 Hz, 1H), 6.78 (d, J=8.0 Hz, 1H), 4.93 (bs, 2H), 4.67 (bs, 2H), 4.57 (bs, 2H).

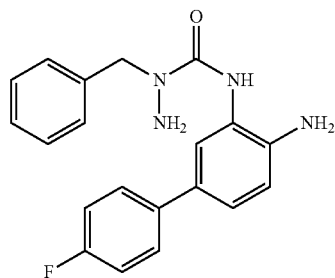
(154)

N-(4-amino-4'-fluoro-[1,1'-biphenyl]-3-yl)-1-benzylhydrazinecarboxamide (154) was prepared by substituting N-methylpropan-1-amine in Scheme 25 with benzylhydrazine and by substituting 5-(cyclopent-1-en-1-yl)-2-nitroaniline in Scheme 25 with 4'-fluoro-4-nitro-[1,1'-biphenyl]-3-amine. ESI+ MS: m/z 351 ([M+H]$^+$). $^1$HNMR (500 MHz, d$^6$-DMSO): δ 8.57 (s, 1H), 7.73 (d, J=1 Hz, 1H), 7.56-7.53 (m, 2H) 7.38-7.35 (m, 2H), 7.31-7.27 (m, 3H), 7.20 (t, J=9.0 Hz, 2H), 7.13 (dd, J=2.0 Hz, 1H), 6.82 (d, J=8.5 Hz, 1H), 4.88 (bs, 2H), 4.66 (s, 2H), 4.57 (s, 2H).

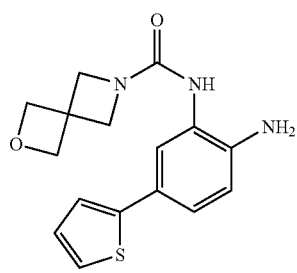
(177)

N-(2-amino-5-(thiophen-2-yl)phenyl)-2-oxa-6-azaspiro[3.3]heptane-6-carboxamide (177) was prepared by substituting N-methylpropan-1-amine in Scheme 25 with 2-oxa-6-azspiro[3.3]heptanes and by substituting 5-(cyclopent-1-en-1-yl)-2-nitroaniline in Scheme 25 with 2-nitro-5-(thiophen-2-yl)aniline. ESI+ MS: m/z 316 ([M+H]$^+$), 1H NMR (500 MHz, d$^6$-DMSO): δ 7.74 (s, 1H), 7.33-7.30 (m, 2H), 7.19-7.17 (m, 2H), 7.03-7.02 (m, 1H), 6.71 (d, J=8.0 Hz, 1H), 5.04 (s, 2H), 4.68 (s, 4H), 4.10-4.06 (m, 4H).

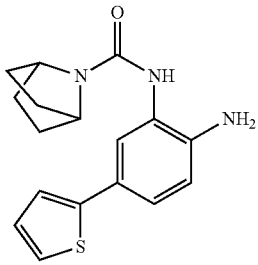
(181)

N-(2-amino-5-(thiophen-2-yl)phenyl)-7-azabicyclo[2.2.1]heptane-7-carboxamide (181) was prepared by substituting substituting N-methylpropan-1-amine in Scheme 25 with 7-azabicyclo[2.2.1]heptane hydrochloride and by substituting 5-(cyclopent-1-en-1-yl)-2-nitroaniline in Scheme 25 with 2-nitro-5-(thiophen-2-yl)aniline. ESI+ MS: m/z 314 ([M+H]$^+$), 1H NMR (500 MHz, d$^6$-DMSO): δ 8.13 (s, 1H), 7.34-7.32 (m, 2H), 7.20-7.18 (m, 2H), 7.03 (t, J=4.5 Hz, 1H), 6.74 (d, J=8.5 Hz, 1H), 4.91 (s, 2H), 3.33 (s, 2H), 1.73 (d, J=7.0 Hz, 4H), 1.42 (d, J=6.5 Hz, 4H).

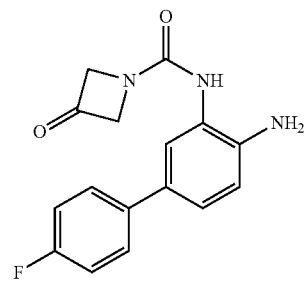
(203)

N-(4-amino-4'-fluoro-[1,1'-biphenyl]-3-yl)-3-oxoazetidine-1-carboxamide (203) was prepared by substituting N-methylpropan-1-amine in Scheme 25 with azetidin-3-one and by substituting 5-(cyclopent-1-en-1-yl)-2-nitroaniline in Scheme 25 with 4'-fluoro-4-nitro-[1,1'-biphenyl]-3-amine. ESI+ MS: m/z 300 ([M+H]$^+$), $^1$HNMR (500 MHz, d$^6$-DMSO): δ 8.13 (s, 1H), 7.54-7.51 (m, 2H), 7.36 (s, 1H), 7.21-7.18 (m, 3H), 6.77 (d, J=8.5 Hz, 1H), 5.08 (s, 2H), 4.77 (s, 4H).

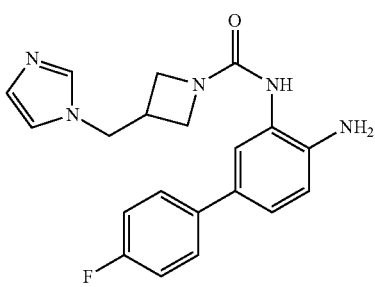
(209)

3-((1H-imidazol-1-yl)methyl)-N-(4-amino-4'-fluoro-[1,1'-biphenyl]-3-yl)azetidine-1-carboxamide (209) was prepared by substituting N-methylpropan-1-amine in Scheme 25 with 1-(azetidin-3-ylmethyl)-1H-imidazole and by substituting 5-(cyclopent-1-en-1-yl)-2-nitroaniline in Scheme 25 with 4'-fluoro-4-nitro-[1,1'-biphenyl]-3-amine. ESI+ MS: m/z 366 ([M+H]⁺). ¹HNMR (400 MHz, d⁶-DMSO): δ 7.76 (S, 1H), 7.67 (s, 1H), 7.52-7.48 (m, 2H), 7.33 (d, J=2.0 Hz, 1H), 7.23-7.14 (m, 4H), 6.93 (s, 1H), 6.75 (d, J=8.0 Hz, 1H), 4.23 (d, J=7.6, 2H), 2.96 (t, J=8.4 Hz, 2H), 3.71-3.67 (m, 2H) 3.00-2.95 (m, 1H).

(210)

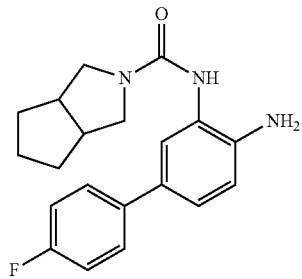

N-(4-amino-4'-fluoro-[1,1'-biphenyl]-3-yl)hexahydrocyclopenta[c]pyrrole-2(1H)-carboxamide (210) was prepared by substituting N-methylpropan-1-amine in Scheme 25 with octahydrocyclopenta[c]pyrrole hydrochloride and by substituting 5-(cyclopent-1-en-1-yl)-2-nitroaniline in Scheme 25 with 4'-fluoro-4-nitro-[1,1'-biphenyl]-3-amine. ESI+ MS: m/z 340 ([M+H]⁺), ¹HNMR (400 MHz, DMSo-d₆): δ 7.55-7.52 (m, 2H), 7.47 (s, 1H), 7.37 (d J=2.0 Hz, 1H) 7.22-7.16 (m, 3H), 6.78 (d J=8.0 Hz, 1H) 4.98 (s, 2H) 3.60 (dd, J₁,₂=8.0 Hz, J₁,₃=10.4 Hz, 2H), 3.66 (d J=3.6 Hz, 2H), 1.81-1.70 (m, 3H), 1.58-1.54 (m, 1H).

(212)

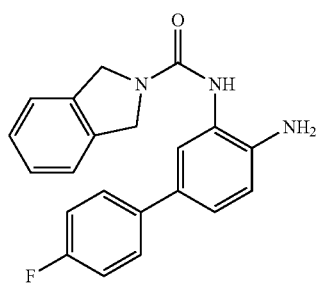

N-(4-amino-4'-fluoro-[1,1'-biphenyl]-3-yl)isoindoline-2-carboxamide (212) was prepared by substituting N-methylpropan-1-amine in Scheme 25 with isoindoline and by substituting 5-(cyclopent-1-en-1-yl)-2-nitroaniline in Scheme 25 with 4'-fluoro-4-nitro-[1,1'-biphenyl]-3-amine. ESI+ MS: m/z 348 ([M+H]⁺), ¹HNMR (400 MHz, d₆-DMSO): δ 7.70 (s, 1H), 7.57-7.54 (m, 2H), 7.44 (d, J=2.0 Hz, 1H), 7.38-7.35 (m, 2H), 7.33-7.30 (m, 2H), 7.23-7.18 (m, 3H), 6.81 (d, J=8.4 Hz, 1H), 5.06 (s, 2H), 4.79 (s, 4H).

(215)

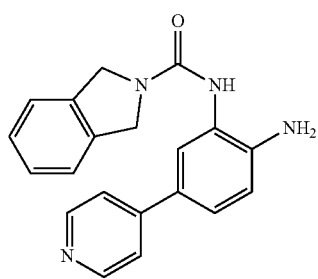

N-(2-amino-5-(pyridin-4-yl)phenyl)isoindoline-2-carboxamide (215) was prepared by substituting N-methylpropan-1-amine in Scheme 25 with isoindoline and by substituting 5-(cyclopent-1-en-1-yl)-2-nitroaniline in Scheme 25 with 5-(pyridin-4-yl)-2-nitroaniline. ESI+ MS: m/z 331 ([M+H]⁺), ¹HNMR (500 MHz, d⁶-DMSO): δ 8.52 (d, J=4.5 Hz, 2H), 7.74 (s, 1H), 7.63 (d, J=6.0 Hz, 3H), 7.47 (d, J=8.5 Hz, 1H), 7.365-7.309 (m, 4H), 6.84 (d, J=8.5 Hz, 1H), 5.40 (bs, 2H), 4.79 (s, 4H).

(216)

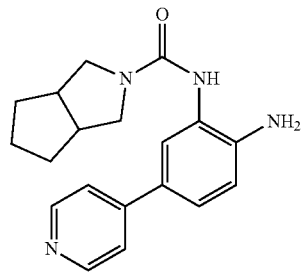

N-(2-amino-5-(pyridin-4-yl)phenyl)hexahydrocyclopenta[c]pyrrole-2(1H)-carboxamide (216) was prepared by substituting N-methylpropan-1-amine in Scheme 25 with octahydrocyclopenta[c]pyrrole hydrochloride and by substituting 5-(cyclopent-1-en-1-yl)-2-nitroaniline in Scheme 25 with 5-(pyridin-4-yl)-2-nitroaniline. ESI+ MS: m/z 323 ([M+H]⁺), ¹HNMR (500 MHz, d⁶-DMSO): δ 8.48 (d, J=6.0 Hz, 2H), 7.52 (t, J=17.5 Hz, 4H), 7.38 (t, J=8.0 Hz, 1H), 6.80 (d, J=5.0 Hz, 1H), 5.21 (s, 2H), 3.17-3.58 (m, 2H), 3.16 (dd, J₁,₂=3.5 Hz, J₁,₃=10.0 Hz, 2H), 2.65 (s, 2H), 1.80-1.72 (m, 3H), 1.58-1.55 (m, 1H), 1.45-1.42 (m, 2H).

(217)

N-(4-amino-4'-fluoro-[1,1'-biphenyl]-3-yl)-5H-pyrrolo[3,4-d]pyrimidine-6(7H)-carboxamide (217) was prepared by substituting N-methylpropan-1-amine in Scheme 25 with 6,7-dihydro-5H-pyrrolo[3,4-d]pyrimidine hydrochloride and by substituting 5-(cyclopent-1-en-1-yl)-2-nitroaniline in Scheme 25 with 4'-fluoro-4-nitro-[1,1'-biphenyl]-3-amine. ESI+ MS: m/z 350 ([M+H]⁺), ¹HNMR (400 MHz, d⁶-DMSO): δ 9.12 (s, 1H), 8.84 (s, 1H), 7.87 (s, 1H), 7.55 (q, J=14 Hz, 2H), 7.40 (d, J=2 Hz, 1H), 7.24-7.19 (m, 3H), 6.80 (d, J=8.4 Hz, 1H), 5.09 (s, 2H), 4.83 (d, J=4 Hz, 4H).

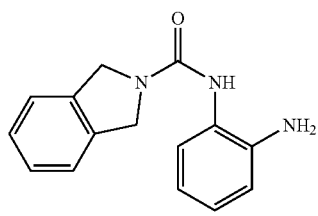

(218)

N-(2-aminophenyl)isoindoline-2-carboxamide (218) was prepared by substituting N-methylpropan-1-amine in Scheme 25 with isoindoline and by substituting 5-(cyclopent-1-en-1-yl)-2-nitroaniline in Scheme 25 with 2-nitroaniline. ESI+ MS: m/z 254 ([M+H]$^+$), $^1$HNMR (400 MHz, d$^6$-DMSO): δ 7.61 (s, 1H), 7.37-7.29 (m, 4H), 7.10 (t, J=8 Hz, 1H), 6.90-6.86 (m, 1H), 6.72 (dd, J$_{1,2}$=1.2 Hz, J$_{1,3}$=8 Hz, 1H), 6.57-6.53 (m, 1H), 4.85 (s, 2H), 4.76 (s, 4H), 4.85 (s, 4H).

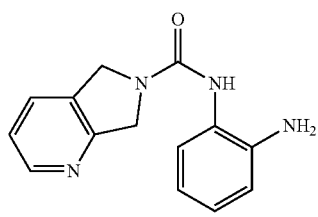

(224)

N-(2-aminophenyl)-5H-pyrrolo[3,4-b]pyridine-6(7H)-carboxamide (224) was prepared by substituting N-methylpropan-1-amine in Scheme 25 with 6,7-dihydro-5H-pyrrolo[3,4-b]pyridine hydrochloride and by substituting 5-(cyclopent-1-en-1-yl)-2-nitroaniline in Scheme 25 with 2-nitroaniline. ESI+ MS: m/z 255 ([M+H]$^+$), $^1$HNMR (300 MHz, MeOD): δ 8.45 (d, J=3.0 Hz, 1H), 7.82 (d, J=6.0 Hz, 1H), 7.36 (dd, J=9.0 Hz, J=6.0 Hz, 1H), 7.10 (d, J=9.0 Hz, 1H), 7.0 (t, J=9.0 Hz, 1H), 6.84 (d, J=9.0 Hz, 1H), 6.72 (t, J=9.0 Hz, 1H), 5.49 (s, 1H), 4.83 (br s, 4H).

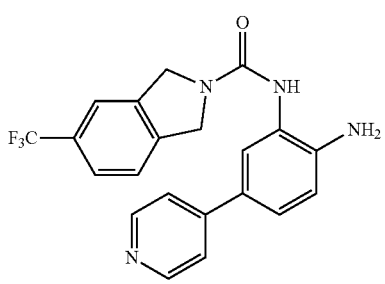

(226)

N-(2-amino-5-(pyridin-4-yl)phenyl)-5-(trifluoromethyl)isoindoline-2-carboxamide (226) was prepared by substituting N-methylpropan-1-amine in Scheme 25 with 5-(trifluoromethyl)isoindoline hydrochloride and by substituting 5-(cyclopent-1-en-1-yl)-2-nitroaniline in Scheme 25 with 5-(pyridin-4-yl)-2-nitroaniline. ESI+ MS: m/z 399 ([M+H]$^+$), $^1$HNMR (400 MHz, d$^6$-DMSO): δ 8.50 (d, J=6.0 Hz, 1H), 7.82 (br s, 1H), 7.77 (br s, 1H), 7.69-7.67 (m, 1H), 7.61-7.54 (m, 4H), 7.43 (dd, J$_{1,2}$=2.0 Hz, J$_{1,3}$=8.4 Hz, 1H), 6.83 (d, J=8.4 Hz, 1H), 5.34 (s, 2H), 4.85 (s, 4H).

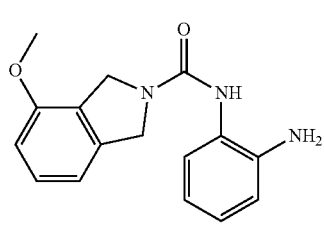

(227)

N-(2-aminophenyl)-4-methoxyisoindoline-2-carboxamide (227) was prepared by substituting N-methylpropan-1-amine in Scheme 25 with 4-methoxyisoindoline hydrochloride and by substituting 5-(cyclopent-1-en-1-yl)-2-nitroaniline in Scheme 25 with 2-nitroaniline. ESI+ MS: m/z 284 ([M+H]$^+$), $^1$HNMR (300 MHz, d$^6$-DMSO): δ 7.63 (s, 1H), 7.30 (t, J=9.0 Hz, 1H), 7.10 (d, J=9.0 Hz, 1H), 6.96-6.83 (m, 3H), 6.71 (d, J=9.0 Hz, 1H), 6.54 (t, J=9.0 Hz, 1H), 4.86 (br s, 2H), 4.73 (br s, 2H), 4.68 (br s, 2H), 3.82 (s, 3H).

(229)

N-(2-aminophenyl)-6,7-dihydro-1H-imidazo[4,5-c]pyridine-5(4H)-carboxamide (229) was prepared by substituting N-methylpropan-1-amine in Scheme 25 with 4,5,6,7-tetrahydro-1H-imidazo[4,5-c]pyridine and by substituting 5-(cyclopent-1-en-1-yl)-2-nitroaniline in Scheme 25 with 2-nitroaniline. ESI+ MS: m/z 258 ([M+H]$^+$), $^1$HNMR (300 MHz, MeOD): δ 7.52 (s, 1H), 7.00-6.80 (m, 2H), 6.79 (d, J=9.0 Hz, 1H), 6.70 (t, J=9.0 Hz, 1H), 4.52 (s, 2H), 3.80 (t, J=6.0 Hz, 2H), 2.71 (t, J=6.0 Hz, 2H).

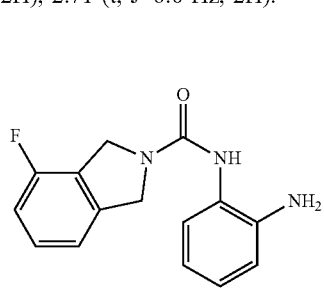

(230)

N-(2-aminophenyl)-4-fluoroisoindoline-2-carboxamide (230) was prepared by substituting N-methylpropan-1-amine in Scheme 25 with 4-fluoroisoindoline and by substituting 5-(cyclopent-1-en-1-yl)-2-nitroaniline in Scheme 25 with 2-nitroaniline. ESI+ MS: m/z 272 ([M+H]$^+$), $^1$HNMR (300 MHz, d$^6$-DMSO): δ 7.72 (s, 1H), 7.45-7.35 (m, 1H), 7.25-7.05 (m, 3H), 6.90 (t, J=9.0 Hz, 1H), 6.72 (d, J=9.0 Hz, 1H), 6.55 (t, J=9.0 Hz, 1H), 4.89 (s, 2H), 4.82 (br s, 2H), 4.80 (br s, 2H).

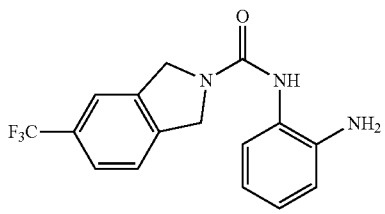
(246)

N-(2-aminophenyl)-5-(trifluoromethyl)isoindoline-2-carboxamide (246) was prepared by substituting N-methylpropan-1-amine in Scheme 25 with 5-(trifluoromethyl) isoindoline hydrochloride and by substituting 5-(cyclopent-1-en-1-yl)-2-nitroaniline in Scheme 25 with 2-nitroaniline. ESI+ MS: m/z 322 ([M+H]+), $^1$HNMR (300 MHz, MeOD): δ 7.68 (s, 1H), 7.65-7.50 (m, 2H), 7.10 (d, J=9.0 Hz, 1H), 7.05-6.97 (m, 1H), 6.85 (d, J=9.0 Hz, 1H), 6.75-6.67 (m, 1H), 4.89 (s, 4H).

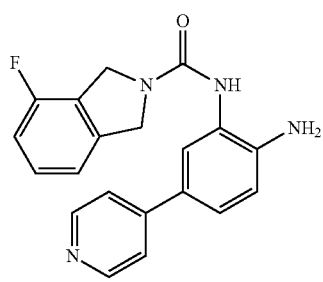
(232)

N-(2-amino-5-(pyridin-4-yl)phenyl)-4-fluoroisoindoline-2-carboxamide (232) was prepared by substituting N-methylpropan-1-amine in Scheme 25 with 4-fluoroisoindoline and by substituting 5-(cyclopent-1-en-1-yl)-2-nitroaniline in Scheme 25 with 5-(pyridin-4-yl)-2-nitroaniline. ESI+ MS: m/z 349 ([M+H]+), $^1$HNMR (400 MHz, d$^6$-DMSO): δ 8.49 (d, J=4.8 Hz, 1H), 7.81 (s, 1H), 7.60-7.50 (m, 3H), 7.45-7.35 (m, 2H), 7.22 (d, J=5.6 Hz, 1H), 7.14 (t, J=5.6 Hz, 1H), 6.82 (d, J=6.8 Hz, 1H), 5.34 (s, 2H), 4.86-4.78 (m, 4H).

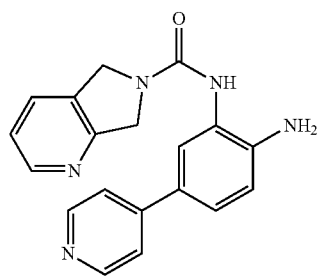
(233)

N-(2-amino-5-(pyridin-4-yl)phenyl)-5H-pyrrolo[3,4-b]pyridine-6(7H)-carboxamide (233) was prepared by substituting N-methylpropan-1-amine in Scheme 25 with 6,7-dihydro-5H-pyrrolo[3,4-b]pyridine and by substituting 5-(cyclopent-1-en-1-yl)-2-nitroaniline in Scheme 25 with 5-(pyridin-4-yl)-2-nitroaniline. ESI+ MS: m/z 332 ([M+H]+), $^1$HNMR (400 MHz, d$^6$-DMSO): δ 8.51-8.48 (m, 3H), 7.82 (d, J=7.6 Hz, 2H), 7.60-7.55 (m, 3H), 7.44 (dd, J$_{1,2}$=2.4 Hz, J$_{1,3}$=8.4 Hz, 1H), 7.35-7.32 (m, 1H), 6.83 (d, J=8.4 Hz, 1H), 5.36 (s, 2H), 4.80 (s, 4H).

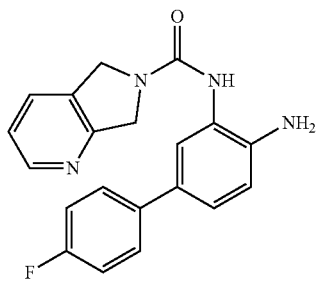
(245)

N-(4-amino-4'-fluoro-[1,1'-biphenyl]-3-yl)-5H-pyrrolo[3,4-b]pyridine-6(7H)-carboxamide (245) was prepared by substituting N-methylpropan-1-amine in Scheme 25 with 6,7-dihydro-5H-pyrrolo[3,4-b]pyridine and by substituting 5-(cyclopent-1-en-1-yl)-2-nitroaniline in Scheme 25 with 4'-fluoro-4-nitro-[1,1'-biphenyl]-3-amine. ESI+ MS: m/z 349 ([M+H]+), $^1$HNMR (400 MHz, d$^6$-DMSO): δ 8.48-8.47 (m, 1H), 7.81-7.79 (m, 2H), 7.57-7.53 (m, 2H), 7.41 (d, J=2.0 Hz, 1H), 7.34-7.31 (m, 1H), 7.23-7.18 (m, 3H), 6.80 (d, J=8.4 Hz, 1H), 5.07 (s, 2H), 4.79 (s, 4H).

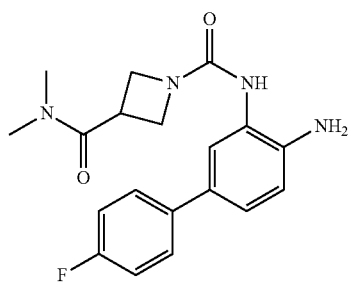
(236)

N1-(4-amino-4'-fluoro-[1,1'-biphenyl]-3-yl)-N3,N3-dimethylazetidine-1,3-dicarboxamide (236) was prepared by substituting N-methylpropan-1-amine in Scheme 25 with N,N-dimethylazetidine-3-carboxamide and by substituting 5-(cyclopent-1-en-1-yl)-2-nitroaniline in Scheme 25 with 4'-fluoro-4-nitro-[1,1'-biphenyl]-3-amine. ESI+ MS: m/z 357 ([M+H]+), $^1$HNMR (400 MHz, d$^6$-DMSO): δ 7.73 (s, 1H), 7.54-7.51 (m, 2H), 7.36 (d, J=2.4 Hz, 1H), 7.21-7.16 (m, 3H), 6.77 (d, J=8.0 Hz, 1H), 4.99 (s, 2H), 4.11-4.01 (m, 4H), 3.72-3.64 (m, 1H), 2.86 (s, 3H), 2.85 (s, 3H).

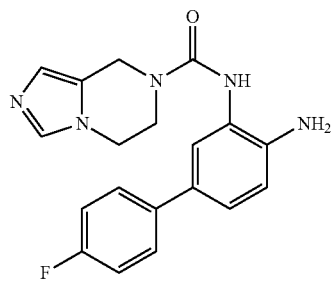
(241)

N-(4-amino-4'-fluoro-[1,1'-biphenyl]-3-yl)-5,6-dihydroimidazo[1,5-a]pyrazine-7(8H)-carboxamide (241) was prepared by substituting N-methylpropan-1-amine in Scheme 25 with 5,6,7,8-tetrahydroimidazo[1,5-a]pyrazine and by substituting 5-(cyclopent-1-en-1-yl)-2-nitroaniline in Scheme 25 with 4'-fluoro-4-nitro-[1,1'-biphenyl]-3-amine.

ESI+ MS: m/z 352 ([M+H]⁺), ¹HNMR (400 MHz, d⁶-DMSO): δ 8.07 (br s, 1H), 7.59 (br s, 1H), 7.54-7.51 (m, 2H), 7.29 (br s, 1H), 7.19-7.16 (m, 3H), 6.76 (t, J=16.4, 2H), 4.96 (br s, 2H), 4.70 (br s, 2H), 4.10-4.09 (m, 2H), 3.83-3.82 (m, 2H).

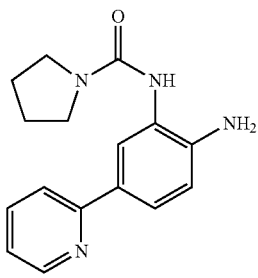
(238)

N-(2-amino-5-(pyridin-2-yl)phenyl)pyrrolidine-1-carboxamide (238) was prepared by substituting N-methylpropan-1-amine in Scheme 25 with pyrrolidine and by substituting 5-(cyclopent-1-en-1-yl)-2-nitroaniline in Scheme 25 with 5-(pyridin-2-yl)-2-nitroaniline. ESI+ MS: m/z 283 ([M+H]⁺), ¹HNMR (400 MHz, d⁶-DMSO): δ 8.52 (d, J=4.4 Hz, 1H), 7.83 (d, J=2.0 Hz, 1H), 7.72-7.71 (m, 2H), 7.63 (dd, J₁,₂=2.0 Hz, J₁,₃=8.4 Hz, 1H), 7.52 (s, 1H), 7.18-7.15 (m, 1H), 6.77 (d, J=8.4 Hz, 1H), 5.13 (s, 2H), 3.38 (t, J=6.4 Hz, 4H), 1.86 (t, J=6.4 Hz, 4H).

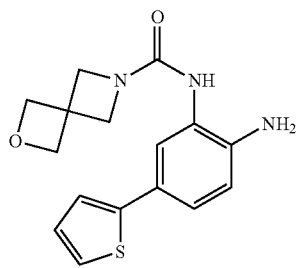
(177)

N-(2-amino-5-(thiophen-2-yl)phenyl)-2-oxa-6-azaspiro[3.3]heptane-6-carboxamide (177) was prepared by substituting N-methylpropan-1-amine in Scheme 25 with 2-oxa-6-azaspiro[3.3]heptane and by substituting 5-(cyclopent-1-en-1-yl)-2-nitroaniline in Scheme 25 with 2-nitro-5-(thiophen-2-yl)aniline. ESI+ MS: m/z 316 ([M+H]⁺), 1H NMR (500 MHz, d⁶-DMSO): δ 9.35 (s, 1H), 8.43 (d, J=2 Hz, 1H), 8.09 (d, J=9 Hz, 1H), 7.75 (d, J=5.5 Hz, 1H), 7.68 (d, J=3.5 Hz, 1H), 7.52 (dd, J=2, 8.5 Hz, 1H), 4.70 (bs, 4H), 4.22 (bs, 4H).

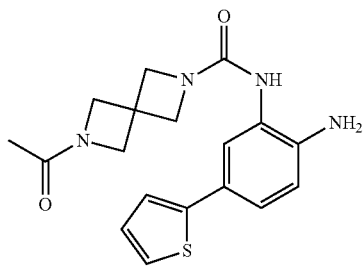
(178)

6-Acetyl-N-(2-amino-5-(thiophen-2-yl)phenyl)-2,6-diazaspiro[3.3]heptane-2-carboxamide (178) can be prepared by substituting N-methylpropan-1-amine in Scheme 25 with tert-butyl 2,6-diazaspiro[3.3]heptane-2-carboxylate and by substituting 5-(cyclopent-1-en-1-yl)-2-nitroaniline in Scheme 25 with 2-nitro-5-(thiophen-2-yl)aniline. ESI+ MS: m/z 357 ([M+H]⁺), 1H NMR (500 MHz, d⁶-DMSO): δ 7.76 (s, 1H), 7.33-7.31 (m, 2H), 7.19-7.17 (m, 2H), 7.03 (dd, J=3.5 Hz, J=5.0 Hz, 1H), 6.71 (d, J=8.5 Hz, 1H), 5.05 (s, 2H), 4.25 (s, 2H), 4.07 (s, 4H), 3.97 (s, 2H), 1.73 (s, 3H).

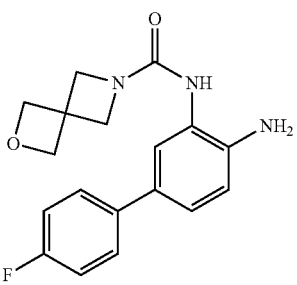
(186)

N-(4-amino-4'-fluoro-[1,1'-biphenyl]-3-yl)-2-oxa-6-azaspiro[3.3]heptane-6-carboxamide (186) can be prepared by substituting N-methylpropan-1-amine in Scheme 25 with 2-oxa-6-azaspiro[3.3]heptanes and by substituting 5-(cyclopent-1-en-1-yl)-2-nitroaniline in Scheme 25 with 4'-fluoro-4-nitro-[1,1'-biphenyl]-3-amine. ESI+ MS: m/z 328 ([M+H]⁺), 1H NMR (500 MHz, d⁶-DMSO): δ 7.73 (s, 1H), 7.51 (dd, I=5.5 Hz, I=8.5 Hz, 2H), 7.32 (d, J=1.5 Hz, 1H), 7.21-7.16 (m, 3H), 6.76 (d, J=8.5 Hz, 1H), 4.98 (s, 2H), 4.68 (s, 4H), 4.10 (s, 4H).

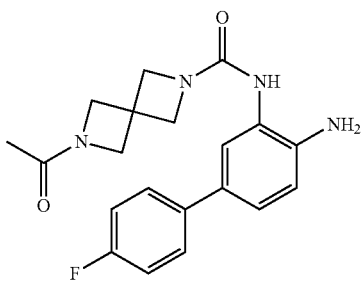
(187)

6-Acetyl-N-(4-amino-4'-fluoro-[1,1'-biphenyl]-3-yl)-2,6-diazaspiro[3.3]heptane-2-carboxamide (187) was prepared by substituting N-methylpropan-1-amine in Scheme 25 with 1-(2,6-diazaspiro[3.3]heptan-2-yl)ethanone and by substituting 5-(cyclopent-1-en-1-yl)-2-nitroaniline in Scheme 25 with 4'-fluoro-4-nitro-[1,1'-biphenyl]-3-amine. ESI+ MS: m/z 369 ([M+H]⁺), 1H NMR (500 MHz, d⁶-DMSO): δ 7.76 (s, 1H), 7.53-7.50 (m, 2H), 7.33 (d, J=1.5 Hz, 1H), 7.21-7.17 (m, 3H), 6.76 (d, J=8.0 Hz, 1H), 4.99 (s, 2H), 4.25 (s, 2H), 4.07 (s, 4H), 3.97 (s, 2H), 1.73 (s, 3H).

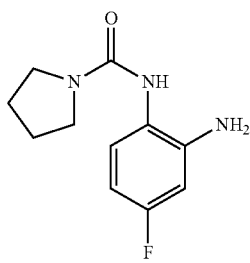

(222)

N-(2-amino-4-fluorophenyl)pyrrolidine-1-carboxamide (222) was prepared by substituting N-methylpropan-1-amine in Scheme 25 with pyrrolidine and by substituting 5-(cyclopent-1-en-1-yl)-2-nitroaniline in Scheme 25 with 4-fluoro-2-nitroaniline. ESI+ MS: m/z 254 ([M+H]+), 1H NMR (00 MHz, d6-DMSO): δ 7.37 (bs, 1H), 6.95 (dd, J$_1$=6 Hz, J$_2$=9 Hz, 1H), 6.47 (dd, J$_1$=3 Hz, J$_2$=12 Hz, 1H), 6.28 (dt, J$_1$=3 Hz, J$_2$=9 Hz, 1H), 5.09 (s, 2H), 3.35-3.31 (m, 4H)m, 1.90-1.81 (m, 4H).

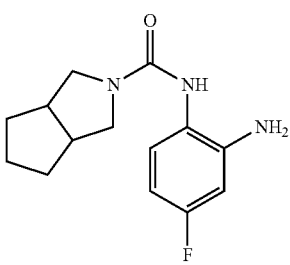

(220)

N-(2-amino-4-fluorophenyl)hexahydrocyclopenta[c]pyrrole-2(1H)-carboxamide (220) was prepared by substituting N-methylpropan-1-amine in Scheme 25 with 3-azabicyclo[3,3,0]octane hydrochloride and by substituting 5-(cyclopent-1-en-1-yl)-2-nitroaniline in Scheme 25 with 4-fluoro-2-nitroaniline. ESI+ MS: m/z 264 ([M+H]$^+$), 1HNMR (300 MHz, CDCl$_3$): δ 7.00-6.93 (m, 1H), 6.50-6.30 (m, 2H), 5.95 (s, 1H), 3.70-3.50 (m, 2H), 3.20-3.10 (m, 2H), 2.80-2.60 (br s, 2H), 1.90-1.70 (m, 3H), 1.70-1.55 (m, 1H), 1.55-1.40 (m, 2H).

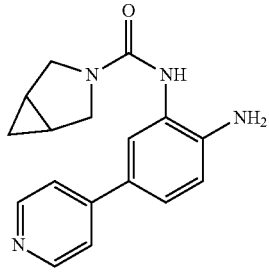

(247)

N-(2-amino-5-(pyridin-4-yl)phenyl)-3-azabicyclo[3.1.0]hexane-3-carboxamide (247) was prepared by substituting N-methylpropan-1-amine in Scheme 25 with 6,7-dihydro-5H-pyrrolo[3,4-b]pyridine and by substituting 5-(cyclopent-1-en-1-yl)-2-nitroaniline in Scheme 25 with 5-(pyridin-4-yl)-2-nitroaniline. ESI+ MS: m/z 295 ([M+H]+); 1H NMR (400 MHz, d6-DMSO): δ 8.50-8.48 (m, 2H), 7.54-7.51 (m, 4H), 7.38 (dd, J=2.4 Hz, J=8.4 Hz), 6.80 (d, J=8.4, 1H), 5.21 (s, 2H), 3.61 (d, J=10.4 Hz), 3.41-3.35 (m, 2H), 1.58 (t, J=7.6 Hz, 2H), 0.72-0.67 (m, 1H), 0.20-0.16 (m, 1H).

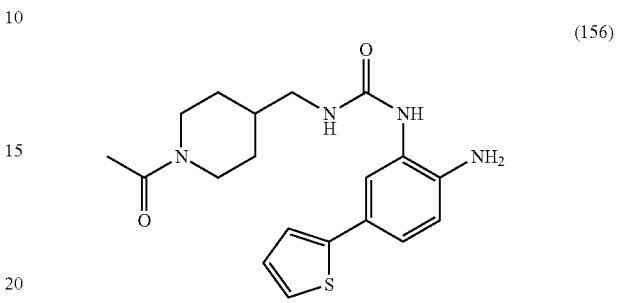

(156)

Synthesis of 1-((1-acetylpiperidin-4-yl)methyl)-3-(2-amino-5-(thiophen-2-yl)phenyl)urea (156)

Scheme 27

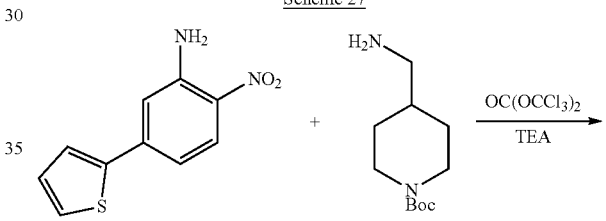

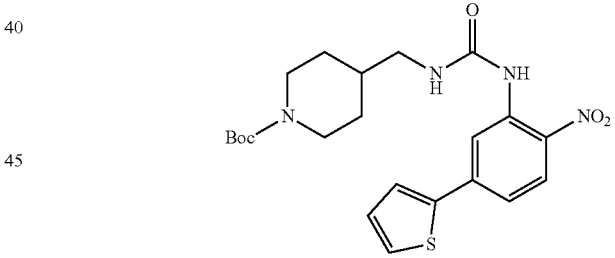

To a solution of 2-nitro-5-(thiophen-2-yl)aniline (0.60 g, 2.72 mmol, 1.0 equiv.) in dichloromethane at 0° C. were added TEA (5 mL, 35.4 mmol, 13 equiv.) and triphosgene (0.81 g, 2.72 mmol, 1.0 equiv.). The mixture was warmed to room temperature and stirred 3 h. The reaction was then cooled to 0° C. and tert-butyl 4-(aminomethyl)piperidine-1-carboxylate (0.88 g, 4.09 mmol, 1.5 equiv.) was then added slowly. The reaction mixture was slowly warmed to room temperature and stirred for 2 h. The reaction was diluted with dichloromethane, washed with water and brine, dried over anhydrous magnesium sulfate, filtered, and concentrated. The crude residue was purified by column chromatography (silica gel, EtOAc/hexanes) to afford tert-butyl 4-((3-(2-nitro-5-(thiophen-2-yl)phenyl)ureido)methyl)piperidine-1-carboxylate (0.31 g, 25% yield).

Scheme 28

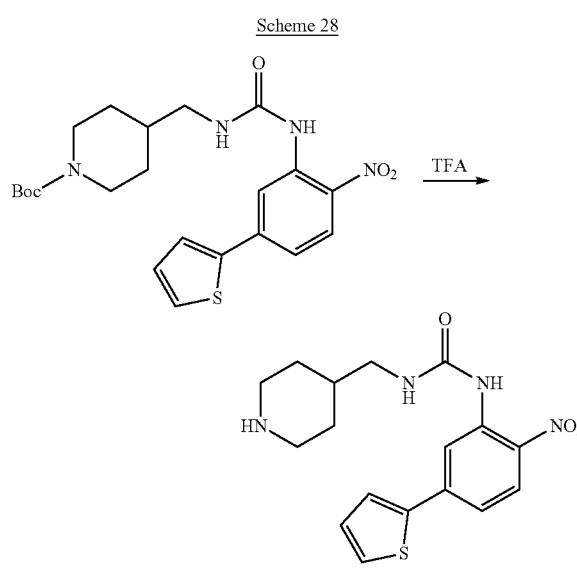

To a solution of tert-butyl 4-((3-(2-nitro-5-(thiophen-2-yl)phenyl)ureido)methyl)piperidine-1-carboxylate (0.30 g, 0.65 mmol) in dichloromethane (15 mL) was added TFA (3 mL) at 0° C. The reaction was warmed to room temperature and stirred for 2 h. The reaction was concentrated. The crude residue was diluted with a saturated aqueous solution of sodium bicarbonate. The obtained solid was filtered, washed with water then washed with ether and pentane to afford 1-(2-nitro-5-(thiophen-2-yl)phenyl)-3-(piperidin-4-ylmethyl)urea (0.20 g, 85% yield).

Scheme 29

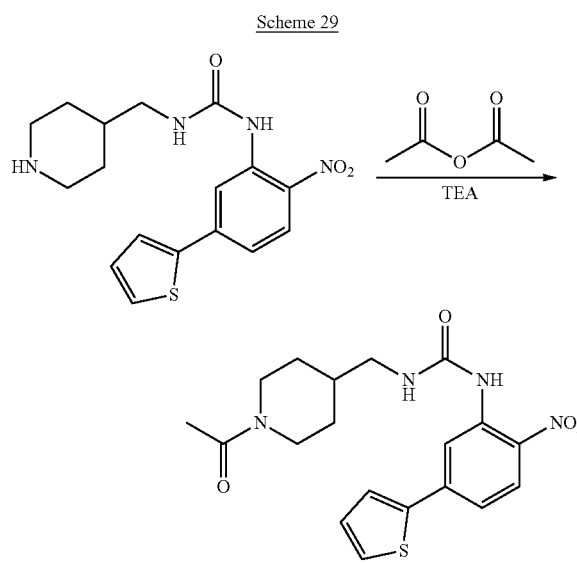

Acetic anhydride (0.03 g, 0.31 mmol, 1.1 equiv.) was added to a solution of 1-(2-nitro-5-(thiophen-2-yl)phenyl)-3-(piperidin-4-ylmethyl)urea (0.10 g, 0.28 mmol, 1.0 equiv.) and triethylamine (60 μL 0.42 mmol, 1.5 equiv.) in dichloromethane (5 mL) at 0° C. The reaction mixture was warmed to room temperature and stirred for 2 h. The reaction was then diluted with water. The product was extracted with dichloromethane, washed with water and brine, dried over sodium sulfate, filtered and concentrated under reduced pressure. The crude solid was purified by column chromatography (silica gel, 5% MeOH/CH$_2$Cl$_2$) to afford 1-((1-acetylpiperidin-4-yl)methyl)-3-(2-nitro-5-(thiophen-2-yl)phenyl)urea (0.09 g, 81% yield).

Scheme 30

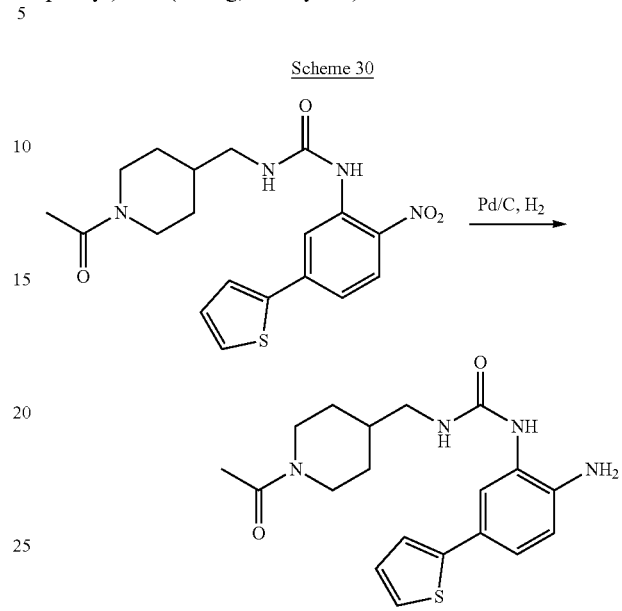

To a solution of 1-((1-acetylpiperidin-4-yl)methyl)-3-(2-nitro-5-(thiophen-2-yl)phenyl)urea (0.09 g, 0.22 mmol) in methanol was added Pd/C (0.03 g, 0.028 mmol, 1.2 equiv.). The reaction mixture was degassed then stirred at room temperature under H$_2$ atmosphere for 1 h. The reaction was filtered through celite and concentrated. The crude solid was washed with ether, and dried under reduced pressure to obtain of pure 1-((1-acetylpiperidin-4-yl)methyl)-3-(2-amino-5-(thiophen-2-yl)phenyl)urea (0.05 g, 60% yield). ESI+ MS: m/z 373 ([M]$^+$). 1H NMR (500 MHz, d$^6$-DMSO): δ 7.66 (d, J=2.0 Hz, 1H), 7.58 (s, 1H), 7.33 (d, J=5.0 Hz, 1H), 7.17 (d, J=3.5 Hz, 1H), 7.10 (dd, J=3.5 Hz, 1H), 7.04-7.02 (m, 1H), 6.72 (d, J=8.0 Hz, 1H), 6.31 (t, J=6.0 Hz, 1H), 4.89 (bs, 2H), 4.36 (d, J=13.0 Hz, 1H), 3.81 (d, J=13.5 Hz, 1H), 3.0-2.96 (m, 3H), 1.90 (s, 3H), 1.71-1.64 (m, 3H), 1.10-1.07 (m, 1H), 0.98-0.95 (m, 1H).

One skilled in the art will recognize that other compounds described below can be prepared in a similar manner:

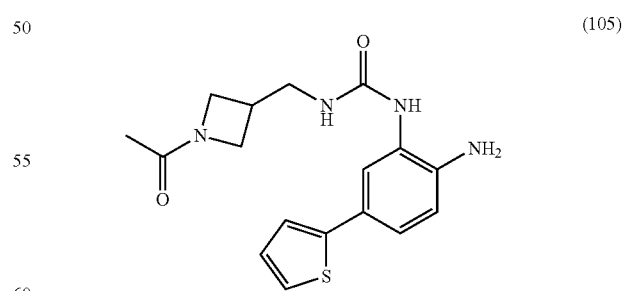

(105)

1-((1-acetylazetidin-3-yl)methyl)-3-(2-amino-5-(thiophen-2-yl)phenyl)urea (105) was prepared by substituting tert-butyl 4-(aminomethyl)piperidine-1-carboxylate in Scheme 27 with tert-butyl 3-(aminomethyl)azetidine-1-carboxylate. ESI+ MS: m/z 345 ([M+H]$^+$), 1H NMR (500 MHz, d$^6$-DMSO): δ 7.68-7.60 (m, 2H), 7.36-7.30 (m, 1H), 7.22-

7.00 (m, 3H), 6.75-6.70 (m, 1H), 6.48-6.42 (m, 1H), 4.92 (bs, 2H), 4.15-4.02 (m, 1H), 3.90-3.70 (m, 2H), 3.60-3.50 (m, 1H), 3.40-3.20 (m, 2H), 2.80-2.60 (m, 1H), 1.73 (s, 3H).

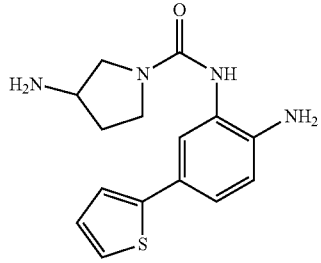

(109)

3-amino-N-(2-amino-5-(thiophen-2-yl)phenyl)pyrrolidine-1-carboxamide (109) was prepared by substituting tert-butyl 4-(aminomethyl)piperidine-1-carboxylate in Scheme 27 with tert-butyl pyrrolidin-3-ylcarbamate. ESI+ MS: m/z 303 ([M+H]$^+$).

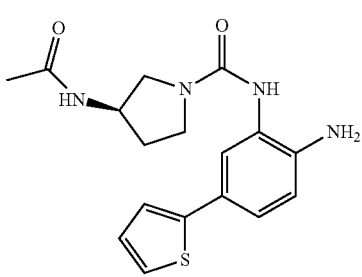

(110)

(R)-3-acetamido-N-(2-amino-5-(thiophen-2-yl)phenyl)pyrrolidine-1-carboxamide (110) was prepared by substituting tert-butyl 4-(aminomethyl)piperidine-1-carboxylate in Scheme 27 with (R)-tert-butyl pyrrolidin-3-ylcarbamate. ESI+ MS: m/z 345 ([M+H]$^+$), 1H NMR (500 MHz, d$^6$-DMSO): δ 8.13 (d, J=6.5 Hz, 1H), 7.55 (bs, 1H), 7.37-7.32 (m, 2H), 7.22-7.16 (m, 2H), 7.03 (dd, J=3.5, 5.0 Hz, 1H), 6.73 (d, J=8.0 Hz, 1H), 5.02 (s, 2H), 4.28-4.20 (m, 1H), 3.62-3.58 (m, 1H), 3.58-3.40 (m, 2H), 3.23-3.20 (m, 1H), 2.09-2.02 (m, 1H), 1.83 (s, 3H), 1.83-1.75 (m, 1H).

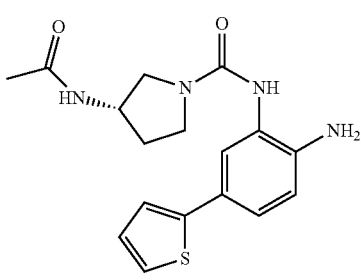

(111)

(S)-3-acetamido-N-(2-amino-5-(thiophen-2-yl)phenyl)pyrrolidine-1-carboxamide (111) was prepared by substituting tert-butyl 4-(aminomethyl)piperidine-1-carboxylate in Scheme 27 with (S)-tert-butyl pyrrolidin-3-ylcarbamate. ESI+ MS: m/z 345 ([M+H]$^+$), 1H NMR (500 MHz, d$^6$-DMSO): δ 8.13 (d, J=6.5 Hz, 1H), 7.55 (bs, 1H), 7.37-7.32 (m, 2H), 7.22-7.16 (m, 2H), 7.03 (dd, J=3.5, 5.0 Hz, 1H), 6.73 (d, J=8.0 Hz, 1H), 5.02 (s, 2H), 4.28-4.20 (m, 1H), 3.62-3.58 (m, 1H), 3.58-3.40 (m, 2H), 3.23-3.20 (m, 1H), 2.09-2.02 (m, 1H), 1.83 (s, 3H), 1.83-1.75 (m, 1H).

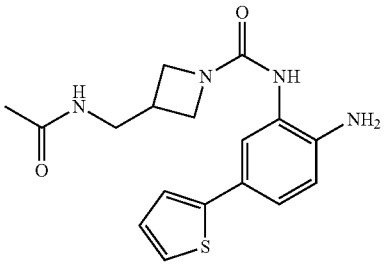

(139)

3-(acetamidomethyl)-N-(2-amino-5-(thiophen-2-yl)phenyl)azetidine-1-carboxamide (139) was prepared by substituting tert-butyl 4-(aminomethyl)piperidine-1-carboxylate in Scheme 27 with tert-butyl (azetidin-3-ylmethyl)carbamate. ESI+ MS: m/z 345 ([M+H]$^+$), 1H NMR (500 MHz, d$^6$-DMSO): δ 8.01 (bs, 1H), 7.65 (bs, 1H), 7.38-7.30 (m, 2H), 7.20-7.14 (m, 2H), 7.06-7.00 (m, 1H), 6.72 (d, J=8.5 Hz, 1H), 5.04 (s, 2H), 3.96 (t, J=8.5 Hz, 2H), 3.63 (t, J=5.5 Hz, 2H), 3.30-3.20 (m, 2H), 2.68-2.60 (m, 1H), 1.82 (s, 3H).

(141)

6-acetamido-N-(2-amino-5-(thiophen-2-yl)phenyl)-3-azabicyclo[3.1.0]hexane-3-carboxamide (141) was prepared by substituting tert-butyl 4-(aminomethyl)piperidine-1-carboxylate in Scheme 27 with tert-butyl 3-azabicyclo[3.1.0]hexan-6-ylcarbamate. ESI+ MS: m/z 357 ([M+H]$^+$), 1H NMR (500 MHz, d$^6$-DMSO): δ 7.99 (s, 1H), 7.51 (s, 1H), 7.35-7.30 (m, 2H), 7.22-7.16 (m, 2H), 7.03 (dd, J=4.0 Hz, 1H), 6.72 (d, J=8.0 Hz, 1H), 5.00 (s, 2H), 3.66 (d, J=10.0 Hz, 2H), 3.43 (d, J=10.0 Hz, 2H), 2.42-2.35 (m, 1H), 1.78 (s, 3H), 2.20-2.14 (m, 2H).

(162)

1-((1-Acetylazetidin-3-yl)methyl)-3-(4-amino-4'-fluoro-[1,1'-biphenyl]-3-yl)urea (162) was prepared by substituting tert-butyl 4-(aminomethyl)piperidine-1-carboxylate in Scheme 27 with tert-butyl 3-(aminomethyl)azetidine-1-carboxylate and 2-nitro-5-(thiophen-2-yl)aniline in Scheme 27 with 4'-fluoro-4-nitro-[1,1'-biphenyl]-3-amine. ESI+ MS: m/z 357 ([M+H]⁺); 1H NMR (500 MHz, d⁶-DMSO): δ 7.65-7.60 (m, 2H), 7.56-7.50 (m, 2H), 7.19 (t, J=9.0 Hz, 2H), 7.09 (d, J=6.5 Hz, 1H), 6.76 (d, J=8.5 Hz, 1H), 6.46 (t, J=6.0 Hz, 1H), 4.86 (s, 2H), 4.12 (t, J=8.0 Hz, 1H), 3.85-3.78 (m, 2H), 3.56-3.53 (m, 1H), 3.31-3.26 (m, 2H), 2.70-2.67 (m, 1H), 1.72 (s, 3H).

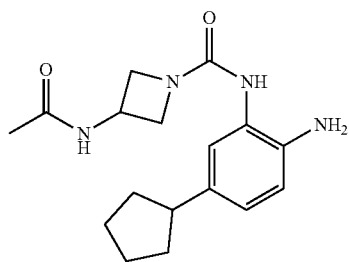

(135)

3-acetamido-N-(2-amino-5-cyclopentylphenyl)azetidine-1-carboxamide (135) was prepared by substituting tert-butyl 4-(aminomethyl)piperidine-1-carboxylate in Scheme 27 with tert-butyl azetidin-3-ylcarbamate and by substituting 2-nitro-5-(thiophen-2-yl)aniline with 5-cyclopentyl-2-nitroaniline. ESI+ MS: m/z 317 ([M+H]⁺), 1H NMR (500 MHz, d⁶-DMSO): δ 8.47 (d, J=7.0 Hz, 1H), 7.69 (s, 1H), 6.89 (d, J=1.5 Hz, 1H), 6.75 (dd, J=1.5, 8.5 Hz, 1H), 6.62 (d, J=8.5 Hz, 1H), 4.61 (bs, 2H), 4.45-4.35 (m, 1H), 4.12 (t, J=8.0 Hz, 2H), 3.72 (dd, J=5.5, 8.0 Hz, 2H), 1.83-1.74 (m, 1H), 1.96-1.86 (m, 2H), 1.83 (s, 3H), 1.78-1.65 (m, 2H), 1.65-1.54 (m, 2H), 1.48-1.38 (m, 2H).

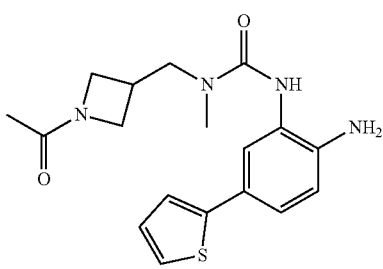

(199)

1-((1-Acetylazetidin-3-yl)methyl)-3-(2-amino-5-(thiophen-2-yl)phenyl)-1-methylurea (199) was prepared by substituting tert-butyl 4-(aminomethyl)piperidine-1-carboxylate in Scheme 27 with tert-butyl 3-((methylamino)methyl)azetidine-1-carboxylate. ESI+ MS: m/z 359 ([M+H]⁺); 1H NMR (500 MHz, d⁶-DMSO): δ 7.75 (s, 1H), 7.32 (d, J=5.5 Hz, 1H), 7.27 (s, 1H), 7.19 (m, 2H), 7.02 (t, J=4.0 Hz, 1H), 6.73 (d, J=8.0, 1H), 4.95 (s, 2H), 4.14 (t, J=8.5 Hz, 1H), 3.88-3.83 (m, 2H), 3.58-3.53 (m, 3H), 2.96 (s, 3H), 2.83 (m, 1H), 1.71 (s, 3H).

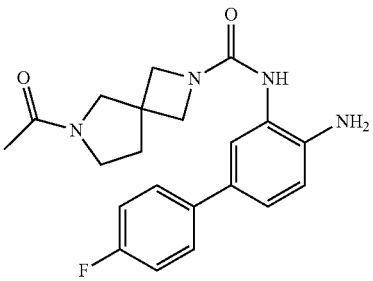

(202)

6-acetyl-N-(4-amino-4'-fluoro-[1,1'-biphenyl]-3-yl)-2,6-diazaspiro[3.4]octane-2-carboxamide (202) was prepared by substituting tert-butyl 4-(aminomethyl)piperidine-1-carboxylate in Scheme 27 with tert-butyl 2,6-diazaspiro[3.4]octane-6-carboxylate 2-nitro-5-(thiophen-2-yl)aniline in Scheme 27 with 4'-fluoro-4-nitro-[1,1'-biphenyl]-3-amine. ESI+ MS: m/z 383 ([M+H]⁺), ¹HNMR (500 MHz, CDCl₃): δ 7.73 (d, J=19.5 Hz, 1H), 7.54-7.51 (m, 2H), 7.37-7.36 (m, 1H), 7.21-7.17 (m, 3H), 6.77 (dd, J₁,₂=2.5 Hz, J₁,₃=8.0 Hz, 1H), 5.01 (s, 2H), 3.93-3.83 (m, 4H), 3.61 (s, 1H), 3.47-3.45 (m, 2H), 3.32-3.29 (m, 1H), 2.12 (t, J=7.0 Hz, 1H), 2.03 (t, J=7.0 Hz, 1H), 1.93 (d, J=5.5 Hz, 3H).

Alternatively, the nitro group reduction can be carried out using zinc and ammonium formate as previously described and one skilled in the art will recognize that other compounds described below can be prepared in a similar manner:

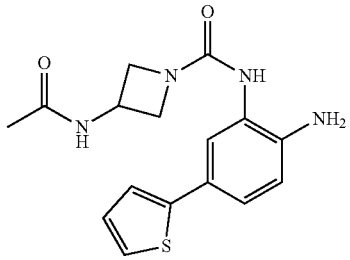

(134)

3-acetamido-N-(2-amino-5-(thiophen-2-yl)phenyl)azetidine-1-carboxamide (134) was prepared by substituting tert-butyl 4-(aminomethyl)piperidine-1-carboxylate in Scheme 27 with tert-butyl azetidin-3-ylcarbamate. ESI+ MS: m/z 331 ([M+H]⁺), 1H NMR (500 MHz, d⁶-DMSO): δ 8.49 (d, J=6.0 Hz, 1H), 7.77 (s, 1H), 7.36-7.32 (m, 2H), 7.22-7.16 (m, 2H), 7.03 (dd, J=3.5, 5.0 Hz, 1H), 6.72 (d, J=8.5 Hz, 1H), 5.05 (s, 2H), 4.44-4.40 (m, 1H), 4.17 (t, J=8.0 Hz, 2H), 3.76 (dd, J=6.0, 9.0 Hz, 2H), 1.83 (s, 3H).

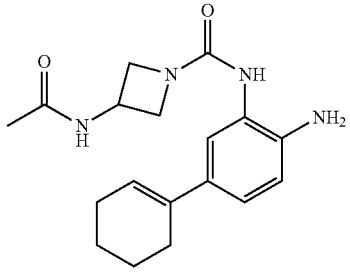

(136)

3-acetamido-N-(4-amino-2',3',4',5'-tetrahydro-[1,1'-biphenyl]-3-yl)azetidine-1-carboxamide (136) was prepared by tert-butyl 4-(aminomethyl)piperidine-1-carboxylate in Scheme 27 with tert-butyl azetidin-3-ylcarbamate and by substituting 2-nitro-5-(thiophen-2-yl)aniline with 5-(1-cyclohexenyl)-2-nitroaniline. ESI+ MS: m/z 329 ([M+H]$^+$), 1H NMR (500 MHz, d$^6$-DMSO): δ 8.48 (d, J=6.5 Hz, 1H), 7.68 (s, 1H), 7.08 (d, J=2.0 Hz, 1H), 6.94 (dd, J=1.5, 8.5 Hz, 1H), 6.63 (d, J=8.5 Hz, 1H), 5.91 (bs, 1H), 4.80 (s, 2H), 4.45-4.36 (m, 1H), 4.13 (t, J=8.0 Hz, 2H), 3.72 (dd, J=6.0, 9.0 Hz, 2H), 2.29-2.22 (m, 2H), 2.16-2.10 (m, 2H), 1.83 (s, 3H), 1.72-1.65 (m, 2H), 1.60-1.53 (m, 2H).

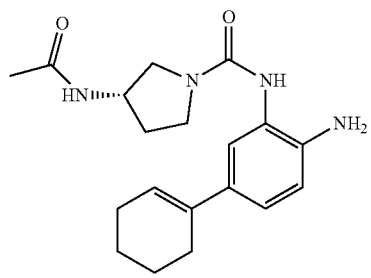

(112)

(S)-3-acetamido-N-(4-amino-2',3',4',5'-tetrahydro-[1,1'-biphenyl]-3-yl)pyrrolidine-1-carboxamide (112) was prepared by substituting tert-butyl 4-(aminomethyl)piperidine-1-carboxylate in Scheme 27 with (S)-tert-butyl pyrrolidin-3-ylcarbamate and by substituting 2-nitro-5-(thiophen-2-yl)aniline with 5-(1-cyclohexenyl)-2-nitroaniline. ESI+ MS: m/z 343 ([M+H]$^+$), 1H NMR (500 MHz, d$^6$-DMSO): δ 8.11 (d, J=6.5 Hz, 1H), 7.45 (s, 1H), 7.10 (d, J=1.0 Hz, 1H), 6.94 (dd, J=1.0, 8.0 Hz, 1H), 6.64 (d, J=8.0 Hz, 1H), 5.91 (bs, 1H), 4.78 (s, 2H), 4.28-4.20 (m, 1H), 3.62-3.54 (m, 1H), 3.50-3.38 (m, 2H), 3.22-3.16 (m, 1H), 2.30-2.24 (m, 2H), 2.16-2.10 (m, 2H), 2.10-2.00 (m, 1H), 1.82 (s, 3H), 1.82-1.74 (m, 1H), 1.72-1.64 (m, 2H), 1.60-1.54 (m, 2H).

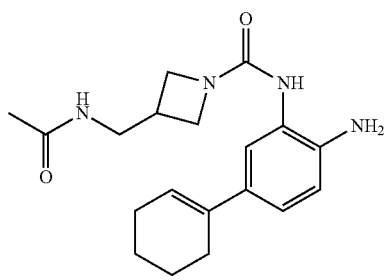

(140)

3-(acetamidomethyl)-N-(4-amino-2',3',4',5'-tetrahydro-[1,1'-biphenyl]-3-yl)azetidine-1-carboxamide (140) was prepared by substituting tert-butyl 4-(aminomethyl)piperidine-1-carboxylate in Scheme 27 with tert-butyl (azetidin-3-ylmethyl)carbamate and by substituting 2-nitro-5-(thiophen-2-yl)aniline with 5-(1-cyclohexenyl)-2-nitroaniline. ESI+ MS: m/z 343 ([M+H]$^+$), 1H NMR (500 MHz, d$^6$-DMSO): δ 8.00 (t, J=5.5 Hz, 1H), 7.56 (s, 1H), 7.09 (d, J=2.0 Hz, 1H), 6.93 (dd, J=2.0, 8.0 Hz, 1H), 6.62 (d, J=8.0 Hz, 1H), 5.91 (bs, 1H), 4.79 (s, 2H), 3.92 (t, J=8.0 Hz, 2H), 3.59 (dd, J=5.5, 8.5 Hz, 2H), 3.25 (t, J=6.0 Hz, 2H), 2.65-2.55 (m, 1H), 2.29-2.22 (m, 2H), 2.15-2.10 (m, 2H), 1.82 (s, 3H), 1.72-1.65 (m, 2H), 1.60-1.53 (m, 2H).

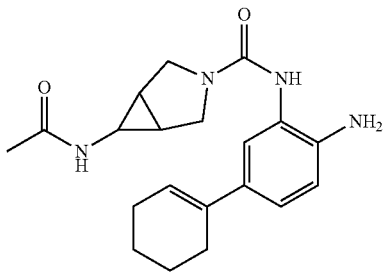

(142)

6-acetamido-N-(4-amino-2',3',4',5'-tetrahydro-[1,1'-biphenyl]-3-yl)-3-azabicyclo[3.1.0]hexane-3-carboxamide (142) was prepared by substituting tert-butyl 4-(aminomethyl)piperidine-1-carboxylate in Scheme 27 with tert-butyl 3-azabicyclo[3.1.0]hexan-6-ylcarbamate and by substituting 2-nitro-5-(thiophen-2-yl)aniline with 5-(1-cyclohexenyl)-2-nitroaniline. ESI+ MS: m/z 355 ([M+H]$^+$), 1H NMR (500 MHz, d$^6$-DMSO): δ 7.99 (d, J=3.0 Hz, 1H), 7.42 (s, 1H), 7.06 (d, J=2.0 Hz, 1H), 6.94 (dd, J=2.0, 8.0 Hz, 1H), 6.63 (d, J=8.0 Hz, 1H), 5.91 (bs, 1H), 4.75 (s, 2H), 3.64 (d, J=10.5 Hz, 2H), 3.40 (d, J=10.5 Hz, 2H), 2.38-2.34 (m, 1H), 2.28-2.24 (m, 2H), 2.14-2.08 (m, 2H), 1.78 (s, 3H), 1.72-1.64 (m, 4H), 1.60-1.54 (m, 2H).

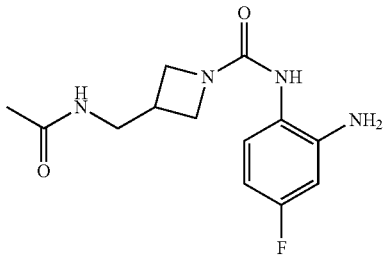

(228)

3-(acetamidomethyl)-N-(2-amino-4-fluorophenyl)azetidine-1-carboxamide (228) was prepared by substituting tert-butyl 4-(aminomethyl)piperidine-1-carboxylate in Scheme 27 with tert-butyl (azetidin-3-ylmethyl)carbamate and by substituting 2-nitro-5-(thiophen-2-yl)aniline with 4-fluoro-2-nitroaniline. ESI+ MS: m/z 281 ([M+H]+); 1H NMR (400 MHz, d6-DMSO): δ 7.99 (m, 1H), 7.51 (s, 1H), 6.95 (dd, J=6.4 Hz, J=8.8 Hz, 1H), 6.46 (dd, J=2.8 Hz, J=11.2 Hz, 1H), 6.29-6.24 (m, 1H), 5.09 (s, 2H), 3.90 (t, J=8.4 Hz, 2H), 3.59-3.55 (m, 2H), 3.24 (t, J=6.4 Hz, 2H), 2.62-2.59 (m, 1H), 1.81 (s, 3H).

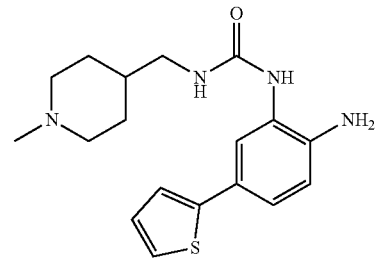

(155)

Synthesis of 1-(2-Amino-5-(thiophen-2-yl)phenyl)-3-((1-methylpiperidin-4-yl)methyl)urea (155)

Scheme 31

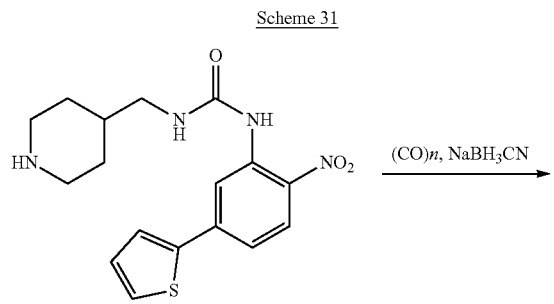

To a solution of 1-(2-nitro-5-(thiophen-2-yl)phenyl)-3-(piperidin-4-ylmethyl)urea in acetonitrile (16 mL) and dichloromethane (8 mL) 0° C. was added formaldehyde. The reaction was warmed to room temperature then stirred for 1 h. Sodium cyanoborohydride was then added and the reaction was stirred for an additional hour. The reaction was quenched with a saturated aqueous solution of sodium bicarbonate. The product was extracted with ethyl acetate. The combined organic layers were washed with water and brine, dried, filtered and evaporated under reduced pressure. The crude residue was purified by column chromatography (silica gel, 5% MeOH/CH$_2$Cl$_2$) to afford 1-(2-nitro-5-(thiophen-2-yl)phenyl)-3-(piperidin-4-ylmethyl)urea (0.045 g, 43% yield).

Scheme 32

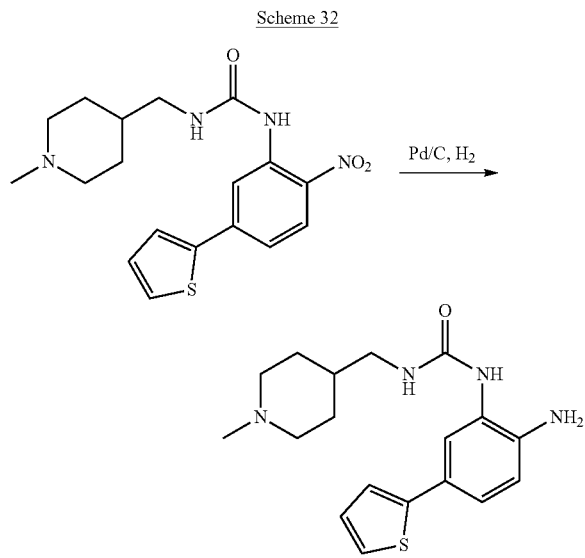

To a solution of 1-(2-nitro-5-(thiophen-2-yl)phenyl)-3-(piperidin-4-ylmethyl)urea (0.045 g, 0.12 mmol, 1.0 equiv.) in methanol was added Pd/C (0.02 g, 0.02 mmol, 0.16 equiv.). The reaction mixture was stirred at room temperature under H$_2$ balloon pressure for 1 h. The reaction was filtered through celite and concentrated under reduced pressure. The crude solid was washed with ether to obtain of pure 1-(2-Amino-5-(thiophen-2-yl)phenyl)-3-((1-methylpiperidin-4-yl)methyl)urea (0.03 g, 67% yield). ESI+ MS: m/z 345 ([M]$^+$). 1H NMR (500 MHz, d$^6$-DMSO): δ 7.66 (d, J=1.5 Hz, 1H), 7.56 (s, 1H), 7.33 (d, J=5.0 Hz, 1H), 7.17 (d, J=3.0 Hz, 1H), 7.10 (dd, J=3.5 Hz, 1H), 7.03 (t, J=4.0 Hz, 1H), 6.71 (d, J=7.5 Hz, 1H), 6.27 (t, J=5.5 Hz, 1H), 4.88 (bs, 2H), 2.98 (t, J=5.5 Hz, 2H), 2.77 (d, J=11.0 Hz, 2H), 2.16 (s, 3H), 1.85 (m, 2H), 1.63 (d, J=4.5 Hz, 2H), 1.36-1.33 (m, 1H), 1.20-1.13 (m, 3H).

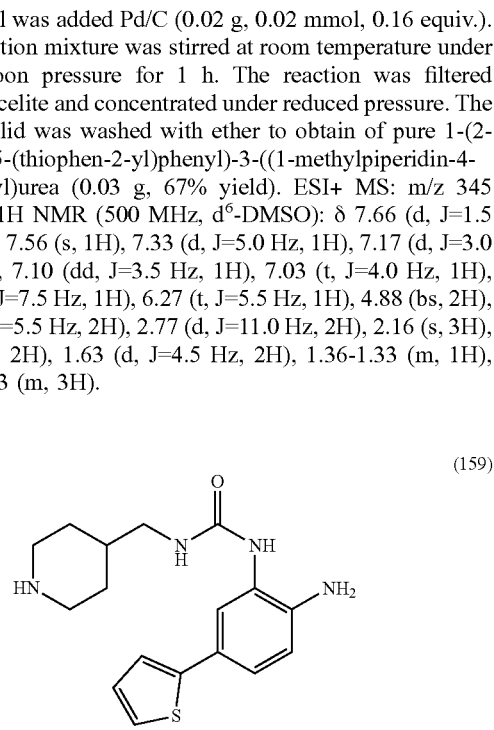

(159)

Synthesis of 1-(2-amino-5-(thiophen-2-yl)phenyl)-3-(piperidin-4-ylmethyl)urea (159)

Scheme 33

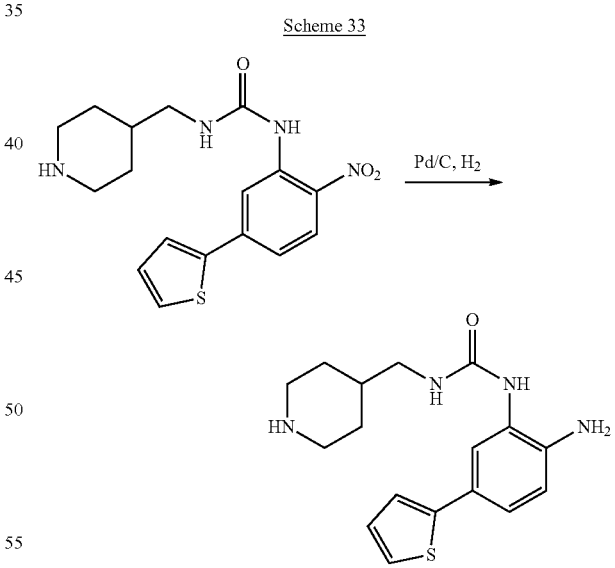

To a solution of 1-(2-nitro-5-(thiophen-2-yl)phenyl)-3-(piperidin-4-ylmethyl)urea (0.10 g, 0.28 mmol, 1.0 equiv.) in methanol was added Pd/C (0.03 g, 0.03 mmol, 0.10 equiv.). The reaction mixture was stirred at room temperature under H$_2$ balloon pressure for 1 h. The reaction was filtered through celite and concentrated under reduced pressure. The crude solid was washed with ether to obtain of pure 1-(2-amino-5-(thiophen-2-yl)phenyl)-3-(piperidin-4-ylmethyl)urea (0.06 g, 65% yield). ESI+ MS: m/z 331 ([M]$^+$); 1H NMR (500 MHz, d$^6$-DMSO): δ 7.64 (d, J=12.0 Hz, 2H), 7.33 (d, J=5.5 Hz, 1H), 7.17 (d, J=3.0 Hz, 1H), 7.10-7.09 (m, 1H), 7.03 (t, J=5.0 Hz, 1H), 6.71 (d, J=8.0 Hz, 1H), 6.34 (m, 1H), 4.90-4.89 (bs, 2H), 3.16 (d, J=12.5 Hz, 2H), 2.99 (t, J=6.0 Hz, 3H), 2.65 (t, J=12.5 Hz, 2H), 1.71 (d, J=13.0 Hz, 1H), 1.62-1.60 (m, 2H), 1.20-1.13 (m, 2H).

One skilled in the art will recognize that other compounds described below can be prepared in a similar manner:

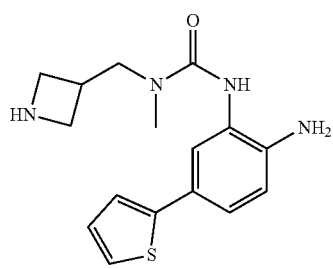
(165)

3-(2-Amino-5-(thiophen-2-yl)phenyl)-1-(azetidin-3-ylmethyl)-1-methylurea (165) was prepared by substituting tert-butyl 4-(aminomethyl)piperidine-1-carboxylate in Scheme 27 with tert-butyl 3-((methylamino)methyl)azetidine-1-carboxylate. ESI+ MS: m/z 317 ([M+H]⁺); 1H NMR (500 MHz, d⁶-DMSO): δ 7.27 (d, J=4.0 Hz, 1H), 7.15 (s, 1H), 7.05-6.96 (m, 2H), 6.88 (s, 1H), 6.62 (d, J=8.0 Hz, 1H), 5.57 (bs, 1H), 4.76-4.68 (m, 3H), 3.38 (s, 2H), 3.18-3.16 (m, 1H), 3.03 (t, J=9.0 Hz, 1H), 2.97 (s, 3H), 2.82 (t, J=9.5 Hz, 1H), 2.06 (bs, 1H).

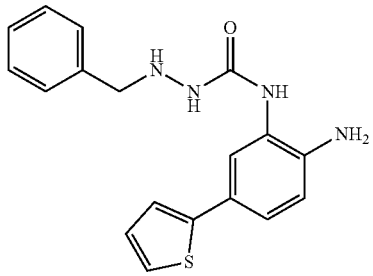
(146)

N-(2-amino-5-(thiophen-2-yl)phenyl)-2-benzylhydrazinecarboxamide (146) was prepared by substituting tert-butyl 4-(aminomethyl)piperidine-1-carboxylate in Scheme 27 with benzylhydrazine. ESI+ MS: m/z 339 ([M+H]⁺), 1H NMR (500 MHz, d⁶-DMSO): 7.97 (bs, 1H), 7.60 (bs, 1H), 7.50-7.41 (m, 3H), 7.38-7.24 (m, 4H), 7.18-7.10 (m, 2H), 7.06-7.03 (m, 1H), 6.73 (d, J=8.5 Hz, 1H), 5.26 (bs, 1H), 4.77 (bs, 2H), 3.90 (d, J=4.5 Hz, 2H).

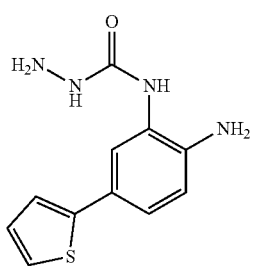
(147)

N-(2-amino-5-(thiophen-2-yl)phenyl)hydrazinecarboxamide (147) was prepared by substituting tert-butyl 4-(aminomethyl)piperidine-1-carboxylate in Scheme 27 with tert-butyl hydrazinecarboxylate. ESI+ MS: m/z 249 ([M+H]⁺), 1H NMR (500 MHz, d⁶-DMSO): 8.03 (s, 1H), 7.65 (s, 1H), 7.39 (s, 1H), 7.34 (d, J=5.0 Hz, 1H), 7.19 (d, J=3.0 Hz, 1H), 7.13 (dd, J=8.5; 1.5 Hz, 1H), 7.04 (t, J=4.5 Hz, 1H), 6.75 (d, J=8.5 Hz, 1H), 4.93 (s, 2H), 4.32 (s, 2H).

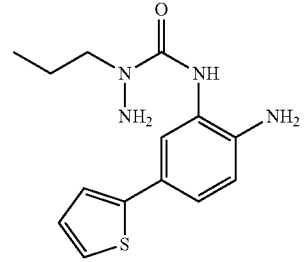
(172)

N-(2-amino-5-(thiophen-2-yl)phenyl)-1-propylhydrazinecarboxamide (172) was prepared by substituting tert-butyl 4-(aminomethyl)piperidine-1-carboxylate in Scheme 27 with tert-butyl 1-propylhydrazinecarboxylate. ESI+ MS: m/z 291 ([M]⁺). 1H NMR (500 MHz, d⁶-DMSO): δ 8.54 (s, 1H), 7.70 (s, 1H), 7.34 (d, J=5.0 Hz, 1H), 7.19 (d, J=3.0 Hz, 1H), 7.12-7.10 (m, 1H), 7.04-7.03 (m, 1H), 6.76 (d, J=8.0 Hz, 1H), 4.88 (s, 2H), 4.66 (s, 2H), 3.39 (t, J=7.0 Hz, 2H), 1.60-1.56 (m, 2H), 0.85 (t, J=7.5 Hz, 3H).

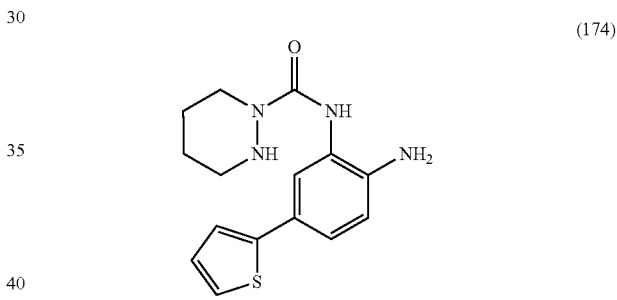
(174)

N-(2-amino-5-(thiophen-2-yl)phenyl)tetrahydropyridazine-1(2H)-carboxamide (174) was prepared by substituting tert-butyl 4-(aminomethyl)piperidine-1-carboxylate in Scheme 27 with tert-butyl tetrahydropyridazine-1(2H)-carboxylate. ESI+ MS: m/z 303 ([M+H]⁺); 1H NMR (500 MHz, d⁶-DMSO): δ 8.45 (s, 1H), 7.70 (s, 1H), 7.34 (d, J=5.0 Hz, 1H), 7.19 (d, J=2.5 Hz, 1H), 7.12 (d, J=8.0, 1H), 7.03 (m, 1H), 6.76 (d, J=8.0 Hz, 1H), 4.86-4.82 (m, 3H), 3.30 (s, 2H), 2.85 (bs, 2H), 1.57 (bs, 4H).

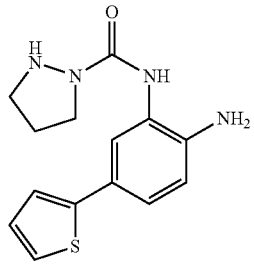
(185)

N-(2-amino-5-(thiophen-2-yl)phenyl)pyrazolidine-1-carboxamide (185) can be prepared by substituting tert-butyl 4-(aminomethyl)piperidine-1-carboxylate in Scheme 27 with tert-butyl pyrazolidine-1-carboxylate. ESI+ MS: m/z 289 ([M+H]⁺), 1H NMR (500 MHz, d⁶-DMSO): δ 8.40 (s, 1H), 7.70 (s, 1H), 7.33 (d, J=5.0 Hz, 1H), 7.19 (d, J=3.5 Hz, 1H), 7.13 (d, J=8.0 Hz, 1H), 7.03 (t, J=4.0 Hz, 1H), 6.77 (d, J=8.5 Hz, 1H), 5.08 (m, 1H), 4.88 (s, 2H), 3.38 (t, J=7.5 Hz, 2H), 2.86 (q, J=7.0 Hz, 2H), 1.97 (m, 2H).

(194)

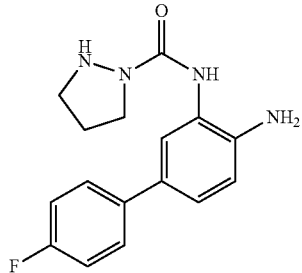

N-(4-amino-4'-fluoro-[1,1'-biphenyl]-3-yl)pyrazolidine-1-carboxamide (194) was prepared by substituting tert-butyl 4-(aminomethyl)piperidine-1-carboxylate in Scheme 27 with tert-butyl pyrazolidine-1-carboxylate and by substituting 2-nitro-5-(thiophen-2-yl)aniline with 4'-fluoro-4-nitro-[1,1'-biphenyl]-3-amine. ESI+ MS: m/z 301 ([M+H]⁺). ¹HNMR (500 MHz, d⁶-DMSO): δ 8.42 (s, 1H), 7.67 (s, 1H), 7.54-7.52 (m, 2H), 7.20 (t, J=9.0 Hz, 2H), 7.11 (d, J=6.5 Hz, 1H), 6.81 (d, J=8.5 Hz, 1H), 5.08 (t, J=8.5 Hz, 1H), 4.83 (s, 2H), 3.38 (t, J=7.0 Hz, 2H), 2.88-2.83 (m, 2H), 2.00-1.95 (m, 2H).

(193)

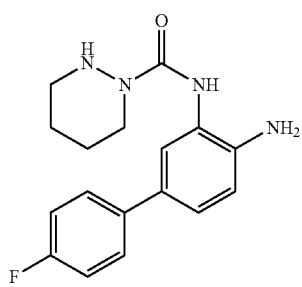

N-(2-amino-5-(thiophen-2-yl)phenyl)tetrahydropyridazine-1(2H)-carboxamide (193) can be prepared by substituting tert-butyl 4-(aminomethyl)piperidine-1-carboxylate in Scheme 27 with tert-butyl tetrahydropyridazine-1(2H)-carboxylate and by substituting 2-nitro-5-(thiophen-2-yl)aniline with 4'-fluoro-4-nitro-[1,1'-biphenyl]-3-amine. ESI+ MS: m/z 315 ([M+H]⁺), 1H NMR (500 MHz, d⁶-DMSO): δ 8.46 (s, 1H), 7.68 (s, 1H), 7.55-7.52 (m, 2H), 7.20 (t, J=9.0 Hz, 2H), 7.11 (d, J=8.5 Hz, 1H), 6.82 (d, J=8.0 Hz, 1H), 4.83 (bs, 2H), 3.49 (bs, 2H), 2.85 (bs, 2H), 1.58 (bs, 4H).

(235)

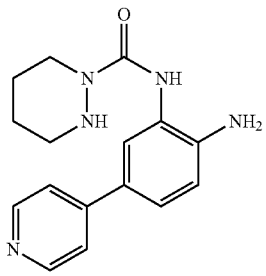

N-(2-amino-5-(pyridin-4-yl)phenyl)tetrahydropyridazine-1(2H)-carboxamide (235) can be prepared by substituting tert-butyl 4-(aminomethyl)piperidine-1-carboxylate in Scheme 27 with tert-butyl tetrahydropyridazine-1(2H)-carboxylate and by substituting 2-nitro-5-(thiophen-2-yl)aniline in Scheme 27 with 2-nitro-5-(pyridin-4-yl)aniline. ESI+ MS: m/z 298 ([M+H]⁺), 1H NMR (500 MHz, d⁶-DMSO): δ 8.50 (d, J=7.0 Hz, 2H), 8.45 (s, 1H), 7.82 (s, 1H), 7.53 (d, J=7.5 Hz, 2H), 7.33 (d, J=10.0 Hz, 1H), 6.84 (d, J=10.5 Hz, 1H), 5.08 (s, 2H), 4.83 (t, J=9.0 Hz, 1H), 3.51 (bs, 2H), 2.86 (bs, 2H), 1.58 (bs, 4H).

(92)

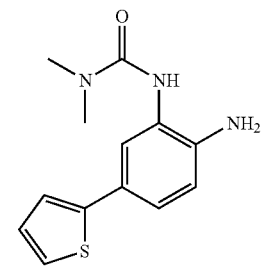

Synthesis of the 3-(2-amino-5-(thiophen-2-yl)phenyl)-1,1-dimethylurea (92)

Scheme 34

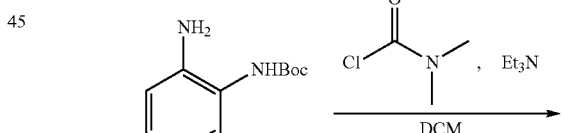

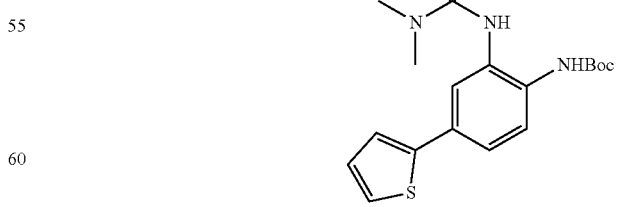

To a solution of tert-butyl 2-amino-4-(thiophen-2yl)phenylcarbamate (0.12 g, 0.41 mmol, 1.0 equiv.) in pyridine (2 mL) was added a solution of dimethylcarbamic chloride (0.07 g, 0.62 mmol, 1.5 equiv.) in toluene (0.3 mL). The resulting solution was stirred at room temperature overnight. The crude residue was diluted with water (10 mL) and extracted with ethyl acetate (10 mL×2). The combined organic layers were washed with water (10 mL), dried, filtered and concentrated. The crude residue was washed with petroleum ether (5 mL) to afford tert-butyl (2-(3,3-dimethylureido)-4-(thiophen-2-yl)phenyl)carbamate (0.12 g, 80% yield).

Scheme 35

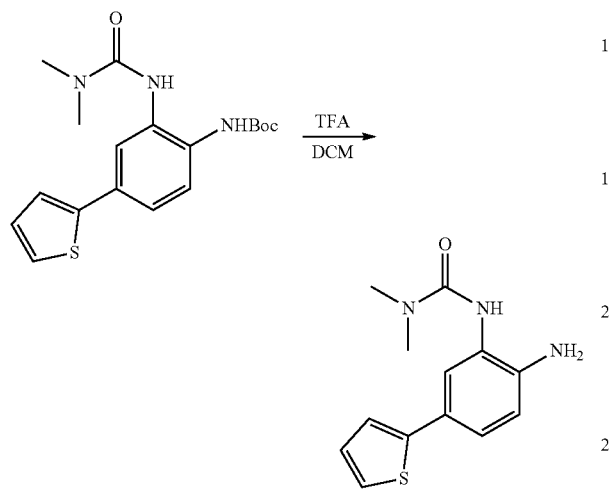

To a solution of tert-butyl (2-(3,3-dimethylureido)-4-(thiophen-2-yl)phenyl)carbamate (115 mg, 0.32 mmol) in dichloromethane (5 mL) was added TFA (2 mL) at 0° C. The reaction was warmed to room temperature and stirred for 1 h. The reaction was concentrated. The crude residue was diluted with ethyl acetate (30 mL) and washed with a saturated aqueous solution of sodium bicarbonate, then water (20 mL), dried over sodium sulfate, filtered and concentrated. The obtained residue was washed with hexane (2 mL) to afford 3-(2-amino-5-(thiophen-2-yl)phenyl)-1,1-dimethylurea (65 mg, 83% yield). ESI+ MS: m/z 262 ([M]$^+$). 1H NMR (500 MHz, d$^6$-DMSO): δ 7.68 (s, 1H), 7.34 (d, J=5.0, 1H), 7.29 (d, J=2.0, 1H), 7.19 (dd, J=4.5, 2.0, 2H), 7.04 (m, 1H), 6.73 (d, J=8.5, 1H), 5.00 (s, 2H), 2.93 (s, 6H).

One skilled in the art will recognize that other compounds described below can be prepared in a similar manner:

(107)

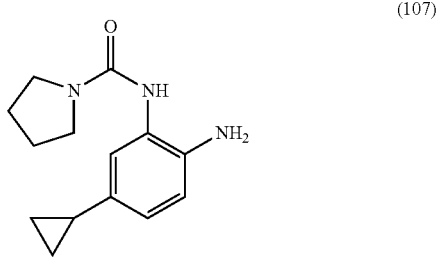 [SMILES: Nc1ccc(C2CC2)cc1NC(=O)N1CCCC1]

N-(2-amino-5-cyclopropylphenyl)pyrrolidine-1-carboxamide (107) was prepared by substituting dimethylcarbamic chloride in Scheme 34 with pyrrolidine-1-carbonyl chloride and by substituting tert-butyl (2-amino-4-(thiophen-2-yl)phenyl)carbamate in Scheme 34 with tert-butyl (2-amino-4-cyclopropylphenyl)carbamate. ESI+ MS: m/z 246 ([M+H]$^+$), 1H NMR (500 MHz, d$^6$-DMSO): δ 7.39 (s, 1H), 6.78 (s, 1H), 6.60 (s, 2H), 4.59 (s, 2H), 3.40-3.37 (m, 2H), 1.86-1.83 (m, 4H), 1.76-1.70 (m, 1H), 0.82-0.77 (m, 2H), 0.49-0.45 (m, 2H).

(120)

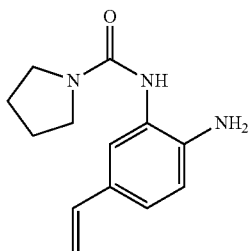

N-(2-amino-5-vinylphenyl)pyrrolidine-1-carboxamide (120) was prepared by substituting dimethylcarbamic chloride in Scheme 34 with pyrrolidine-1-carbonyl chloride and by substituting tert-butyl (2-amino-4-(thiophen-2-yl)phenyl)carbamate in Scheme 34 with tert-butyl (2-amino-4-vinylphenyl)carbamate. ESI+ MS: m/z 403 ([M+H]$^+$), 1H NMR (500 MHz, d$^6$-DMSO): δ 7.44 (s, 1H), 7.15 (s, 1H), 6.99 (d, J=9 Hz, 1H), 6.66 (d, J=8 Hz, 1H), 6.53 (dd, J=11.5 Hz, 6.5 Hz, 1H), 5.46 (d, J=18 hz, 1H), 4.98 (s, 2H), 4.94 (d, J=11 Hz, 1H), 3.40-3.35 (m, 4H0, 1.90-1.75 (m, 1H).

(121)

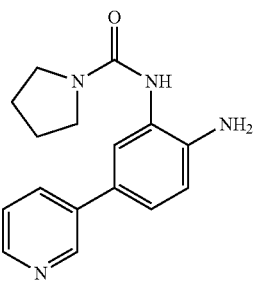

Synthesis of the N-(2-amino-5-(pyridin-3-yl)phenyl)pyrrolidine-1-carboxamide (121)

Scheme 36

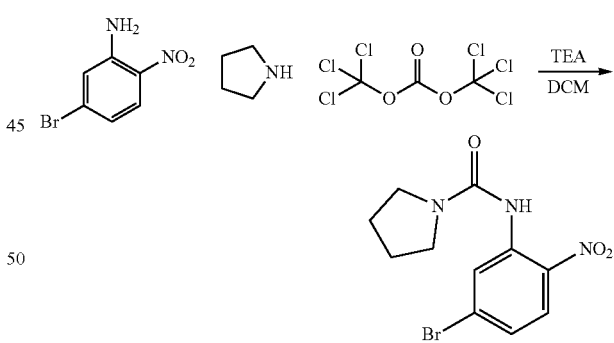

To a solution of 5-bromo-2-nitroaniline (1 g, 4.61 mmol) in dichloromethane (15 mL) were added TEA (8.35 mL, 59.9 mmol, 1.3 eq.) and triphosgene (1.37 g, 4.61 mmol, 1 equiv.) at 0° C. The mixture was stirred for three hours at room temperature and the pyrolidine (0.39 g, 5.53 mmol, 1.2 equiv.) was added slowly. The reaction was stirred for an additional two hours. The reaction crude was diluted with dichloromethane and washed with water and brine. The organic layers were dried over MgSO$_4$, filtered and evaporated. The residue was purified by column chromatography on eluting ethyl acetate and hexane to allow N-(2-amino-5-bromophenyl)pyrrolidine-1-carboxamide (0.45 g, 31% yield).

Scheme 37

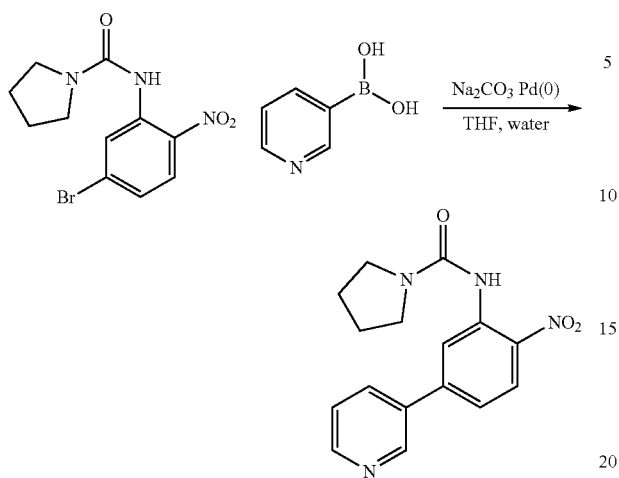

To a solution of N-(2-amino-5-bromophenyl)pyrrolidine-1-carboxamide (0.26 g, 0.72 mmol) in THF (10 mL) and water (5 mL) were added pyridin-3-ylboronic acid (0.13 g, 1.07 mmol, 1.5 equiv.), sodium bicarbonate (0.11 g, 1.07 mmol, 1.5 equiv.) and palladium(O) (0.08 g, 0.07 mmol, 0.1 equiv.). The reaction mass was stirred at 90° C. for sixteen hours. The reaction crude was filtered on a celite bed and diluted in ethyl acetate. The organic layers were washed with water and brine then dried over $Na_2SO_4$ and concentrated. The residue was purified by column chromatography on eluting ethyl acetate and hexane to allow N-(2-amino-5-(pyridin-3-yl)phenyl)pyrrolidine-1-carboxamide (0.14 g, 63% yield).

To a solution of N-(2-amino-5-(pyridin-3-yl)phenyl)pyrrolidine-1-carboxamide (0.07 g, 0.22 mmol) in methanol was added Pd/C (0.03 g, 0.24 mmol, 1.05 equiv.). The reaction mixture was degassed then stirred at room temperature under $H_2$ atmosphere for 1 h. The reaction was filtered through celite and concentrated. The crude solid was washed with ether, and dried under reduced pressure to obtain of pure N-(2-amino-5-(pyridin-3-yl)phenyl)pyrrolidine-1-carboxamide (0.04 g, 56% yield). ESI+ MS: m/z 283 ([M]+). 1H NMR (500 MHz, $d^6$-DMSO): δ 8.76 (d, J=1.5 Hz, 1H), 8.42 (d, J=3.5 Hz, 1H), 7.90 (d, J=7.5 Hz, 1H), 7.50 (s, 1H), 7.44 (d, J=2 Hz, 1H), 7.39 (dd, J=4.5 Hz, 3 Hz, 1H), 7.27 (dd, J=2 Hz, 6 Hz, 1H), 6.82 (d, J=8.5 Hz, 1H), 5.07 (s, 2H), 3.39 (m, 4H), 1.87 (m, 4H).

Scheme 38

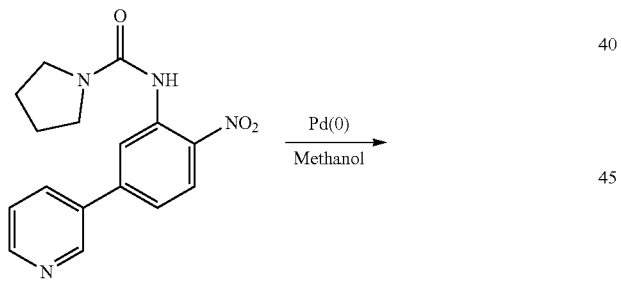

(168)

Synthesis of the N-(2-amino-5-(pyrazin-2-yl)phenyl)pyrrolidine-1-carboxamide (168)

Scheme 39

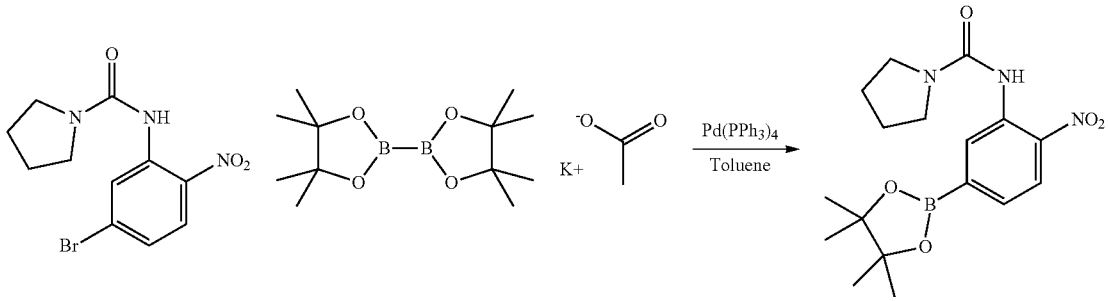

225

To a solution of N-(2-amino-5-bromophenyl)pyrrolidine-1-carboxamide (0.5 g, 1.59 mmol) in toluene (25 mL) were added 4,4,4',4',5,5,5',5'-octamethyl-2,2'-bi(1,3,2-dioxaborolane) (0.60 g, 2.39 mmol, 1.5 equiv.), potassium acetate (0.46 g, 4.78 mmol, 3.0 equiv.) and Pd(PPh$_3$)$_4$ (0.19 g, 0.16 mmol, 0.1 equiv.). The mixture was heated to 110° C. After vigorously stirring for four hours, the solution was diluted with water, filtered through celite and washed with ethyl acetate. The organic layers were dried over Mg2SO4 and concentrated. The residue was purified by flash column by eluting ethyl aceate and hexane to allow N-(2-nitro-5-(4,4,5,5-tetramethyl-1,3,2-dioxaborolan-2-yl)phenyl)pyrrolidine-1-carboxamide (0.64 g, 40% yield).

Scheme 40

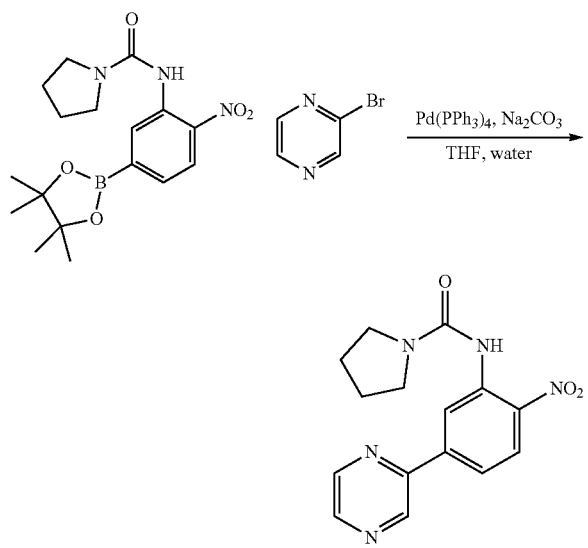

To a solution of N-(2-nitro-5-(4,4,5,5-tetramethyl-1,3,2-dioxaborolan-2-yl)phenyl)pyrrolidine-1-carboxamide (0.20 g, 0.55 mmol) was added at room temperature sodium bicarbonate (0.09 g, 0.80 mmol, 1.45 equiv.), 2-bromopyrazine (0.14 g, 0.89 mmol, 1.6 equiv.) and palladium (0.07 g, 0.06 mmol, 0.1 equiv). The reaction was refluexed for fourteen hours. The crude reaction was filtered and concentrated. The residue was diluted into water and washed with ethyl acetate, the concentrated. The obtained was purified through column chromatography by eluting ethyl acetate and hexane to allow N-(2-nitro-5-(pyrazin-2-yl)phenyl)pyrrolidine-1-carboxamide (0.12 g, 70% yield).

Scheme 41

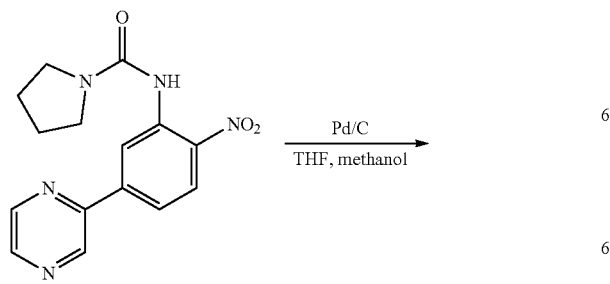

226

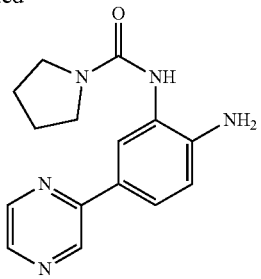

To a solution of 1 N-(2-nitro-5-(pyrazin-2-yl)phenyl)pyrrolidine-1-carboxamide (0.11 g, 0.35 mmol) in methanol (6 mL) and THF (6 mL) was added Pd/C (0.04 g, 0.94 mmol, 0.33 equiv.). The reaction mixture was degassed then stirred at room temperature under H$_2$ atmosphere for 1 h. The reaction was filtered through celite and concentrated. The crude solid was washed with ether, and dried under reduced pressure to obtain of pure N-(2-amino-5-(pyrazin-2-yl)phenyl)pyrrolidine-1-carboxamide (0.07 g, 70% yield). ESI+ MS: m/z 284 ([M+H]$^+$), 1H NMR (500 MHz, d$^6$-DMSO): δ 9.30 (s, 1H), 8.55 (s, 1H), 8.40-8.39 (m, 1H), 7.88 (s, 1H), 7.71-7.69 (m, 1H), 7.53 (s, 1H), 6.81 (d, J=8.5 Hz, 1H), 5.31 (s, 2H), 3.40-3.37 (m, 4H), 1.86 (m, 4H).

(1)

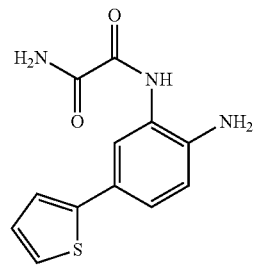

Synthesis of N1-(2-amino-5-(thiophen-2-yl)phenyl)oxalamide (1)

Scheme 42

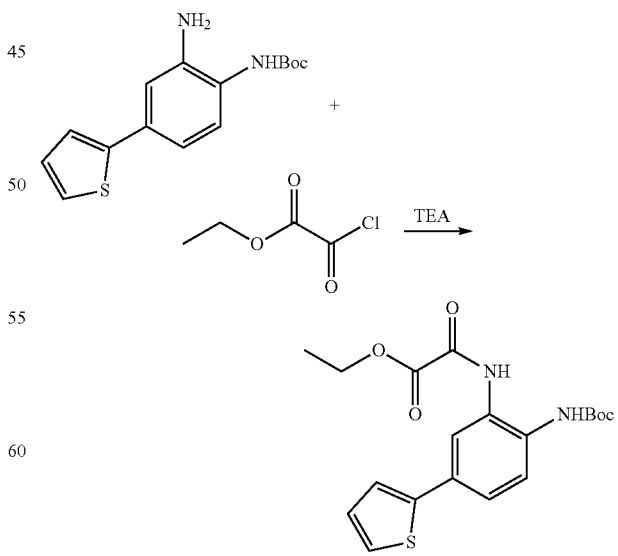

To a solution of tert-butyl (2-amino-4-(thiophen-2-yl)phenyl)carbamate (1.0 g, 3.44 mmol) in dichloromethane (10 mL) was added ethyl oxalyl chloride (0.6 mL, 5.17 mmol, 1.5 equiv.) and TEA (1.2 mL, 8.61 mmol, 2.5 equiv.) at 0° C. The reaction was warmed to room temperature and stirred for 4 h. The reaction was then diluted with dichloromethane and water. The combined organic layers were washed with water and brine, dried over Na$_2$SO$_4$ and then concentrated under reduced pressure. The crude material was purified by column chromatography (silica gel, EtOAc/hexanes) to afford ethyl 2-((2-((tert-butoxycarbonyl)amino)-5-(thiophen-2-yl)phenyl)amino)-2-oxoacetate (1.0 g, 74% yield).

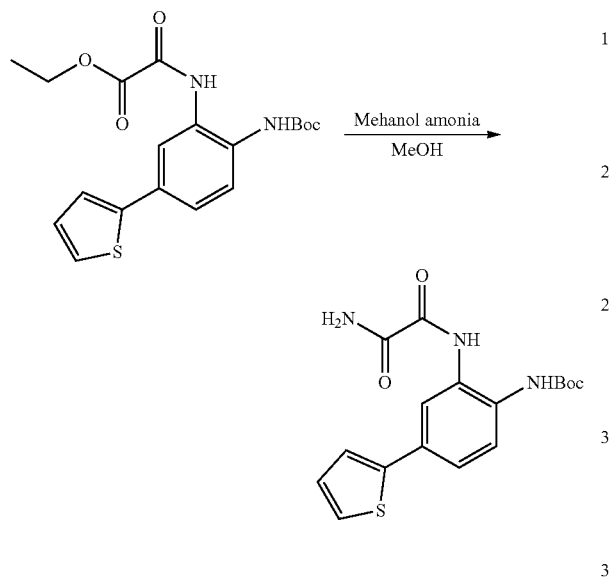

To a solution of ethyl 2-((2-((tert-butoxycarbonyl)amino)-5-(thiophen-2-yl)phenyl)amino)-2-oxoacetate (0.2 g, 0.512 mmol) in MeOH (2 mL) was added methanolic ammonia (5 mL, 0.512 mmol, 1 equiv.) in a sealed tube. The reaction was stirred at room temperature for five h. The obtained white solid was filtered and dried to afford tert-butyl (2-(2-amino-2-oxoacetamido)-4-(thiophen-2-yl)phenyl)carbamate (0.11 g, 59% yield).

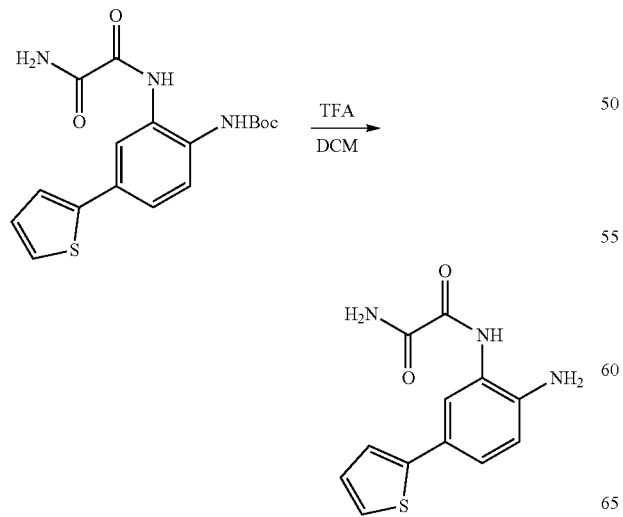

To a solution of tert-butyl (2-(2-amino-2-oxoacetamido)-4-(thiophen-2-yl)phenyl)carbamate (0.1 g, 0.28 mmol) in DCM (3 mL) was added TFA (1 mL, 13 mmol) at 0° C. The reaction was warmed to room temperature and stirred for 2 h. The reaction was then concentrated under reduced pressure. The residue was basified with a saturated aqueous solution of Na$_2$CO$_3$. The obtained solid was filtered, washed with water and ether then dried to afford N1-(2-amino-5-(thiophen-2-yl)phenyl)oxalamide (40 mg, 55% yield). ESI+ MS: m/z 262 ([M+H]$^+$), 1H NMR (500 MHz, d$^6$-DMSO): δ 9.89 (s, 1H), 8.24 (s, 1H), 7.94 (s, 1H), 7.59 (d, J=2.0 Hz, 1H), 7.6 (d, J=5 Hz, 1H), 7.29-7.26 (m, 1H), 7.23 (d, J=4.0 Hz, 1H), 7.05 (t, J=4.0 Hz, 1H), 6.80 (d, J=9.0 Hz, 1H), 5.16 (s, 2H).

One skilled in the art will recognize that other compounds described below were prepared in a similar manner to the procedures described above.

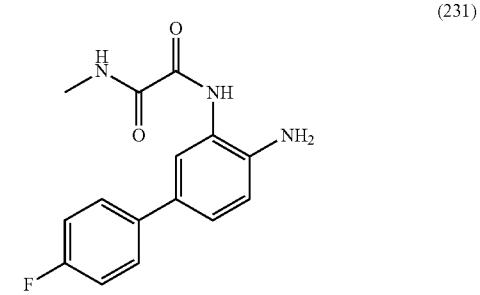 [SMILES: CNC(=O)C(=O)Nc1cc(-c2ccc(F)cc2)ccc1N]

(231)

N1-(4-amino-4'-fluoro-[1,1'-biphenyl]-3-yl)-N2-methyloxalamide (231) was prepared by substituting methanolic ammonia in Scheme 43 with methanamine (2N solution in THF) and by substituting tert-butyl (2-amino-4-(thiophen-2-yl)phenyl)carbamate in Scheme 42 with tert-butyl (3-amino-4'-fluoro-[1,1'-biphenyl]-4-yl)carbamate. In this case, boc deprotection was substituted by a nitro reduction using palladium/hydrogen as described earlier. ESI– MS: m/z 286 ([M–H]$^-$), 1H NMR (400 MHz, d6-DMSO): δ 9.95 (s, 1H), 8.84 (d, J=5.2 Hz, 1H), 7.56-7.53 (m, 3H), 7.29-7.18 (m, 3H), 6.84 (d, J=8.4 Hz, 1H), 5.09 (s, 2H), 2.75 (s, 3H).

(213)

Synthesis of N-(4-amino-4'-fluoro-[1,1'-biphenyl]-3-yl)-3-((dimethylamino)methyl)azetidine-1-carboxamide (213)

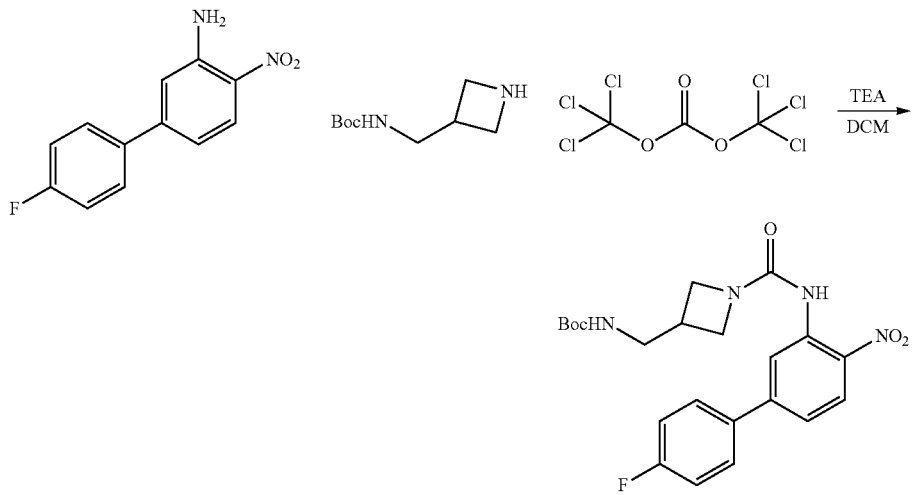

Scheme 45

To a solution of 4'-fluoro-4-nitro-[1,1'-biphenyl]-3-amine (1.5 g, 6.46 mmol) in DCM (50 mL) were added triphosgene (1.917 g, 6.46 mmol) and TEA (8.5 g, 84 mmol) at 0° C. The reaction mixture was stirred at room temperature for two hours. tert-butyl azetidin-3-ylmethylcarbamate (1.203 g, 6.46 mmol) was then added at 0° C. and the reaction mixture was stirred at room temperature for four hours. The reaction crude was diluted with saturated citric acid solution and extracted with DCM. The organic layer was washed with water, brine, dried over $Na_2SO_4$, filtered and concentrated to yield crude residue which was purified by column chromatography eluting with 30% EtOAc in Hexane to afford tert-butyl ((1-((4'-fluoro-4-nitro-[1,1'-biphenyl]-3-yl)carbamoyl)azetidin-3-yl)methyl)carbamate (2 g, 69.7% yield).

Scheme 46

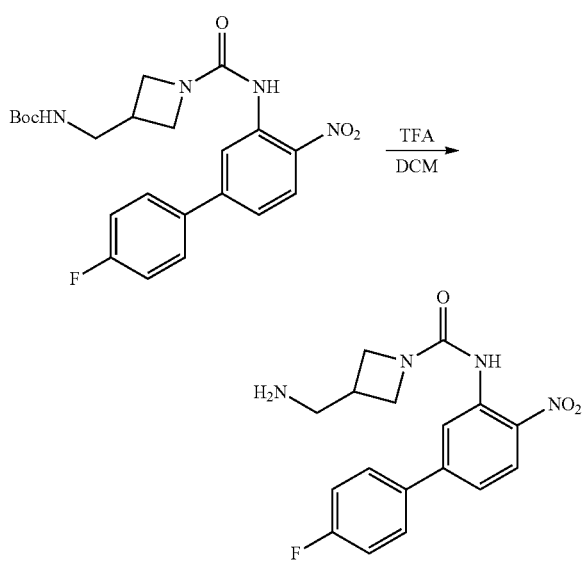

To a solution of tert-butyl (1-(4'-fluoro-4-nitrobiphenyl-3-ylcarbamoyl)azetidin-3-yl)methylcarbamate (2.0 g, 4.5 mmol) in DCM (60 mL) was added TFA (8 mL, 104 mmol) at 0° C. The reaction was warmed to room temperature and stirred for 2 h. The reaction was then concentrated under reduced pressure. The residue was basified with a saturated aqueous solution of $NaHCO_3$ and extracted with a 15% MeOH in DCM. The organic layer was dried over $Na_2SO_4$ and concentrated to afford 3-(aminomethyl)-N-(4'-fluoro-4-nitro-[1,1'-biphenyl]-3-yl)azetidine-1-carboxamide (1.6 g, 100% yield) as yellow syrup which is used in the next step as such without any further purification.

Scheme 47

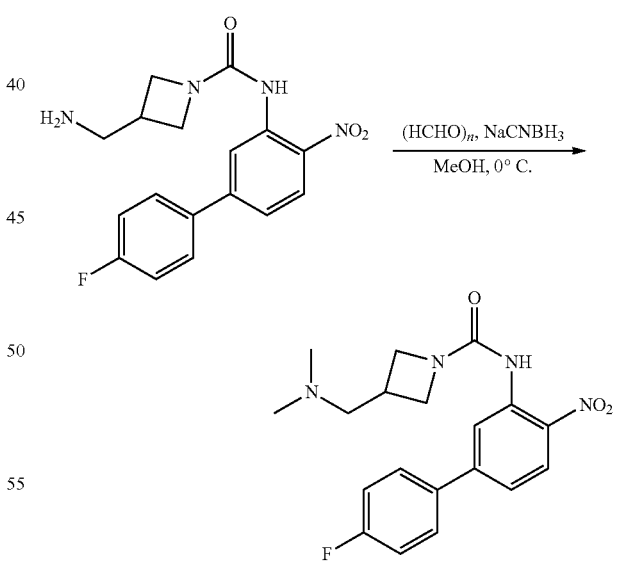

To a solution of 3-(aminomethyl)-N-(4'-fluoro-4-nitro-[1,1'-biphenyl]-3-yl)azetidine-1-carboxamide (2 g, 5.81 mmol) in MeOH (50 mL) were added formaldehyde (1.74 g, 58.1 mmol) and acetic acid (1.74 g, 29.0 mmol) at room temperature and stirred for 1 h. $NaCNBH_3$ (1.46 g, 23.23 mmol) was then added at 0° C. The reaction mixture was stirred at room temperature for two hours. The reaction was quenched with saturated $NaHCO_3$ and extracted with EtOAc. The organic layer was washed with water, brine and dried over Na$_2$SO$_4$. The organic layer was concentrated under vacuum to afford crude residue which was purified by column chromatography eluting with 2% MeOH in DCM to yield 3-((dimethylamino)methyl)-N-(4'-fluoro-4-nitro-[1,1'-biphenyl]-3-yl)azetidine-1-carboxamide (1.69 g, 78% yield).

Scheme 48

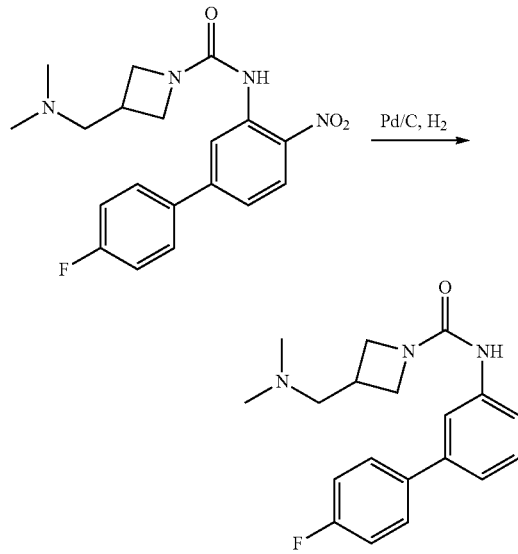

To a solution of 3-((dimethylamino)methyl)-N-(4'-fluoro-4-nitro-[1,1'-biphenyl]-3-yl)azetidine-1-carboxamide (1.7 g, 4.57 mmol, 1.0 eq.) in methanol (100 mL) and was added 10% Pd/C (1.0 g, 0.94 mmol). The reaction mixture was stirred 2 h under a hydrogen atmosphere. The reaction was then filtered and the filtrate was concentrated under reduced pressure to give N-(4-amino-4'-fluoro-[1,1'-biphenyl]-3-yl)-3-((dimethylamino)methyl)azetidine-1-carboxamide (35 mg, 3% yield) as an off-white solid. ESI+ MS: m/z 343 ([M+H]$^+$), $^1$HNMR (500 MHz, DMSO-d$_6$): δ 7.61 (s, 1H), 7.53-7.51 (m, 2H), 7.36 (d, J=2.0 Hz, 1H), 7.21-7.15 (m, 3H), 6.76 (d, J=8.5 Hz, 1H), 4.98 (s, 2H), 3.99 (t, J=8.0 Hz, 2H), 3.58 (dd, J$_{1,2}$=6.0 Hz, J$_{1,3}$=8.0 Hz, 2H), 2.72-2.69 (m, 1H), 2.45-2.44 (m, 2H), 2.13 (s, 6H).

Example 3: Inhibition of Histone Deacetylase Enzymatic Activity

The following trypsin-coupled protocol and Caliper protocol described herein was used to assay the compounds of the invention.
Trypsin Coupled Assay:
HDAC1-KineticIC50-3 Hr PreIncubation
Working Stocks
   1× HDAC Assay Buffer:
      50 mM HEPES (GIBCO 15630-114), 100 mM KCl, 0.001% Tween-20 (Zymed 00-3005), 0.05% BSA (Invitrogen, P2489), pH 7.4
   1.5× HDAC+1.5× Trypsin: 225 nM Trypsin(Worthinton)+0.18 µg/ml HDAC1 (BPS Inc) in assay buffer
   300× Trypsin stock is made up in HDAC Assay Buffer, aliquoted and stored at −80° C.
   3× Substrate: 18 µM Substrate in assay buffer
   BPS Enzyme and Substrate amounts (per well)

| HDAC | class | Enz amount | [Substrate] (µM) | Substrate |
|---|---|---|---|---|
| HDAC1 | Ia | 3.5 ng* | 6* | 1600* |

Protocol (Costar 3573 384-Well Plate—Black/Black Bottom)
Assay is performed at room temp. reagents are stored on ice
1) Add 20 µl of enzyme+trypsin in assay buffer (Combi)
2) Pin transfer compounds (100 nl pins)
3) incubate 3 hours at room temp
4) Add 10 ul of 3× substrate in assay buffer (Combi)
5) centrifuge: 1 min at 1000 rpm
6) Kinetic assay: read plates on Envision with excitation=355 nm; emission=460 nm for 7 times with interval of 10 min
7) use slope from 20 min~60 min (linear range) for data analysis
HDAC2-KineticIC50-3 Hr PreIncubation
Working Stocks
   1× HDAC Assay Buffer:
      50 mM HEPES (GIBCO 15630-114), 100 mM KCl, 0.001% Tween-20 (Zymed 00-3005), 0.05% BSA (Invitrogen, P2489), pH 7.4
   1.5× HDAC+1.5× Trypsin: 225 nM Trypsin(Worthinton)+0.2 µg/ml HDAC2 (BPS Inc) in assay buffer
   300× Trypsin stock is made up in HDAC Assay Buffer, aliquoted and stored at −80° C.
   3× Substrate: 13.8 µM Substrate in assay buffer
   BPS Enzyme and Substrate amounts (per well)

| HDAC | class | Enz amount | [Substrate] (µM) | Substrate |
|---|---|---|---|---|
| HDAC2 | Ia | 4 ng* | 4.5* | 1600* |

Protocol (Costar 3573 384-Well Plate—Black/Black Bottom)
Assay is performed at room temp. reagents are stored on ice
1) Add 20 µl of enzyme+trypsin in assay buffer (Combi)
2) Pin transfer compounds (100 nl pins)
3) incubate 3 hours at room temp
4) Add 10 µl of 3× substrate in assay buffer (Combi)
5) centrifuge: 1 min at 1000 rpm
6) Kinetic assay: read plates on Envision with excitation=355 nm; emission=460 nm for 7 times with interval of 10 min
7) use slope from 20 min-60 min (linear range) for data analysis
Protocol: HDAC3-KineticIC50-3 Hr PreIncubation
Working Stocks
   1× HDAC Assay Buffer:
      50 mM HEPES (GIBCO 15630-114), 100 mM KCl, 0.001% Tween-20 (Zymed 00-3005), −0.05% BSA (Invitrogen, P2489), pH 7.4
   1.5× HDAC: 0.1 µg/ml HDAC3 (BPS Inc) in assay buffer
   3× Substrate+3× Trpsin: 28.5 µM Substrate+450 nMTrpsin in assay buffer
   300× Trypsin stock is made up in HDAC Assay Buffer, aliquoted and stored at −80° C.
   BPS Enzyme and Substrate amounts (per well)

| HDAC | class | Enz amount | [Substrate] (µM) | Substrate |
|---|---|---|---|---|
| HDAC3 | Ia | 2 ng* | 9.5* | 1600* |

Protocol (Costar 3573 384-Well Plate—Black/Black Bottom)

Assay is performed at room temp. reagents are stored on ice
1) Add 20 µl of enzyme+trypsin in assay buffer (Combi)
2) Pin transfer compounds (100 nl pins)
3) incubate 3 hours at room temp
4) Add 10 µl of 3× substrate in assay buffer (Combi)
5) centrifuge: 1 min at 1000 rpm
6) Kinetic assay: read plates on Envision with excitation=355 nm; emission=460 nm for 7 times with interval of 10 min
7) use slope from 20 min~60 min (linear range) for data analysis The compounds of the invention were assayed for histone deacetylase inhibitory activity. The data is presented in the tables below. The data is presented whereby the letter "A" means the compound has an $IC_{50}$ between 0.0000001 µM≤0.1 µM, the letter "B" means the compound has an $IC_{50}$ between 0.11 µM≤1 µM, the letter "C" means the compound has an $IC_{50}$ between 1.1 µM≤5 µM, the letter "D" means the compound has an $IC_{50}$ between 5.1 µM≤30 µM, the letter "E" means the compound has an $IC_{50}$>30 µM. It will be recognized by one skilled in the art that the compounds can be assessed against other histone deacetylase enzymes and that the presentation of data is illustrative and in no way intended to limit the scope of the present invention. The compounds of the invention can be assayed against a range of histone deacetylase enzymes depending upon the performance activity desired to be gathered. Furthermore, the letters "A", "B", "C", "D" and "E" are also illustrative and in no way is intended to limit the scope of the present invention. For example, the symbol "E" is not meant to indicate that a compound necessarily lacks activity or utility but rather that its $IC_{50}$ value against the indicated histone deacetylase enzyme is greater than 30 µM.

TABLE 2

| Cmpd No | HDAC1 Kinetic IC50 (uM) | HDA2 Kinetic IC50 (uM) | HDAC3 Kinetic IC50 (uM) | HDAC1 Caliper IC50 (uM) | HDAC2 Caliper IC50 (uM) | HDAC3 Caliper IC50 (uM) |
|---|---|---|---|---|---|---|
| 3 | B | B | C | B | B | B |
| 2 | C | B | C | | | |
| 24 | C | B | E | | | |
| 23 | D | D | D | | | |
| 6 | D | C | E | | | |
| 21 | D | C | C | | | |
| 1 | C | B | C | C | C | C |
| 120 | C | B | C | | | |
| 4 | A | A | C | A | B | B |
| 81 | C | B | D | | | |
| 30 | A | A | B | A | A | B |
| 27 | C | C | D | | | |
| 12 | B | B | C | A | A | B |
| 11 | C | B | D | | | |
| 22 | B | B | D | B | B | C |
| 16 | A | A | B | A | A | B |
| 13 | A | A | C | A | A | B |
| 5 | C | C | D | | | |
| 45 | A | A | C | A | A | C |
| 17 | A | A | C | A | A | C |
| 83 | D | D | E | | | |
| 76 | B | B | C | | | |
| 36 | E | E | E | | | |
| 35 | A | A | C | A | A | C |
| 19 | B | B | E | | | |
| 46 | B | B | D | | | |
| 34 | C | B | D | | | |
| 78 | D | D | E | | | |
| 20 | B | C | D | | | |
| 47 | C | B | D | | | |

TABLE 2-continued

| Cmpd No | HDAC1 Kinetic IC50 (uM) | HDA2 Kinetic IC50 (uM) | HDAC3 Kinetic IC50 (uM) | HDAC1 Caliper IC50 (uM) | HDAC2 Caliper IC50 (uM) | HDAC3 Caliper IC50 (uM) |
|---|---|---|---|---|---|---|
| 49 | A | A | D | A | B | C |
| 32 | A | A | B | A | A | B |
| 40 | A | A | C | A | B | C |
| 59 | C | C | D | | | |
| 48 | B | B | C | | | |
| 8 | C | D | E | | | |
| 73 | C | B | D | B | B | C |
| 42 | B | B | D | | | |
| 10 | D | D | E | | | |
| 43 | E | D | E | | | |
| 9 | C | C | D | | | |
| 31 | B | B | E | | | |
| 26 | C | C | E | | | |
| 61 | C | B | D | | | |
| 89 | B | B | D | B | B | C |
| 68 | A | A | C | A | A | C |
| 37 | D | D | E | | | |
| 85 | B | B | C | | | |
| 59 | D | C | E | | | |
| 82 | D | D | E | | | |
| 62 | E | D | E | | | |
| 69 | B | B | D | | | |
| 79 | C | B | C | | | |
| 80 | D | D | E | | | |
| 41 | D | D | E | | | |
| 33 | B | A | D | | | |
| 66 | B | B | D | | | |
| 15 | B | A | C | B | B | B |
| 91 | B | A | C | A | A | B |
| 64 | C | B | D | | | |
| 38 | C | C | C | | | |
| 75 | D | C | E | | | |
| 57 | A | A | C | A | B | C |
| 44 | B | B | D | | | |
| 55 | C | B | E | | | |
| 58 | D | C | D | | | |
| 65 | B | A | D | | | |
| 51 | C | C | D | | | |
| 53 | B | B | E | B | B | C |
| 39 | A | A | D | A | A | C |
| 72 | C | B | D | B | B | C |
| 54 | A | A | C | A | A | B |
| 18 | A | A | C | A | A | B |
| 86 | B | A | C | | | |
| 74 | D | D | E | | | |
| 87 | A | A | C | | | |
| 88 | B | A | C | | | |
| 90 | C | B | E | | | |
| 25 | A | A | C | A | A | B |
| 67 | B | A | C | A | A | C |
| 52 | C | B | D | | | |
| 60 | B | B | C | B | B | C |
| 77 | D | C | D | | | |
| 63 | B | B | C | B | B | B |
| 70 | C | B | D | B | B | D |
| 56 | A | A | C | A | B | C |
| 96 | A | B | C | | | |
| 97 | D | C | C | | | |
| 106 | A | A | C | A | A | B |
| 124 | A | A | D | A | A | C |
| 128 | A | A | D | A | B | C |
| 129 | A | A | C | A | A | C |
| 130 | B | B | D | | | |
| 98 | A | A | C | A | B | C |
| 133 | A | A | C | A | B | C |
| 114 | A | A | D | | | |
| 109 | B | B | E | | | |
| 92 | A | A | C | | | |
| 107 | D | D | C | D | D | C |
| 113 | A | A | D | A | A | D |
| 115 | A | A | D | | | |
| 116 | B | B | D | | | |
| 131 | C | C | E | | | |
| 100 | B | B | C | | | |
| 126 | A | A | D | A | B | D |

TABLE 2-continued

| Cmpd No | HDAC1 Kinetic IC50 (uM) | HDA2 Kinetic IC50 (uM) | HDAC3 Kinetic IC50 (uM) | HDAC1 Caliper IC50 (uM) | HDAC2 Caliper IC50 (uM) | HDAC3 Caliper IC50 (uM) |
|---|---|---|---|---|---|---|
| 104 | D | D | D | | | |
| 95 | B | B | D | | | |
| 137 | A | A | C | | | |
| 117 | A | A | C | | | |
| 94 | A | B | D | | | |
| 122 | A | A | D | | | |
| 123 | A | A | C | | | |
| 139 | A | A | C | A | B | C |
| 105 | C | B | D | | | |
| 141 | A | A | D | | | |
| 110 | A | A | D | | | |
| 111 | A | A | D | | | |
| 134 | A | A | D | A | B | C |
| 140 | C | B | D | | | |
| 138 | B | C | E | | | |
| 127 | D | D | E | | | |
| 136 | C | C | E | | | |
| 135 | B | C | E | | | |
| 108 | C | B | D | | | |
| 132 | C | C | E | | | |
| 112 | C | B | E | | | |
| 119 | A | A | D | | | |
| 142 | B | B | C | | | |
| 145 | B | B | C | B | B | C |
| 125 | A | A | D | | | |
| 93 | C | B | D | | | |
| 146 | B | B | D | | | |
| 147 | A | B | C | | | |
| 143 | B | A | D | | | |
| 144 | A | A | C | A | B | C |
| 118 | A | A | C | A | A | C |
| 121 | B | A | B | A | B | B |
| 177 | A | A | C | | | |
| 14 | | | | A | B | C |
| 50 | D | C | E | | | |
| 103 | | | | A | A | D |
| 152 | D | C | E | | | |
| 153 | D | C | D | | | |
| 154 | C | B | C | | | |
| 155 | C | B | E | | | |
| 156 | A | A | C | | | |
| 157 | B | B | D | | | |
| 158 | A | A | D | | | |
| 159 | B | B | D | | | |
| 160 | A | A | C | | | |
| 161 | D | C | E | | | |
| 162 | C | B | D | | | |
| 163 | | | | B | B | C |
| 164 | | | | A | A | C |
| 165 | E | E | E | | | |
| 166 | B | A | C | | | |
| 167 | B | A | B | | | |
| 168 | B | B | D | | | |
| 169 | B | B | C | | | |
| 170 | B | A | B | | | |
| 171 | A | B | C | | | |
| 172 | A | A | B | | | |
| 173 | E | D | E | | | |
| 174 | | | | A | A | B |
| 175 | C | C | D | | | |
| 176 | E | D | E | | | |
| 177 | | | | A | B | C |
| 178 | | | | A | B | D |
| 181 | C | C | D | | | |
| 182 | | | | A | A | C |
| 185 | A | A | B | | | |
| 186 | A | A | D | A | B | C |
| 187 | A | A | D | B | B | E |
| 191 | | | | B | B | C |
| 193 | | | | A | A | B |
| 194 | | | | A | A | B |
| 200 | C | B | D | | | |
| 195 | C | C | E | | | |
| 196 | E | D | E | | | |
| 197 | D | D | E | | | |
| 198 | C | C | D | | | |
| 199 | B | B | E | | | |
| 201 | E | E | E | | | |
| 202 | | | | A | B | C |
| 203 | | | | A | B | C |
| 204 | | | | B | B | C |
| 205 | | | | B | B | D |
| 206 | | | | D | D | C |
| 207 | | | | D | D | B |
| 208 | | | | A | B | C |
| 209 | | | | A | B | c |
| 210 | | | | A | A | C |
| 211 | | | | A | B | E |
| 212 | | | | A | A | B |
| 213 | | | | B | C | D |
| 214 | | | | A | A | D |
| 215 | | | | A | A | C |
| 216 | | | | A | A | D |
| 217 | | | | A | A | C |
| 218 | | | | A | B | A |
| 219 | | | | B | B | B |
| 220 | | | | E | D | C |
| 221 | | | | E | D | C |
| 222 | | | | D | D | B |
| 223 | | | | C | C | B |
| 224 | | | | A | B | A |
| 225 | | | | C | D | E |
| 226 | | | | A | A | D |
| 227 | | | | A | A | A |
| 228 | | | | D | E | C |
| 229 | | | | C | D | B |
| 230 | | | | A | B | A |
| 231 | | | | C | D | D |
| 232 | | | | A | A | D |
| 233 | | | | A | A | D |
| 234 | | | | B | C | A |
| 235 | | | | B | B | D |
| 236 | | | | A | B | C |
| 237 | | | | D | E | C |
| 238 | | | | A | B | E |
| 239 | | | | C | C | D |
| 240 | | | | E | D | D |
| 241 | | | | A | B | C |
| 242 | | | | A | A | C |
| 243 | | | | D | D | B |
| 244 | | | | B | B | B |
| 245 | | | | A | A | C |
| 246 | | | | B | B | B |

Example 4

Methods:

Learning tests: All behavioral testing is described in Fischer et al., Neuron 48, 825-838 (2005).

Fear Conditioning Tests:

Context-dependent fear conditioning. Training consists of a 3 min exposure of mice to the conditioning box (context) followed by a foot shock (2 sec, 0.5/0.8/1.0 mA, constant current). The memory test is performed 24 hr later by re-exposing the mice for 3 min into the conditioning context. Freezing, defined as a lack of movement except for heart beat and respiration associated with a crouching posture, is recorded every 10 sec by two trained observers (one is unaware of the experimental conditions) during 3 min (a total of 18 sampling intervals). The number of observations indicating freezing obtained as a mean from both observers is expressed as a percentage of the total number of observations. For short term memory test, the memory test is performed 3 hrs after the foot shock training.

Tone-dependent fear conditioning. Training consists of a 3 min exposure of mice to the conditioning box (context), followed by a tone [30 sec, 20 kHz, 75 dB sound pressure level (SPL)] and a foot shock (2 sec, 0.8 tnA, constant current). The memory test is performed 24 hr later by exposing the mice for 3 min to a novel context followed by an additional 3 min exposure to a tone (10 kHz, 75 dB SPL). Freezing is recorded every 10 sec by two nonbiased observers as described above.

Morris water maze test. The water maze paradigm is performed in a circular tank (diameter 1.8 m) filled with opaque water. A platform (11×11 cm) is submerged below the water's surface in the center of the target quadrant. The swimming path of the mice is recorded by a video camera and analyzed by the Videomot 2 software (TSE). For each training session, the mice are placed into the maze consecutively from four random points of the tank. Mice are allowed to search for the platform for 60 s. If the mice do not find the platform within 60 s, they are gently guided to it. Mice are allowed to remain on the platform for 15 s. Two training trials are given every day; the latency for each trial is recorded for analysis. During the memory test (probe test), the platform is removed from the tank, and the mice are allowed to swim in the maze for 60 s.

Spatial working memory on elevated T-maze. Mice are maintained on a restricted feeding schedule at 85% of their free-feeding weight. Spatial working memory is first assessed on an elevated plastic T-maze. This consists of a start arm (47×10 cm) and two identical goal arms (35×10 cm), surrounded by a 10 cm high wall. A plastic food well is located 3 cm from the end of each goal arm. The maze is located 1 m above the floor in a well lit laboratory that contained various prominent distal extramaze cues. The mice are habituated to the maze, and to drinking sweetened, condensed milk, over several days before spatial non-matching-to-place testing.

Each trial consists of a sample run and a choice run. On the sample run, the mice are forced either left or right by the presence of a plastic block, according to a pseudorandom sequence (with equal numbers of left and right turns per session, and with no more than two consecutive turns in the same direction). A reward consisting of 0.07 ml of sweetened, condensed milk (diluted 50/50 with water) is available in the food well at the end of the arm. The block is then removed, and the mouse is placed, facing the experimenter, at the end of the start arm and allowed a free choice of either arm. The time interval between the sample run and the choice run is approximately 15 s. The animal is rewarded for choosing the previously unvisited arm (that is, for alternating). Mice are run one trial at a time with an inter-trial interval (ITI) of approximately 10 min. Each daily session consists of 4 trials, and mice receive 24 trials in total.

Cannulation and injection: Microcannula are inserted into the lateral brain ventricles as described by Fischer et al., J. Neurosci 22, 3700-7 (2002).

Immunoblotting and staining: Lysates for immunoblotting are prepared as described by Fischer et al. Neuron 48, 825-838 (2005). To isolate histones, brain tissue is homogenized in TX-buffer (50 mM Tris HCl, 150 mM NaCl, 2 mM EDTA, 1% Triton-100) and incubated at 4° C. for 15 min prior to centrifugation at 200 rpm for 10 min. After a wash-step in TX-buffer the pellet is dissolved in TX-buffer containing 0.2M HCl and incubated on ice for 30 min, before a second centrifugation at 10000 rpm for 10 min. The supernatant is either dialysed or directly used for immunoblotting. Antibodies are used in 1:1000 concentrations. All antibodies detecting histones and anti-PSD-95 are from e.g., Upstate (Lake Placid, N.Y.). Anti-synaptophysin (SVP38) is from e.g., Sigma. Anti-neuronal nuclei (neuN) and anti-growth associated protein (Gap43) are from e.g., Chemicon (Temecula, Calif.) and anti-N-cadherin, anti-beta-catenin are from e.g., Santa Cruz (Santa Cruz, Calif.). Immunostaining is performed as described by Fischer et al., Neuron 48, 825-838 (2005). Antibodies mentioned above are used in a 1:500 dilution. Anti-MAP-2 antibody (e.g., Sigma) is used in a 1:200 dilution.

Statistical analysis: The data are analyzed by unpaired student's t test and one-way ANOVA (ANalyis Of VAriance). One-way ANOVA followed by post-hoc Scheffe's test is employed to compare means from several groups.

Example 5

Compounds of the invention are tested for their ability to reinstatement learning behavior through inhibition of HDAC. Brain atrophy occurs during normal aging and is an early feature of neurodegenerative diseases associated with impaired learning and memory. Only recently have mouse models with extensive neurodegeneration in the forebrain been reported. One of these models is the bi-transgenic CK-p25 Tg mice where expression of p25, a protein implicated in various neurodegenerative diseases (Cruz, J., et al., Curr. Opin. Neurobiol. 14, 390-394 (2004)), is under the control of the CamKII promoter and can be switched on or off with a doxycycline diet (Fisher, A. et al., Neuron 48, 471-83 (2003); Cruz, J. et al., Neuron 40, 471-83 (2003)). Post-natal induction of p25 expression for 6 weeks causes learning impairment that is accompanied by severe synaptic and neuronal loss in the forebrain.

Specifically, compounds of the invention are tested for their ability to reinstate learning behavior and to recover access to long-term memories in CK-p25 Tg mice that had developed synaptic and neuronal loss. p25 is induced in 11 month old CK-p25 Tg mice for 6 weeks. Afterwards p25 expression is repressed and one group of CK-p25 Tg mice are subjected to daily or intermittent (e.g every other day) injection of a compound of the invention for a period of time (e.g. 1-4 weeks), whereas the other group receives saline injection. Subsequently all mice, including a control group that do not express p25, are subjected to fear conditioning and water maze learning. To this end, p25 expression is induced in 11-month old CK-p25 mice for 6 weeks, before one group is injected daily or intermittently (e.g every other day) for a period of time (e.g. 1-4 weeks) with a compound of the invention whereas the control group receives saline. The freezing behavior and spatial learning of vehicle vs. compound treated groups are compared and levels of synaptic marker proteins are measured. Freezing is defined as a lack of movement except for heart beat and respiration associated with a crouching position. Brain atrophy and hippocampal neuronal loss are also evaluated.

The effect of HDAC inhibition using a compound of the invention on the recovery of inaccessible long-term memories is evaluated. Eleven month old CK-p25 Tg mice are trained in the fear conditioning paradigm and returned to their home cages for 4 weeks. Subsequently p25 is induced for 6 weeks before the mice are injected with either saline (vehicle) or a compound of the invention for a period of time. Afterwards all mice, including a vehicle injected control groups that did not express p25 and a group of compound-injected control mice that were not trained, are subjected the memory test. The freezing behavior and spatial learning of vehicle vs. compound treated groups are compared and levels of synaptic marker proteins are measured.

Brain atrophy and hippocampal neuronal loss are also evaluated. A significant reduction in freezing behavior during the memory test (P<0.0001) test, suggests the loss of consolidated long-term memories.

Example 6

Compounds of the invention are tested to determine their effect on plasticity factors in CK-p25 Tg mice that developed severe neurodegeneration. p25 is induced in 11 month old CK-p25 Tg mice for 6 weeks. Afterwards p25 expression is repressed and one group of CK-p25 Tg mice is subjected to daily or intermittent (e.g every other day) compound injections for a period of time (e.g 1-4 weeks), whereas the other group receives saline injection. Hippocampal neuronal loss is evaluated for compound and vehicle treated mice for example, by comparing images showing hippocampal NeuN and MAP-2 staining and using immunoblots from the hippocampus and cortex of all groups.

Example 7

Compounds of the invention are tested to determine their effect on learning, basal anxiety, explorative behavior and brain plasticity. C57BL/6J mice are subjected to fear conditioning and are injected intraperitoneally [ip] with a compound of the invention or saline immediately afterwards. Freezing behavior is evaluated during a memory test performed 24 h later.

C57BL/6J mice are implanted with microcannulae into the lateral brain ventricles (icv) and are injected with either a compound of the invention or vehicle immediately after fear conditioning. Freezing behavior is evaluated during a memory test performed 24 h later.

C57BL/6J mice are injected [ip] daily or intermittmently with a compound of the invention or saline for a period of time (e.g 1-4 weeks) before all mice are subjected to the elevated plus maze and open field test. MAP-2 immunoreactivity (IR) in the hippocampus is evaluated and compound treated and vehicle treated mice compared. Markers for brain plasticity are measured.

Example 8

Compound of the invention are tested to determine their ability to recover spatial memories. CK-p25 Tg mice in which p25 expression is repressed and control mice are trained in the water maze paradigm until all mice reliably find the hidden platform. Afterwards all mice are returned to their home cages for 4 weeks to allow the consolidation of hippocampus independent long-term memories. Afterwards p25 expression is induced for 6 weeks, followed by p25 repression. One group of CK-p25 Tg mice are injected daily or intermittently (e.g every other day) with a compound of the invention, whereas the other group is injected with vehicle. Pilot studies have shown that a probe test, commonly used to analyze memory retrieval in the water maze paradigm, is not a reliable read out to analyze long-term memory retrieval. In fact, without extensive re-training even wild type mice show no significant preference for the target quadrant when tested 10 weeks after the training in a probe test. To measure the retrieval of long-term memory mice are instead exposed to only 2 reminder-training sessions on a single day. The mean escape latency during the reminder-training sessions is compared to control mice that did not receive the initial training. Escape latency is evaluated for compound treated and control mice.

Example 9

Compounds of the invention are tested to determine the specific acetylation mark elicited by the compound which is relevant to the treatment of Rubinstein Taybi. Sagittal brain sections of Rubinstein Taybi CBP+/− mice are immunostained to detect levels of AcH2B in hippocampal neurons. Western blot analysis of hippocampal protein extracts from CBP+/− and WT mice using antibodies against 13-actin, H2B (nonacetylated), AcH2A, AcH3 and AcH4 is used to reveal AcH2B level. Quantification of Western blot analysis shows the differences in the level of p-actin, total H2B, AcH2A, and AcH3.

Example 10

Compounds of the invention were evaluated in primary neuronal culture for determining HDAC inhibitor effects in cells. E17 embryonic mouse forebrain was dissociated into a single cell suspension by gentle trituration following trypsin/DNAse digestion. Cells were plated at a density of 12,500 cells per well in poly-D-lysine/laminin-coated black/clear bottom 96-well plates (BD Biosciences #BD356692) in Neurobasal medium containing 2% B27, and 1% pen/strep. Cultures were treated with HDAC inhibitors for 24 h starting on the third day after plating at varying inhibitor concentrations.

Compounds of the invention were evaluated to determine the functional measures of compounds' cellular HDAC activity (Immunoflourescent analysis). Imaging of neurons was performed using automated microscopy. After 24 h of HDAC inhibitor treatment, formaldehyde dissolved in phosphate-buffered saline (PBS) was added directly to the wells for a final concentration of 4%. Cells were fixed for 10 minutes at room temperature. Following two washes with phosphate-buffered saline, cells were permeabilized and blocked with blocking buffer composed of 0.1% Triton X-100, 2% BSA in PBS. For immunofluorescence imaging of histone modifications, cells were stained with anti-acetyl-H3K9 (Millipore, cat #07-352) or anti-Ac-H4K12 (Millipore, cat #04-119) antibodies, and Alexa488-conjugated secondary antibody (Molecular Probes). Cellular nuclei were identified by staining with Hoechst 33342 (Invitrogen, H3570). Cell nuclei and histone acetylation signal intensity were detected and measured using a laser-scanning microcytometer (Acumen eX3, TTP Laptech). Acumen Explorer software was used to identify a threshold of histone acetylation signal intensity such that, in the absence of HDAC inhibitor, >99.5% of cells had intensity levels below the threshold. In the presence of HDAC inhibitors, cells with histone acetylation signal intensities above the threshold were scored as "bright green nuclei". The percentage of nuclei scoring as bright green was quantitated for each HDAC inhibitor. This percentage was then normalized to DMSO controls. Representative images of histone acetylation staining in neurons (with dendrites stained by anti-Map2B antibody (EnCor) and Alexa-555-conjugated secondary antibody (Molecular Probes); shown in red) in the absence and presence of HDAC inhibitors were taken on a Zeiss Observer Z1 microscope.

Example 11

Materials and Methods: CBP mutant mice (B6.Cg-Tg (Camk2a-Crebbp*)1364Tabe/J) are obtained from, example, the Jackson lab. Expression of this FLAG-epitope tagged, dominant negative truncation of the CREB-binding protein (FLAG-CBPA1, lacking the coding sequence for amino acids 1084-2441) is spatially directed to neurons in the forebrain (hippocampus, amygdala, striatum, and cortex) and temporally directed to postnatal development by the CaMKIIa promoter. This dominant negative mutant form of CBP (designed to interrupt transcription factors utilizing CBP as a co-activator for the expression of their target genes) is expressed from the transgene at 95% of endogenous CBP levels in the hippocampus and 84% of endogenous CBP levels in the cortex. Hemizygous mice exhibit hippocampus-dependent memory deficits (such as reduced long-term potentiation, defective spatial learning, and impaired contextual fear conditioning) with none of the developmental impairments observed in CBP-deficient mutant models. The CBP mutant hemizygous mice and their control littermates are injected daily of intermittently (e.g every other day) with vehicle or a compound of the invention for a period of time (e.g 10 days). On day 11, mice are trained in contextual fear conditioning paradigm (Training consists of a 3 min exposure of mice to the conditioning box (context, TSE) followed by a foot shock (2 sec, 0.8 mA, constant current). One hour after training, mice are injected with compounds of the invention or vehicle. On day 12 mice are returned to the training box and the freezing behavior were monitored and recorded. References: Learn Mem. 2005 March-April; 12(2):111-9. Transgenic mice expressing a truncated form of CREB-binding protein (CBP) exhibit deficits in hippocampal synaptic plasticity and memory storage. Wood M A, Kaplan M P, Park A, Blanchard E J, Oliveira A M, Lombardi T L, Abel T.

CBP (+/−) heterozygous mice represent a model of the human disease syndrome of Rubinstien Taybi. It is the same genetic mutation which is believed to be casual in humans. People affected by this syndrome have memory/cognition and developmental deficits. Using the dosing paradigm (e.g., 1 mg/kg, QD, 10 days) compounds of the invention are tested for their ability to restore the memory of these mice to an equivalent level as found in the wild-type littermates.

Example 12

Materials and Methods: CK/p25 mouse is an inducible neurodegenerative disease mouse model. The bi-transgenic mice are created by crossing the CamK2a-tTA and the tetO-p25 Tg mouse lines. In the presence of doxycyclin, the expression of p25 is suppressed. When doxycyclin is removed, the expression of p25 is strongly induced in the forebrain. Six weeks of p25 induction causes massive neuronal loss, elevated beta-amyloid peptide production, tau associated pathology, and impairment in learning and memory. For these experiments, doxycyclin is removed from 3-month old CK/p25 mice and the control littermates for 6 weeks. The mice are subsequently injected with compounds of the invention or vehicle for a period of time (e.g. 10 days). After that time period (e.g., on day 11), mice are trained in contextual fear conditioning paradigm (training consisted of a 3 min exposure of mice to the conditioning box (context, TSE) followed by a foot shock (2 sec, 0.8 mA, constant current). One hour after training, mice are injected with a compound of the invention or vehicle. On day 12 mice are returned to the training box and the freezing behavior is monitored and recorded. References: Cruz J C, et al. Neuron 2003, 40:471-483; Fischer A, et al, Neuron, 2005, 48: 825-838; Fischer A, et al., Nature 2007, 447: 178-182.

The p25 vehicle group represents non-induced vehicle treated mice, the p25/CK vehicle group represents the induced untreated mice. The control group consists of the tetO-p25 Tg mice fed on normal diet, which do not express p25. The compounds of the invention are tested for their ability to restore contextual fear conditioning learning. The brain pathology of p25 is reminiscent of human patients with neurodegeneration and memory impairment.

Example 13

Mice are trained using contextual fear conditioning paradigm on day 0. For example, training consists of a 3 min exposure of mice to the conditioning box (context, TSE) followed by three foot shocks (2 sec, 0.8 mA, constant current with 15-seconds-intervals). From day 1, mice are trained in extinction trials. For each training day, mice are twice exposed to the conditioning box for 3 min without foot shock (two extinction trials/day). One hour after the first trial, mice are injected with a compound of the invention (e.g., 30 mg/1 (g, i.p.). One hour after the injection, the second extinction trial is performed. The freezing time in each individual trial is measured.

Example 14

For the memory reconsolidation paradigm, after the fear extinction training as described above, mice are re-housed in the home cage for one month. Mice are subsequently re-expose to the conditioning box for 3 min, their freezing behavior is measured. It is well established that after the fear memory extinction trials, fear memory will spontaneously recover after resting in the home cage for a period of time. The speculated mechanism for fear extinction is to trigger the formation of new memory which competes with fear memory and in turn reduces the fear response. Conversely, reconsolidation based fear memory extinction paradigm has been proposed to directly modify the activated fear memory, so that the reduced fear response does not spontaneously recover (Extinction-reconsolidation boundaries: key to per attenuation of fear memories. Monfils M H, Cowansage K K, Klann E, LeDoux J E. Science. 2009 May 15; 324(5929): 951-5. Epub 2009 Apr. 2).

Compounds of the invention are tested in several dosing paradigms in terms of frequency and dose in multiple disease states. The experiments above can show treatment is beneficial for extinction of aversive memories. In an embodiment, the compounds of the present invention in conjunction with proper training paradigm lead to permanent erasing of fear memory.

Example 15: Caliper Endpoint Assay

The following non-trypsin coupled in-vitro HDAC enzymatic endpoint assay was used to assay the compounds of the invention. Below is a standardized protocol for running HDAC selectivity panel on Caliper LabChip EZ-Reader Instrument.

The Caliper HDAC Assay Buffer (acronym HAB, 1 liter) was prepared as follows:

| Components: | Final Concentration: | Catalog #s: |
|---|---|---|
| 100 mL 1M KCL | 100 mM | Sigma #9541-500G |
| 50 mL 1M HEPES, pH 7.4 | 50 mM | Sigma #H3375-1KG |

-continued

| Components: | Final Concentration: | Catalog #s: |
|---|---|---|
| 1 mL 10% BSA | 0.01% *(important) | SeraCare #AP-4510-80-100G |
| 20 uL 50% Tween-20 | 0.001% | Zymed #00-3005-20 mL |

The buffer was added to 1 liter Milli-Q water and store at 4° C. *BSA final concentration cannot exceed 0.01% for use on the Caliper instrument. HDAC enzymes 1 to 9 were purchased from BPS Bioscience (see table below for catalog #s).

The substrate (stock conc.) was prepared as follows:
Substrate A (aka HS-C2 (structure shown below): 10 mM/2 mM in 100% DMSO)—final conc. 2 μM—HDACs 1, 2, 3, 6
Substrate B (aka HS-CF$_3$ (structure shown below): 10 mM/2 mM in 100% DMSO)—final conc. 2 μM—HDACs 4, 5, 7, 8, 9

The quench inhibitor (stock conc.) was LBH (structure shown below). The instrument buffer was ProfilerPro Separation Buffer (e.g., Caliper #760367). The instrument chip was LabChip EZ Reader II 12-Sipper Off-Chip Mobility Shift Chip (e.g., Caliper #760404).

The Caliper peptide structures HS-C2 and HS-CF$_3$ are shown below and prepared according to the synthetic procedure described in U.S. patent application Ser. No. 61/628,562 entitled "Fluorescent Substrates for Determining Lysine Deacetylase Activity" filed Nov. 2, 2011.

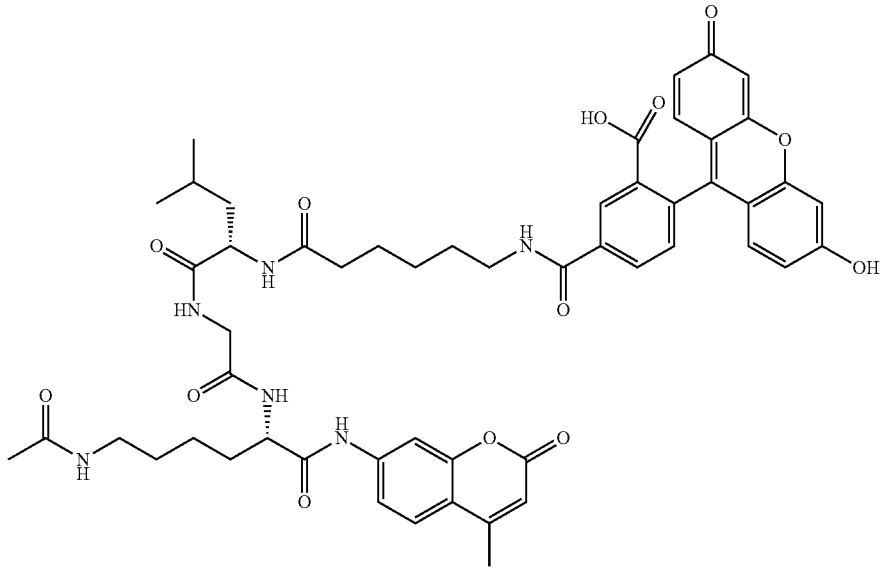

Substrate A

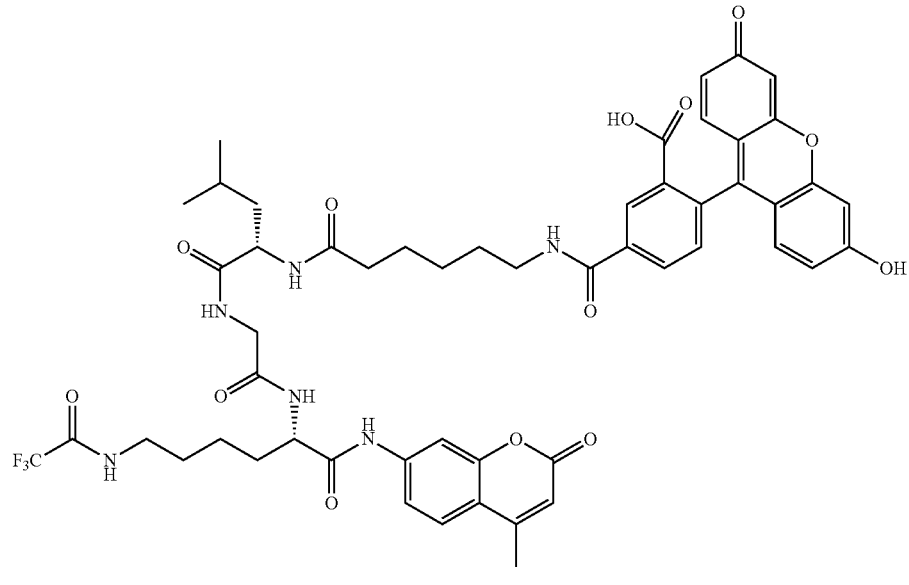

Substrate B

LBH quench structure is:

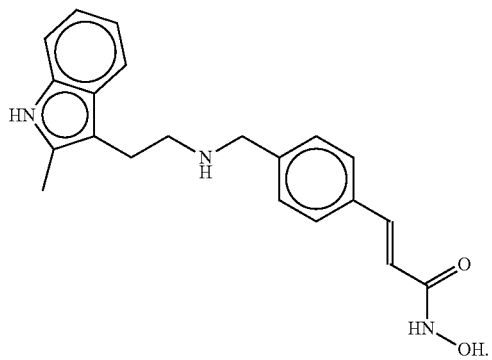

(LBH)

The protocol was carried out as follows:
1. Caliper LabChip and 1 μM Marker (peptide in separation buffer) were prepared for instrument run.
2. Warm up Caliper HAB buffer to room temperature
3. Pin 100 nl compd. into 20 μl 1.5× solution HDACs and preincubate 3 hrs at room temperature
4. Add 10 μl 3× solution acetylated substrate to initiate the reaction for 50 minutes.
5. Stop reaction with 5 μL of 10 μM LBH solution (~1.4 uM final)
6. Mix plate
7. Read plate on EZ Reader instrument. Separate substrate and product peaks by capillary electrophoresis and read fluorescence from both substrate and product.

8. Run parameters were as follows:

|  | Pressure | Upstream votage | Downstream votage | Post sample buffer sip time | Final delay | Peak order |
|---|---|---|---|---|---|---|
| HS-C2 | −1.3 | −500 | −1500 | 35 | 90 | Product first |
| HS-CF3 | −1.3 | −500 | −1500 | 35 | 90 | Product first |

Below is the HDAC and Peptide concentration table.

| HDAC | BPS Cat. # | Peptide | Peptide Conc. (μM) | Stock enz. (μM) | Final enz. (nM) | Conversion % @ 1 hr |
|---|---|---|---|---|---|---|
| 1 | 50051 | C2 | 2 | 4.82 | 5 | 27% |
| 2 | 50002 | C2 | 2 | 44 | 3 | 20% |
| 2T | (#X083-59 XTAL sol'n 0.9 mg/ml) | C2 | 2 | 19.1 | 0.5 |  |
| 3 | 50003 | C2 | 2 | 7.67 | 5 | 30% |
| 4 | 50004 | CF3 | 2 | 26.6 | 0.5 | 38% |
| 5 | 50045 | CF3 | 2 | 0.567 | 1 | 17% |
| 6 | 50006 | C2 | 2 | 5.66 | 2 | 29% |
| 7 | 50007 | CF3 | 2 | 8.97 | 0.5 | 45% |
| 8 | 50008 | CF3 | 2 | 12.93 | 0.5 | 22% |
| 9 | 50009 | CF3 | 2 | 57.99 | 3 | 25% |

Preparation of Substrates A and B:

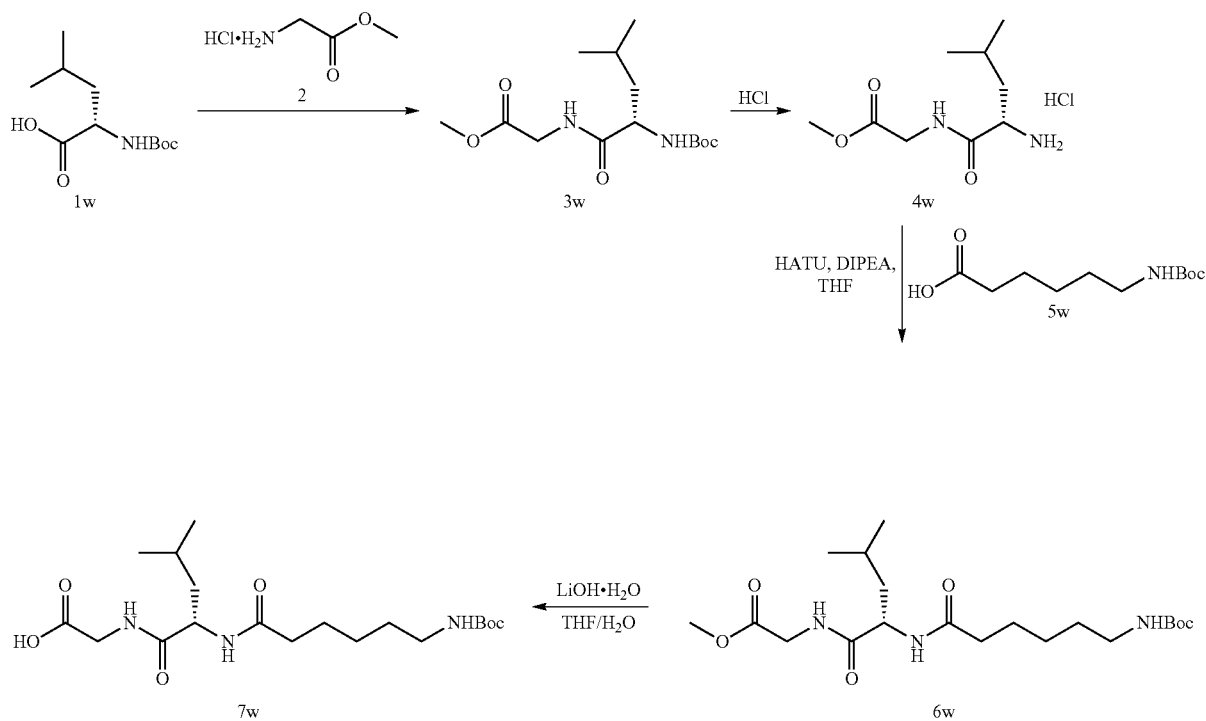

Scheme 1X

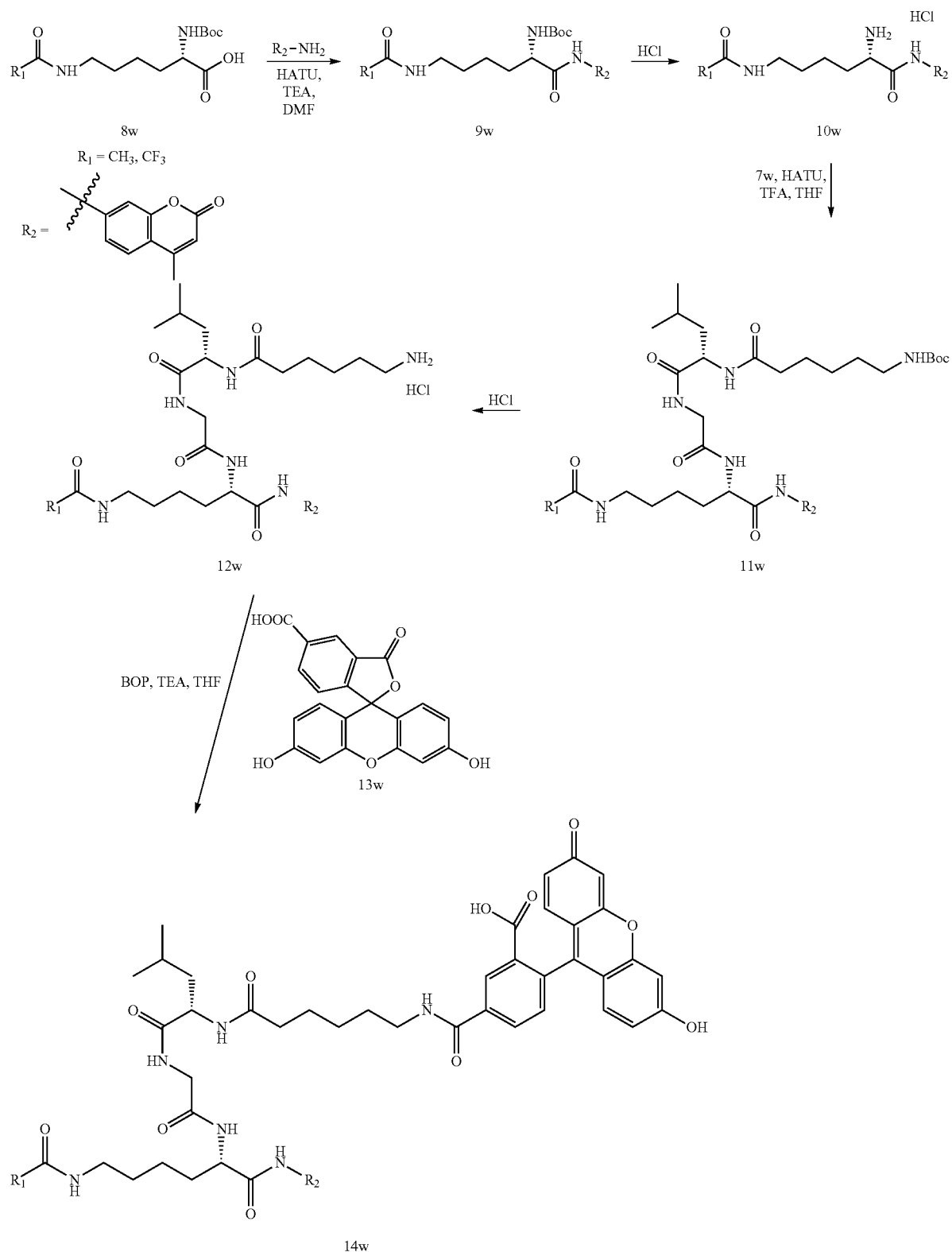

In one aspect, substrates A and B were prepared as follows. To a solution of (S)-2-((tert-butoxycarbonyl) amino)-4-methylpentanoic acid (1w) in THF was added methyl 2-aminoacetate hydrochloride (2w), Et$_3$N and HATU. The mixture was stirred at room temperature for 16 h. The reaction was filtered through Celite. The reaction filtrate was diluted with 100 mL of water and stirred for 15 min. The suspension was filtered off, rinsed with water and dried to afford (S)-methyl 2-(2-((tert-butoxycarbonyl)amino)-4-methylpentanamido)acetate (3w).

To a solution of (S)-methyl 2-(2-((tert-butoxycarbonyl)amino)-4-methylpentanamido) acetate (3w) in 1,4-dioxane was added a 5M solution of HCl in 1,4-dioxane at room temperature. The reaction was stirred at room temperature for 16 h. The reaction mixture was filtered to afford (S)-methyl 2-(2-amino-4-methylpentanamido)acetate hydrochloride (4w) as the filtered solid.

To a solution of (S)-methyl 2-(2-amino-4-methylpentanamido)acetate hydrochloride (4w) in THF was added 6-((tert-butoxycarbonyl)amino) hexanoic acid, HATU and DIPEA. The reaction was stirred at room temperature for 18 h. The mixture was then filtered through Celite. The filtrate was concentrated under reduced pressure and the crude residue was purified by column chromatography (silica gel, $CH_2Cl_2$/MeOH=50/1) to give (S)-methyl 13-isobutyl-2,2-dimethyl-4,11,14-trioxo-3-oxa-5,12,15-triazaheptadecan-17-oate (6w) as a white solid.

To a solution of (S)-methyl 13-isobutyl-2,2-dimethyl-4,11,14-trioxo-3-oxa-5,12,15-triazaheptadecan-17-oate (6w) in THF was added a solution of $LiOH.H_2O$ in water at room temperature. After 3 h, the reaction mixture was concentrated, diluted with water and acidified with a 1N aqueous solution of HCl to about pH 4-5. The mixture was stirred for 15 min and the white precipitate formed was filtered off, rinsed with water, and dried to afford (S)-13-isobutyl-2,2-dimethyl-4,11,14-trioxo-3-oxa-5,12,15-triazaheptadecan-17-oic acid (7w).

To a solution of 8w in DMF at room temperature was added 7-amino-4-methyl-2H-chromen-2-one, HATU and triethylamine. The reaction was stirred at room temperature for 2 h. A saturated solution of sodium bicarbonate was added. The product was extracted with ethyl acetate. The combined organic layers were washed with water, dried over sodium sulfate, filtered and concentrated under reduced pressure. The crude residue was purified by prep-HPLC to afford 9w.

To a solution of 9w in 1,4-dioxane was added a 5M solution of HCl in 1,4-dioxane. The reaction was stirred at room temperature for 3 h. The mixture was concentrated under reduced pressure to afford 10w.

To a solution of 10w in THF was added 7, HATU and triethylamine. The reaction was stirred at room temperature for 3 h. A saturated solution of sodium bicarbonate was added. The product was extracted with ethyl acetate. The combined organic layers were washed with water, dried over sodium sulfate, filtered and concentrated under reduced pressure. The crude material was purified by silica gel column (prep-HPLC) to afford 11w.

To a solution of 11w in 1,4-dioxane and was added a 5M solution of HCl in 1,4-dioxane. The reaction was stirred at room temperature for 3 h. The reaction was then concentrated and dried under reduced pressure to afford 12w.

To a solution of 12w in THF at room temperature was added 13w, BOP and triethylamine. The reaction was stirred at room temperature for 22 h. The mixture was then filtered through Celite. The filtrate was concentrated under reduced pressure. The crude residue was purified by prep-HPLC to give 14w.

Figure 1B:
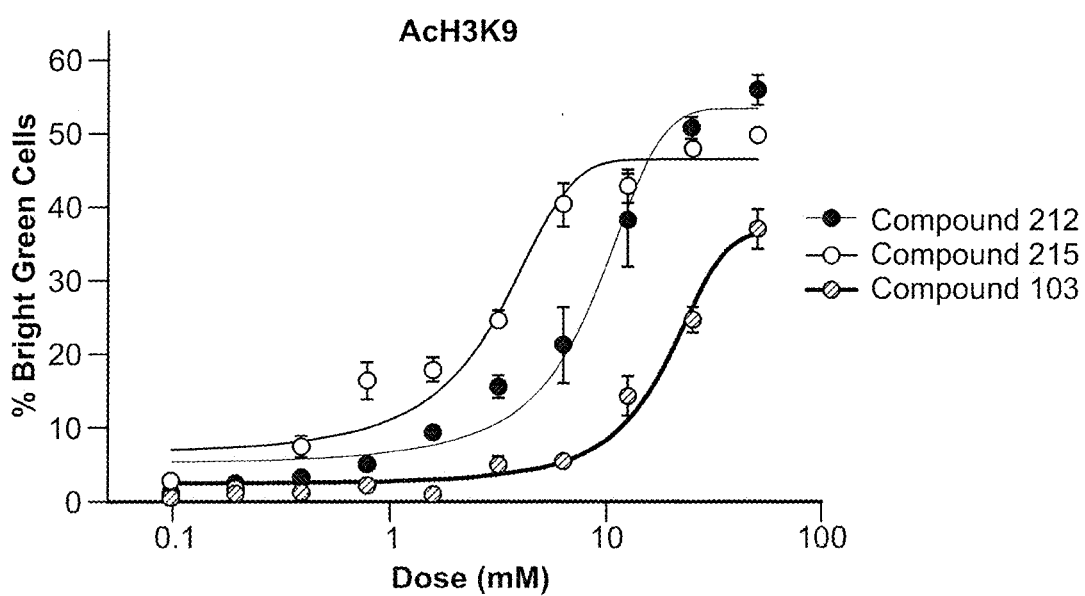
FIGS. 1B and 1D are dose response curves of histone acetylation (AcH3K9) in primary neuronal cultures by compounds of the invention.
Figure 1C:
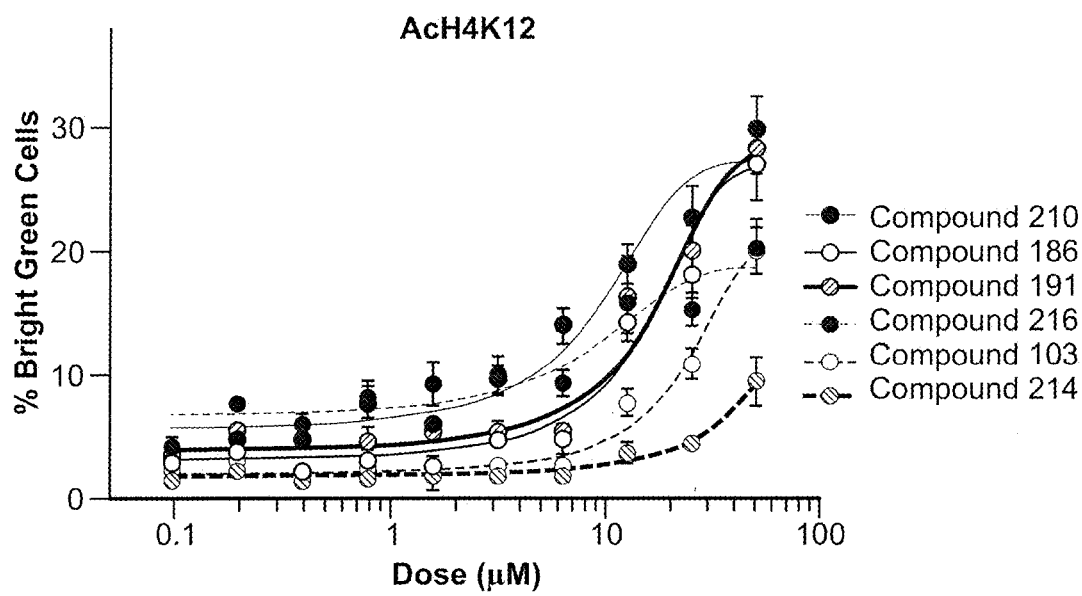
Figure 1D:
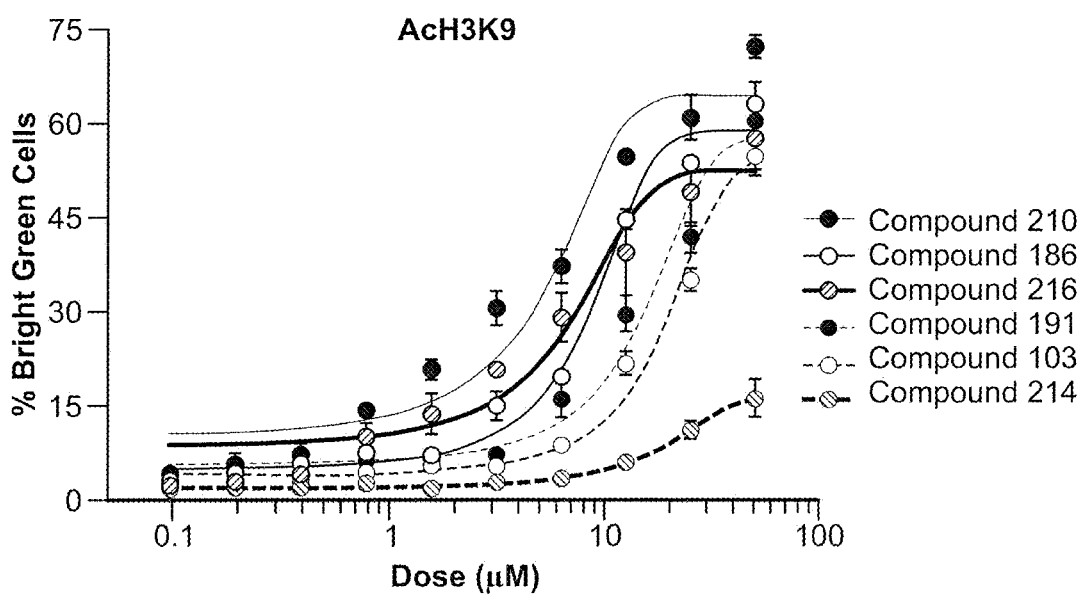

Example 16: Histone Acetylation Changes in Neuronal Cell Culture After Treatment with Compounds of the Invention Primary cultured mouse forebrain neurons were treated for 24 hours with compounds of the invention, and the resulting increases in histone acetylation were measured with immunofluorescence assays. FIGS. 1A, 1B, 1C and 1D show dose response curves for induction of acetylation of histone H4 lysine 12, and histone H3 lysine 9 for compounds of the invention. Specifically, FIG. 1A and FIG. 1C are dose response curves of histone acetylation (AcH4K12) in primary neuronal cultures by compounds of the invention. FIG. 1B and FIG. 1D are dose response curves of histone acetylation (AcH3K9) in primary neuronal cultures by compounds of the invention. For FIGS. 1A, 1B, 1C, and 1D, the cultures were treated for 24 hours with compounds of the invention at the indicated doses and histone acetylation was measured in an immunofluorescence assay. The percentage of cells with strong histone acetylation staining (bright green cells) was quantitated and averaged across duplicate samples from two independent cultures.

The protocol for primary neuronal culture was carried out as follows. E17 embryonic mouse forebrain was dissociated into a single cell suspension by gentle trituration following trypsin/DNAse digestion. Cells were plated into poly-D-lysine/laminin coated black/clear bottom 96-well plates (e.g., BD Biosciences #BD356692), 6-well plates, or 10 cm plates in Neurobasal medium containing 2% B27, and 1% pen/strep. Cultures were treated with compounds of the invention for 24 h starting on the thirteenth day after plating at varying concentrations of the compounds of the invention.

The protocol for histone acetylation immunofluorescence assays using primary neuronal culture was carried out as follows. Imaging of neurons was performed using automated microscopy. After 24 h of treatment by compounds of the invention, formaldehyde dissolved in phosphate-buffered saline (PBS) was added directly to the wells for a final concentration of 4%. Cells were fixed for 10 minutes at room temperature. Following two washes with phosphate-buffered saline, cells were permeabilized and blocked with blocking buffer composed of 0.1% Triton X-100, 2% BSA in PBS. For immunofluorescence imaging of histone modifications, cells were stained with anti-acetyl-H3K9 (e.g., Millipore, cat #07-352) or anti-Ac-H4K12 (e.g., Millipore, cat #04-119) antibodies, and Alexa488-conjugated secondary antibody (e.g., Molecular Probes). Cellular nuclei were identified by staining with Hoechst 33342 (e.g., Invitrogen, H3570). Cell nuclei and histone acetylation signal intensity were detected and measured using a laser-scanning microcytometer (e.g., Acumen eX3, TTP Laptech). Acumen Explorer software was used to identify a threshold of histone acetylation signal intensity such that, in the absence of compounds of the invention, >99.5% of cells had intensity levels below the threshold. In the presence of the compounds of the invention, cells with histone acetylation signal intensities above the threshold were scored as "bright green nuclei". The percentage of nuclei scoring as bright green was quantitated for compounds of the invention. This percentage was then normalized to DMSO controls.

Figure 2:
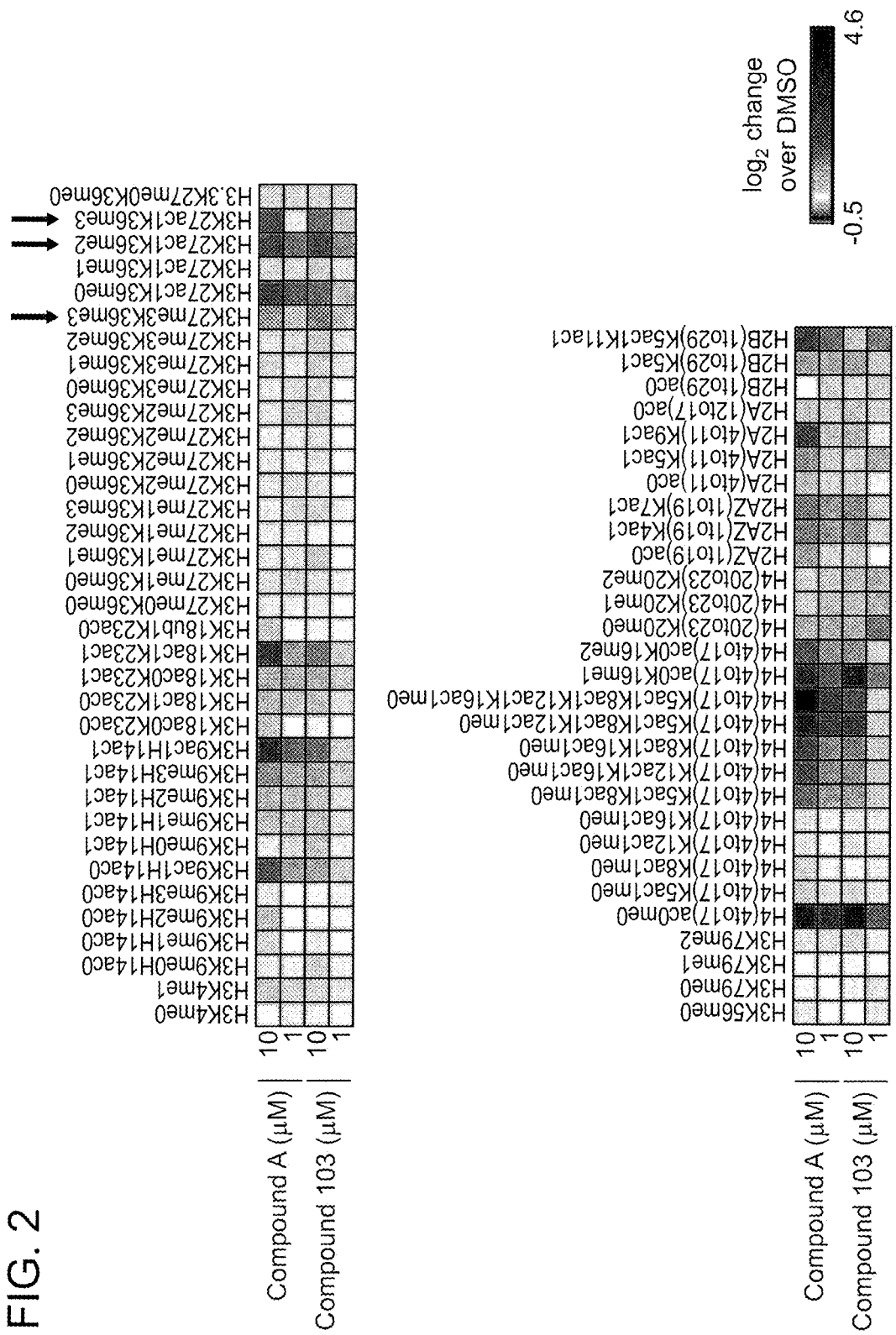
FIG. 2 is a heat map indicating changes in histone acetylation and methylation states regulated by treatment of primary neuronal cultures with compound 103 or compound A (positive control).

Example 17: Use of Mass Spectrometry for Identification of Changes in Histone Acetylation and Methylation States Induced in Neurons by Treatment with Compounds of the Invention The protocol was carried out as follows. Large-scale primary neuronal cultures were treated with compound 103 (at 1 and 10 μM) for 24 hours, and cells were harvested for mass spectrometry analysis of histone acetylation and methylation according to methods developed by S. L. Peach et al. (see Quantitative assessment of "ChIP-grade" antibodies directed against histone modifications reveals patterns of co-occurring marks on histone protein molecules; Molecular & Cellular Proteomics, published on Mar. 21, 2012 as manuscript M111.015941). FIG. 2 is a heat map indicating changes in histone acetylation and methylation states regulated by treatment of primary neuronal cultures with compound 103 of the invention or compound A (positive control). Specifically, FIG. 2 is a heat map indicating the mass spectrometry characterization of histone acetylation and methylation states regulated treatment of neuronal cultures with compounds of the invention. Primary neuronal cultures were treated for 24 hours at the indicated doses. Arrows indicate the histone marks states induced equipotently by control compound A and compound 103.

Changes in many histone marks were induced in a dose-dependent manner. However, in the case of three specific histone mark states (AcH3K27/di- or tri-MeH3K36; triMeH3K27/triMeH3K36), compound A and compound 103 were equipotent. Thus, these three sets of histone marks may represent specific states that respond selectively to inhibition of HDACs 1/2.

Primary Neuronal Culture:

E17 embryonic mouse forebrain was dissociated into a single cell suspension by gentle trituration following trypsin/DNAse digestion. Cells were plated into poly-D-lysine/laminin coated black/clear bottom 96-well plates (e.g., BD Biosciences #BD356692), 6-well plates, or 10 cm plates in Neurobasal medium containing 2% B27, and 1% pen/strep. Cultures were treated with compounds of the invention for 24 h starting on the thirteenth day after plating at varying concentrations of the compounds of the invention.

Mass Spectrometry Determination of Histone Acetylation and Methylation States:

Primary neuronal cultures grown in 10 cm plates (3 million cells/plate) were treated for 24 hours with compound 103 (1 µM and 10 µM). Cells were harvested for proteomic analysis of histone acetylation and methylation states. Nuclei were purified from harvested cells, and histones were collected by acid extraction. Mass spectrometric analysis was used to identify the indicated histone acetylation and methylation states (Peach S L, et al.).

Example 18: Identification of Gene Expression Changes Upon Treatment with Compounds of the Invention in Neurons Changes in histone acetylation and methylation are key events in the regulation of gene transcription (Bannister A J, et al. Cell Res. 21:381-95). Thus, HDAC inhibitors that alter histone mark states in cells also induce changes in gene expression (e.g. Chang J, et al. Br J Cancer. 2012 Jan. 3; 106(1):116-25). Evidence suggests that HDAC isoforms have unique roles in controlling the expression of neuronal genes; some genes appear to be regulated by the coordinated actions of multiple HDACs; other genes seem to be uniquely regulated by specific HDACs (Guan J S, et al. Nature. 2009 May 7; 459(7243):55-60).

Genome-wide transcript profile studies were performed to assess the cellular activity of compounds of the invention, downstream from their immediate effects on histone acetylation and methylation, and to discover gene expression signatures that were specific phenotypes of HDAC1/2 inhibition. For these assays, primary cultured neurons were treated with compound A or compound 215 (at 10 µM) for 24 hours, and then harvested RNA for transcript profile analysis on Illumina microarrays.

1130 genes were found to be up or down-regulated by at least 1.5 fold (p<0.05; one-way ANOVA test) by compound 215. Of these, 109 were regulated to approximately the same extent by compound A and compound 215 (fold changes equivalent within +/− 10%). Table 3 lists a functionally well-annotated subset of these 109 genes, and indicates the directionality and fold changes induced by compound A and compound 215. These 109 genes were regulated by compound 215, which is a selective HDAC1,2 inhibitor.

This functionally annotated set consists of 34 genes that were up regulated, and 43 genes that were down-regulated, by compound A and compound 215. These gene expression phenotypes may represent a signature of selective inhibition of HDACs1/2.

TABLE 3

Genes regulated by compound 215 in neuronal cell cultures.

| Gene | Fold Change compound 215 | Fold Change compound A |
|---|---|---|
| Cdr2 | 1.9 | 2.1 |
| Rgs4 | 2.0 | 2.0 |
| Eno2 | 1.8 | 1.9 |
| Tpst2 | 1.8 | 1.7 |
| Rcl1 | 1.7 | 1.7 |
| Ramp3 | 1.7 | 1.7 |
| Nes | 1.6 | 1.6 |
| Nsf | 1.5 | 1.6 |
| Abca7 | 1.6 | 1.6 |
| Tmem86a | 1.5 | 1.6 |
| Ina | 1.6 | 1.6 |
| Il11ra1 | 1.5 | 1.6 |
| Urod | 1.6 | 1.6 |
| Fchsd1 | 1.5 | 1.6 |
| Smyd3 | 1.5 | 1.6 |
| St8sia5 | 1.4 | 1.5 |
| Tmem184b | 1.5 | 1.5 |
| Actn4 | 1.4 | 1.5 |
| Wipi1 | 1.5 | 1.5 |
| Arsa | 1.5 | 1.5 |
| Snhg11 | 1.4 | 1.5 |
| Pou3f1 | 1.5 | 1.5 |
| Galnt2 | 1.4 | 1.5 |
| Med10 | 1.5 | 1.5 |
| Adam15 | 1.4 | 1.5 |
| Ddn | 1.4 | 1.5 |
| Eif4ebp1 | 1.7 | 1.5 |
| Dok5 | 1.5 | 1.5 |
| Bbc3 | 1.6 | 1.5 |
| Lmtk2 | 1.6 | 1.5 |
| Adrbk2 | 1.5 | 1.5 |
| Cry2 | 1.5 | 1.5 |
| Reep6 | 1.5 | 1.4 |
| Zfyve27 | 1.5 | 1.4 |
| Rap2c | −1.5 | −1.4 |
| Scn2a1 | −1.5 | −1.4 |
| Rundc3b | −1.5 | −1.4 |
| Marcksl1 | −1.6 | −1.4 |
| Idh1 | −1.5 | −1.4 |
| Pccb | −1.5 | −1.5 |
| Sltm | −1.5 | −1.5 |
| Dcx | −1.5 | −1.5 |
| Lass2 | −1.4 | −1.5 |
| Aqp4 | −1.5 | −1.5 |
| Polr3k | −1.4 | −1.5 |
| Fam131a | −1.5 | −1.5 |
| Hist1h2an | −1.5 | −1.5 |
| Gabrg2 | −1.6 | −1.5 |
| Pgam5 | −1.5 | −1.5 |
| Hist1h2ad | −1.7 | −1.5 |
| Ccdc53 | −1.5 | −1.5 |
| Suv420h1 | −1.6 | −1.5 |
| Hist1h2ai | −1.6 | −1.5 |
| Efha1 | −1.5 | −1.5 |
| Fbxo6 | −1.5 | −1.5 |
| Mgat3 | −1.4 | −1.6 |
| Dctn6 | −1.4 | −1.6 |
| Lsm5 | −1.4 | −1.6 |
| Chchd1 | −1.5 | −1.6 |

TABLE 3-continued

Genes regulated by compound 215 in neuronal cell cultures.

| Gene | Fold Change compound 215 | Fold Change compound A |
| --- | --- | --- |
| Astn1 | −1.4 | −1.6 |
| Npm3-ps1 | −1.5 | −1.6 |
| Dis3l | −1.5 | −1.6 |
| Mrpl48 | −1.5 | −1.6 |
| Smarca1 | −1.6 | −1.6 |
| Gpr22 | −1.7 | −1.6 |
| Aldoc | −1.5 | −1.6 |
| Hist1h2af | −1.6 | −1.6 |
| Hmgn2 | −1.7 | −1.7 |
| Cenpa | −1.7 | −1.7 |
| Taf9b | −1.7 | −1.8 |
| Jazf1 | −1.6 | −1.8 |
| Mrpl54 | −1.7 | −1.8 |
| Ppp1r9a | −1.8 | −1.8 |
| Nasp | −1.7 | −1.9 |
| Pbk | −1.7 | −1.9 |
| Lor | −2.1 | −2.0 |
| Nxph2 | −1.9 | −2.1 |

The protocol for genome-wide transcript profiling assays was carried out as follows. E17 embryonic mouse forebrain was dissociated into a single cell suspension by gentle trituration following trypsin/DNAse digestion. Primary neuronal cultures grown in 6-well plates were treated for 24 hours with compound 215 at 10 µM. RNA was isolated with the RNeasy kit (e.g., Qiagen) according to the manufacturer's instructions. cDNA was synthesized using ArrayScript (e.g., Ambion). Triplicate samples were collected and analyzed using Illumina mouse whole-genome-6 microarrays. Total RNA from the samples was normalized to 20 ng/µl, and the Illumina® TotalPrep™-96 RNA Amplification Kit (e.g., Applied Biosystems, PN #4393543) protocol was used for amplification in a semi automated process. The total RNA underwent reverse transcription to synthesize first-strand cDNA. This cDNA was then converted into a double-stranded DNA template for transcription. In vitro transcription synthesized aRNA and incorporated a biotin-conjugated nucleotide. The aRNA was then purified to remove unincorporated NTPs, salts, enzymes, and inorganic phosphate. Labeled cRNA was normalized to 150 ng/µl and hybridized to Illumina's MouseWG-6 v2.0 Expression BeadChip. The labeled RNA strand was hybridized to the bead on the BeadChip containing the complementary gene-specific sequence. After 16 hours of hybridization, the beadchips were washed and stained using a Cy3 streptavidin conjugate. Illumina's BeadArray Reader was used to measure the fluorescence intensity at each addressed bead location. Raw data were annotated with Genome Studio (Illumina), and then quantile normalized and baseline transformed to the median of the DMSO control samples using GeneSpring software (Agilent). Probes failing to score as "present" in 100% of samples from at least one treatment condition were removed. A statistical threshold ($p<0.05$, paired t-test with Benjamini-Hochberg multiple comparisons correction) and a fold change criterion ($\geq 1.5$) were then applied to generate lists of genes up- and down-regulated by compound 215.

Example 19: Biochemical Profiling of Compounds of the Invention Using Native HDAC2 Complex Enzymatic Assays In cells, HDACs1/2 are assembled into large multi-protein complexes. Three major complexes containing HDACs1/2 have been found to bind to the non-selective hydroxamic acid HDAC inhibitor SAHA: CoREST, NuRD, and SIN3 (Bantscheff M, et al. Nat Biotechnol. 2011 March; 29(3):255-65).

The ability of compounds of the invention to selectively inhibit HDACs1/2 to effect unique conformational changes in the enzymes induced by assembly into these multi-protein complexes, which are not achieved by the recombinant free enzymes tested in the in vitro assays, was evaluated. HDAC2 complexes from mouse forebrain were immuno-precipitated. The following determinations were made: 1) known complex members (CoREST, mSin3a, and Mta3), but not HDAC3, were present in the HDAC2 immunoprecipitates (FIG. 3A); 2) the immunoprecipitated HDAC2 complexes were enzymatically active, as confirmed by one of our standard in vitro assays (FIG. 3B); 3) the effects of compound A, compound 215, and a negative control compound on this enzymatic activity. FIG. 3C shows that both compound A and compound 215 inhibited the enzymatic activity of the HDAC2 immunoprecipitate, whereas the negative control compound produced no inhibition, indicating that HDAC2 is sensitive to inhibition by compounds of the invention in the context of its endogenous multi-protein complexes.

Figure 3A:
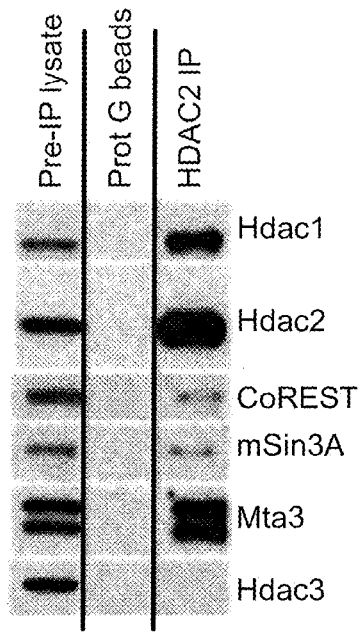
FIG. 3A is a Western blot showing detection of HDACs 1, 2 and 3 and known members of endogenous HDAC2 complexes in immunoprecipitated HDAC2 complexes.
Figure 3B:
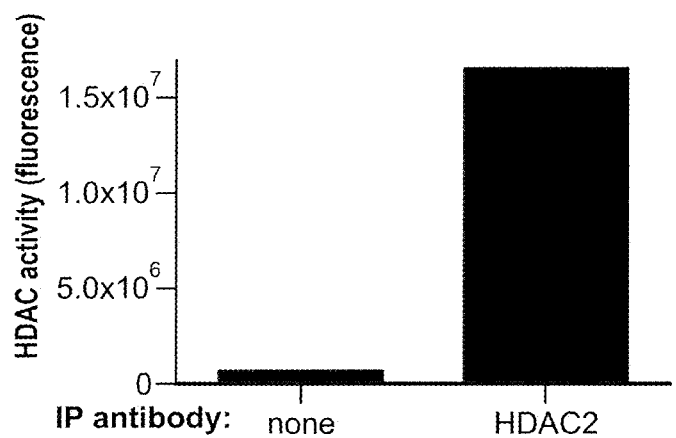
FIG. 3B is a bar chart indicating the enzymatic activity of the immunoprecipitated HDAC2 complexes from mouse forebrain.
Figure 3C:
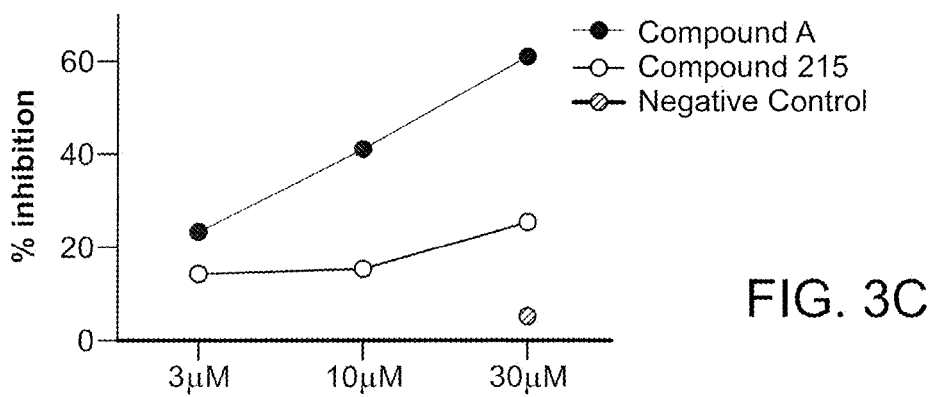
FIG. 3C is a graph indicating the % inhibition of enzymatic activity over time by compounds of the invention or compound A (positive control).

FIG. 3A, FIG. 3B, and FIG. 3C indicate that HDAC2 complexes immunoprecipitated from mouse forebrain are enzymatically active and sensitive to inhibition by compounds of the invention. FIG. 3A is a Western blot showing detection of HDACs 1, 2 and 3 and known members of endogenous HDAC2 complexes in immunoprecipitated HDAC2 complexes. FIG. 3B is a bar chart indicating the enzymatic activity of the immunoprecipitated HDAC2 complexes from mouse forebrain. Immunoprecipitates were added to an in vitro enzymatic assay containing MAZ1600 substrate, incubated for 22 hours prior to fluorescence detection of the activity. FIG. 3C is a graph indicating the % inhibition of enzymatic activity over time by compounds of the invention or compound A (positive control). The HDAC2 immunoprecipitates were incubated for three hours in the presence of the indicated compounds and then added to the MAZ1600 in vitro enzymatic assay for three hours of incubation prior to fluorescence detection.

Example 20: Learning and Memory—In Vivo Biomarker Analysis and Efficacy Studies in Normal Mice and a Mouse Model of Neurodegeneration, CK-p25 Mice Compound 54 and compound 103 were examined for their efficacy in the model behavior paradigm, the contextual fear conditioning task as described in Example 4. It was found that daily injections of either compound 54 or compound 103 (10 mg/kg daily i.p.) enhanced associative learning in wildtype mice (see FIG. 4). This experiment was repeated in an inducible mouse model of neurodegeneration, the CK-p25 mouse (see FIG. 5). This mouse model recapitulates many of the hallmarks of Alzheimer's disease (e.g. profound neuronal loss in the forebrain, increased β-amyloid peptide production, tau hyperphosphorylation, and severe cognitive impairment). Following the treatment of CK-p25 mice with either compound 54 (10 mg/kg daily i.p.) or compound 103 (1 mg/kg daily i.p.), it was observed that these compounds were able to ameliorate the cognitive deficits compared to vehicle treatment.

FIG. 4 is a bar chart indicating increased freezing in a contextual fear conditioning paradigm following administration of compounds of the invention or compound A (positive control; 10 mg/kg) in wild type mice. Administration of compound 54 (10 mg/kg), compound 103 (10 mg/kg), or compound A (positive control; 10 mg/kg) for ten days prior to fear conditioning training enhances associative learning in wild type mice (n=10 per group). *P<0.05, P<0.01, *P<0.001, using Tukey's test after ANOVA.

FIG. 5 is a bar chart indicating increased freezing in a contextual fear conditioning paradigm following administration of compounds of the invention or compound A (positive control; 1 mg/kg) in 6-week induced CK-p25 mice (neurodegenerative mouse model). Administration of compound 54 (10 mg/kg), compound 103 (1 mg/kg), or compound A (positive control; 1 mg/kg) enhances associative learning in 6-week induced CK-p25mice (numbers in histogram columns=animal n's). *P<0.05, P<0.01, *P<0.001, using Tukey's test after ANOVA.

After completing the behavioral tests, the mice were sacrificed and their brain tissue was subjected to either immunohistochemistry or immunoblotting. Immunoblotting experiments demonstrated that compound 54 administration marginally increased global histone acetylation in the hippocampus (see FIG. 6A, FIG. 6B, and FIG. 7). In addition, compound 103 administration at 1 mg/kg substantially decreased immunoreactivity for glial fibrillary acidic protein (GFAP) in the brains of treated animals, indicating reduced astrogliosis and inflammation (see FIG. 8A and FIG. 8B).

Figure 6B:
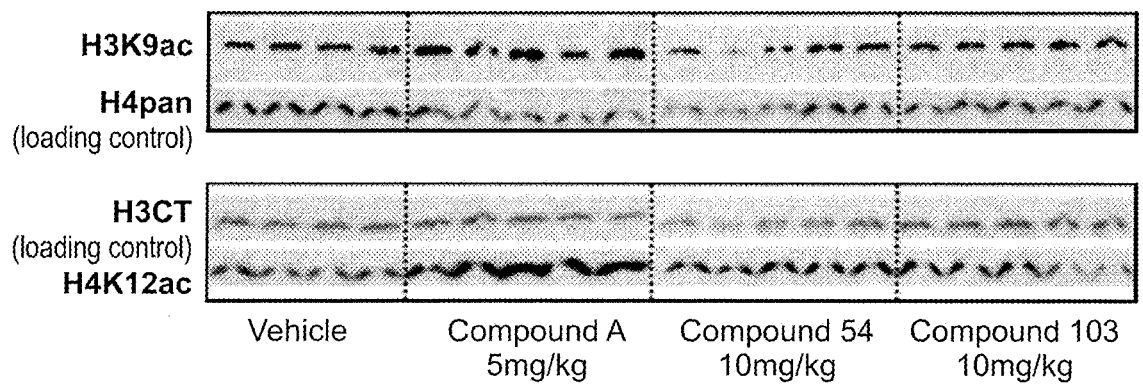
FIG. 6B shows the representative Western blots.

FIG. 6A and FIG. 6B indicate that chronic administration (10 days) of compound 54 (10 mg/kg) and compound 103 (10 mg/kg) increases the acetylation of histone loci H3K9 and/or H4K12 in the cortex of normal mice. Compound A is the positive control. FIG. 6A is a bar chart indicating the relative histone acetylation of H3K9 and H4K12 in C57BL/6 mouse cortex following chronic administration of compounds of the invention or compound A (positive control) compared to untreated (vehicle) mice. FIG. 6B shows the representative Western blots.

Figure 7:
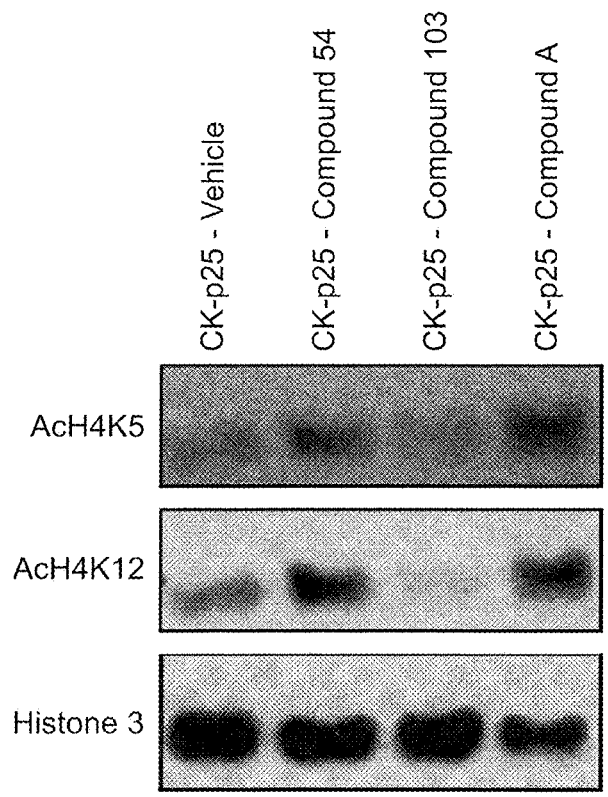
FIG. 7 is an immunoblot analysis of histone acetylation (AcH4K5 and AcH4K12) in CK-p25 mouse hippocampus following chronic administration of compounds of the invention or compound A (positive control).

FIG. 7 is an immunoblot analysis of histone acetylation (AcH4K5 and AcH4K12) in CK-p25 mouse hippocampus following the chronic administration of compounds of the invention or compound A (positive control). Chronic administration of compound 54 (10 mg/kg) marginally increases acetylation of histone residues, H4K5 and H4K12, in CK-p25 mice (n=3 per group).

Figure 8A:
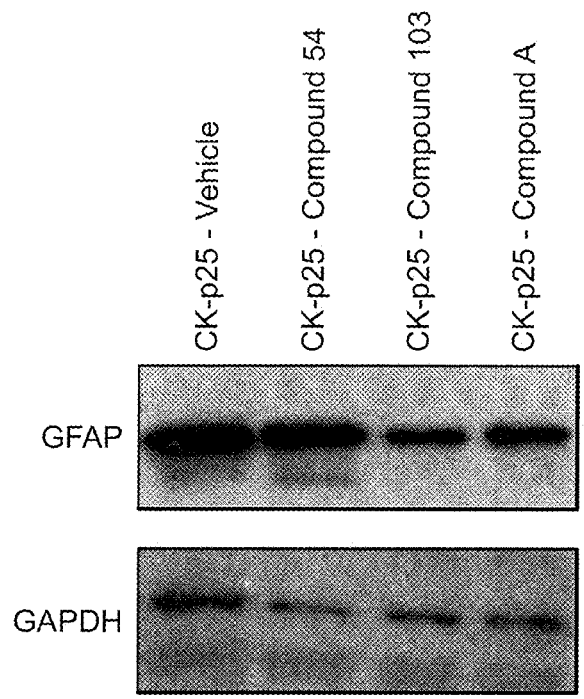
FIG. 8A is a Western blot showing the decrease of GFAP protein after administration of compound 103.
Figure 8B:
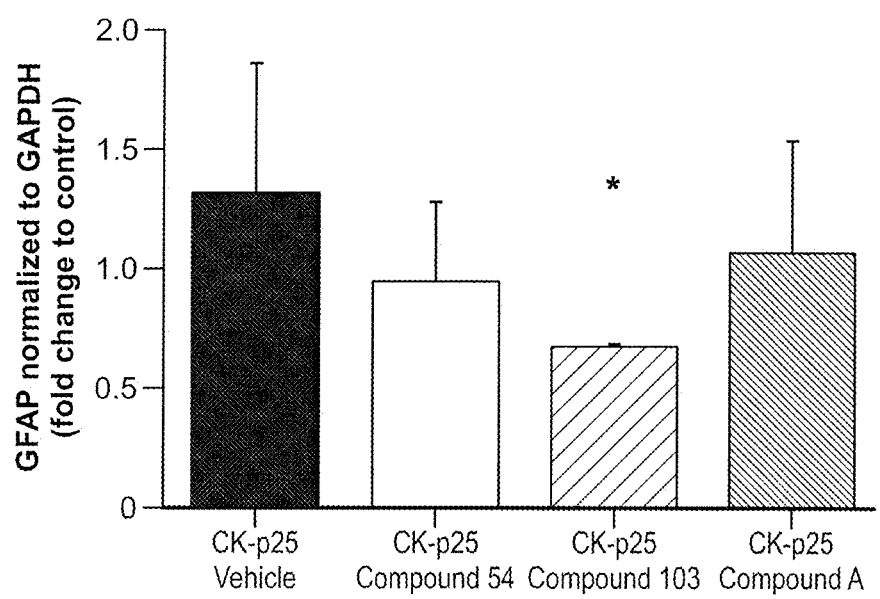
FIG. 8B is a bar chart indicating the level of GFAP normalized to GAPDH.

FIGS. 8A and 8B indicate that the administration of compound 103 (1 mg/kg) significantly decreases GFAP protein levels, an astrocytic marker commonly associated with brain inflammation (n=2). FIG. 8A is a Western blot showing the decrease of GFAP protein after administration of compound 103 of the invention. FIG. 8B is a bar chart indicating the level of GFAP normalized to GAPDH. *P<0.05, **P<0.01, using Student t test.

Specifically, the above results directed to acetylation in mouse cortex were obtained by a 2-step Crude Protein Lysis protocol, which was adapted from 'Lysis of Mammalian Cells and Tissue in Gel-Loading Buffer,' from Molecular Cloning: A Laboratory Manual, Book #3, Chapter 18 (Detection and Analysis of Proteins Expressed from Cloned Genes), pages 62-63.

For whole frozen mouse brain, the follow procedures were carried out:
1. On ice, thaw frozen tissue and dissect whole cortex using major neuroanatomical landmarks.
   a. Immediately homogenize carefully in 250 uL of ice-cold suspension buffer. 100 uL was used for tissue approx. 2-3 mm$^3$ and was adjust as needed. 1.5 mL disposable pestles (e.g., Fisher cat #03-392-100) were used.
   b. As soon as possible, add an equal volume of 2× SDS gel-loading buffer, pipetting up and down to mix.
2. Place the sample at 95° C. for 5 min.
3. Shear viscous chromosomal DNA by smoothly passaging through 23-25 gauge hypodermic needle (2-3×) or by sonicating briefly (the needle method also worked fine). Avoid foaming/bubbles.
4. Centrifuge the sample at 10,000 g for 10 min at room temperature, transferring supernatant to fresh tube.
5. Aliquot sample as needed based on protein concentration.

The suspension buffer was prepared using 0.1M NaCl, 0.01M TrisCl (pH 7.6), and 0.001M EDTA (pH 8.0). The buffer could have be prepared ahead and stored at room temperature. Just before use, the following was added: 1× phosphatase/protease inhibitor cocktail (e.g., ThermoFisher "HALT," cat #78440), and 5 mM Sodium Butyrate (HDAC inhibitor).

The 2× SDS gel-loading buffer was prepared using 100 mM TrisCl (pH 6.8), 4% SDS, and 20% glycerol. The buffer could have been prepared ahead and stored at room temperature. Just before use, the following was added: 200 mM dithiothreitol (from 1M stock) and 5 mM Sodium Butyrate (HDAC inhibitor).

Further, the Western blots above were obtained as follows. 10 ug cortical extract per sample on BioRad 15% Tris-HCl Gel at 150V was resolved for 1 hour. The sample was transfer to PVDF at 350 mA for 1 hour. The membranes were blocked with TBST+5% milk for 1 hour, then incubated overnight with primary antibody against i) H3K9ac (e.g., Millipore #07-352); ii) H3-Cterminus (e.g., Millipore #07-108); iii) H4K12ac (e.g., Millipore #04-119); or iv) Histone H4 (H4pan, e.g., Millipore #07-108). The membranes were subsequently incubated with secondary HRP-linked antibodies against i) Mouse IgG (e.g., Cell Signaling #7076) or ii) Rabbit IgG (e.g., Cell Signaling #7074) for 1 hour. Chemiluminescent signal was generated using Supersignal West Dura Extended Duration Substrate (ThermoFisher #34076) and radiographic film. Quantification was executed using Image J software (e.g., NIH).

Example 21: In Vivo Efficacy in Mood Related Behaviors

The compounds of the invention were tested in various behavioral paradigms. The compounds of the invention were prepared at the beginning of each experiment (10-12 aliquots per experiment) in aliquots. All aliquots were frozen and only thawed one time for administration. Each aliquot contained the appropriate concentration of compounds of the invention in 100% DMSO. Prior to administration, aliquots were removed, thawed, and prepared as:
45% PEG400/45% saline (0.9% NaCl)/10% DMSO: 200 ul DMSO, 900 ul PEG400, 900 ul Saline 30% Cremophor EL/65% Saline/5% DMSO: 100 ul DMSO, 600 ul Cremophor, 1300 ul Saline. Aliquots were discarded each day and fresh compound was prepared each day. About 2 mls of compound for each day for each drug (2 ml is the amount used for the calculations below) were made.

Administration of compounds of the invention was carried out as follows. Each mouse was administered compounds of the invention daily at approximately the same time each day. Mice were weighed daily as a gross measure of overall tolerability of the compounds of the invention. Mice were administered the appropriate dose of the compound of the invention at either 5 mls or 10 mls/kg, depending on the solubility of the compound the invention. Mice were returned to the home cage immediately after for the first 5 days of dosing. For the rest of dosing, mice were run in various behavioral paradigms (detailed below) and administered compounds of the invention after the completion of the behavior runs. Thus, all behavioral data were obtained 18-24 hours after the previous drug administration. All behavior data should reflect the chronic effects of the compounds of the invention and not acute effects of each of the compounds of the invention.

The behavioral assays were prepared as follows. For the amphetamine-induced hyperactivity (AIH) assay, mice were habituated on day 1 (day 6 of compound administration), baseline motor activity was obtained on day 2 (day 7 of compound administration), and the effects of the compounds of the invention on the amphetamine response were obtained on day 3 (day 8 of compound administration).

Specifically, AIH was examined in eight identical open-field chambers (16.5"×16"×12"; AccuScan Instruments, Columbus, Ohio). See FIGS. 9A, 9B, 10A and 10B. Activity was detected by infrared beam breaks and recorded automatically by VersaMax software (AccuScan). Daily sessions were automatically binned in 5 minute intervals (VersaDat; AccuSacn) for statistical analysis. AIH was run over three consecutive days.

Figure 9A:
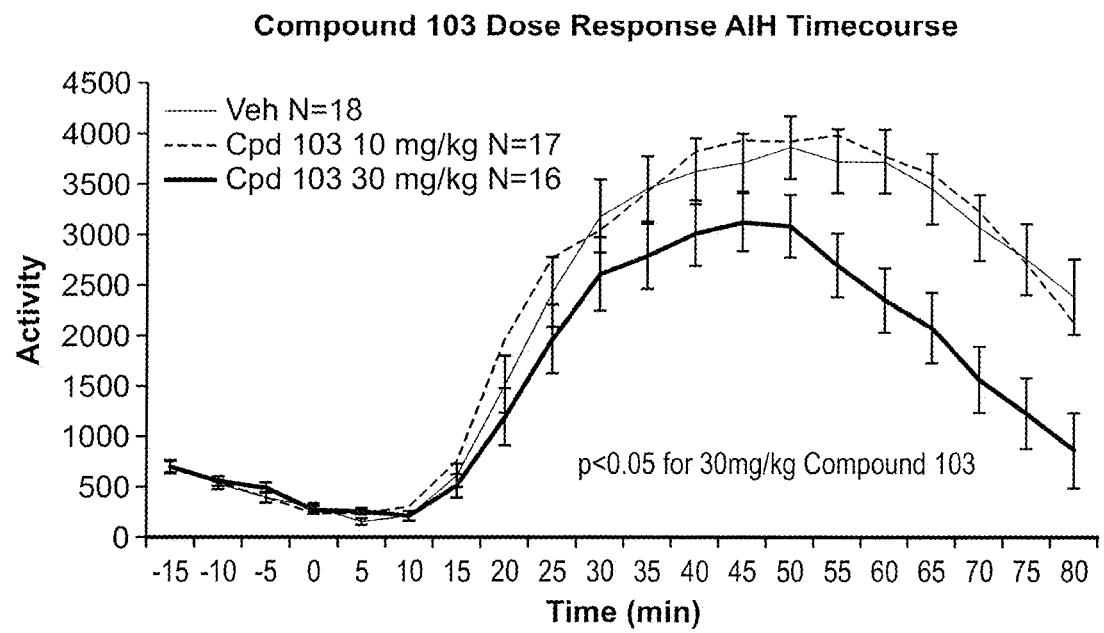
FIG. 9A is a line graph of the total locomotor activity over time (min) in C57BL/6 mice after chronic administration of compound 103 of the invention in the amphetamine induced hyperactivity (AIH) mouse model.
Figure 9B:
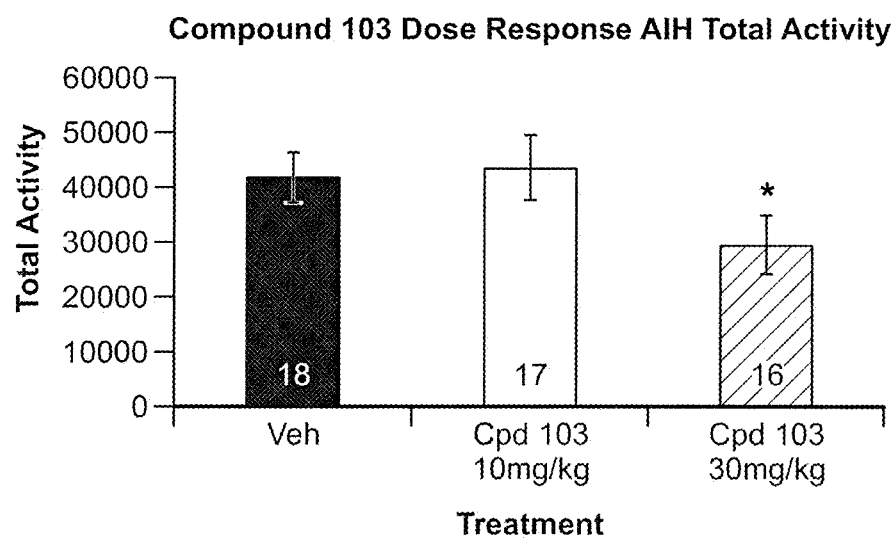
FIG. 9B is a bar chart of the total activity during the test period.

FIG. 9A and FIG. 9B indicate that chronic administration (8 days) of compound 103 (30 mg/kg) in normal mice attenuates the response in amphetamine induced hyperactivity. FIG. 9A is a line graph of the total locomotor activity over time (min) in C57BL/6 mice after chronic administration of compound 103 of the invention in the amphetamine induced hyperactivity (AIH) mouse model. FIG. 9B is a bar chart of the total activity during the test period.

Figure 10A:
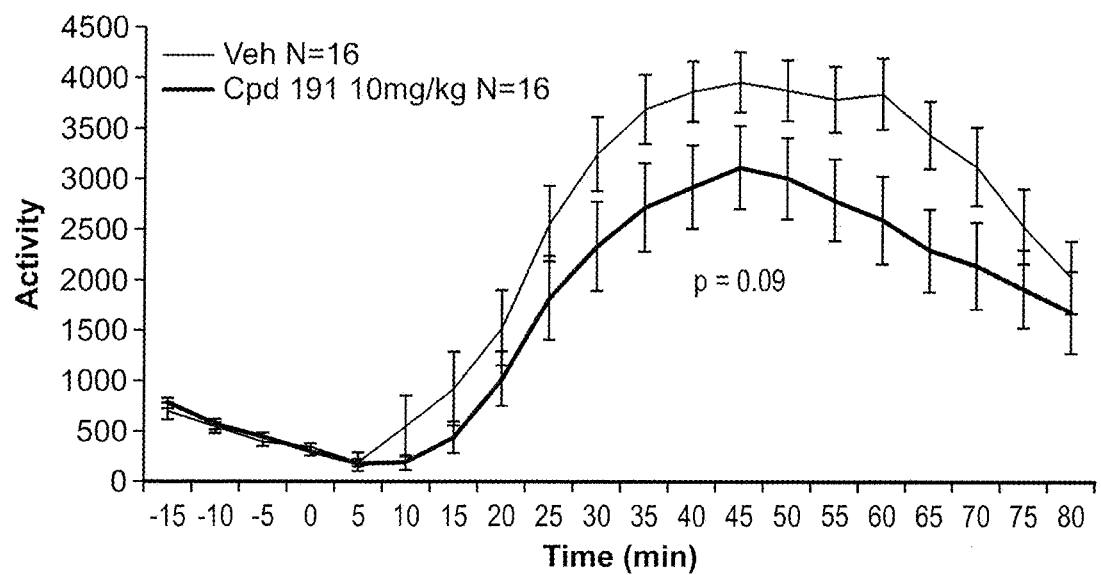
FIG. 10A is a graph of the total locomotor activity over time (min) in C57BL/6 mice following chronic administration of compound 191 of the invention in AIH.
Figure 10B:
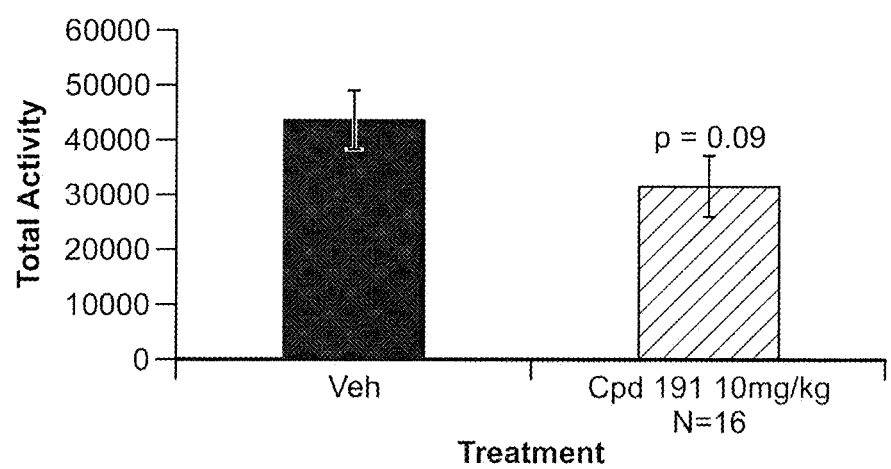
FIG. 10B is a bar chart of the total activity during the test period.

FIG. 10A and FIG. 10B indicate that the chronic administration (8 days) of compound 191 (10 mg/kg) in normal mice attenuates the response in amphetamine induced hyperactivity. FIG. 10A is a graph of the total locomotor activity over time (min) in C57BL/6 mice following chronic administration of compound 191 of the invention in AIH. FIG. 10B is a bar chart of the total activity during the test period. Decreased locomotor activity is indicative of an antimanic phenotype.

Figure 11:
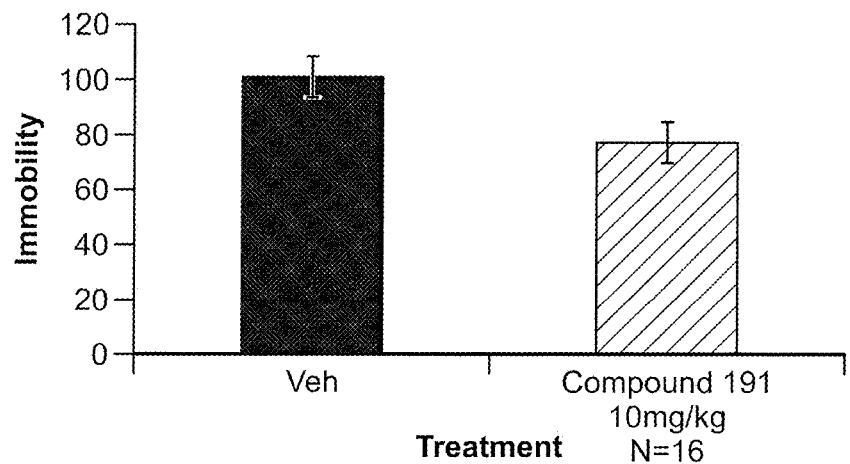
FIG. 11 is a bar chart indicating that chronic administration of compound 191 in C57BL/6 mice decreases the immobility time during the forced swim test.
Figure 12:
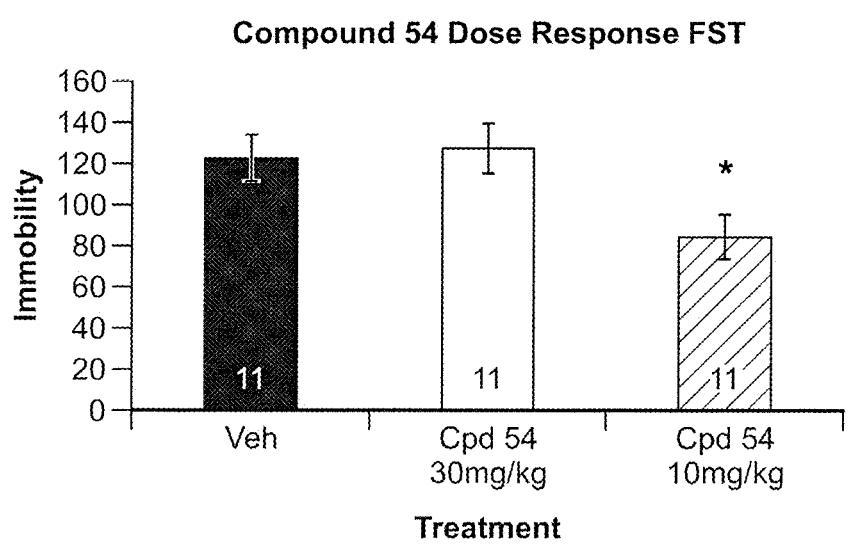
FIG. 12 is a bar chart indicating that chronic administration of compound 54 in C57BL/6 mice decreases the immobility time during the forced swim test.

For the forced-swim test (FST), mice were exposed to the 6 minute test on day 9 of compound administration (See FIG. 11 and FIG. 12). Specifically, mice were placed in one of five identical cylindrical chambers (24 cm×15 cm) filled ~½ way with warm water (26±2°). The FST was run in one day for 6 minutes and behavior was scored automatically (EthoVision; Noldus) for the final 4 minutes of the session.

FIG. 11 is a bar chart indicating that chronic administration of compound 191 in C57BL/6 mice decreases the immobility time during the forced swim test. Decreased immobility is indicative of an antidepressant phenotype.

FIG. 12 is a bar chart indicating that chronic administration of compound 54 in C57BL/6 mice decreases the immobility time during the forced swim test. Decreased immobility is indicative of an antidepressant phenotype.

Further, tissue collection and biochemistry analysis were carried out on day 10. Mice were treated with compounds of the invention and tissue was collected one hour after the final administration. Mice were sacrificed via cervical dislocation and the brains were rapidly removed and immediately flash frozen on dry ice. Cortex and striatum were then dissected from whole brain and tissue was prepared and analyzed. Specific details of tissue collection, dissection and Western Blotting can be found in Example 20. (see 2-step Crude Protein Lysis protocol and details on Western blots).

The invention claimed is:
1. A compound having formula I:

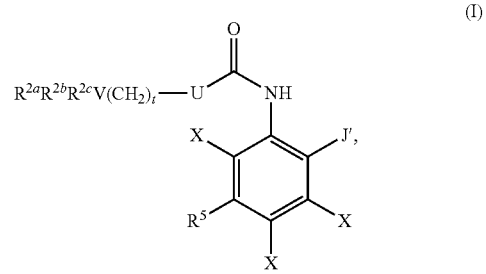

or a pharmaceutically acceptable salt, hydrate, or solvate thereof, wherein:
U is a single bond;
J' is $NH_2$;
V is C;
X is hydrogen;
taken together two of $R^{2a}$, $R^{2b}$, and $R^{2c}$ form a $C_4$-$C_5$ cycloalkyl ring or $C_4$-$C_5$ cycloalkenyl ring, and the remaining $R^{2a}$, $R^{2b}$, or $R^{2c}$ is absent or selected from hydrogen, halogen, OH, $NH_2$, and $C_1$-$C_8$ alkyl, wherein said cycloalkyl ring formed by taking together two of $R^{2a}$, $R^{2b}$, and $R^{2c}$ is substituted with one or more $R^x$, and said cycloalkenyl ring formed by taking together two of $R^{2a}$, $R^{2b}$, and $R^{2c}$ is unsubstituted or substituted with one or more $R^x$;
each $R^x$ is independently selected from $(CH_2)_zNH_2$, $(CH_2)_z NHR^3$, $(CH_2)_zNR^3R^3$, $OR^3$, $OCF_3$, $OCH_2F$, $OCHF_2$, $(CH_2)_z$-heterocyclic ring, hydroxyl, halogen, $C_1$-$C_8$ alkyl, $(C_1$-$C_8$ alkyl)$CF_3$, $(C_1$-$C_8$ alkyl)OH, C(O)$R^3$, $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_zNR^4C(O)R^4$;
or:
taken together only two $R^x$ form: i) a $C_3$-$C_4$ or $C_7$-$C_8$, cycloalkyl ring, or 3 to 8 membered, saturated or partially unsaturated, heterocyclic ring, wherein said cycloalkyl ring and heterocyclic ring are unsubstituted or substituted with one or more $R^z$; or ii) an aromatic ring or heteroaromatic ring, wherein said aromatic ring and heteroaromatic ring are unsubstituted or substituted with one or more $R^z$; and
optionally each remaining $R^x$ is independently selected from $(CH_2)_zNH_2$, $(CH_2)_zNHR^3$, $(CH_2)_zNR^3R^3$, $OR^3$, $OCF_3$, $OCH_2F$, $OCHF_2$, $(CH_2)_z$-heterocyclic ring, hydroxyl, halogen, $C_1$-$C_8$ alkyl, $(C_1$-$C_8$ alkyl)$CF_3$, $(C_1$-$C_8$ alkyl)OH, C(O)$R^3$, $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_zNR^4C(O)R^4$;
each $R^z$ is independently selected from halogen, $C_1$-$C_4$ alkyl, OH, $OR^3$, $CF_3$, $OCF_3$, $OCH_2F$, $OCHF_2$, $NH_2$, $NHR^3$, $NR^3R^3$, and $C(O)CH_3$;
each instance of $R^3$ is $C_1$-$C_8$ alkyl;
each instance of $R^4$ is independently selected from $C_1$-$C_8$ alkyl and $CF_3$;
$R^5$ is hydrogen;
t is 0; and
z is selected from 0, 1, 2, and 3.
2. The compound of claim 1 or a pharmaceutically acceptable salt, hydrate, or solvate thereof, wherein $R^{2a}R^{2b}R^{2c}V$— is

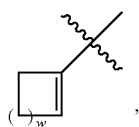

wherein w is selected from 1 and 2.

3. The compound of claim 1, wherein the compound is of the formula:

| No. | Formula |
|---|---|
| 219 | 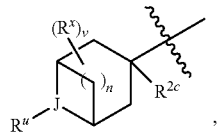 or |
| 223 | 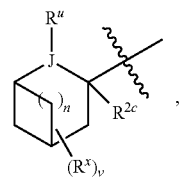 | or a pharmaceutically acceptable salt, hydrate, or solvate thereof.

4. The compound of claim 1, or a pharmaceutically acceptable salt, hydrate, or solvate thereof, wherein the cycloalkenyl ring formed by taking together two of $R^{2a}$, $R^{2b}$, and $R^{2c}$ is unsubstituted.

5. The compound of claim 1, or a pharmaceutically acceptable salt, hydrate, or solvate thereof, wherein:
the cycloalkyl ring and cycloalkenyl ring formed by taking together two of $R^{2a}$, $R^{2b}$, and $R^{2c}$ are substituted with one or more $R^x$; and
each $R^x$ is independently selected from $(CH_2)_zNH_2$, $(CH_2)_z NHR^3$, $(CH_2)_zNR^3R^3$, $OR^3$, $OCF_3$, $OCH_2F$, $OCHF_2$, $(CH_2)_z$-heterocyclic ring, hydroxyl, halogen, $C_1$-$C_8$ alkyl, ($C_1$-$C_8$ alkyl)$CF_3$, ($C_1$-$C_8$ alkyl)OH, C(O)$R^3$, $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_zNR^4C(O)R^4$.

6. The compound of claim 1, or a pharmaceutically acceptable salt, hydrate, or solvate thereof, wherein:
the cycloalkyl ring and cycloalkenyl ring formed by taking together two of $R^{2a}$, $R^{2b}$, and $R^{2c}$ are substituted with two or more $R^x$;
taken together only two $R^x$ form a $C_3$-$C_4$ or $C_7$-$C_8$, cycloalkyl ring, or 3 to 8 membered, saturated or partially unsaturated, heterocyclic ring, wherein said cycloalkyl ring and heterocyclic ring are unsubstituted or substituted with one or more $R^z$; and optionally:
each remaining $R^x$ is independently selected from $(CH_2)_z$ $NH_2$, $(CH_2)_zNHR^3$, $(CH_2)_zNR^3R^3$, $OR^3$, $OCF_3$, $OCH_2F$, $OCHF_2$, $(CH_2)_z$-heterocyclic ring, hydroxyl, halogen, $C_1$-$C_8$ alkyl, ($C_1$-$C_8$ alkyl)$CF_3$, ($C_1$-$C_8$ alkyl) OH, C(O)$R^3$, $(CH_2)_zC(O)NH_2$, $(CH_2)_zC(O)NHR^3$, $(CH_2)_zC(O)NR^3R^3$, $(CH_2)_zNHC(O)R^4$, and $(CH_2)_z$ $NR^4C(O)R^4$.

7. The compound of claim 1, or a pharmaceutically acceptable salt, hydrate, or solvate thereof, wherein $R^{2a}R^{2b}R^{2c}V$— is:

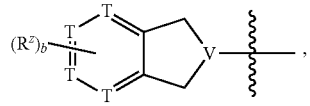

wherein:
J is selected from N, O, CH, C, and S;
when J is N, CH, or C, $R^u$ is selected from hydrogen, $C_1$-$C_8$ alkyl, ($C_1$-$C_8$ alkyl)$CF_3$, ($C_1$-$C_8$ alkyl)OH, and C(O)$R^{3a}$; and when J is O or S, $R^u$ is absent;
$R^{3a}$ is $C_1$-$C_8$ alkyl;
n is 0; and
is selected from 0, 1, 2, 3, 4, 5, 6, and 7.

8. The compound of claim 1, or a pharmaceutically acceptable salt, hydrate, or solvate thereof, wherein $R^{2a}R^{2b}R^{2c}V$— is:

wherein:
J is selected from CH and C;
$R^u$ is selected from hydrogen, $C_1$-$C_8$ alkyl, ($C_1$-$C_8$ alkyl) $CF_3$, ($C_1$-$C_8$ alkyl)OH, and C(O)$R^{3a}$; $R^{3a}$ is $C_1$-$C_8$ alkyl;
n is 0; and
is selected from 0, 1, 2, 3, 4, 5, 6, and 7.

9. The compound of claim 1, or a pharmaceutically acceptable salt, hydrate, or solvate thereof, wherein:
the cycloalkyl ring and cycloalkenyl ring formed by taking together two of $R^{2a}$, $R^{2b}$, and $R^{2c}$ are substituted with two or more $R^x$;
taken together only two $R^x$ form an aromatic ring, wherein said aromatic ring is unsubstituted or substituted with one or more $R^z$; and optionally:
each remaining $R^x$ is independently selected from $(CH_2)_z$ $NH_2$, $(CH_2)_zNHR^3$, $(CH_2)_zNR^3R^3$, $OR^3$, $OCF_3$, $OCH_2F$, $OCHF_2$, $(CH_2)_z$-heterocyclic ring, hydroxyl, halogen, $C_1$-$C_8$ alkyl, ($C_1$-$C_8$ alkyl)$CF_3$, ($C_1$-$C_8$ alkyl) OH, C(O)$R^3$, $(CH_2)_zC(O)NH_2$, $(CH_2)_zC(O)N H R^3$, $(CH_2)_zC(O)NR^3R^3$, $(CH_2)_zN HC(O) R^4$, and $(CH_2)_z$ $NR^4C(O)R^4$.

10. The compound of claim 1, or a pharmaceutically acceptable salt, hydrate, or solvate thereof, wherein $R^{2a}R^{2b}R^{2c}V(CH_2)_tU$— is:

wherein:

V is CH;

each instance of T is independently CH, CR$^z$, or N;

each R$^z$ is independently selected from halogen, C$_1$-C$_4$ alkyl, OH, OR$^3$, CF$_3$, OCF$_3$, OCH$_2$F, OCHF$_2$, NH$_2$, NHR$^3$, NR$^3$R$^3$, and C(O)CH$_3$;

b is 0; and each instance of R$^3$ is C$_1$-C$_8$ alkyl.

11. The compound of claim 10, or a pharmaceutically acceptable salt, hydrate, or solvate thereof, wherein each instance of T is independently CH or CR$^z$.

12. The compound of claim 1, or a pharmaceutically acceptable salt, hydrate, or solvate thereof, wherein the remaining R$^{2a}$, R$^{2b}$, or R$^{2c}$ is absent or hydrogen.

13. The compound of claim 1, or a pharmaceutically acceptable salt thereof.

14. The compound of claim 1, or a pharmaceutically acceptable salt thereof, wherein the compound is of the formula:

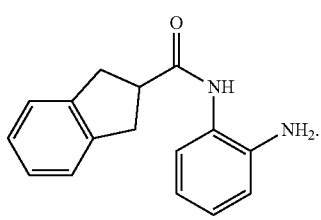

(223)

15. The compound of claim 1, or a pharmaceutically acceptable salt, hydrate, or solvate thereof, wherein:

the cycloalkyl ring and cycloalkenyl ring formed by taking together two of R$^{2a}$, R$^{2b}$, and R$^{2c}$ are substituted with two or more R$^x$;

taken together only two R$^x$ form a heteroaromatic ring, wherein said heteroaromatic ring is unsubstituted or substituted with one or more R$^z$; and optionally:

each remaining R$^x$ is independently selected from (CH$_2$)$_z$NH$_2$, (CH$_2$)$_z$NHR$^3$, (CH$_2$)$_z$NR$^3$R$^3$, OR$^3$, OCF$_3$, OCH$_2$F, OCHF$_2$, (CH$_2$)$_z$-heterocyclic ring, hydroxyl, halogen, C$_1$-C$_8$ alkyl, (C$_1$-C$_8$ alkyl)CF$_3$, (C$_1$-C$_8$ alkyl)OH, C(O)R$^3$, (CH$_2$)$_z$C(O)NH$_2$, (CH$_2$)$_z$C(O)NH R$^3$, (CH$_2$)$_z$C(O)NR$^3$R$^3$, (CH$_2$)$_z$NHC(O) R$^4$, and (CH$_2$)$_z$NR$^4$C(O)R$^4$.

16. A pharmaceutical composition comprising:

an effective amount of a compound of claim 1, or a pharmaceutically acceptable salt, hydrate, or solvate thereof; and a pharmaceutical carrier, diluent, or excipient.

17. A kit containing one or more of: the compounds of claim 1, and pharmaceutically acceptable salts, hydrates, and solvates thereof.

18. A compound of formula I:

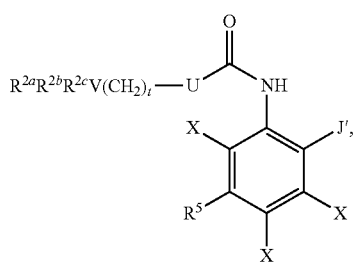

(I)

or a pharmaceutically acceptable salt, hydrate, solvate, or prodrug thereof, wherein:

J' is NH$_2$;

X is hydrogen;

R$^5$ is hydrogen;

U is a single bond;

t is selected from 0, 1, and 2;

R$^{2a}$R$^{2b}$R$^{2c}$V— is selected from:

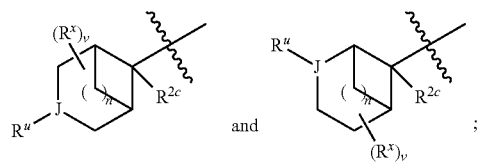

and

J is selected from N, O, CH, C, and S;

when J is N, CH, or C, R$^u$ is selected from hydrogen, C$_1$-C$_8$ alkyl, (C$_1$-C$_8$ alkyl)CF$_3$, (C$_1$-C$_8$ alkyl)OH, and C(O)R$^{3a}$; and when J is O or S, R$^u$ is absent;

R$^{3a}$ is C$_1$-C$_8$ alkyl;

n is 0, 1, or 2;

v is selected from 0, 1, 2, 3, 4, 5, 6, 7, and 8;

R$^{2c}$ is selected from hydrogen, halogen, OH, NH$_2$, and C$_1$-C$_8$ alkyl;

or R$^{2a}$R$^{2b}$R$^{2c}$V(CH$_2$)$_t$U— is

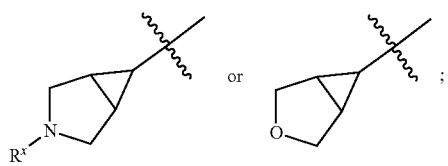

or

;

each R$^x$ is independently selected from (CH$_2$)$_z$NH$_2$, (CH$_2$)$_z$ NHR$^3$, (CH$_2$)$_z$NR$^3$R$^3$, OR$^3$, OCF$_3$, OCH$_2$F, OCHF$_2$, (CH$_2$)$_z$-aromatic ring, (CH$_2$)$_z$-heterocyclic ring, hydroxyl, halogen, C$_1$-C$_8$ alkyl, (C$_1$-C$_8$ alkyl)CF$_3$, (C$_1$-C$_8$ alkyl)OH, C(O)R$^3$, (CH$_2$)$_z$C(O)NH$_2$, (CH$_2$)$_z$C(O)NHR$^3$, (CH$_2$)$_z$C(O)NR$^3$R$^3$, (CH$_2$)$_z$NHC(O)R$^4$, and (CH$_2$)$_z$NR$^4$C(O)R$^4$;

or taken together two R$^x$ attached to the same carbon atom of a cycloalkyl, cycloalkenyl, or heterocyclic ring form =O;

or taken together two R$^x$ form a C$_3$-C$_8$ cycloalkyl ring, C$_4$-C$_8$ cycloalkenyl ring, or 3 to 8 membered, saturated or partially unsaturated, heterocyclic ring, wherein said cycloalkyl ring, cycloalkenyl ring, and heterocyclic ring are unsubstituted or substituted with one or more R$^z$;

or taken together two R$^x$ form an aromatic ring or heteroaromatic ring, wherein said aromatic ring and heteroaromatic ring are unsubstituted or substituted with one or more R$^z$;

each R$^z$ is independently selected from halogen, C$_1$-C$_4$ alkyl, OH, OR$^3$, CF$_3$, OCF$_3$, OCH$_2$F, OCHF$_2$, NH$_2$, NHR$^3$, NR$^3$R$^3$, and C(O)CH$_3$;

each instance of R$^3$ is independently selected from C$_1$-C$_8$ alkyl and O(C$_1$-C$_8$ alkyl);

each instance of R$^4$ is independently selected from C$_1$-C$_8$ alkyl and CF$_3$; and z is selected from 0, 1, 2, and 3.

19. The compound of claim 18, or a pharmaceutically acceptable salt thereof.

20. A pharmaceutical composition comprising:
an effective amount of a compound of claim 18, or a pharmaceutically acceptable salt, hydrate, solvate, or prodrug thereof; and
a pharmaceutical carrier, diluent, or excipient.

21. A kit containing one or more of: the compounds of claim 18, and pharmaceutically acceptable salts, hydrates, solvates, and prodrugs thereof.

22. A method of treating a condition in a subject in need thereof comprising administering to the subject in need thereof an effective amount of a compound of claim 1, or a pharmaceutically acceptable salt, hydrate, or solvate thereof, wherein the condition is a disease.

23. The method of claim 22, wherein the condition is a cancer.

24. The method of claim 22, wherein the compound or a pharmaceutically acceptable salt, hydrate, or solvate thereof is administered by a route selected from oral, parenteral, intramuscular, intranasal, sublingual, intratracheal, inhalation, ocular, vaginal, rectal, and intracerebroventricular.

25. The method of claim 22, wherein the condition is hematologic cancer.

26. The method of claim 25, wherein the hematologic cancer is selected from the group consisting of acute myeloid leukemia, acute promyelocytic leukemia, acute lymphoblastic leukemia, chronic myelogenous leukemia, and myelodysplastic syndromes.

27. The method of claim 22, wherein the condition is lymphoma.

28. The method of claim 22, wherein the condition is non-Hodgkin's lymphoma.

29. The method of claim 22, wherein the condition is diffuse large B-cell lymphoma.

30. A method of improving memory in a normal subject comprising administering to the normal subject an effective amount of a compound of claim 1, or a pharmaceutically acceptable salt, hydrate, or solvate thereof.

31. A method of increasing synaptic density, synaptic plasticity, or dendritic density in neurons in a subject in need of such increase comprising administering to the subject in need of such increase an effective amount of a compound of claim 1, or a pharmaceutically acceptable salt, hydrate, or solvate thereof.

32. A method of treating a condition in a subject in need thereof comprising administering to the subject in need thereof an effective amount of a compound of claim 18, or a pharmaceutically acceptable salt, hydrate, solvate or prodrug thereof, wherein the condition is a neoplastic disease.

33. The method of claim 32, wherein the condition is hematologic cancer.

34. The method of claim 32, wherein the condition is lymphoma.

35. The method of claim 32, wherein the condition is non-Hodgkin's lymphoma.

36. The method of claim 32, wherein the condition is diffuse large B-cell lymphoma.

37. The method of claim 33, wherein the hematologic cancer is selected from the group consisting of acute myeloid leukemia, acute promyelocytic leukemia, acute lymphoblastic leukemia, chronic myelogenous leukemia, and myelodysplastic syndromes.

38. A method of improving memory in a normal subject comprising administering to the normal subject an effective amount of a compound of claim 18, or a pharmaceutically acceptable salt, hydrate, solvate, or prodrug thereof.

39. A method of increasing synaptic density, synaptic plasticity, or dendritic density in neurons in a subject in need of such increase comprising administering to the subject in need of such increase an effective amount of a compound of claim 18, or a pharmaceutically acceptable salt, hydrate, solvate, or prodrug thereof.

* * * * *

UNITED STATES PATENT AND TRADEMARK OFFICE
CERTIFICATE OF CORRECTION

PATENT NO. : 10,662,199 B2
APPLICATION NO. : 15/786134
DATED : May 26, 2020
INVENTOR(S) : Edward Holson et al.

Page 1 of 1

It is certified that error appears in the above-identified patent and that said Letters Patent is hereby corrected as shown below:

In the Claims

In Claim 7, at Column 260, Line 20, the text "is selected" should be replaced with the text --v is selected--.

In Claim 8, at Column 260, Line 40, the text "is selected" should be replaced with the text --v is selected--.

In Claim 22, at Column 263, Line 13, the text "a disease" should be replaced with the text --a neoplastic disease--.

Signed and Sealed this
Fourteenth Day of July, 2020

Andrei Iancu
*Director of the United States Patent and Trademark Office*